(12) United States Patent
Hyde et al.

(10) Patent No.: US 8,637,636 B2
(45) Date of Patent: *Jan. 28, 2014

(54) PEPTIDE SYNTHESIS APPARATUSES

(75) Inventors: Roderick A. Hyde, Redmond, WA (US); Edward K. Y. Jung, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 290 days.

This patent is subject to a terminal disclaimer.

(21) Appl. No.: 12/829,566

(22) Filed: Jul. 2, 2010

(65) Prior Publication Data

US 2010/0331215 A1  Dec. 30, 2010

Related U.S. Application Data

(63) Continuation of application No. 11/821,375, filed on Jun. 22, 2007, now Pat. No. 7,777,002, which is a continuation-in-part of application No. 11/478,540, filed on Jun. 29, 2006, now Pat. No. 7,754,854.

(51) Int. Cl.
*C07K 1/02* (2006.01)
*C07K 2/00* (2006.01)

(52) U.S. Cl.
USPC ............. 530/333; 530/300; 530/350; 930/10; 930/20

(58) Field of Classification Search
None
See application file for complete search history.

(56) References Cited

U.S. PATENT DOCUMENTS

| | | | |
|---|---|---|---|
| 5,562,622 A | 10/1996 | Tihon | |
| 5,635,400 A | 6/1997 | Brenner | |
| 5,700,667 A * | 12/1997 | Marble et al. | 435/91.3 |
| 6,457,361 B1 | 10/2002 | Takeuchi et al. | |
| 6,555,360 B1 | 4/2003 | Srienc et al. | |
| 6,562,622 B1 | 5/2003 | Coia et al. | |
| 6,620,587 B1 | 9/2003 | Taussig et al. | |
| 6,722,200 B2 | 4/2004 | Roukes et al. | |
| 6,846,638 B2 | 1/2005 | Shipwash | |
| 7,247,448 B2 | 7/2007 | Erdmann et al. | |
| 7,879,973 B2 * | 2/2011 | Hyde et al. | 530/333 |
| 7,879,974 B2 * | 2/2011 | Hyde et al. | 530/333 |
| 7,879,975 B2 * | 2/2011 | Hyde et al. | 530/333 |
| 7,888,465 B2 * | 2/2011 | Hyde et al. | 530/333 |
| 7,910,695 B2 * | 3/2011 | Hyde et al. | 530/333 |
| 7,923,533 B2 * | 4/2011 | Hyde et al. | 530/333 |
| 7,977,070 B2 * | 7/2011 | Hyde et al. | 435/69.1 |
| 2003/0100000 A1 | 5/2003 | Martin | |
| 2005/0064465 A1 * | 3/2005 | Dettloff et al. | 435/6 |
| 2005/0260653 A1 | 11/2005 | Labaer et al. | |
| 2006/0073478 A1 * | 4/2006 | Fink et al. | 435/6 |
| 2006/0078888 A1 | 4/2006 | Griffiths et al. | |
| 2006/0223178 A1 | 10/2006 | Barber et al. | |
| 2007/0119510 A1 | 5/2007 | Kartalov et al. | |
| 2009/0081643 A1 | 3/2009 | Preminger et al. | |

FOREIGN PATENT DOCUMENTS

| WO | WO 2004/050825 A2 | 6/2004 |
|---|---|---|
| WO | WO 2004/104178 A2 | 12/2004 |

OTHER PUBLICATIONS

U.S. Appl. No. 11/478,551, Hyde et al.
U.S. Appl. No. 11/478,550, Hyde et al.
U.S. Appl. No. 11/478,549, Hyde et al.
U.S. Appl. No. 11/478,548, Hyde et al.
U.S. Appl. No. 11/478,546, Hyde et al.
U.S. Appl. No. 11/478,540, Hyde et al.
U.S. Appl. No. 11/478,539, Hyde et al.
U.S. Appl. No. 11/478,382, Hyde et al.
U.S. Appl. No. 11/478,326, Hyde et al.
U.S. Appl. No. 11/478,308, Hyde et al.
Adelman, M.R.; Blobel, Gunter; Sabatini, David D.; "An Improved Cell Fractionation Procedure for the Preparation of Rat Liver Membrane-Bound Ribosomes"; The Journal of Cell Biology; Bearing a date of 1973; pp. 191-205; vol. 56; located at: www.jcb.org.
Asahara, Haruichi; Uhlenbeck, Olke C.; "Predicting the Binding Affinities of Misacylated tRNAs for *Thermus thermophilus* EF-Tu-GTP"; Biochemistry; Bearing dates of 2005 and Jul. 29, 2005; pp. 11254-11261; vol. 44, No. 33; American Chemical Society.
Beaulande, Melanie; Tarbouriech, Nicolas; Hartlein, Michael; "Human Cytosolic Asparaginyl-tRNA Synthetase: cDNA Sequence, Functional Expression in *Escherichia coli* and Characterization as Human Autoantigen"; Nucleic Acids Research; bearing a date of 1998; pp. 521-524; vol. 26, No. 2; Oxford University Press.
Beebe, David J.; Mensing, Glennys A.; Walker, Glenn M.; "Physics and Applications of Microfluidics in Biology"; Annual Review of Biomedical Engineering; bearing a date of 2002; pp. 261-286; vol. 4; Annual Reviews; located at: arjournals.annualreviews.org.
Beringer, Malte; Bruell, Christian; Xiong, Liqun; Pfister, Peter; Bieling, Peter; Katunin, Vladimir I.; Mankin, Alexander S.; Bottger, Erik C.; Rodnina, Marina V.; "Essential Mechanisms in the Catalysis of Peptide Bond Formation on the Ribosome"; The Journal of Biological Chemistry; bearing a date of Oct. 28, 2005; pp. 36065-36072; vol. 280, No. 43; The American Society for Biochemistry and Molecular Biology, Inc.
Bessho, Yoshitaka; Hodgson, David R.W.; Suga, Hiroaki; "Research Article: A tRNA Aminoacylation System for Non-Natural Amino Acids Based on a Programmable Ribozyme"; Nature Biotechnology; bearing dates of Jul. 2002; pp. 723-728; vol. 20; Nature Publishing Group; located at: http://biotech.nature.com.

(Continued)

*Primary Examiner* — Christopher M Gross
(74) *Attorney, Agent, or Firm* — Dorsey & Whitney LLP

(57) ABSTRACT

Methods, apparatus, systems, computer programs and computing devices related to biologically assembling and/or synthesizing peptides and/or proteins are disclosed.

29 Claims, 38 Drawing Sheets

(56) References Cited

OTHER PUBLICATIONS

Blanchard, Scott C.; Gonzalez, Ruben L., Jr.; Kim, Harold D.; Chu, Steven; Puglisi, Joseph D.; "Articles: tRNA Selection and Kinetic Proofreading in Translation"; Nature Structural & Molecular Biology; bearing a date of Oct. 2004; pp. 1008-1014; vol. 11, No. 10; Nature Publishing Group; located at: http://www.nature.com/natstructmolbiol.
Blanchard, Scott C.; Kim, Harold D.; Gonzalez, Ruben L., Jr.; Puglisi, Joseph D.; Chu, Steven; "Biophysics: tRNA Dynamics on the Ribosome During Translation"; PNAS; bearing a date of Aug. 31, 2004; pp. 12893-12898; vol. 101, No. 35; The National Academy of Sciences of the USA; located at: www.pnas.org/chi/doi/10.1073/pnas.0403884101.
Bocchetta, Maurizio; Xiong, Liqun; Mankin, Alexander S.; "23S rRNA Positions Essential for tRNA Binding in Ribosomal Functional Sites"; Proceedings of the National Academy of Sciences; bearing a date of Mar. 1998; pp. 3525-3530; vol. 95; The National Academy of Sciences; located at: http://www.pnas.org.
Brandt, Ole; Hoheisel, Jorg D.; "Opinion: Peptide Nucleic Acids on Microarrays and Other Biosensors"; Trends in Biotechnology; bearing a date of Dec. 2004; pp. 617-622; vol. 22, No. 12; Elsevier Ltd; located at: www.sciencedirect.com
Brune, Martin; Hunter, Jackie L.; Howell, Steven A.; Martin, Stephen R.; Hazlett, Theodore L.; Corrie, John E.T.; Webb, Martin R.; "Mechanism of Inorganic Phosphate Interaction with Phosphate Binding Protein from *Escherichia coli*"; Biochemistry; bearing a date of 1998; pp. 10370-10380; vol. 37; American Chemical Society.
Burns, Mark A.; Johnson, Brian N.; Brahmasandra, Sundaresh N.; Handique, Kalyan; Webster, James R.; Krishnan, Madhavi; Sammarco, Timothy S.; Man, Piu M.; Jones, Darren; Heldsinger, Dylan; Mastrangelo, Carlos H.; Burke, David T.; "Reports: An Integrated Nanoliter DNA Analysis Device"; Science Magazine; bearing a date of Oct. 16, 1998; pp. 484-487; vol. 282; located at: www.sciencemag.com.
Capone, John P.; Sharp, Phillip A.; Rajbhandary, Uttam L.; "Amber, Ochre and Opal Suppressor tRNA Genes Derived From a Human Serine tRNA Gene"; The EMBO Journal; bearing a date of 1985; pp. 213-221; vol. 4, No. 1; IRL Press Limited, Oxford, England.
Cheng, Slew Bang; Skinner, Cameron D.; Taylor, Justine; Attiya, Said; Lee, William E.; Piceill, Gilles; Harrison, D. Jed; "Development of a Multichannel Microfluidic Analysis System Employing Affinity Capillary Electrophoresis for Immunoassay"; Analytical Chemistry; bearing a date of Apr. 1, 2001; pp. 1472-1479; vol. 73, No. 7; American Chemical Society.
Chin, Jason W.; Cropp, T. Ashton; Anderson, J. Christopher; Mukherji, Mridul; Zhang, Zhiwen; Schultz, Peter G.; "Reports: An Expanded Eukaryotic Genetic Code"; Science; bearing a date of Aug. 15, 2003; pp. 964-967; vol. 301; located at: www.sciencemag.org.
Curran, James F.; Yarus, Michael; "Rates of Aminoacyl-tRNA Selection at 29 Sense Codons in Vivo"; Journal of Molecular Biology; bearing a date of 1989; pp. 65-77; vol. 209; Academic Press Limited.
Dale, Taraka; Uhlenbeck, Olke C.; "Letter to the Editor: Binding of Misacylated tRNAs to the Ribosomal A Site"; RNA; bearing a date of 2005; pp. 1610-1615; vol. 11; Cold Spring Harbor Laboratory Press—RNA Society.
Dale, Taraka; Uhlenbeck, Olke C.; "Opinion: Amino Acid Specificity in Translation"; Trends in Biochemical Sciences; bearing a date of Dec. 2005; pp. 659-665; vol. 30, No. 12; Elsevier Ltd; located at: www.sciencedirect.com.
Deisingh, Anil K.; "I-Section: MEMS Technology in Analytical Chemistry"; The Analyst; bearing a date of 2003; pp. 9-11; vol. 128; The Royal Society of Chemistry.
Dittmar, Kimberly A.; Goodenbour, Jeffrey M.; Pan, Tao; "Tissue-Specific Differences in Human Transfer RNA Expression"; PLOS Genetics; bearing a date of Dec. 2006; pp. 2107-2115; vol. 2, No. 12 e221; located at: www.plosgenetics.org.
Dorywalska, Magdalena; Blanchard, Scott C.; Gonzalez, Ruben L., Jr.; Kim, Harold D.; Chu, Steven; Puglisi, Joseph D.; "Site-Specific Labeling of the Ribosome for Single-Molecule Spectroscopy"; Nucleic Acids Research; bearing a date of 2005; pp. 182-189; vol. 33, No. 1; Oxford University Press.
Englisch, Sabine; Englisch, Uwe; Von Der Haar, Friedrich; Cramer, Friedrich; "The Proofreading of Hydroxy Analogues of Leucine and Isoleucine by Leucyl-tRNA Synthetases from *E. coli* and Yeast"; Nucleic Acids Research; bearing a date of 1986; pp. 7529-7539; vol. 14, No. 19; IRL Press Limited, Oxford, England.
Flick, Jeffrey S.; Thorner, Jeremy; "Genetic and Biochemical Characterization of a Phosphatidylinositol-Specific Phospholipase C in *Saccharomyces cerevisiae*"; Molecular and Cellular Biology; bearing a date of Sep. 1993; pp. 5861-5876; vol. 13, No. 9; American Society for Microbiology.
Forster, Anthony C.; Tan, Zhongping; Nalam, Madhavi N.L.; Lin, Hening; Qu, Hui; Cornish, Virginia W.; "Programming Peptidomimetic Syntheses by Translating Genetic Codes Designed de novo"; Biochemistry; bearing a date of May 27, 2003; pp. 6353-6357; vol. 100, No. 11; PNAS.
Gabriel, Kaigham J.; "Machines, Materials and Manufacturing: Engineering Microscopic Machines"; Scientific American; bearing a date of Sep. 1995; pp. 150-153; Scientific American, Inc.
Gau, Jen-Jr; Lan, Esther H.; Dunn, Bruce; Ho, Chih-Ming; Woo, Jason C.S.; "A MEMS Based Amperometric Detector for *E. coli* Bacteria Using Self-Assembled Monolayers"; Biosensors & Bioelectronics; bearing a date of 2001; pp. 745-755; vol. 16; Elsevier Science B.V.
Gilchrist, Michael A.; Wagner, Andreas; "A Model of Protein Translation including Codon Bias, Nonsense Errors, and Ribosome Recycling"; Journal of Theoretical Biology; bearing a date of Apr. 21, 2006; pp. 417-434; vol. 239, No. 4; Elsevier Ltd; located at: www.elsevier.com/locate/yjtbi and www.sciencedirect.com.
Giordano, B.C.; Ferrance, J.; Swedberg, S.; Huhmer, A.F.R.; Landers, J.P.; "Polymerase Chain Reaction in Polymeric Microchips: DNA Amplification in Less Than 240 Seconds"; Analytical Biochemistry; bearing a date of 2001; pp. 124-132; vol. 291; Academic Press; located at: http://www.idealibrary.com.
Hartman, Matthew C.T.; Josephson, Kristopher; Szostak, Jack W.; "Enzymatic Aminoacylation of tRNA with Unnatural Amino Acids"; PNAS; bearing a date of Mar. 21, 2006; pp. 4356-4361; vol. 103, No. 12; The National Academy of Sciences of the USA; located at: www.pnas.org/cgi/doi/10.1073/pnas.0509219103.
Henderson, Matthew P.A.; Billen, Lieven P.; Kim, Peter K.; Andrews, David W.; "Cell-Free Analysis of Tail-Anchor Protein Targeting to Membranes"; Methods; bearing a date of 2007; pp. 427-438; vol. 41; Elsevier, Inc.; located at: www.sciencedirect.com or www.elsevier.com/locate/ymeth.
Hendrickson, Tamara L.; Crécy-Lagard, Valérie De; Schimmel, Paul; "Incorporation of NonNatural Amino Acids Into Proteins"; Annual Reviews of Biochemistry; Bearing a date of 2004; pp. 147-176; vol. 73; Annual Reviews.
Hodgson, David R.W.; Sanderson, John M.; "Tutorial Review: The Synthesis of Peptides and Proteins Containing Non-Natural Amino Acids"; Chemistry Society Review; bearing a date of 2004; pp. 422-430; vol. 33; The Royal Society of Chemistry; located at: www.rsc.org/csr.
Hoffmann, A.; Roeder, R.G.; "Purification of His-Tagged Proteins in Non-Denaturing Conditions Suggests a Convenient Method for Protein Interaction Studies"; Nucleic Acids Research; bearing a date of Aug. 23, 1991; pp. 6337-6338; vol. 19, No. 22; Laboratory of Biochemistry and Molecular Biology, The Rockefeller University, New York, NY, USA.
Hohsaka, Takahiro; Ashizuka, Yuki; Murakami, Hiroshi; Sisido, Masahiko; "Five-Base Codons for Incorporation of Nonnatural Amino Acids into Proteins"; Nucleic Acids Research; bearing a date of 2001; pp. 3646-3651; vol. 29, No. 17; Oxford University Press.
Hohsaka, Takahiro; Ashizuka, Yuki; Taira, Hikaru; Murakami, Hiroshi; Sisido, Masahiko; "Incorporation of Nonnatural Amino Acids into Proteins by Using Various Four-Base Codons in an *Escherichia coli* inVitro Translation System"; Biochemistry; bearing a date of 2001; pp. 11060-11064; vol. 40; American Chemical Society.
Huang, Yanyi; Castrataro, Piero; Lee, Cheng-Chung; Quake, Stephen R.; "Communication: Solvent Resistant Microfluidic DNA Synthe-

(56) References Cited

OTHER PUBLICATIONS sizer"; Lab on a Chip; bearing a date of 2007; pp. 24-26; vol. 7; The Royal Society of Chemistry; located at: www.rsc.org/loc.

Huh, Dongeun; Mills, K.L.; Zhu, Xiaoyue; Burns, Mark A.; Thouless, M.D.; Takayama, Shuichi; "Letters: Tuneable Elastomeric Nanochannels for Nanofluidic Manipulation"; Nature Materials; bearing a date of Jun. 2007; pp. 424-428; vol. 6; Nature Publishing Group; located at: www.nature.com/naturematerials.

Hyun, Soonsil; Hyun Lee, Kyung; Yu, Jaehoon; "A Strategy for the Design of Selective RNA Binding Agents. Preparation and RRE RNA Binding Affinities of a Nemycin-Peptide Nucleic Acid Heteroconjungate Library"; Bioorganic & Medicinal Chemistry Letters; bearing a date of 2006; pp. 4757-4759; vol. 16; Elsevier Ltd.; located at: www.sciencedirect.com.

Ibba, Michael; "Science's Compass: Persectives: Protein Synthesis: Discriminating Right From Wrong"; Science; bearing a date of Oct. 5, 2001; pp. 70-71; vol. 294; located at: www.sciencemag.org.

Ibrahim, Nader G.; Burke, James P.; Beattie, Diana S.; "The Sensitivity of Rat Liver and Yeast Mitochondrial Ribosomes to Inhibitors of Protein Synthesis"; The Journal of Biological Chemistry; bearing a date of Nov. 10, 1974; pp. 6806-6811; vol. 249, No. 21; located at: www.jbc.org.

Jackson, R.J.; Napthine, S.; Brierley, I.; Development of a tRNA-Dependent in Vitro Translation System; RNA; bearing a date of 2001; pp. 765-773; vol. 7; RNA Society; located at: www.majournal.org.

Jankowsky, Eckhard; Strunk, Gunther; Schwenzer, Bernd; "Peptide Nucleic Acid (PNA) is Capable of Enhancing Hammerhead Ribozyme Activity with Long But Not With Short RNA Substrates"; Nucleic Acids Research; bearing a date of 1997; pp. 2690-2693; vol. 25, No. 14; Oxford University Press.

Joseph, Simpson; Noller, Harry F.; "Mapping the rRNA Neighborhood of the Acceptor End of tRNA in the Ribosome"; The EMBO Journal; bearing a date of 1996; pp. 910-916; vol. 15, No. 4; Oxford University Press.

Kapp, Lee D.; Lorsch, Jon R.; "The Molecular Mechanics of Eukaryotic Translation"; Annual Review of Biochemistry; bearing a date of 2004; pp. 657-704; vol. 73; Annual Reviews.

Köhrer, Caroline; Sullivan, Eric L.; Rajbhandary, Uttam L.; "Complete Set of Orthogonal $21^{st}$ Aminoacyl-tRNA Synthetase-Amber, Ochre and Opal Suppressor tRNA Pairs: Concomitant Suppression of Three Different Termination Codons in an mRNA in Mammalian Cells"; Nucleic Acids Research; bearing a date of 2004; pp. 6200-6211; vol. 32, No. 21; Oxford University Press.

Kopp, Martin U.; De Mello, Andrew J.; Manz, Andreas; "Reports: Chemical Amplification: Continuous-Flow PCR on a Chip"; Science Magazine; bearing a date of May 15, 1998; pp. 1046-1048; vol. 280; located at: www.sciencemag.org.

Korencic, Dragana; Soll, Dieter; Ambrogelly, Alexandre; "A One-Step Method for In Vitro Production of tRNA Transcripts"; Nucleic Acids Research; bearing a date of 2002; pp. 1-4; vol. 30, No. 20 e105; Oxford University Press.

Kourouklis, Dimitrios; Murakami, Hiroshi; Suga, Hiroaki; "Programmable ribozymes for mischarging tRNA with nonnatural amino acids and their applications to translation"; Methods; bearing a date of 2005; pp. 239-244; vol. 36; Elsevier Inc.; located at: www.sciencedirect.com.

Lariviere, Frederick J.; Wolfson, Alexey D.; Uhlenbeck, Olke C.; "Reports: Uniform Binding of Aminoacyl-tRNAs to Elongation Factor Tu by Thermodynamic Compensation"; Science; bearing a date of Oct. 5, 2001; pp. 165-168; vol. 294; located at: www.sciencemag.org.

Lee, Byeong J.; De La Pena, Pilar; Tobian, Janet A.; Zasloff, Michael; Hatfield, Dolph; "Unique Pathway of Expression of an Opal Suppressor Phosphoserine tRNA"; Biochemistry—Proceedings of the National Academy of Sciences; bearing a date of Sep. 1987; pp. 6384-6388; vol. 84.

Link, A. James; Tirrell, David A.; "Reassignment of Sense Condons in Vivo" Methods; bearing a date of 2005; pp. 291-298; vol. 36; Elsevier Inc.; located at: www.sciencedirect.com.

Lodder, Michiel; Wang, Bixun; Hecht, Sidney M.; "The N-pentenoyl Protecting Group for Aminoacyl-tRNAs" Methods; bearing a date of 2005; pp. 245-251; vol. 36; Elsevier Inc.; located at: www.sciencedirect.com.

Magota, Koji; Otsuji, Nozomu; Miki, Takeyoshi; Horiuchi, Tadao; Tsunasawa, Susumu; Kondo, Jun; Sakiyama, Fumio; Amemura, Mitsuko; Morita, Takashi; Shinagawa, Hideo; Nakata, Atsuo; "Nucleotide Sequence of the phoS Gene, the Structural Gene for the Phosphate-Binding Protein of *Escherichia coli*"; Journal of Bacteriology; bearing a date of Mar. 1984; pp. 909-917; vol. 157, No. 3; American Society for Microbiology.

Margulies, Marcel; Egholm, Michael; Altman, William E.; Attiya, Said; Bader, Joel S.; Bemben, Lisa A.; Berka, Jan; Braverman, Michael S.; Chen, Yi-Ju; Chen, Zhoutao; Dewell, Scott B.; Du, Lei; Fierro, Joseph M.; Gomes, Xavier V.; Godwin, Brian C.; He, Wen; Helgesen, Scott; Ho, Chun He; Irzyk, Gerard P.; Jando, Szilveszter C.; Alenquer, Maria L.I.; Jarvie, Thomas P.; Jirage, Kshama B.; Kim, Jong-Bum; Knight, James R.; Lanza, Janna R.; Leamon, John H.; Lefkowitz, Steven M.; Lei, Ming; Li, Jing; Lohman, Kenton L.; Lu, Hong; Makhijani, Vinod B.; McDade, Keith E.; McKenna, Michael P.; Myers, Eugene W.; Nickerson, Elizabeth; Nobile, John R.; Plant, Ramona; Puc, Bernard P.; Ronan, Michael T.; Roth, George T.; Sarkis, Gary J.; Simons, Jan Fredrik; Simpson, John W.; Srinivasan, Maithreyan; Tartaro, Karrie R.; Tomasz, Alexander; Vogt, Kari A.; Volkmer, Greg A.; Wang, Shally H.; Wang, Yong; Weiner, Michael P.; Yu, Pengguang; Begley, Richard F.; Rothberg, Jonathan M.; "Genome sequencing in microfabricated high-density picolitre reactors"; Nature; bearing a date of Sep. 15, 2005; pp. 376-380; vol. 437; Nature Publishing Group.

Mhlanga, Musa M.; Vargas, Diana Y.; Fung, Cindy W.; Kramer, Fred Russell; Tyagi, Sanjay; "tRNA-Linked Molecular Beacons for Imaging mRNAs in the Cytoplasm of Living Cells"; Nucleic Acids Research; bearing a date of 2005; pp. 1902-1912; vol. 33, No. 6; The Author—Oxford University Press.

Moraes, Christopher; Simmons, Craig A.; Sun, Yu; "Cell Mechanics Meets MEMS"; CSME Bulletin SCGM; bearing a date of Fall 2006; pp. 15-18; Mechanical and Industrial Engineering, Institute of Biomaterials and Biomedical Engineering, University of Toronto.

Moriyama, Kei; Kimoto, Michiko; Mitsui, Tsuneo; Yokoyama, Shigeyuki; Hirao, Ichiro; "Site-Specific Biotinylation of RNA Molecules by Transcription Using Unnatural Base Pairs"; Nucleic Acids Research; bearing a date of Aug. 19, 2005; pp. 1-8; vol. 33, No. 15 e129; The Author—Oxford University Press.

Mothes, Walther; Heinrich, Sven U.; Graf, Roland; Nilsson, Ingmarie; Von Heijne, Gunnar; Brunner, Josef; Rapoport, Tom A.; "Molecular Mechanism of Membrane Protein Integration into the Endoplasmic Reticulum"; Cell; bearing a date of May 16, 1997; pp. 523-533; vol. 89; Cell Press.

Nagata, Hideya; Hirano, Ken; Tabuchi, Mari; Baba, Yoshinobu; "Application of the Thermal Lens Microscope as a Detector of the Biopolymer in Microchip Electrophoresis"; $7^{th}$ International Conference on Miniaturized Chemical and Biochemical Analysis Systems; bearing a date of Oct. 5-9, 2003; pp. 367-370.

Noren, Christopher J.; Anthony-Cahill, Spencer J.; Suich, Daniel J.; Noren, Karen A.; Griffith, Michael C.; Schultz, Peter G.; "In Vitro Suppression of an Amber Mutation by a Chemically Aminoacylated Transfer RNA Prepared by Runoff Transcription"; Nucleic Acids Research; bearing a date of Jan. 11, 1990; pp. 83-88; vol. 18, No. 1; Department of Chemistry, University of California, Berkeley, CA; located at: http://www.pubmedcentral.nih.gov/articlerender.fcgi?artid=330206.

Okoh, Michael P.; Hunter, Jackie L.; Corrie, John E.T.; Webb, Martin R.; "A Biosensor for Inorganic Phosphate Using a Rhodamine-Labeled Phosphate Binding Protein"; Biochemistry; bearing a date of 2006; pp. 14764-14771; vol. 45; American Chemical Society.

Pavlov, Michael Yu; Ehrenberg, Mans; "Rate of Translation of Natural mRNAs in an Optimized in Vitro System"; Archives of Biochemistry and Biophysics; bearing a date of Apr. 1, 1996; pp. 9-16; vol. 328, No. 1; Academic Press, Inc.

Pfisterer, J.; Buetow, D.E.; "In Vitro Reconstitution of the Mitochondrial Translation System of Yeast"; Biochemistry—Proceedings of the National Academy of Sciences; bearing a date of Aug.

(56) References Cited

OTHER PUBLICATIONS

1981; pp. 4917-4921; vol. 78, No. 8; Department of Physiology and Biophysics, University of Illinois, Urbana, Illinois.

Polla, Dennis L.; Erdman, Arthur G.; Robbins, William P.; Markus, David T.; Diaz-Diaz, Jorge; Rizq, Raed; Nam,Yunwoo; Brickner, Hui Tao; "Microdevices in Medicine"; Annual Review of Biomedical Engineering; bearing a date of 2000; pp. 551-576; vol. 2; located at: arjournals.annualreviews.org.

Ramakrishnan, V.; "Ribosome Structure and the Mechanism of Translation"; Cell; bearing a date of Feb. 22, 2002; pp. 557-572; vol. 108; Cell Press.

Robertson, Stephanie A.; Noren, Christopher J.; Anthony-Cahill, Spencer J.; Griffith, Michael C.; Schulz, Peter G.; "The Use of 5'-phospho-2 Deoxyribocytidylylriboadenosine as a Facile Route to Chemical Aminoacylation of tRNA"; Nucleic Acids Research; bearing a date of 1989; pp. 9649-9660; vol. 17, No. 23; Department of Chemistry, University of California, Berkeley, CA.

Rothschild, Kenneth J.; Gite, Sadanand; "tRNA-mediated Protein Engineering"; Biotechnology; bearing a date of 1999; pp. 64-70; vol. 10; Elsevier Science Ltd.; located at: http://biomednet.com/elecref/0958166901000064.

Saito, Hirohide; Kourouklis, Dimitrios; Suga, Hiroaki; "An in Vitro Evolved Precursor tRNA with Aminoacylation Activity"; The EMBO Journal; bearing a date of 2001; pp. 1797-1806; vol. 20, No. 7; European Molecular Biology Organization.

Sampson, Jeffrey R.; Uhlenbeck, Olke C.; "Biochemical and Physical Characterization of an Unmodified Yeast Phenylalanine Transfer RNA Transcribed in Vitro"; Biochemistry—Proceedings of the National Academy of Sciences; bearing a date of Feb. 1988; pp. 1033-1037; vol. 85; Department of Chemistry and Biochemistry—University of Colorado.

Sato, Kiichi; Tokeshi, Manabu; Odake, Tamao; Kimura, Hiroko; Ooi, Takeshi; Nakao, Masayuki; Kitamori, Takehiko; "Integration of an Immunosorbent Assay System: Analysis of Secretory Human Immunoglobulin A on Polystyrene Beads in a Microchip"; Analytical Chemistry; bearing a date of Mar. 15, 2000; pp. 1144-1147; vol. 72, No. 6; American Chemical Society.

Sato, Kiichi; Yamanaka, Maho; Hagino, Tomokazu; Tokeshi, Manabu; Kimura, Hiroko; Kitamori, Takehiko; "Paper: Microchip-Based Enzyme-Linked Immunosorbent Assay (microELISA) System with Thermal Lens Detection"; Miniaturisation for Chemistry, Biology & Bioengineering—Lab on a Chip; bearing a date of 2004; pp. 570-575; vol. 4; The Royal Society of Chemistry.

Schmeing, T. Martin, Huang, Kevin S.; Strobel, Scott A.; Steitz, Thomas A.; "Letters: An Inducted-fit Mechanism to Promote Peptide Bond Formation and Exclude Hydrolysis of Peptidyl-tRNA"; Nature; bearing a date of Nov. 24, 2005; pp. 520-524; vol. 438; Nature Publishing Group.

Seiser, Robert M.; Nicchitta, Christopher V.; "The Fate of Membrane-bound Ribosomes Following the Termination of Protein Synthesis"; The Journal of Biological Chemistry; bearing a date of Oct. 27, 2000; pp. 33820-33827; vol. 275, No. 43; The American Society for Biochemistry and Molecular Biology, Inc.; located at: http://www.jbc.org.

Shimizu, Yoshihiro; Inoue, Akio; Tomari, Yukihide; Suzuki, Tsutomu; Yokogawa, Takashi; Nishikawa, Kazuya; Ueda, Takuya; "Research Article: Cell-free Translation Reconstituted With Purified Components"; Nature Biotechnology; bearing a date of Aug. 2001; pp. 751-755; vol. 19; Nature Publishing Group; located at: http://biotech.nature.com.

Shimizu, Yoshihiro; Kanamori, Takashi; Ueda, Takuya; "Protein synthesis by Pure Translation Systems"; Methods; bearing a date of 2005; pp. 299-304; vol. 36; Elsevier Inc.; located at: www.sciencedirect.com.

Shipwash, Edward; "Microarrays for Amino Acid Analysis and Protein Sequencing"; bearing a date of Aug. 10, 1999; pp. 1-21; located at: http://arxiv.org/abs/physics/9908021.

Shutes, Adam; Der, Channing J.; "Real-Time in Vitro Measurement of GTP Hydrolysis"; Methods; bearing a date of 2005; pp. 183-189; vol. 37; Elsevier, Inc.; located at: www.sciencedirect.com and www.elsevier.com/locate/ymeth.

Sievers, Annette; Beringer, Malte; Rodnina, Marina V.; Wolfenden, Richard; "Biochemistry: The Ribosome as an Entropy Trap"; PNAS; bearing a date of May 25, 2004; pp. 7897-7901; vol. 101, No. 21; The National Academy of Sciences of the USA; located at: www.pnas.org/cgi/doi/10.1073/pnas.0402488101.

Sisido, Masahiko; Ninomiya, Keiko; Ohtsuki, Takashi; Hohsaka, Takahiro; "Four-base Condon/Anticondon Strategy and Non-Enzymatic Aminoacylation for Protein Engineering With Non-natural Amino Acids"; Methods; bearing a date of 2005; pp. 270-278; vol. 36; Elsevier Inc.; located at: www.sciencedirect.com.

Spirin, Alexander S.; Baranov, Vladimir I.; Ryabova, Lubov A.; Ovodov, Sergey Yu.; Alakhov, Yuly B.; "A Continuous Cell-Free Translation System Capable of Producing Polypeptides in High Yield"; Science; bearing a date of Nov. 25, 1998; pp. 1162-1164; vol. 242, No. 4882; Institute of Protein Research, Academy of Sciences of the USSR.

Squires, Todd M.; Quake, Stephen R.; "Microfluidics: Fluid Physics at the Nanoliter Scale"; Reviews of Modern Physics; bearing dates of Oct. 6, 2005 and Jul. 2005; pp. 977-1026; vol. 77; The American Physical Society.

Steege, Deborah A.; "A Nucleotide Change in the Anticodon of an *Escherichia coli* Serine Transfer RNA Results in supD-Amber Suppression"; Nucleic Acids Research; bearing a date of 1983; pp. 3823-3832; vol. 11, No. 11; IRL Press Limited, Oxford, England.

Stone, H.A.; Stroock, A.D.; Ajdari, A.; "Engineering Flows in Small Devices: Microfluidics Toward a Lab-on-a-Chip"; Annual review of Fluid Mechanics; bearing a date of 2004; pp. 381-411, Cl-C4; vol. 36; Annual Reviews; located at: arjournals.annualreviews.org.

Sundberg, Steven A.; "High-throughput and ultra-high-throughput screening: solution- and cell-based approaches"; Analytical Biotechnology; bearing a date of 2000; pp. 47-53; vol. 11; Elsevier Science Ltd.

Taira, Hikaru; Hohsaka, Takahiro; Sisido, Masahiko; "In Vitro Selection of tRNAs for Efficient Four-Base Decoding to Incorporate Non-Natural Amino Acids into Proteins in an *Escherichia coli* Cell-Free Translation System"; Nucleic Acids Research; bearing a date of 2006; pp. 1653-1662; vol. 34, No. 5; Oxford University Press.

Takahashi, Shuntaro; Akita, Ryoko; Furusawa, Hiroyuki; Shimizu, Yoshihiro; Ueda, Takuya; Okahata, Yoshio; "Kinetic Analysis of Ribosome Binding Process onto mRNA Using a Quartz-Crystal Microbalance"; Nucleic Acids Symposium Series; bearing a date of 2006; pp. 49-50; vol. 50; Oxford University Press.

Takeishi, Keiichi; Ukita, Tyunosin; "Characterization of Two Species of Methionine Transfer Ribonucleic Acid from Bakers' Yeast"; The Journal of Biological Chemistry; bearing a date of Nov. 10, 1968; pp. 5761-5769; vol. 243, No. 21; located at: www.jbc.org.

Taki, Masumi; Hohsaka, Takahiro; Murakami, Hiroshi; Taira, Kazunari; Sisido, Masahiko; "Position-Specific Incorporation of a Fluorophore-Quencher Pair into a Single Streptavidin Through Orthogonal Four-Base Codon/Anticodon Pairs"; Journal of the American Chemical Society; bearing a date of 2002; pp. 14586-14590; vol. 124; American Chemical Society.

Taki, Masumi; Kuno, Atsushi; Matoba, Shinsuke; Kobayashi, Yuki; Futami, Junichiro; Murakami, Hiroshi; Suga, Hiroaki; Taira, Kazunari; Hasegawa, Tsunemi; Sisido, Masahiko; "Leucyl/Phenylalanyl-tRNA-Protein Transferase-Mediated Chemoenzymatic Coupling of N-Terminal Arg/Lys Units in Post-Translationally Processed Proteins with Non-Natural Amino Acids"; ChemBioChem; bearing a date of 2006; pp. 1676-1679; vol. 7; Wiley-VCH Verlag GmbH & Co. KGaA, Weinheim.

Tan, Zhongping; Blacklow, Stephen C.; Cornish, Virginia W.; Forster, Anthony C.; "De Novo Genetic Codes and Pure Translation Display"; Methods; bearing a date of 2005; pp. 279-290; vol. 36; Elsevier Inc.; located at: www.sciencedirect.com.

"Tech Tip #5: Attach an Antibody onto Glass, Silica or Quartz Surface"; Pierce; bearing a date of 2006; pp. 1-4; Pierce Biotechnology, Inc.

(56) References Cited

OTHER PUBLICATIONS

Ulbrich, Beate; Czempiel, Winfried; Bass, Rolf; "Mammalian Mitochondrial Ribosomes"; European Journal of Biochemistry; bearing a date of 1980; pp. 337-343; vol. 108; FEBS.

Vanzi, Francesco; Takagi, Yasuharu; Shuman, Henry; Cooperman, Barry S.; Goldman, Yale E.; "Mechanical Studies of Single Ribosome/mRNA Complexes"; Biophysical Journal; bearing a date of Sep. 2005; pp. 1909-1919; vol. 89; Biophysical Society.

Vanzi, Francesco; Vladimirov, Serguei; Knudsen, Charlotte R.; Goldman, Yale E.; Cooperman, Barry S.; "Report: Protein Synthesis by Single Ribosomes"; RNA; bearing a date of 2003; pp. 1174-1179; vol. 9; Cold Spring Harbor Laboratory Press—RNA Society.

Varenne, Stanislas; Buc, Jean; Lloubes, Roland; Lazdunski, Claude; "Translation is a Non-Uniform Process: Effect of tRNA Availability on the Rate of Elongation of Nascent Polypeptide Chains"; Journal of Molecular Biology; bearing a date of 1984; pp. 549-576; vol. 180; Academic Press Inc.

Wilding, Peter; Kricka, Larry J.; Cheng, Jing; Hvichia, Gia; Shoffner, Mann A.; Fortina, Paolo; "Integrated Cell Isolation and Polymerase Chain Reaction Analysis Using Silicon Microfilter Chambers"; Analytical Biochemistry; bearing a date of 1998; pp. 95-100; vol. 257; Academic Press.

Woese, Carl R.; "Perspective: Translation: in Retrospect and Prospect"; RNA; bearing a date of 2001; pp. 1055-1067; vol. 7, No. 8; Cambridge University Press.

Woese, Carl R.; Olsen, Gary J.; Ibba, Michael; Soll, Dieter; "Aminoacyl-tRNA Synthetases, the Genetic Code, and the Evolutionary Process" Microbiology and Molecular Biology Reviews; bearing a date of Mar. 2000; pp. 202-236; vol. 64, No. 1; American Society for Microbiology.

Xia, Xuhua; "How Optimized is the Translational Machinery in *Escherichia coli, Salmonella typhimurium* and *Saccharomyces cerevisiae*?"; Genetics; bearing a date of May 1998; pp. 37-44; vol. 149; Genetics Society of America.

Xie, Jianming; Schultz, Peter G.; "An Expanding Genetic Code"; Methods; bearing a date of 2005; pp. 227-238; vol. 36; Elsevier Inc.; located at: www.sciencedirect.com.

Zhang, Wenhua; Baskaran, Rajashree; Turner, Kimberly L.; "Nonlinear Behavior of a Parametric Resonance-Based Mass Sensor"; Proceedings of IMECE2002-33261 ASME International Mechanical Engineering Congress & Exposition; bearing a date of Nov. 17-22, 2002; pp. 1-5; New Orleans, Louisiana; ASME.

Champe, et al.; Biochemistry $2^{nd}$ Edition, Lippincott's Illustrated Reviews; 1994; pp. 389-400; J. B. Lippincott Company, Philadelphia, PA.

Kelly M.; "Mainframe Graphics on a Microcomputer: Display Tektronix-type Plots on Your Microcomputer"; Byte; Oct. 1983; vol. 8; pp. 439-442.

Menninger Jr.; "Computer Simulation of Ribosome Editing"; Journal of Molecular Biology; 1983; vol. 171; pp. 383-399.

Schilling-Bartetzko, Susanne,; Bartetzko, Andreas; Nierhaus, Knud H.; "Kinetic and Thermodynamic Parameters for tRNA Binding to the Ribosome and for the Translocation Reaction", The Journal of Biological Chemistry, Mar. 5, 1992, 4703-4712, vol. 267, No. 7, The American Society for Biochemistry and Molecular Biology, Inc., USA.

Jungbauer et al.; "Experimental and Computational Analysis of Translation Products in Apomyoglobin Expression"; J. Mol. Biol.; 2006; pp. 1121-1143; vol. 357; Elsevier Ltd.

Takahashi et al.; "Ribosome Display for Selection of Active Dihydrofolate Reductase Mutants Using Immobilized Methotrexate on Agarose Beads"; FEBS Letters; 2002; pp. 106-110; vol. 514; Elsevier Science B.V.

Excerpt from Webster's New World Medical Dictionary; "ELISA"; bearing a date of 2003; printed on Mar. 26, 2010; one page; located at: http://www.credoreference.com/entry/webstermed/elisa.

Glaser, Ralf W.; "CBEIA: programs for simulation of ELISA experiments and affinity determination"; Journal of Immunological Methods; bearing a date of 1993; pp. 141-142; vol. 160; Elsevier Science Publishers B.V.

Marahiel et al.; "Modular Peptide Synthetases Involved in Nonribosomal Peptide Synthesis"; Chemical Reviews; bearing a date of 1997; pp. 2651-2673; vol. 97, No. 7; American Chemical Society.

Pavlov, et al.; "Synthesis of region-labelled proteins for NMR studies by in vitro translation of column-coupled mRNAs"; Biochimie; bearing a date of 1997; pp. 415-422; vol. 79; Societe francaise de biochimie et biologie moleculair; Elsevier, Paris.

\* cited by examiner

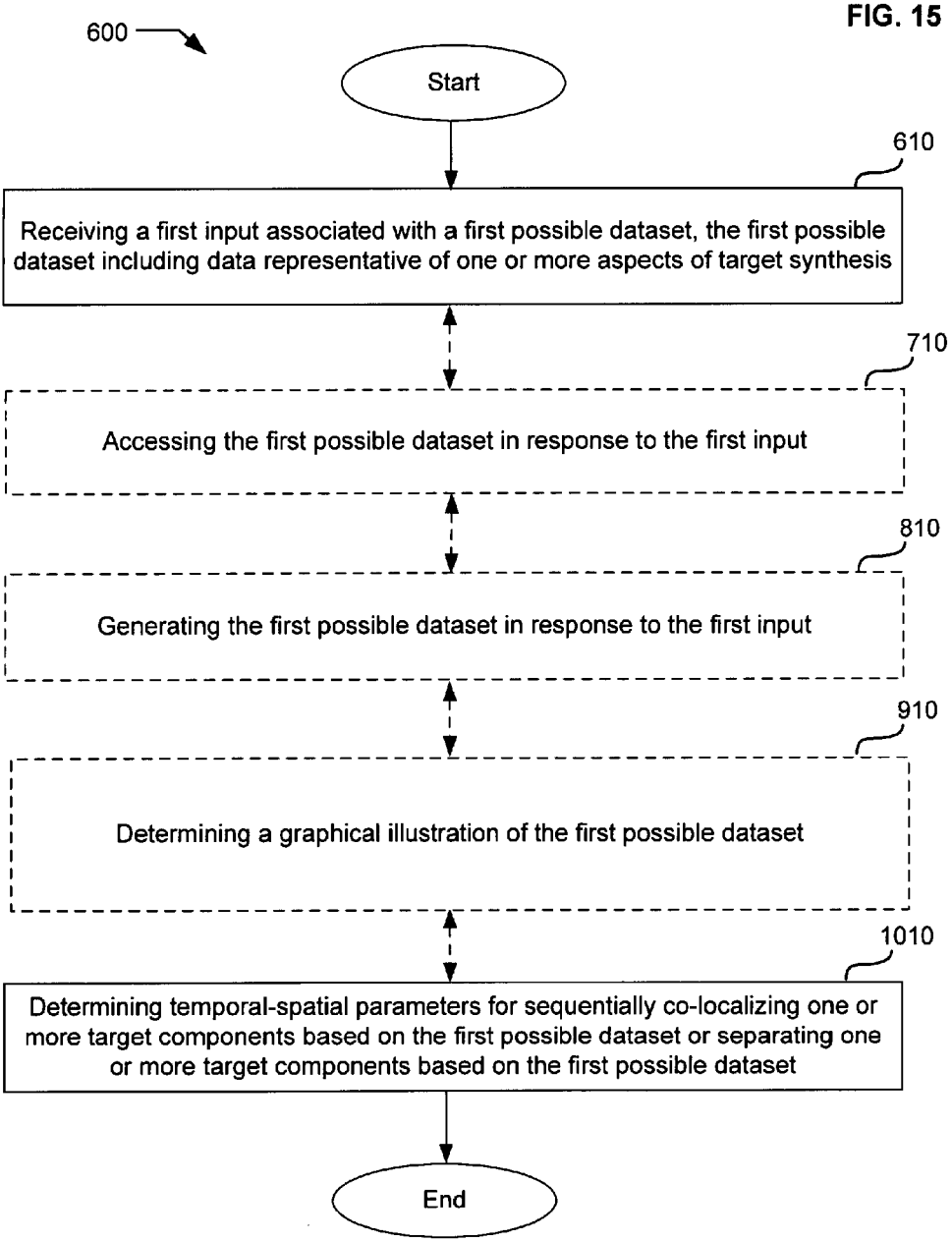

Receiving a first input associated with a first possible dataset, the first possible dataset including data representative of one or more aspects of target synthesis

| 6100 Receiving the first input associated with the first possible dataset, the first input including data representative of one or more of amino acid incorporation into one or more peptides, biological assembler activity, nucleic acid translocation, or tRNA release | 6101 Receiving the first input associated with the first possible dataset, the first input including data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA |

| 6102 Receiving a first data entry associated with the first possible dataset | 6103 Receiving a first data entry associated with the first possible dataset, the first data entry including data representative of one or more of amino acid incorporation into one or more peptides, biological assembler activity, nucleic acid translocation, or tRNA release | 6104 Receiving a first data entry associated with the first possible dataset, the first data entry including data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA |

| 6105 Receiving a first data entry from one or more peptide synthesis units | 6106 Receiving a first data entry from one or more of one or more monitoring units, or one or more computing units | 6107 Receiving a first data entry from a graphical user interface | 6108 Receiving a first data entry from at least one submission element of a graphical user interface | 6109 Receiving a first data entry at least partially identifying one or more elements of the first possible dataset |

| 6110 Receiving a first input associated with monitoring one or more of amino acid incorporation, biological assembly activity, nucleic acid translocation, or tRNA release | 6111 Receiving the first input associated with monitoring one or more of presence or absence, concentration, or composition of one or more of one or more charge tRNA or one or more tRNA |

Accessing the first possible dataset in response to the first input

| 7100 Accessing the first possible dataset in response to the first input, the first input including data representative of one or more of amino acid incorporation into one or more peptides, biological assembler activity, nucleic acid translocation, or tRNA release | 7101 Accessing the first possible dataset in response to the first input, the first input including data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA |

| 7102 Accessing the first possible dataset by associating data representative of one or more of amino acid incorporation into one or more peptides, biological assembler activity, nucleic acid translocation, or tRNA release with one or more elements of the first possible dataset | 7103 Accessing the first possible dataset by associating data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA with one or more elements of the first possible dataset | 7104 Accessing the first possible dataset by corresponding data representative of one or more of amino acid incorporation into one or more peptides, biological assembler activity, nucleic acid translocation, or tRNA release with one or more elements of the first possible dataset |

| 7105 Accessing the first possible dataset by corresponding data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA with one or more elements of the first possible dataset | 7106 Receiving a first request associated with the first possible dataset | 7107 Receiving a first request associated with the first possible dataset, the first request selecting one or more target | 7108 Receiving a first request from a graphical user interface |

| 7109 Receiving a first request from at least one submission element of a graphical user interface | 7110 Receiving a first request from at least one submission element of a graphical user interface, the first request providing instructions identifying one or more target components | 7111 Receiving a first request from at least one submission element of a graphical user interface, the first request specifying one or more target components and at least one other instruction |

Generating the first possible dataset in response to the first input

8100 Generating the first possible dataset in response to the first input, the first input including data representative of one or more of amino acid incorporation into one or more peptides, biological assembler activity, nucleic acid translocation, or tRNA release 8101 Generating the first possible dataset in response to the first input, the first input including data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA 8102 Generating the first possible dataset by associating data representative of one or more of amino acid incorporation into one or more peptides, biological assembler activity, nucleic acid translocation, or tRNA release with one or more elements of the first possible dataset 8103 Generating the first possible dataset by associating data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA with one or more elements of the first possible dataset 8104 Generating the first possible dataset by corresponding data representative of one or more of amino acid incorporation into one or more peptides, biological assembler activity, nucleic acid translocation, or tRNA release with one or more elements of the first possible dataset 8105 Generating the first possible dataset by corresponding data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA with one or more elements of the first possible dataset

PEPTIDE SYNTHESIS APPARATUSES

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation of U.S. patent application Ser. No. 11/821,375 (now U.S. Pat. No. 7,777,002), entitled METHODS FOR ARBITRARY PEPTIDE SYNTHESIS, naming Roderick A. Hyde; Edward K. Y. Jung and Lowell L. Wood, Jr. as inventors, filed 22, Jun. 2007, which is a continuation-in-part of U.S. patent application Ser. No. 11/478,540 (now U.S. Pat. No. 7,754,854), entitled METHODS FOR ARBITRARY PEPTIDE SYNTHESIS, naming Roderick A. Hyde; Edward K. Y. Jung and Lowell L. Wood, Jr. as inventors, filed 29, Jun. 2006.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at //www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BRIEF DESCRIPTION OF THE FIGURES

FIG. 15 shows an operational flow representing illustrative embodiments of operations related to determining temporal-spatial parameters for co-localizing and/or separating one or more target components based on a first possible dataset.

FIG. 16 shows optional embodiments of the operational flow of FIG. 15.

FIG. 17 shows optional embodiments of the operational flow of FIG. 15.

FIG. 18 shows optional embodiments of the operational flow of FIG. 15.

DETAILED DESCRIPTION

Figure 1:
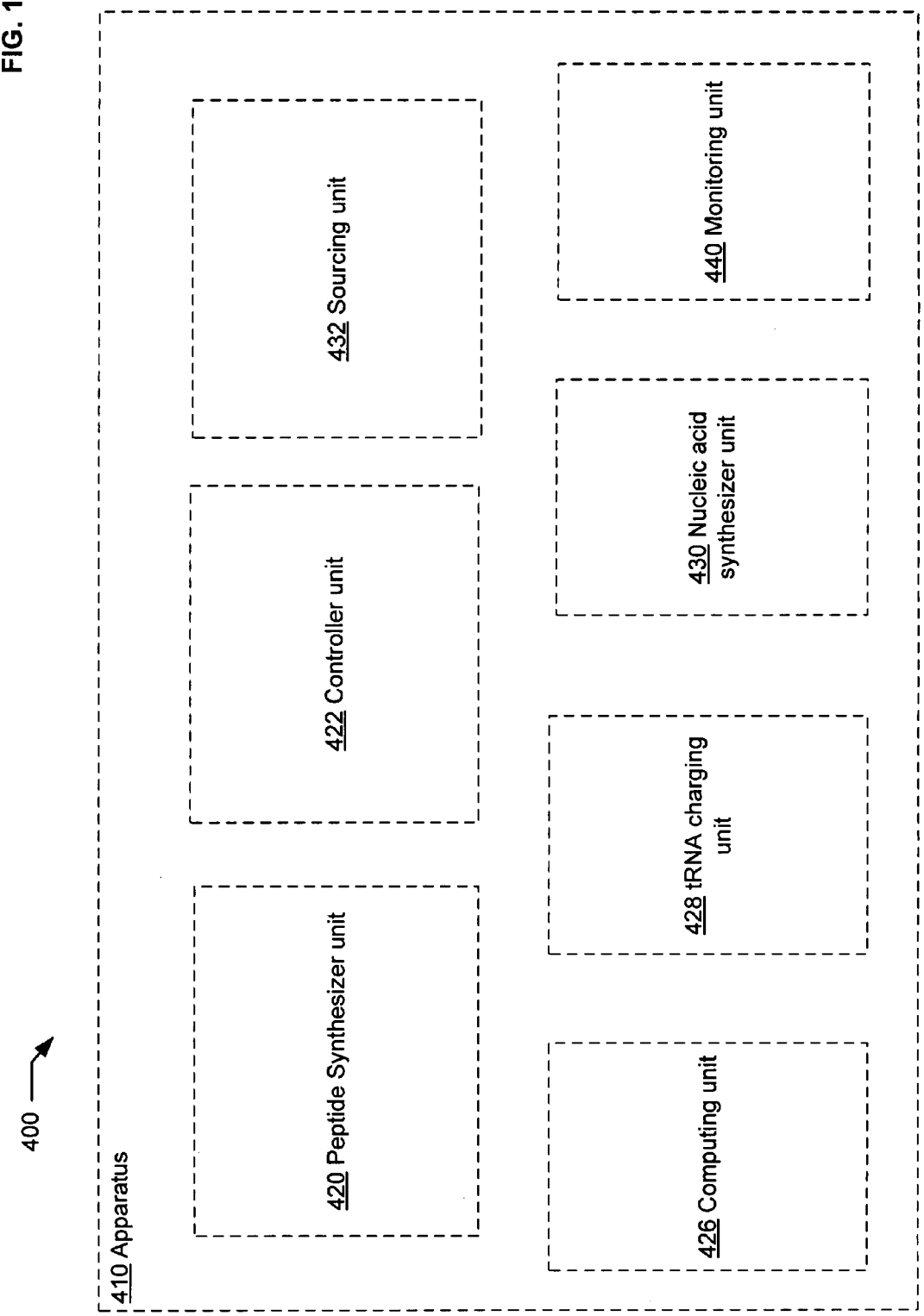
FIG. 1 shows a schematic of an illustrative apparatus in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

This disclosure is drawn, inter alia, to methods, apparatus, computer programs and computing devices related to biologically assembling and/or synthesizing peptides and/or proteins.

As used herein, the term "peptide, peptides, protein, proteins" means polypeptide molecules formed from linking various amino acids in a defined order. The link between one amino acid residue and the next forms a bond, including but not limited to an amide or peptide bond, or any other bond that can be used to join amino acids. The peptides/proteins may include any polypeptides of two or more amino acid residues. The peptides/proteins may include any polypeptides including, but not limited to, ribosomal peptides and non-ribosomal peptides. The peptides/proteins may include natural and unnatural amino acid residues. The number of amino acid residues optionally includes, but is not limited to, at least 5, 10, 25, 50, 100, 200, 500, 1,000, 2,000 or 5,000 amino acid residues. The number of amino acid residues optionally includes, but is not limited to, 2 to 5,000, 2 to 2,000, 2 to 1,000, 2 to 500, 2 to 250, 2 to 100, 2 to 50, 2 to 25, 2 to 10, 5 to 5,000, 5 to 2,000, 5 to 1,000, 5 to 500, 5 to 250, 5 to 100, 5 to 50, 10 to 5,000, 10 to 2,000, 10 to 1,000, 10 to 500, 10 to 250, to 100, or 10 to 50.

As used herein, the term "amino acid or amino acids" means any molecule that contains both amino and carboxylic acid functional groups, including, but not limited to, alpha amino acids in which the amino and carboxylate functionalities are attached to the same carbon, the so-called $\alpha$-carbon. Amino acids may include natural amino acids, unnatural amino acids, and arbitrary amino acids.

As used herein, the term "natural amino acid" includes, but is not limited to, one or more of the amino acids encoded by the genetic code. The genetic codes of all known organisms encode the same 20 amino acid building blocks with the rare exception of selenocysteine and pyrrolysine (Methods (2005) 36:227-238). In some embodiments, natural amino acids may also include, but not be limited to, any one or more of the amino acids found in nature. In some embodiments, these natural amino acids may include, but not be limited to, amino acids from one or more of plants, microorganisms, prokaryotes, eukaryotes, protozoa or bacteria. In some embodiments, natural amino acids may include, but are not limited to, amino acids from one or more of mammals, yeast, *Escherichia coli*, or humans.

As used herein, the term "unnatural amino acid" may include any amino acid other than the amino acids encoded by the genetic code. In some embodiments, unnatural amino acids may include, but not be limited to, modified or derivatized amino acids encoded by the genetic code. In some embodiments, unnatural amino acids may include, but not be limited to, modified or derivatized amino acids of any one or more of the amino acids found in nature. In some embodiments, unnatural amino acids may include, but not be limited to, modified or derivatized amino acids from one or more of plants, microorganisms, prokaryotes, eukaryotes, protozoa, bacteria, mammals, yeast, *E. coli*, or humans.

Unnatural amino acids are known in the art including, but not limited to, those containing spectroscopic probes, post-translational modification, metal chelators, photoaffinity labels, D-enantiomers, as well as other functional groups and modified structures (e.g. Methods 36 (2005) 227-238; Annu. Rev. Biochem. (2004) 73:147-176; Science (2003) 301:964-967; Royal Society of Chemistry (2004) 33:422-430).

As used herein, the term "arbitrary amino acid or arbitrary amino acids" means any amino acid that is not the amino acid coded for by the tRNA codon recognition site as determined by the genetic code. In some embodiments, arbitrary amino acids are natural or unnatural amino acids.

As used herein, the term "amino acid residue or amino acid residues" means the remainder of an amino acid incorporated into a peptide/protein.

As used herein, the term "tRNA, tRNAs, transfer RNA or transfer RNAs" means an RNA chain that transfers an amino acid to a growing polypeptide chain. The tRNA has sites for amino acid attachment and codon recognition. In some embodiments, tRNA includes natural, unnatural, and arbitrary tRNA.

As used herein, the term "natural tRNA" means one or more tRNA known in nature that transfer an amino acid to a growing polypeptide chain. In some embodiments, natural tRNA includes, but is not limited to, tRNA that transfer one or more of the natural amino acids that are encoded by the genetic code. In some embodiments, natural tRNA include, but are not limited to, natural tRNA from one or more of plants, microorganisms, prokaryotes, eukaryotes, protozoa, bacteria, mammals, yeast, *E. coli*, humans, or archae.

As used herein, the term "unnatural tRNA" means any tRNA, other than tRNA known in nature, which transfers an amino acid to a growing polypeptide chain. In some embodiments, unnatural tRNA may include, but are not limited to, modified or derivatized natural tRNA. In some embodiments, unnatural tRNA may include, but are not limited to, modified or derivatized natural tRNA from one or more of plants, microorganisms, prokaryotes, eukaryotes, protozoa, bacteria, mammals, yeast, *E. coli*, humans, or archae. In some embodiments, unnatural tRNA may include, but are not limited to, tRNA with altered sites for amino acid attachment, and/or tRNA with altered acceptor stems, and/or tRNA with altered sites for codon recognition (the anticodon). In some embodiments, unnatural tRNA is recombinant tRNA.

As used herein, the term "arbitrary tRNA" means a tRNA that has been modified or derivatized such that the amino acid attachment site may bind one or more amino acids other than the amino acid specified by the codon recognition site based on the genetic code. The amino acid may be natural or unnatural. Arbitrary tRNA may also include tRNA that have been modified or derivatized such that the amino acid attachment site may bind one or more different amino acids (natural or unnatural), while the codon recognition site may recognize one or more of one or more stop codons, one or more singlet codons, one or more doublet codons, one or more triplet codons, one or more quadruplet codons, one or more quintuplet codons, one or more sextuplet codons or others. Stop codons include ochre (TAA), amber (TAG and opal (TGA).

Methods for modifying tRNA including, but not limited to, the anti-codon, the amino acid attachment site, and/or the acceptor stem to allow incorporation of unnatural and/or arbitrary amino acids are known in the art (Methods (2005) 36:227-238 Methods (2005) 36:270-278; Annu. Rev. Biochem. (2004) 73:147-176; Nucleic Acids Research (2004) 32:6200-6211PNAS (2003) 100:6353-6357; Royal Society of Chemistry (2004) 33:422-430).

As used herein, the term "anti-stop codon tRNA" means a tRNA having a stop codon recognition site. In some embodiments, the anti-stop codon tRNA may be charged with one or more natural, one or more unnatural, or one or more arbitrary amino acids. In some embodiments, the anti-stop codon tRNA may be a natural, an unnatural, or an arbitrary tRNA.

As used herein, the term "charged tRNA or charged tRNAs" means tRNA that has an amino acid bound at the amino acid attachment site. During peptide synthesis, the aminoacyl group is transferred to the nascent peptide, releasing the tRNA. As used herein, the term "released tRNA" means the tRNA remaining after the charged tRNA has donated the attached amino acid to the nascent polypeptide. In some embodiments, the charged tRNA may be natural, unnatural and/or arbitrary.

As used herein, the term "natural charged tRNA" means a natural tRNA that has an amino acid bound at the amino acid attachment site. In some embodiments, the natural tRNA has one or more of a natural or an unnatural amino acid bound at the amino acid attachment site.

As used herein, the term "unnatural charged tRNA" means an unnatural tRNA that has an amino acid bound at the amino acid attachment site. In some embodiments, the unnatural tRNA has one or more of a natural or an unnatural amino acid bound at the amino acid attachment site.

As used herein, the term "arbitrary charged tRNA or tRNA charged with arbitrary amino acids" means a tRNA that has an amino acid bound at the amino acid attachment site, and that amino acid is different from the amino acid specified by the codon recognition site of the tRNA based on the genetic code. In some embodiments, the bound amino acid is a natural or an unnatural amino acid. In some embodiments, the codon recognition site includes, but is not limited to, a stop codon recognition site, a singlet codon recognition site, a doublet codon recognition site, a triplet codon recognition site, a quadruplet codon recognition site, a quintuplet codon recognition site, or a sextuplet codon recognition site.

As used herein, the term "charging or aminoacylation" is a process of adding an aminoacyl group to a compound. Methods for charging natural, unnatural and/or arbitrary tRNA with natural, unnatural and/or arbitrary amino acids are known in the art, and include, but are not limited to, chemical aminoacylation, biological misacylation, acylation by modified aminoacyl tRNA synthetases, ribozyme-based, and protein nucleic acid-mediated methods (Methods (2005) 36:227-238; Methods (2005) 36:39-244; Methods (2005) 36:245-251; Methods (2005) 36:270-278; Methods (2005) 36:291-298; Annu. Rev. Biochem. (2004) 73:147-176; Nucleic Acids Research (2004) 32:6200-6211; Royal Society of Chemistry (2004) 33:422-430); Nature (2002) 20:723-728.

As used herein, the term "aminoacyl tRNA synthetase or aaRs" means an enzyme that catalyzes the binding of one or more amino acids to a tRNA to form an aminoacyl-tRNA (or charged tRNA). In some embodiments, the synthetase binds the appropriate amino acid to one or more tRNA molecules. In some embodiments, the synthetase mediates a proofreading reaction to ensure high fidelity of tRNA charging. In some embodiments, the synthetase does not mediate a proofreading reaction to ensure high fidelity of tRNA charging.

As used herein, the term "natural aminoacyl tRNA synthetases" means aminoacyl tRNA synthetases known in nature that add an aminoacyl group to a tRNA. In some embodiments, natural aminoacyl tRNA synthetases include, but are not limited to, aminoacyl tRNA synthetases that add one or more of the natural aminoacyl groups that are encoded by the genetic code. In some embodiments, natural aminoacyl tRNA synthetases include, but are not limited to, natural aminoacyl tRNA synthetases from one or more of plants, microorganisms, prokaryotes, eukaryotes, protozoa, bacteria, mammals, yeast, *Escherichia coli*, or humans.

The term "unnatural aminoacyl tRNA synthetase" means any aminoacyl tRNA synthetase, other than aminoacyl tRNA synthetases known in nature that add an aminoacyl group to a tRNA. In some embodiments, unnatural aminoacyl tRNA synthetases may include, but are not limited to, modified or derivatized natural aminoacyl tRNA synthetases. In some embodiments, unnatural aminoacyl tRNA synthetases may include, but are not limited to, modified or derivatized natural aminoacyl tRNA synthetases from one or more of plants, animals, microorganisms, prokaryotes, eukaryotes, protozoa, bacteria, mammals, yeast, *E. coli*, or humans. In some embodiments, unnatural aminoacyl tRNA synthetases may include, but are not limited to, aminoacyl tRNA synthetases with altered aminoacyl specificity and/or altered tRNA specificity, and/or altered editing ability As used herein, the term "altered specificity" means that the specificity typically observed in nature has been changed. In some embodiments, altered specificity includes, but is not limited to, broadening the specificity to include, for example, recognition of additional amino acids, and/or additional tRNA. In some embodiments, altered specificity includes, but is not limited to, changing the identity of the aminoacyl group and/or tRNA from the aminoacyl group and/or tRNA recognized in nature.

Modified aminoacyl tRNA synthetases are known in the art, and include but are not limited to, aminoacyl tRNA synthetases with relaxed substrate specificity through active site mutations as well as aminoacyl tRNA synthetases with attenuated proofreading activity (e.g. Methods (2005) 36:227-238; Methods (2005) 36:291-298; Annu. Rev. Biochem. (2004) 73:147-176; Science (2003) 301:964-967; Microbiology and Molecular Biology Reviews (2000) 64:202-236).

As used herein, the term "biological assembler or biological assemblers" means any mechanism that utilizes one or more biological components to synthesize one or more peptides/proteins. In some embodiments, biological assemblers are peptide/protein assemblers. In some embodiments, biological assemblers are partially or completely isolated, purified, or separated from cells, other cellular material, and/or tissues. In some embodiments, biological assemblers are encompassed by a semi-permeable membrane and/or membrane-bound. In some embodiments, biological assemblers are modified, non-natural or recombinant. In some embodiments, biological assemblers include, but are not limited to, one or more of ribosome-based assemblers and nonribosome-based assemblers.

As used herein, the term "ribosome-based assemblers" means biological assemblers that include, but are not limited to, one or more ribosomes. The ribosomes may be one or more of eukaryotic ribosomes and/or prokaryotic ribosomes. In some embodiments, the ribosome-based assemblers are partially or completely isolated, purified, or separated from cells, other cellular material, and/or tissues. In some embodiments, the ribosomes are from mitochondria and/or chloroplasts. The ribosomes may be from one or more of plants, animals, microorganisms, prokaryotes, eukaryotes, protozoa, bacteria, mammals, yeast, *E. coli*, and/or humans.

As used herein, the term "nonribosome-based assemblers" means biological assemblers that do not include ribosomes. In some embodiments, the nonribosome-based assemblers use one or more elements of a modular enzyme complex in which there is a common core structure, and optionally include one or more different modules to perform additional manipulations on the evolving product. In some embodiments, the nonribosome-based assemblers are partially or completely isolated, purified, or separated from one or more of one or more unicellular organisms, one or more plants, or one or more fungi.

As used herein, the term "biological assembler components or components of the biological assemblers" means one or more biological elements, and/or one or more non-biological elements, that make up the biological assemblers. In some embodiments, the components of one or more biological assemblers include, but are not limited to, one or more of one or more ribosomes, one or more ribosome subunits, one or more ribosomal RNA (rRNA) molecules, one or more protein molecules, one or more translation factors, one or more enzymes, one or more energy sources or one or more molecular chaperones. In some embodiments, biological assembler components include, but are not limited to, one or more of one or more elements of a modular enzyme complex or one or more additional enzyme modules. In some embodiments, the components include, but are not limited to, one or more of one or more prokaryotic components, one or more eukaryotic components, one or more mitochondrial components, and/or one or more chloroplastic components.

Methods of partially and/or completely purifying or isolating natural, non-natural, and/or recombinant components of biological assemblers, including both ribosomal and non-ribosomal components, and re-assembling functional peptide/protein synthetic machinery are known in the art (e.g. Methods (2005) 36:279-290; Methods (2005) 36:299-304; PNAS (2003) 100:6353-6357; Nature (2001) 19:751-755; Royal Society of Chemistry (2004) 33:422-430). Methods for partially or completely encapsulating isolated and/or purified biological assemblers and/or biological assembler components within natural or artificial semi-permeable membranes, or partially or completely integrating isolated and/or purified biological assemblers and/or biological assembler components within natural or artificial semi-permeable membranes are known in the art (e.g. Cell (1997) 89:523-533; J. Cell Biology (1973) 56:191-205; J. Biol. Chem. (2000) 43:33820-33827).

As used herein, the term "components of peptide and/or target synthesis" or "peptide and/or target synthesis components" or the equivalent means one or more biological components that may be optionally included in one or more of the aspects described herein. As an example, peptide synthesis components may include, but are not limited to, one or more biological assemblers, one or more biological assembler components, one or more charged tRNA, and/or one or more nucleic acids. Peptide synthesis components may also include, but are not limited to, one or more tRNA, one or more amino acids, one or more tRNA charging components, one or more nucleic acids, and one or more nucleic acid charging components.

In one aspect, the disclosure is drawn to methods for peptide synthesis. Some methods comprise sequentially providing two or more charged tRNA to one or more identifiable locations. Some methods comprise co-localizing sequentially two or more charged tRNA with one or more biological assemblers. Some methods comprise co-localizing sequentially one or more biological assemblers with two or more charged tRNA, wherein at least two of the two or more tRNA are located at one or more different locations. Some methods comprise assembling a target peptide by co-localizing sequentially one or more biological assemblers and two or more charged tRNA.

In some embodiments, one or more methods include synthesizing a target peptide by providing two or more charged tRNA to one or more identifiable locations. In some embodiments, one or more methods include synthesizing a target peptide by co-localizing sequentially two or more charged tRNA with one or more biological assemblers. In some embodiments, one or more methods include synthesizing a target peptide by co-localizing sequentially one or more biological assemblers with two or more charged tRNA, wherein at least two of the two or more charged tRNA are at one or more different locations.

Some embodiments include one or more methods of extra-cellular peptide synthesis comprising co-localizing sequentially two or more charged tRNA with one or more biological assemblers in vitro. Some embodiments include one or more methods of extra-cellular peptide synthesis comprising sequentially providing two or more charged tRNA to one or more identifiable locations at one or more first identifiable time intervals in vitro. Some embodiments include one or more methods of extra-cellular peptide synthesis comprising co-localizing sequentially one or more biological assemblers with two or more charged tRNA, wherein at least two of the two or more charged tRNA are located at one or more different locations in vitro. Some embodiments include one or more methods of extra-cellular peptide synthesis comprising assembling a target peptide in vitro by co-localizing sequentially one or more biological assemblers, and two or more charged tRNA. In some embodiments, the one or more methods are cell-free.

In some embodiments, one or more methods include determining and/or selecting an assembly order; and co-localizing two or more charged tRNA with one or more biological assemblers based on the assembly order. In some embodiments, one or more methods include determining and/or selecting an assembly order; and providing two or more charged tRNA to one or more identifiable locations at one or more first identifiable time intervals based on the assembly order. In some embodiments, one or more methods include determining and/or selecting an assembly order; and co-localizing one or more biological assemblers with two or more charged tRNA based on the assembly order, wherein at least two of the two or more charged tRNA are located at one or more different locations. In some embodiments, one or more methods include determining and/or selecting an assembly order; and assembling a target peptide by co-localizing one or more biological assemblers, and two or more charged tRNA.

As used herein, the term "assembly order" means the process (or sequence) by which the one or more components of target peptide synthesis are provided and/or co-localized and then optionally removed and/or separated.

In some embodiments, one or more methods further comprise eliminating and/or removing and/or separating, optionally sequentially, one or more components of peptide synthesis, optionally including, but not limited to, one or more biological assemblers, one or more nucleic acids, one or more biological assembler components, one or more charged tRNA, and/or one or more tRNA. In some embodiments, one or more methods further comprise consuming, optionally sequentially, two or more charged tRNA. In some embodiments, one or more methods further comprise eliminating and/or removing and/or separating, optionally sequentially, two or more charged tRNA and/or one or more released tRNA. In some embodiments, one or more methods further include separating, optionally sequentially, one or more biological assemblers from two or more charged tRNA and/or one or more released tRNA, wherein at least two of the two or more charged tRNA and/or released tRNA are located at one or more different locations. In some embodiments, one or more methods further include separating, optionally sequentially, one or more biological assemblers and two or more charged tRNA and/or one or more released tRNA.

As used herein, the term "co-localizing or providing or assembling" means any process resulting in one or more components being in the same place at the same time. By "in the same place at the same time" is meant physical proximity such that the one or more components are capable of interaction on a molecular level. Co-localizing may include, commingling, combining, mixing, assembling, aggregating, injecting, or other similar processes.

As used herein, the term "synthesizing" means any process resulting in one or more components being combined and/or added to a prior component. For example, a process that results in combining two or more amino acids to form a peptide, or a process that results in combining two or more nucleotides to form a nucleic acid.

As used herein, the term "removing or eliminating or separating" means one or more processes that result in one or more peptide synthesis components being no longer located in the same place. In some embodiments, one or more peptide synthesis components are at least partially removed and/or eliminated and/or consumed and/or separated. In some embodiments, one or more components are moved to another location.

In illustrative embodiments, charged tRNA are at least partially consumed when the attached amino acid is donated to the nascent polypeptide. In some embodiments, charged tRNA not incorporated into the nascent polypeptide may be partially or completely removed (and/or separated and/or eliminated) from one or more locations. In some embodiments, tRNA remaining after the previously attached amino acid is donated to the nascent polypeptide are partially or completely removed and/or eliminated from one or more locations. In illustrative embodiments, one or more charged tRNA and/or one or more tRNA are separated from one or more biological assemblers. In illustrative embodiments, one or more biological assemblers are separated from one or more charged tRNA and/or one or more tRNA. In illustrative embodiments, one or more biological assemblers are removed from one or more locations.

As used herein, the term "sequentially" when modifying processes, such as, the processes including, for example, co-localizing, providing, removing, and/or eliminating, means any process that includes a temporal aspect such that the process acts upon one or more components at subsequent times. Sequentially may include, but is not limited to, any process that acts upon one or more components in a defined order. Sequentially may include, but is not limited to, any process that acts on one or more components one after another.

Generic processes useful for co-localizing, providing, eliminating, removing, separating and/or assembling, and including sequential processes, are known in the art and include, but are not limited to, one or more of automated methods, mechanical methods, computer and/or software-controlled methods, and fluid flow. Fluid flow includes, but is not limited to, nanofluidics and microfluidics. Nanofluidics and microfluidics include, but are not limited to, continuous flow microfluidics and digital microfluidics, and have been developed for use in biological systems (Annu. Rev. Fluid Mech. (2004) 36:381-411; Annu. Rev. Biomed. Eng. (2002) 4:261-86; Science (1988) 242:1162-1164, Rev. Mod. Phys. (2005) 77:977-1026).

In illustrative embodiments, fluid flow is used to "flow" charged tRNA into association (co-localization) with biological assemblers and to "flow" excess charged tRNA and/or released tRNA out of association (co-localization) with biological assemblers. In illustrative embodiments, fluid flow is used to sequentially "flow" one type of charged tRNA after another into association with biological assemblers and to sequentially "flow" one type of excess charged tRNA and/or released tRNA after another out of association with biological assemblers. In illustrative embodiments, fluid flow is used to "flow" biological assemblers into association (co-localization) with charged tRNA and to "flow" biological assemblers away from excess charged tRNA and/or released tRNA. In illustrative embodiments, fluid flow is used to sequentially "flow" one or more biological assemblers to locations containing one type of charged tRNA after another and to sequentially "flow" biological assemblers away from one type of excess charged tRNA and/or released tRNA after another.

In illustrative embodiments, one or more charged tRNA are provided in the order of a target peptide sequence with each subsequent charged tRNA being provided after the aminoacyl residue from the prior charged tRNA is incorporated into a nascent polypeptide. In illustrative embodiments, excess charged tRNA and/or released tRNA are removed/eliminated/separated before subsequent charged tRNA are provided.

In illustrative embodiments, one or more biological assemblers are co-localized with one or more charged tRNA in the order of a target peptide sequence with each subsequent co-localization occurring after the aminoacyl residue from the prior charged tRNA is incorporated into a nascent polypeptide. In illustrative embodiments, biological assemblers are removed/separated from excess charged tRNA and/or released tRNA prior to co-localization with subsequent charged tRNA.

In some embodiments, one or more methods includes co-localizing and/or providing and/or assembling, optionally sequentially, one or more peptide synthesis components at one or more identifiable time intervals. In some embodiments, one or more methods include providing, optionally sequentially, two or more charged tRNA to one or more identifiable locations at one or more first identifiable time intervals. In some embodiments, one or more methods include co-localizing, optionally sequentially, two or more charged tRNA with one or more biological assemblers at one or more first identifiable time intervals. In some embodiments, one or more methods include co-localizing sequentially one or more biological assemblers with two or more charged tRNA at one or more first identifiable time intervals, wherein at least two of the two or more charged tRNA are located at one or more different locations. In some embodiments, one or more methods include assembling a target peptide by co-localizing sequentially one or more biological assemblers and two or more charged tRNA at one or more first identifiable time intervals.

In some embodiments, one or more methods further include separating and/or removing and/or eliminating and/or consuming, optionally sequentially, one or more peptide synthesis components at one or more identifiable time intervals. In some embodiments, one or more methods further include removing and/or separating, optionally sequentially, two or more charged tRNA and/or one or more released tRNA from one or more biological assemblers at one or more second identifiable time intervals. In some embodiments, one or more methods further include separating, optionally sequentially, one or more biological assemblers from two or more charged tRNA and/or one or more released tRNA at one or more second identifiable time intervals, wherein at least two of the two or more charged tRNA and/or released tRNA are located at one or more different locations. In some embodiments, one or more methods further include assembling a target peptide by separating, optionally sequentially, one or more biological assemblers and two or more charged tRNA and/or the released tRNA at one or more second identifiable time intervals.

As used herein, the term "identifiable time interval" means a discrete amount of time that is optionally knowable, determinable, and/or calculable. The term "one or more identifiable time intervals", is used herein to indicate time intervals for one or more processes. The one or more identifiable time intervals may be the same or different for different processes and/or elements of processes. The one or more identifiable time intervals may be the same or different for synthesis of different target peptides. One of skill in the art is able to determine appropriate one or more identifiable time intervals based on the teachings herein and in the art. The one or more identifiable time intervals may be designated "first", "second", "third", "fourth", "fifth", "sixth", "seventh", "eighth", "ninth", "tenth", and so on for clarity to indicate that the time interval may, or may not, be the same as other time intervals. Labeling one or more time intervals with the same numeral may indicate the same or similar time intervals unless context indicates otherwise.

In some embodiments, one or more identifiable time intervals are at least partially based on a predicted rate of incorporation of two or more amino acids into one or more peptides. In some embodiments, one or more identifiable time intervals are at least partially based on a predicted rate of activity of one or more biological assemblers. In some embodiments, one or more identifiable time intervals are at least partially based on a predicted rate of translocation of one or more nucleic acids. In some embodiments, one or more identifiable time intervals are at least partially based on a predicted rate of release of tRNA.

In some embodiments, one or more first identifiable time intervals and/or one or more second identifiable time intervals are from approximately 0.001 seconds to approximately 0.1 seconds. In some embodiments, one or more first identifiable time intervals and/or one or more second identifiable time intervals are approximately 0.01 seconds.

Many aspects of biological peptide synthesis, both in cells and in cell-free systems, have been studied using a variety of natural and unnatural components (Cell (2002) 108:557-572, Ann. Rev. Biochem. (2004) 73:657-704, Methods (2005) 36:279-290, Methods (2005) 36:299-304), and provide a basis for predicting appropriate time intervals for addition and removal of target components for peptide synthesis. Rates of incorporation of a variety of natural, unnatural, and arbitrary amino acids into nascent peptides are known in the art for a variety of biological systems, including but not limited to, eukaryotic and prokaryotic systems. The corresponding rate of release of the tRNA following incorporation of the amino acyl residue has also been studied. The rate of activity of a variety of eukaryotic and prokaryotic cells and cell-free systems for peptide synthesis is known in the art (Molecular Biology of the Cell (2002) 343-344, J. Mol. Biol. (1984):549-576, J. Mol. Biol. (1989) 209:65-77, Methods (2005) 36:279-290). The rate of translocation of nucleic acids in these systems has also been studied. The rate of in vivo ribosomal incorporation of amino acids into a protein is primarily limited by elongation (dominated by acquisition rate of the cognate charged tRNA) and (for polyribosomal translation) by ribosomal initiation (Genetics (1998) 149:37-44; Journal of Theoretical Biology (2006) 239:417-434).

In some embodiments, one or more identifiable time intervals may include from approximately 0.001 seconds to approximately 0.1 seconds. In one or more embodiments, one or more identifiable time intervals may include, but are not limited to, from 0.001 to 0.1, from 0.005 to 0.1, from 0.01 to 0.1, from 0.05 to 0.1, from 0.001 to 0.05, from 0.001 to 0.01, and from 0.001 to 0.005 seconds. In some embodiments, one or more identifiable time intervals may include approximately 0.01 seconds. In some embodiments, one or more identifiable time intervals may include, but are not limited to, approximately 0.001, 0.005, 0.01, 0.05, and 0.1 seconds.

In some illustrative embodiments, charged tRNA may be "flowed" at predetermined time intervals. One or more of the time intervals may be of the same length, of different lengths, of arbitrary lengths, of random lengths, of variable lengths, of fixed lengths, and/or of sequential lengths. In some embodiments, the time interval is determined, partially or completely, by the length of time needed and/or useful to incorporate each additional amino acid residue into the nascent polypeptide, and/or by the length of time needed and/or useful to remove excess charged tRNA and/or released tRNA from association (co-localization) with the ribosomal assemblers. In some embodiments, the time interval is determined, partially or completely, by internal and/or external feedback. In some embodiments, the internal and/or external feedback is partially or completely, related to the length of time needed to incorporate each additional amino acid residue into the nascent polypeptide and/or by the length of time needed and/or useful to remove excess charged tRNA and/or released tRNA from association (co-localization) with the ribosomal assemblers.

In some embodiments, one or more methods may further include, monitoring amino acid incorporation into one or more peptides, biological assembler activity, nucleic acid translocation, and/or tRNA release. In some embodiments, one or more methods further include, monitoring presence or absence, concentration, and/or composition of charged tRNA and/or tRNA.

Methods for measuring and/or monitoring amino acid incorporation into one or more peptides, biological assembler activity, nucleic acid translocation, or tRNA release are known in the art and include, but are not limited to spectroscopy, fluorescence spectroscopy, surface plasmon resonance imaging, nuclear magnetic resonance imaging, and/or immunoassays. Methods for measuring presence or absence, concentration, and/or compositions of charged tRNA or tRNA are known in the art, and include, but are not limited to, spectroscopy, fluorescence spectroscopy, surface plasmon resonance imaging, nuclear magnetic resonance imaging, and/or immunoassays.

In some embodiments, one or more methods may include co-localizing and/or providing and/or assembling, optionally sequentially, one or more peptide synthesis components at one or more identifiable time intervals, wherein the one or more identifiable time intervals are at least partially based on measurements of amino acid incorporation into one or more peptides, biological assembler activity, nucleic acid translocation, and/or tRNA release. In some embodiments, the one or more identifiable time intervals are at least partially based on measurements of availability of one or more nucleic acid codons.

In some embodiments, one or more methods include providing, optionally sequentially, two or more charged tRNA to one or more identifiable locations at one or more first identifiable time intervals, wherein the one or more first identifiable time intervals are at least partially based on, but are not limited to, amino acid incorporation into one or more peptides, biological assembler activity, nucleic acid translocation, and/or tRNA release. In some embodiments, one or more methods include co-localizing sequentially two or more charged tRNA with one or more biological assemblers at one or more first identifiable time intervals, wherein the one or more first identifiable time intervals are at least partially based on, but are not limited to, amino acid incorporation into one or more peptides, biological assembler activity, nucleic acid translocation, and/or tRNA release. In some embodiments, one or more methods include co-localizing sequentially one or more biological assemblers with two or more charged tRNA at one or more first identifiable time intervals, wherein at least two of the two or more charged tRNA are located at one or more different locations, and wherein the one or more first identifiable time intervals are at least partially based on, but are not limited to, amino acid incorporation into one or more peptides, biological assembler activity, nucleic acid translocation, and/or tRNA release. In some embodiments, one or more methods include assembling a target peptide by co-localizing sequentially one or more biological assemblers with two or more charged tRNA at one or more first identifiable time intervals, and wherein the one or more first identifiable time intervals are at least partially based on, but are not limited to, amino acid incorporation into one or more peptides, biological assembler activity, nucleic acid translocation, and/or tRNA release. In some embodiments, the one or more first identifiable time intervals are at least partially based on measurements of availability of one or more nucleic acid codons.

In some embodiments, one or more methods may include removing and/or separating and/or consuming and/or eliminating, optionally sequentially, one or more peptide synthesis components at one or more identifiable time intervals, wherein the one or more identifiable time intervals are at least partially based on measurements and/or monitoring of amino acid incorporation into one or more peptides, biological assembler activity, nucleic acid translocation, and/or tRNA release. In some embodiments, the one or more identifiable time intervals are at least partially based on measurements and/or monitoring of availability of one or more nucleic acid codons.

In some embodiments, one or more methods further include removing and/or separating, optionally sequentially, two or more charged tRNA and/or one or more tRNA from one or more biological assemblers at one or more second identifiable time intervals, wherein the one or more second identifiable time intervals are at least partially based on, but are not limited to, amino acid incorporation into one or more peptides, biological assembler activity, nucleic acid translocation, and/or tRNA release. In some embodiments, one or more methods further include removing and/or separating one or more biological assemblers from two or more charged tRNA and/or one or more tRNA at one or more second identifiable time intervals, wherein the two or more charged tRNA are located at one or more different locations, and wherein the one or more second identifiable time intervals are at least partially based on, but are not limited to, amino acid incorporation into one or more peptides, biological assembler activity, nucleic acid translocation, and/or tRNA release. In some embodiments, one or more methods further include removing and/or separating one or more biological assemblers and two or more charged tRNA and/or one or more tRNA at one or more second identifiable time intervals, and wherein the one or more second identifiable time intervals are at least partially based on, but are not limited to, amino acid incorporation into one or more peptides, biological assembler activity, nucleic acid translocation, and/or tRNA release. In some embodiments, the one or more second identifiable time intervals are at least partially based on measurements of availability of one or more nucleic acid codons.

In some embodiments, one or more methods may include co-localizing and/or providing and/or assembling, optionally sequentially, one or more peptide synthesis components at one or more identifiable time intervals, wherein the one or more identifiable time intervals are at least partially based on measurements of concentrations of charged tRNA and/or released tRNA. In some embodiments, the one or more identifiable time intervals are at least partially based on measurements of presence or absence of one or more charged tRNA and/or one or more tRNA. In some embodiments, the one or more identifiable time intervals are at least partially based on measurements of presence or absence of one or more anticodons on one or more charged tRNA and/or one or more tRNA.

In some embodiments, one or more methods include providing, optionally sequentially, two or more charged tRNA at one or more identifiable locations at one or more first identifiable time intervals, wherein the one or more first identifiable time intervals are at least partially based on measurements of concentrations of, presence or absence of, and/or composition of one or more charged tRNA and/or one or more released tRNA. In some embodiments, one or more methods include co-localizing sequentially two or more charged tRNA with one or more biological assemblers at one or more first identifiable time intervals, wherein the one or more first identifiable time intervals are at least partially based on measurements of concentrations of, presence or absence of, and/or composition of one or more charged tRNA and/or one or more released tRNA. In some embodiments, one or more methods include co-localizing sequentially one or more biological assemblers with two or more charged tRNA at one or more first identifiable time intervals, wherein at least two of the two or more charged tRNA are located at one or more different locations, and wherein the one or more first identifiable time intervals are at least partially based on measurements of concentrations of, presence or absence of, and/or composition of one or more charged tRNA and/or one or more released tRNA. In some embodiments, one or more methods include assembling a target peptide by co-localizing sequentially one or more biological assemblers with two or more charged tRNA at one or more first identifiable time intervals, and wherein the one or more first identifiable time intervals are at least partially based on measurements of concentrations of, presence or absence of, and/or composition of one or more charged tRNA and/or one or more released tRNA. In some embodiments, the one or more first identifiable time intervals are at least partially based on the presence or absence of one or more anti-codons on one or more charged tRNA and/or released tRNA.

In some embodiments, one or more methods may further include removing and/or separating and/or consuming and/or eliminating, optionally sequentially, one or more peptide synthesis components at one or more identifiable time intervals, wherein the one or more identifiable time intervals are at least partially based on measurements of concentrations of charged tRNA or released tRNA. In some embodiments, the one or more identifiable time intervals are at least partially based on measurements of presence or absence of one or more of the two or more charged tRNA or of the one or more tRNA. In some embodiments, the one or more identifiable time intervals are at least partially based on measurements of presence or absence of one or more anti-codons on one or more of the two or more charged tRNA or the one or more tRNA.

In some embodiments, one or more methods further include removing and/or separating, optionally sequentially, one or more charged tRNA and/or one or more tRNA from one or more biological assemblers at one or more second identifiable time intervals, wherein the one or more second identifiable time intervals are at least partially based on measurements of concentrations of, presence or absence of, and/or composition of one or more charged tRNA and/or released tRNA. In some embodiments, one or more methods further include removing and/or separating, optionally sequentially, one or more biological assemblers from two or more charged tRNA at one or more second identifiable time intervals, wherein at least two of the two or more charged tRNA are located at one or more different locations, and wherein the one or more second identifiable time intervals are at least partially based on measurements of concentrations of, presence or absence of, and/or composition of one or more charged tRNA and/or released tRNA. In some embodiments, one or more methods further include separating, optionally sequentially, one or more biological assemblers and two or more charged tRNA at one or more second identifiable time intervals, and wherein the one or more second identifiable time intervals are at least partially based on measurements of concentrations of, presence or absence of, and/or composition of one or more charged tRNA and/or released tRNA. In some embodiments, the one or more second identifiable time intervals are at least partially based on the presence or absence of one or more anti-codons on one or more charged tRNA and/or released tRNA.

In some embodiments, one or more methods may include one or more identifiable time intervals. Such identifiable time intervals may include for example, but are not limited to, one or more of one or more first identifiable time intervals, one or more second identifiable time intervals, one or more third identifiable time intervals, one or more fourth identifiable time intervals, one or more fifth identifiable time intervals, and/or one or more sixth identifiable time intervals. In some embodiments, one or more identifiable time intervals may be the same as one or more other identifiable time intervals. In some embodiments, one or more of identifiable time intervals may be different from one or more other identifiable time intervals. In some embodiments, each identifiable time interval is determined separately.

In illustrative embodiments, one or more methods may include a first identifiable time interval for the (optionally sequential) co-localization of biological assemblers and charged tRNA. The one or more methods may also include a second identifiable time interval for the removal and/or separation (optionally sequential) of the biological assemblers from charged tRNA. These time intervals may be the same or different.

In illustrative embodiments, one or more methods may include a first identifiable time interval for the (optionally sequential) co-localization of charged tRNA with biological assemblers. The one or more methods may also include a second identifiable time interval for the removal and/or separation (optionally sequential) of the charged tRNA from the biological assemblers. These time intervals may be the same or different. The one or more methods may also include a third/fourth/fifth identifiable time interval for the co-localization of the biological assemblers and/or biological assembler components and/or nucleic acids, for example, at an identifiable location. These time intervals may all be the same as each other, or one or more may be different. In some embodiments, one or more of these time intervals will be different from the first and/or second identifiable time intervals.

In some embodiments, one or more methods include providing and/or co-localizing two or more charged tRNA, wherein two or more of the two or more charged tRNA have the same anti-codon and are optionally charged with different amino acids. In some embodiments, one or more methods include providing and/or co-localizing two or more charged tRNA, wherein two or more of the two or more charged tRNA are optionally charged with the same amino acids and have different anti-codons. In some embodiments, one or more methods include co-localizing one or more biological assemblers with two or more charged tRNA, wherein at least two of the two or more charged tRNA are at one or more different locations, and wherein two or more of the two or more charged tRNA have the same anti-codon and are optionally charged with different amino acids. In some embodiments, one or more methods include co-localizing one or more biological assemblers with two or more charged tRNA, wherein at least two of the two or more charged tRNA are at one or more different locations, and wherein two or more of the two or more charged tRNA are optionally charged with the same amino acids and have different anti-codons. In some embodiments, one or more methods include co-localizing one or more biological assemblers and two or more charged tRNA, wherein two or more of the two or more charged tRNA have the same anti-codon and are optionally charged with different amino acids. In some embodiments, one or more methods include co-localizing one or more biological assemblers and two or more charged tRNA, wherein two or more of the two or more charged tRNA are optionally charged with the same amino acids and have different anti-codons.

In illustrative embodiments, two of the charged tRNA may have traditional stop anti-codons, for example AUU, but one may be charged with glycine and the other with methionine, for example. In illustrative embodiments, two of the charged tRNA may have traditional stop anti-codons, for example one may have AUU and the other AUC, but both tRNA may be charged with glycine, for example. In illustrative embodiments, two of the charged tRNA may have traditional cysteine anti-codons, for example ACA, but one may be charged with glycine and the other with methionine, for example. In illustrative embodiments, one of the two charged tRNA may have a traditional cysteine anti-codon, for example ACA, while the other may have a traditional histidine anti-codon, for example GUA, but both tRNA may be charged with glycine, for example.

In some embodiments, one or more methods comprises sequentially co-localizing and/or providing two or more charged anti-stop codon tRNA to one or more identifiable locations. In some embodiments, one or more methods comprises sequentially providing two or more charged anti-stop codon tRNA to one or more biological assemblers. In some embodiments, one or more methods comprises sequentially co-localizing one or more biological assemblers with two or more charged anti-stop codon tRNA, wherein at least two charged tRNA are located at one or more different locations. In some embodiments, one or more methods comprises sequentially co-localizing one or more biological assemblers and two or more charged anti-stop codon tRNA.

In some embodiments, one or more methods include 3 or more, 4 or more, 5 or more, 6 or more, 8 or more, 10 or more, 15 or more, 20 or more, or 50 or more charged anti-stop codon tRNA. In some embodiments, one or more methods include from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 100, 10 to 50, 10 to 25, 20 to 500, 20 to 250, 20 to 100, or 20 to 50 charged anti-stop codon tRNA.

In some embodiments, the two or more charged anti-stop codon tRNA have two different anti-stop codon recognition sites. In some embodiments, the two or more charged anti-stop codon tRNA with two different anti-stop codon recognition sites are sequentially co-localized and/or provided in an alternating anti-stop codon recognition site sequence. In some embodiments, biological assemblers are sequentially co-localized with the two or more charged anti-stop codon tRNA in an alternating anti-stop codon recognition site sequence. In some embodiments, the charged anti-stop codon tRNA with two different anti-stop codon recognition sites optionally have aminoacyl groups that change irrespective and/or unrelated to of the identity of the tRNA anti-stop codon. In some embodiments, the method includes at least 2, at least 3, at least 4, at least 5, at least 6, at least 8, at least 10, at least 15, at least 20, or at least 25 charged anti-stop codon tRNA having two different anti-stop codon recognition sites. In some embodiments, the method includes from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 10, 10 to 50, 10 to 25, 20 to 500, 20 to 250, 20 to 100, or 20 to 50 charged anti-stop codon tRNA having two different anti-stop codon recognition sites.

In some embodiments, one or more methods include sequentially co-localizing and/or providing three or more charged anti-stop codon tRNA having three different anti-stop codon recognition sites in a repeating anti-stop codon recognition site sequence. In some embodiments, one or more methods include sequentially co-localizing one or more biological assemblers with three or more charged anti-stop codon tRNA having three different anti-stop codon recognition sites in a repeating anti-stop codon recognition site sequence, wherein at least two charged tRNA are located at one or more different locations. In some embodiments, one or more methods include sequentially co-localizing one or more biological assemblers and three or more charged anti-stop codon tRNA having three different anti-stop codon recognition sites in a repeating anti-stop codon recognition site sequence.

In some embodiments, the three or more charged anti-stop codon tRNA with three different anti-stop codon recognition sites, optionally have aminoacyl groups that change irrespective and/or unrelated to of the identity of the tRNA anti-stop codon. In some embodiments, one or more methods include at least 3, at least 4, at least 5, at least 6, at least 8, at least 10, at least 15, at least 20, or at least 25 charged anti-stop codon tRNA having three different anti-stop codon recognition sites in a repeating anti-stop codon recognition site sequence. In some embodiments, one or more methods include 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 100, 10 to 50, 10 to 25, 20 to 500, 20 to 250, 20 to 100, or 20 to 50 charged anti-stop codon tRNA having three different anti-stop codon recognition sites in a repeating anti-stop codon recognition site sequence.

In some embodiments, one or more methods include sequentially providing two or more charged tRNA in a target sequence to one or more identifiable locations. In some embodiments, one or more methods include sequentially co-localizing two or more charged tRNA with one or more biological assemblers in a target sequence. In some embodiments, one or more methods include co-localizing sequentially one or more biological assemblers with two or more charged tRNA in a target sequence, wherein at least two of the two or more charged tRNA are at one or more different locations. In some embodiments, one or more methods include co-localizing sequentially one or more biological assemblers and two or more charged tRNA in a target sequence.

In some embodiments, one or more methods further include determining the target sequence for sequentially providing two or more charged tRNA to one or more identifiable locations. In some embodiments, one or more methods further include determining the target sequence for sequentially co-localizing two or more charged tRNA with one or more biological assemblers. In some embodiments, one or more methods further include determining the target sequence for co-localizing sequentially the one or more biological assemblers with the two or more charged tRNA, wherein at least two of the two or more charged tRNA are at one or more different locations. In some embodiments, one or more methods further include determining the target sequence for co-localizing sequentially the one or more biological assemblers and the two or more charged tRNA.

In some embodiments, the target sequence is determined based on criteria including, but not limited to, a target peptide sequence, a nucleic acid protein coding sequence, a biological assembler, and/or one or more biological assembler components. In some embodiments, the target sequence is determined based on criteria including, but not limited to, user designations, target output, computer predictions, availability, predicted synthetic time, and/or cost.

In some embodiments, one or more methods include providing and/or co-localizing two or more charged tRNA sequentially at one or more identifiable locations at one or more identifiable time intervals, wherein the one or more identifiable locations contain one or more biological assemblers and/or one or more nucleic acids. In some embodiments, the one or more nucleic acids have a defined and/or target and/or selected protein coding sequence.

In some embodiments, one or more methods include co-localizing sequentially two or more charged tRNA with one or more peptide assemblers, one or more ribosome-based assemblers, one or more nonribosome-based assemblers, one or more prokaryotic ribosome-based assemblers, one or more eukaryotic ribosome-based assemblers, one or more *E. coli* ribosome-based assemblers, and/or one or more mitochondrial ribosome-based assemblers. In some embodiments, one or more methods include co-localizing sequentially one or more biological assemblers, one or more ribosome-based assemblers, one or more nonribosome-based assemblers, one or more prokaryotic ribosome-based assemblers, one or more eukaryotic ribosome-based assemblers, one or more E. coli ribosome-based assemblers, and/or one or more mitochondrial ribosome-based assemblers with two or more charged tRNA, wherein at least two of the two or more charged tRNA are at one or more different locations. In some embodiments, one or more methods include co-localizing sequentially one or more biological assemblers, one or more ribosome-based assemblers, one or more nonribosome-based assemblers, one or more prokaryotic ribosome-based assemblers, one or more eukaryotic ribosome-based assemblers, one or more E. coli ribosome-based assemblers, and/or one or more mitochondrial ribosome-based assemblers and two or more charged tRNA.

In some embodiments, one or more methods include providing one or more first charged tRNA to one or more identifiable locations; providing one or more second charged tRNA to the one or more identifiable locations; and optionally repeating. In some embodiments, one or more methods further comprise providing one or more third charged tRNA to one or more identifiable locations. In some embodiments, one or more methods comprises co-localizing one or more first charged tRNA with one or more biological assemblers; co-localizing one or more second charged tRNA with one or more biological assemblers; and optionally repeating. In some embodiments, one or more methods further comprise co-localizing one or more third charged tRNA with one or more biological assemblers. In some embodiments, one or more methods include co-localizing one or more biological assemblers with one or more first charged tRNA at one or more first locations; co-localizing the one or more biological assemblers with one or more second charged tRNA at one or more second locations; and optionally repeating. In some embodiments, one or more methods further include co-localizing one or more biological assemblers with one or more third charged tRNA at one or more third locations. In some embodiments, one or more methods include co-localizing one or more biological assemblers and one or more first charged tRNA at one or more first locations; co-localizing the one or more biological assemblers and one or more second charged tRNA at one or more second locations; and optionally repeating. In some embodiments, one or more methods further include co-localizing one or more biological assemblers and one or more third charged tRNA at one or more third locations.

In some embodiments, one or more methods further comprise providing one or more additional charged tRNA to one or more identifiable locations. In some embodiments, one or more methods further comprise co-localizing one or more additional charged tRNA with one or more biological assemblers. In some embodiments, one or more methods further comprise co-localizing one or more biological assemblers with one or more additional charged tRNA, wherein the one or more additional charged tRNA are optionally at one or more different locations. In some embodiments, one or more methods further comprise co-localizing one or more biological assemblers and one or more additional charged tRNA.

In some embodiments, the one or more first charged tRNA is optionally the same as and/or optionally different from the one or more second charged tRNA. In some embodiments, the one or more first charged tRNA includes a stop codon recognition site, and the one or more second charged tRNA includes a stop codon recognition site. In some embodiments, the one or more first charged tRNA stop codon recognition site is different from the one or more second charged tRNA stop codon recognition site. In some embodiments, the one or more third charged tRNA includes a stop codon recognition site that is optionally the same as the one or more first charged tRNA stop codon recognition site and/or the one or more second charged tRNA stop codon recognition site, or optionally different from the one or more first charged tRNA stop codon recognition site and/or the one or more second charged tRNA stop codon recognition site. In some embodiments, the one or more additional charged tRNA have stop codon recognition sites. In some embodiments, the one or more additional charged tRNA having stop codon recognition sites are co-localized such that the stop codon recognition sites of the charged tRNA alternate. In some embodiments, the one or more biological assemblers are co-localized with the one or more additional charged tRNA having stop codon recognition sites such that the stop codon recognition sites of the charged tRNA alternate.

In some embodiments, the one or more first charged tRNA, the one or more second charged tRNA, the one or more third charged tRNA, and/or the one or more additional charged tRNA are optionally the same as, or optionally different from, each other. In some embodiments, the tRNA portion of one or more of the one or more first charged tRNA, the one or more second charged tRNA, the one or more third charged tRNA, or the one or more additional charged tRNA are optionally the same as, or optionally different from, each other. In some embodiments, one or more of the anticodon portions of one or more of the one or more first charged tRNA, the one or more second charged tRNA, the one or more third charged tRNA, or the one or more additional charged tRNA are one or more stop codon recognition sites. In some embodiments, the amino acid portion of one or more of the one or more first charged tRNA, the one or more second charged tRNA, the one or more third charged tRNA, or the one or more additional charged tRNA are optionally the same as, or optionally different from, each other.

In some embodiments, one or more methods comprises co-localizing one or more first charged tRNA with one or more biological assemblers, the one or more first charged tRNA charged with one or more first arbitrary amino acid; removing one or more first tRNA, the one or more first tRNA released during peptide synthesis; co-localizing one or more second charged tRNA with one or more biological assemblers, the one or more second charged tRNA charged with one or more second arbitrary amino acid; removing one or more second tRNA, the one or more second tRNA released during peptide synthesis; and optionally repeating. In some embodiments, the method includes co-localizing one or more biological assemblers with one or more first charged tRNA in one or more first locations, the one or more first charged tRNA charged with one or more first arbitrary amino acid; removing one or more first tRNA, the one or more first tRNA released during peptide synthesis; co-localizing one or more biological assemblers with one or more second charged tRNA at one or more second locations, the one or more second charged tRNA charged with one or more second arbitrary amino acid; removing one or more second tRNA, the one or more second tRNA released during peptide synthesis; and optionally repeating.

In some embodiments, one or more methods include co-localizing one or more biological assemblers with one or more first charged tRNA at one or more first locations, the one or more first charged tRNA charged with one or more arbitrary amino acids; removing the one or more biological assemblers from the one or more first locations; co-localizing the one or more biological assemblers with one or more second charged tRNA at one or more second locations, the second one or more charged tRNA charged with one or more arbitrary amino acids; removing the one or more biological assemblers from the one or more second locations; and optionally repeating. In some embodiments, one or more methods include co-localizing one or more biological assemblers and one or more first charged tRNA at one or more first locations, the first one or more charged tRNA charged with one or more arbitrary amino acids; separating the one or more first charged tRNA and/or one or more released tRNA and the one or more biological assemblers; co-localizing the one or more biological assemblers and one or more second charged tRNA at one or more second locations, the second one or more charged tRNA charged with one or more arbitrary amino acids; separating the one or more second charged tRNA and/or one or more released tRNA and the one or more biological assemblers; and optionally repeating.

In some embodiments, the first arbitrary amino acid is optionally the same as, or optionally different from, the second arbitrary amino acid. In some embodiments, the first tRNA is optionally the same as, or optionally different from, the second tRNA. In some embodiments, the first charged tRNA is optionally the same as, or optionally different from, the second charged tRNA. In some embodiments, the one or more first arbitrary amino acid is the same as the one or more second arbitrary amino acid, and the one or more first tRNA is different from the one or more second tRNA. In some embodiments, the first and the second tRNA have different anti-codons. In some embodiments, the one or more first tRNA is the same as the one or more second tRNA, and the one or more first arbitrary amino acids are different from the one or more second arbitrary amino acids. In some embodiments, the first and the second tRNA have the same anti-codon.

In illustrative embodiments, one or more methods include: providing the first charged tRNA having an anti-codon that recognizes the first codon of the translatable reading frame and having an amino acid attached that is the first amino acid of the target polypeptide; allowing sufficient time for docking of the charged tRNA; providing the second charged tRNA having an anti-codon that recognizes the second codon of the translatable reading frame and having an amino acid attached that is the second amino acid of the target polypeptide; allowing sufficient time for docking of the charged tRNA, peptide bond formation between the first two amino acids, and release of the first tRNA; removal of the first released tRNA; providing the third charged tRNA having an anti-codon that recognizes the third codon of the translatable reading frame and having an amino acid attached that is the third amino acid of the target polypeptide; allowing sufficient time for docking of the charged tRNA, peptide bond formation between the second and the third amino acids, and release of the second tRNA; removal of the second released tRNA; and repeating the process for the target peptide sequence.

In some embodiments, one or more of the methods described herein includes charging one or more tRNA with one or more arbitrary amino acids, one or more natural amino acids or one or more unnatural amino acids. In some embodiments, one or more of the methods described herein includes charging one or more anti-stop codon tRNA with one or more natural amino acids or one or more unnatural amino acids. In some embodiments, aminoacylation is mediated by aminoacyl tRNA synthetases including one or more natural and/or one or more unnatural aminoacyl tRNA synthetases.

In some embodiments, one or more of the methods described herein includes selecting two or more charged tRNA. In some embodiments, two or more charged tRNA are selected at least partially, or completely, based on criteria including, but not limited to, target peptide sequence, a nucleic acid protein coding sequence, a biological assembler, and/or one or more biological assembler components. In some embodiments, the protein coding region of the nucleic acid sequence includes one or more codons selected from the group consisting of two or more stop codons, at least three stop codons, two or more alternating stop codons, one or more singlet codons, one or more doublet codons, one or more triplet codons, one or more quadruplet codons, one or more quintuplet codons, and one or more sextuplet codons. In some embodiments, two or more charged tRNA are selected based on criteria including, but not limited to, user designations, target output, computer predictions, availability, predicted synthetic time, and/or cost.

In some embodiments, one or more of the methods described herein includes selecting one or more biological assemblers. In some embodiments, one or more biological assemblers are selected at least partially based on criteria including, but not limited to, one or more of a target peptide sequence, one or more charged tRNA, or a nucleic acid protein coding sequence. In some embodiments, one or more biological assemblers are selected at least partially based on criteria including, but not limited to, user designations, target output, computer predictions, availability, predicted synthetic time, and cost.

In some embodiments, one or more of the methods described herein includes selecting one or more components of one or more biological assemblers. In some embodiments, one or more biological assembler components are selected at least partially based on criteria including, but not limited to, one or more of a target peptide sequence, one or more charged tRNA, or a nucleic acid protein coding sequence. In some embodiments, one or more biological assembler components are selected at least partially based on criteria including, but not limited to, user designations, target output, computer predictions, availability, predicted synthetic time, and cost.

As used herein, the term "selecting" means any process used to identify for use one or more target components. Processes include, but are not limited to, user selected, user identified, software method analysis, algorithm-based, computer mediated, operations research, optimization, simulation, queuing theory, and/or game theory.

In some embodiments, one or more methods include assembling and/or co-localizing and/or providing one or more components of one or more biological assemblers. In some embodiments, one or more methods include assembling one or more components of the one or more biological assemblers at one or more third identifiable time intervals. In some embodiments, the one or more third identifiable time intervals are at least partially based on a predicted rate of incorporation of two or more amino acids into one or more peptides, a predicted rate of activity of the one or more biological assemblers, a predicted rate of translocation of one of more nucleic acids, and/or a predicted rate of release of tRNA. In illustrative embodiments, one or more methods include assembling one or more first biological assembler components, assembling a target peptide, removing the one or more first biological assembler components, and co-localizing one or more second biological assembler components. In illustrative embodiments, one or more methods include assembling one or more first biological assembler components, commencing synthesis of a target peptide, co-localizing one or more second biological assembler components, and assembling a target peptide.

In some embodiments, one or more methods include assembling one or more components of one or more biological assemblers at one or more third identifiable time intervals, and further comprises monitoring amino acid incorporation into one or more peptides, biological assembler activity, nucleic acid translocation, and/or tRNA release. In some embodiments, one or more methods include assembling one or more components of one or more biological assemblers at one or more third identifiable time intervals, and further include monitoring the presence or absence, concentration, and/or compositions of one or more charged tRNA and/or one or more tRNA. In some embodiments, the one or more identifiable time intervals are at least partially based on availability of one or more nucleic acid codons. In some embodiments, the one or more identifiable time intervals are at least partially based on the concentrations of one or more charged tRNA and/or one or more tRNA. In some embodiments the one or more identifiable time intervals are based on the presence or absence of one or more charged tRNA and/or one or more tRNA. In some embodiments, the one or more identifiable time intervals are based on the presence or absence of one or more anti-codons on one or more charged tRNA and/or one or more tRNA.

In some embodiments, one or more methods of co-localizing sequentially two or more tRNA with one or more biological assemblers, further include co-localizing the one or more biological assemblers at one or more identifiable locations. In some embodiments, one or more methods include co-localizing one or more biological assemblers at one or more identifiable locations at one or more fourth identifiable time intervals. In some embodiments, the one or more fourth identifiable time intervals are at least partially based on a predicted rate of incorporation of one or more amino acids into one or more peptides, a predicted rate of activity of one or more biological assemblers, a predicted rate of translocation of one or more nucleic acids, and/or a predicted rate of release of tRNA. In illustrative embodiments, one or more methods include co-localizing one or more first biological assemblers, assembling a target peptide, removing the one or more first biological assemblers, and co-localizing one or more second biological assemblers.

In some embodiments, one or more methods includes co-localizing one or more biological assemblers at one or more identifiable locations at one or more fourth identifiable time intervals, and further comprises monitoring amino acid incorporation into one or more peptides, biological assembler activity, nucleic acid translocation, and/or tRNA release. In some embodiments, the one or more identifiable time intervals are based on the results of the monitoring. For example, in some embodiments the one or more identifiable time intervals are at least partially based on measurements of amino acid incorporation into one or more peptides, biological assembler activity, nucleic acid translocation, and/or tRNA release. In some embodiments, one or identifiable time intervals are at least partially based on availability of one or more nucleic acid codons.

In some embodiments, one or more methods includes co-localizing one or more biological assemblers at one or more identifiable locations at one or more fourth identifiable time intervals, and further comprises monitoring the presence or absence, concentration, and/or compositions of one or more charged tRNA and/or one or more tRNA released during peptide synthesis. In some embodiments, the one or more identifiable time intervals are based on the results of monitoring. For example, the one or more identifiable time intervals may be at least partially based on the concentrations of one or more charged tRNA and/or one or more tRNA, the presence or absence of one or more charged tRNA and/or one or more tRNA, and/or the presence or absence of one or more anti-codons on one or more charged tRNA and/or one or more tRNA.

In some embodiments, co-localizing, optionally sequentially, two or more charged tRNA with one or more biological assemblers occurs at least partially, and optionally completely, following co-localizing the one or more biological assemblers at one or more identifiable locations. In some embodiments, co-localizing, optionally sequentially, one or more biological assemblers with two or more charged tRNA, wherein at least two of the two or more charged tRNA are at different locations, occurs at least partially, and optionally completely, following co-localizing the two or more charged tRNA at one or more different locations.

As used herein, the term "assembling" means any process resulting in one or more components being in the same place. In some embodiments, the components may be assembled by one or more methods including, but not limited to, one or more of co-localized, provided, injected, aggregated, commingled, combined, mixed or any other similar method.

In illustrative embodiments, fluid flow is used to "flow" one or more components into association (or assemblage). In some embodiments, the components may be all of one type, or of one or more types. In some embodiments, the components may be an admixture of ribosomal and non-ribosomal components, or biological and non-biological components.

As used herein, the term "type" means a difference in kind. For example, "type" as used with biological assemblers and/or biological assembler components may refer to chloroplast versus mitochondrial ribosomal assemblers, or prokaryotic versus eukaryotic ribosomal assemblers, or ribosomal versus nonribosome assemblers. Type may also refer to differences in kind for nucleic acids, for example, DNA versus RNA, or eukaryotic versus prokaryotic, or plasmid versus linear. Type may also refer to differences in kind for charged tRNA and/or tRNA, for example, based on differences in the anti-codon, or eukaryotic versus prokaryotic, or natural versus unnatural. Type may also refer to differences in kind for amino acids, for example, based on differences of natural versus unnatural.

In some embodiments, one or more methods include one or more biological assemblers that are affixed at one or more identifiable locations. In some embodiments, one or more of the methods further comprise affixing one or more biological assemblers at one or more identifiable locations and/or to one or more devices. In some embodiments, one or more of the methods include co-localizing sequentially two or more charged tRNA with one or more biological assemblers, wherein the one or more biological assemblers are affixed at one or more identifiable locations. In some embodiments, one or more methods include affixing one or more nucleic acids at one or more identifiable locations and/or to one or more devices.

In some embodiments, one or more methods include two or more charged tRNA affixed at one or more different locations. In some embodiments, one or more methods include affixing two or more charged tRNA at two or more different locations and/or the two or more different devices. In some embodiments, one or more methods include co-localizing sequentially one or more biological assemblers with two or more charged tRNA, wherein at least two of the two or more charged tRNA are located at one or more different locations, and wherein the at least two of the two or more charged tRNA are affixed at the two or more different locations. In some embodiments, one or more devices include, but are not limited t, one or more microelectromechanical systems (MEMS) devices, beads, and/or immunoassay arrays.

In illustrative embodiments, two or more charged tRNA are affixed in two or more liquid beads. In illustrative embodiments, fluid flow is used to co-localize one or more biological assemblers sequentially with each of the two or more charged tRNA in two or more liquid beads. In illustrative embodiments, excess charged tRNA and/or released tRNA are removed using fluid flow and differential filtration.

In some embodiments, one or more methods include co-localizing sequentially one or more biological assemblers with two or more charged tRNA, wherein at least two of the two or more charged tRNA are located at one or more different locations, and further includes co-localizing the at least two of the two or more charged tRNA at the one or more different locations. In some embodiments, the co-localizing sequentially one or more biological assemblers with the at least two of the two or more charged tRNA occurs at least partially following the co-localizing the at least two of the two or more charged tRNA at the one or more different locations. In some embodiments, one or more methods include co-localizing sequentially one or more biological assemblers with two or more charged tRNA, wherein at least two of the two or more charged tRNA are located at one or more different locations, and further includes removing one or more of the at least two of the two or more charged tRNA or one or more released tRNA from the one or more different locations.

In illustrative embodiments, one or more methods comprise: co-localizing, optionally sequentially, one or more first charged tRNA at one or more first identifiable locations, one or more second charged tRNA at one or more second identifiable locations, and one or more third charged tRNA at one or more third identifiable locations; co-localizing and subsequently removing one or more biological assemblers with the one or more first charged tRNA at the one or more first locations, with the one or more second charged tRNA at the one or more second locations, and/or with the one or more third charged tRNA at the one or more third locations in a target sequence; removing one or more first charged tRNA and/or one or more released tRNA from the one or more first locations, one or more second charged tRNA and/or one or more released tRNA from the one or more second locations, and/or one or more third charged tRNA and/or one or more released tRNA from at the one or more third locations depending on the target sequence; and optionally repeating until a target peptide is synthesized.

In some embodiments, one or more methods include co-localizing sequentially one or more biological assemblers with two or more charged tRNA, wherein at least two of the two or more charged tRNA are located at one or more different locations, and further includes co-localizing the at least two of the two or more charged tRNA at the one or more different locations at one or more identifiable time intervals. In some embodiments, one or more methods include co-localizing sequentially one or more biological assemblers with two or more charged tRNA, wherein at least two of the two or more charged tRNA are located at one or more different locations, and further includes removing one or more of the at least two of the two or more charged tRNA or one or more released tRNA from the one or more different locations at one or more identifiable time intervals. The time intervals for providing the charged tRNA and the time intervals for removing the charged tRNA and/or released tRNA may be the same or different. The one or more identifiable time intervals for providing the charged tRNA and the time intervals for removing the charged tRNA and/or released tRNA are at least partially based on one or more of a predicted rate of incorporation of two or more amino acids into one or more peptides, a predicted rate of activity of the one or more biological assemblers, a predicted rate of translocation of one or more nucleic acids, or a predicted rate of release of tRNA.

In some embodiments, one or more methods include co-localizing sequentially one or more biological assemblers with two or more charged tRNA, wherein at least two of the two or more charged tRNA are located at one or more different locations; co-localizing the at least two of the two or more charged tRNA at the one or more different locations at one or more identifiable time intervals; and further includes monitoring amino acid incorporation into one or more peptides, biological assembler activity, nucleic acid translocation, and/or tRNA release. In some embodiments, one or more methods include co-localizing sequentially one or more biological assemblers with two or more charged tRNA, wherein at least two of the two or more charged tRNA are located at one or more different locations; removing one or more of the at least two of the two or more charged tRNA or one or more released tRNA from the one or more different locations at one or more identifiable time intervals; and further includes monitoring amino acid incorporation into one or more peptides, biological assembler activity, nucleic acid translocation, and/or tRNA release. In some embodiments, the one or more first identifiable time intervals are at least partially based on the results of the monitoring, including but not limited to measurements of the amino acid incorporation into the one or more peptides, the biological assembler activity, the nucleic acid translocation, and/or the tRNA release. In some embodiments, the one or more first identifiable time intervals are at least partially based on availability of one or more nucleic acid codons.

In some embodiments, one or more methods include co-localizing sequentially one or more biological assemblers with two or more charged tRNA, wherein at least two of the two or more charged tRNA are located at one or more different locations; co-localizing the at least two of the two or more charged tRNA at the one or more different locations at one or more identifiable time intervals; and further includes monitoring the presence or absence, concentration, and/or composition of one or more charged tRNA and/or one or more tRNA. In some embodiments, one or more methods include co-localizing sequentially one or more biological assemblers with two or more charged tRNA, wherein at least two of the two or more charged tRNA are located at one or more different locations; removing one or more of the at least two of the two or more charged tRNA or one or more released tRNA from the one or more different locations at one or more identifiable time intervals; and further includes monitoring the presence or absence, concentration, and/or composition of one or more charged tRNA and/or one or more tRNA. In some embodiments, the one or more first identifiable time intervals are at least partially based on the results of the monitoring, including but not limited to the concentration, presence or absence of one or more charged tRNA and/or one or more tRNA, and/or the presence or absence of one or more anti-codons on one or more charged tRNA and/or one or more tRNA.

As used herein, the term "identifiable location" means a position in space and time that can be determined. In some embodiments, one or more identifiable locations are internal to a device or apparatus and/or external to a device or apparatus. In some embodiments, the one or more identifiable locations are moving in time and/or moving in space. In some embodiments, the movement in time and/or space may be one or more of steady, fluctuating, predictable or other type of movement so long as the location can be identified at a particular place and time.

In some embodiments, one or more of the processes and/or elements of processes occur at one or more identifiable locations that may be the same or may be different. In some embodiments the terms, "first", "second", "third", "fourth", "fifth", "sixth", etc. may be used to indicate that the identifiable locations are optionally different identifiable locations. Generally, identifiable locations indicated by the same numeral are the same locations unless context indicates otherwise.

As used herein, the term "different location" means an identifiable location that is in a different position in space and/or time from another identifiable location.

As used herein, the term "devices" means any configuration capable of localizing and/or containing one or more components at least temporarily. Devices may include, but are not limited to, containers, receptacles, semi-permeable membranes, beads of liquid, MEMS, microfluidics devices, arrays, liposomes, and/or surface-tension attached liquids.

As used herein, the term "affixing" means any process that at least temporarily restricts the movement of one or more components in relation to an identifiable location and/or one or more devices. Processes include, but are not limited to, attachment, filtration, ultrafiltration, resins, changes in aperture diameter, optical traps, and/or electric fields. Affixing may be through direct and/or indirect means including, for example, affixing one or more biological assemblers by affixing the one or more nucleic acids that the one or more biological assemblers are translating. Attachment includes, but is not limited to, methods known in the art for attaching membranes to a variety of support structures, for attaching nucleic acids to a variety of support structures, and for attaching proteins to a variety of support structures. Support structures include, but are not limited to, beads, microfluidic devices, MEMS devices, carbon nanotubes, arrays, and/or microstructured surfaces.

In some embodiments, one or more methods include providing and/or co-localizing two or more charged tRNA sequentially into one or more receptacles at one or more identifiable locations. In some embodiments, one or more methods include providing and/or co-localizing two or more charged tRNA sequentially into one or more receptacles at one or more identifiable locations at one or more identifiable time intervals. In some embodiments, one or more methods include injecting sequentially two or more charged tRNA into one or more receptacles containing one or more biological receptors. In some embodiments, the one or more receptacles contain one or more biological assemblers and/or one or more nucleic acids.

In some embodiments, one or more methods include co-localizing sequentially two or more charged tRNA with one or more biological assemblers that are co-localized with one or more nucleic acids. In some embodiments, one or more methods include co-localizing sequentially one or more biological assemblers and two or more charged tRNA, wherein the one or more biological assemblers are co-localized with one or more nucleic acids. In some embodiments, multiple biological assemblers are co-localized with one or more nucleic acids. In some embodiments, multiple biological assemblers are optionally translating one or more nucleic acids at the same time.

In some embodiments, the one or more nucleic acids include, but are not limited to, one or more DNA, one or more cDNA, one or more RNA, and/or one or more mRNA. In some embodiments, one or more nucleic acids may be recombinant, circular, linear, plasmid, double stranded, single stranded, poly-adenylated, or any other form known in the art suitable for protein synthesis. In some embodiments, one or more nucleic acids have a defined and/or selected and/or target protein coding sequence.

As used herein, the term "nucleic acid or nucleic acids" means one or more complex, high-molecular-weight biochemical macromolecules composed of nucleotide chains. Nucleic acids include, but are not limited to, one or more forms of deoxyribonucleic acid (DNA), ribonucleic acid (RNA; includes messenger RNA (mRNA)), and complementary DNA (cDNA; DNA synthesized from an mRNA template).

As used herein, the term "target protein coding sequence" means a translatable reading frame in one or more nucleic acids. In some embodiments, the translatable reading frames are open reading frames that translate into a target peptide using the standard genetic code. In some embodiments, the translatable reading frames do not translate into a target peptide using the standard genetic code.

In some embodiments, the translatable reading frames contain at least one stop codon. In some embodiments, the translatable reading frames have a protein coding sequence having at least 2, at least 3, at least 4, at least 5, at least 6, at least 8, at least 10, at least 15, at least 20, or at least 25 stop codons. In some embodiments, the translatable reading frames have a protein coding sequence having from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 100, 10 to 50, 10 to 25, 20 to 500, 20 to 250, 20 to 100, or 20 to 50 stop codons.

In some embodiments, the stop codons are two different stop codons in an alternating sequence. In some embodiments, the alternating stop codon sequence includes, but is not limited to, at least 2, at least 3, at least 4, at least 5, at least 6, at least 8, at least 10, at least 15, at least 20, or at least 25 alternating stop codons. In some embodiments, the alternating stop codon sequence has from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 100, 10 to 50, 10 to 25, 20 to 500, 20 to 250, 20 to 100, or 20 to 50 alternating stop codons.

In some embodiments, the stop codons are three different stop codons in a repeating sequence. In some embodiments, the repeating stop codon sequence includes, but is not limited to, at least 3, at least 4, at least 5, at least 6, at least 8, at least 10, at least 15, at least 20, or at least 25 repeating stop codons. In some embodiments, the repeating stop codon sequence has from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 100, 10 to 50, 10 to 25, 20 to 500, 20 to 250, 20 to 100, or 20 to 50 repeating stop codons.

In some embodiments, the translatable reading frames contain one or more of at least one singlet codon, at least one doublet codon, at least one triplet codon, at least one quadruplet codon, at least one quintuplet codon, or at least one sextuplet codon. In some embodiments, the translatable reading frames have a protein coding sequence having at least 2, at least 3, at least 4, at least 5, at least 6, at least 8, at least 10, at least 15, at least 20, or at least 25 singlet, doublet, triplet, quadruplet, quintuplet, and/or sextuplet codons. In some embodiments, the translatable reading frames have a protein coding sequence having from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 100, 10 to 50, 10 to 25, 20 to 500, 20 to 250, 20 to 100, or 20 to 50 singlet, doublet, triplet, quadruplet, quintuplet, and/or sextuplet codons.

Methods of synthesizing nucleic acids are known in the art including, but not limited to, chemical and enzymatic synthesis. Proteins/peptides translated from nucleic acids with modified translatable reading frames, including sense codon reassignment are known in the art (e.g. Methods (2005) 36:227-238; Methods (2005) 36:270-278; Methods (2005) 36:279-290; Methods (2005) 36:291-298; Annu. Rev. Biochem. (2004) 73:147-176; Nucleic Acids Research (2004) 32:6200-6211; PNAS (2003) 100:6353-6357)

As used herein, the term "target protein or target protein sequence" means one or more identified and/or selected polypeptide sequences. In some embodiments, the target peptide sequence is directly translatable from the target protein coding sequence of one or more nucleic acids using the genetic code. In some embodiments, the target peptide sequence is not directly translatable from the target protein coding sequence of one or more nucleic acids using the genetic code.

In other embodiments, one or more methods include co-localizing one or more nucleic acids with one or more biological assemblers. Some embodiments include any process that results in one or more components being in the same place. One or more nucleic acids and one or more biological assemblers may be assembled, aggregated, commingled, combined or mixed, or other similar methods. Processes, including sequential processes, are known in the art and include, but are not limited to, one or more of automated methods, mechanical methods, computer and/or software-controlled methods, and fluid flow. Fluid flow includes, but is not limited to, nanofluidics and microfluidics. Nanofluidics and microfluidics include, but are not limited to, continuous flow microfluidics and digital microfluidics, and have been developed for use in biological systems (Annu. Rev. Fluid Mech. (2004) 36:381-411; Annu. Rev. Biomed. Eng. (2002) 4:261-86; Science (1988) 242:1162-1164, Rev. Mod. Phys. (2005) 77:977-1026).

In some embodiments, one or more methods include co-localizing one or more nucleic acids with one or more biological assemblers at one or more fifth identifiable time intervals. In some embodiments, the one or more fifth identifiable time intervals are at least partially based on a predicted rate of incorporation of amino acids into peptides, a predicted rate of activity of biological assemblers, a predicted rate of translocation of nucleic acids and/or a predicted rate of release of tRNA.

In some embodiments, one or more methods that include co-localizing one or more nucleic acids with one or more biological assemblers at one or more fifth identifiable time intervals, further include monitoring amino acid incorporation into peptides, biological assembler activity, nucleic acid translocation, and/or tRNA release. In some embodiments, the results of monitoring one or more of amino acid incorporation into peptides, biological assembler activity, nucleic acid translocation, or tRNA release are at least partially used to identify time intervals for co-localization of nucleic acids. In some embodiments, the one or more fifth identifiable time intervals are at least partially based on availability of one or more nucleic acid codons.

In some embodiments, one or more methods that include co-localizing one or more nucleic acids with one or more biological assemblers at one or more fifth identifiable time intervals, further include monitoring the presence or absence, concentration, and/or compositions of one or more charged tRNA and/or one or more tRNA. In some embodiments, the results of monitoring the presence or absence, concentration, and/or compositions of one or more charged tRNA and/or one or more tRNA are at least partially used to identify time intervals for co-localization of nucleic acids. In some embodiments, the one or more fifth identifiable time intervals are at least partially based on the presence or absence of one or more charged tRNA and/or one or more tRNA, and/or the presence or absence of one or more anti-codons on one or more charged tRNA and/or one or more tRNA.

In some embodiments, one or more methods include co-localizing, optionally sequentially, two or more charged tRNA with one or more biological assemblers at least partially, or optionally completely, following co-localizing one or more nucleic acids with one or more biological assemblers. In some embodiments, one or more methods include co-localizing, optionally sequentially, one or more biological assemblers with two or more charged tRNA, at least partially, or optionally completely, following co-localizing one or more nucleic acids with the one or more biological assemblers. In some embodiments, one or more methods include co-localizing, optionally sequentially, one or more biological assemblers and two or more charged tRNA, at least partially, or optionally completely, following co-localizing one or more nucleic acids with the one or more biological assemblers.

In some embodiments, one or more methods include selecting one or more nucleic acids, including but not limited to, RNA, DNA, cDNA, and mRNA. In some embodiments, the method includes selecting one or more nucleic acids having a selected and/or target protein coding sequence. In some embodiments, one or more nucleic acids are selected based on criteria including, but not limited to, one or more of a target peptide sequence, a target nucleic acid protein coding sequence, one or more charged tRNA, one or more biological assemblers, or one or more biological assembler components. For example, the one or more nucleic acid sequences may be selected at least partially based on the selected target peptide sequence and the selected biological assemblers and/or biological assembler components (e.g. Ef-Tu; Biochemistry (2006) 44:11254-11261). In some embodiments, one or more nucleic acids are selected based on criteria including, but not limited to, user designations, target output, computer predictions, availability, predicted synthetic time, and/or cost.

Some embodiments include any process used to identify for use one or more target components. Processes include, but are not limited to, user selected, user identified, software method analysis, algorithm-based, computer mediated, operations research, optimization, simulation, queuing theory, and/or game theory.

In some embodiments, one or more of the methods described herein includes synthesizing one or more nucleic acids. In some embodiments, one or more nucleic acids are synthesized to have a selected/target protein coding sequence. In yet other embodiments, the method includes synthesizing the one or more nucleic acids using two or more singlet codons, two or more doublet codons, two or more triplet codons, two or more quadruplet codons, two or more quintuplet codons, and/or two or more sextuplet codons. In other embodiments, the method includes synthesizing one or more nucleic acids using two or more stop codons. In some embodiments, the method includes synthesizing one or more nucleic acids using two or more different stop codons or three or more different stop codons. In some embodiments, the nucleic acids are synthesized having alternating stop codons and/or repeating stop codons. In some embodiments, the nucleic acids are synthesized having any one of the translatable reading frames described herein.

As used herein, the term "synthesizing" means any process resulting in two or more nucleotides being joined to form a nucleic acid. Processes to synthesize DNA and RNA are well known to those of skill in the art and include, but are not limited to, one or more of enzymatic or chemical methods such as polymerase chain reaction and phosphoramidite chemistry followed by deprotection, for example.

In some embodiments, one or more methods include synchronizing sequentially providing two or more charged tRNA at one or more identifiable locations, with a selected or target protein coding sequence of one or more nucleic acids. In some embodiments, one or more methods include synchronizing sequentially co-localizing two or more charged tRNA with the one or more biological assemblers, with a selected or target protein coding sequence of one or more nucleic acids. In some embodiments, one or more methods include synchronizing sequentially co-localizing one or more biological assemblers with two or more charged tRNA, with a selected or target protein coding sequence of one or more nucleic acids. In some embodiments, one or more methods include synchronizing sequentially co-localizing one or more biological assemblers and two or more charged tRNA, with a selected or target protein coding sequence of one or more nucleic acids.

In some embodiments, the nucleic acid protein coding sequence and the target protein sequence both follow the standard genetic code, therefore sequential co-localization of charged tRNA also follows the standard genetic code, and synchronization is based on the standard genetic code. In some embodiments, the target protein coding sequence includes one or more modified or unnatural amino acids, and synchronization between the target peptide sequence and the nucleic acid protein coding sequence allows the co-localization of a charged tRNA with standard anti-codon recognition sequence and attached modified/unnatural aminoacyl group. In other embodiments, the nucleic acid protein coding sequence and target protein coding sequence do not follow the standard genetic code, therefore synchronization between the target peptide sequence and the nucleic acid protein coding sequences allows co-localization of charged tRNA with the anti-codon recognition sequences to pair with the nucleic acid codons and attached aminoacyl groups that follow the target protein coding sequence.

In other embodiments, one or more of the methods described herein includes synchronizing synthesizing one or more nucleic acids, with co-localizing two or more charged tRNA with one or more biological assemblers. In other embodiments, one or more of the methods described herein includes synchronizing synthesizing one or more nucleic acids, with co-localizing one or more biological assemblers with two or more charged tRNA, wherein at least two of the two or more charged tRNA are at one or more different locations. In other embodiments, one or more of the methods described herein includes synchronizing synthesizing one or more nucleic acids, with sequentially co-localizing one or more biological assemblers and two or more charged tRNA.

In some embodiments, the nucleic acid protein coding sequence and the target protein sequence both follow the standard genetic code, therefore synchronization of nucleic acid protein coding region synthesis with co-localizing charged tRNA is based on the standard genetic code. In some embodiments, the target protein coding sequence includes one or more modified or unnatural amino acids, therefore synchronization allows a nucleic acid protein coding region to be synthesized with a target sequence to that coordinates with co-localization (and incorporation) of a charged tRNA with an attached modified/unnatural aminoacyl group. In other embodiments, the nucleic acid protein coding sequence and target protein coding sequence do not follow the standard genetic code, therefore synchronization of nucleic acid protein coding region synthesis with co-localizing charged tRNA allows the synthesis of a nucleic acid protein coding sequence with codons that will pair with the charged tRNA anti-codon recognition sequences having attached aminoacyl groups that follow the target protein coding sequence.

In other embodiments, one or more of the methods described herein includes synchronizing synthesizing one or more nucleic acids, and charging one or more tRNA with one or more natural amino acids, one or more arbitrary amino acids, and/or one or more unnatural amino acids. In some embodiments, the nucleic acid protein coding sequence and the target protein sequence both follow the standard genetic code, therefore synchronization of nucleic acid protein coding region synthesis with charging tRNA with amino acids is based on the standard genetic code. In some embodiments, the target protein coding sequence includes one or more modified or unnatural amino acids, therefore synchronization of nucleic acid protein coding region synthesis and tRNA charging allows the coordination of the nucleic acid codon and tRNA anti-codon pairing for the charged tRNA with an attached modified/unnatural aminoacyl group. In other embodiments, the nucleic acid protein coding sequence and target protein coding sequence do not follow the standard genetic code, therefore synchronization of nucleic acid protein coding region synthesis with tRNA charging allows the synthesis of a nucleic acid protein coding sequence with codons that will pair with the charged tRNA anti-codon recognition sequences having attached aminoacyl groups that follow the target protein coding sequence.

As used herein, the term "synchronizing" means any one or more processes coordinating one or more elements of one or more methods. The one or more elements of one or more methods may include, but are not limited to one or more of two or more processes, or one or more processes and one or more target sequences. The one or more processes may include, but are not limited to, user defined, software-based, algorithm-based, computer mediated, operations research, optimization, simulation, queuing theory, and/or game theory.

In some embodiments, one or more methods further comprise partially or completely isolating the one or more target peptide following synthesis. Methods for isolating proteins are well-known in the art.

In one aspect, the disclosure is drawn to one or more apparatus for peptide synthesis. In some embodiments, any one of the methods described herein may be performed on one or more apparatus.

FIG. 1 shows a schematic 400 of an illustrative apparatus 410 for biologically synthesizing peptides in which embodiments may be implemented. The apparatus 410 is optionally operable for extra-cellular and/or cell-free peptide synthesis. In some embodiments, the peptide synthesis is in vitro. The apparatus may optionally be, or include, one or more units including, but not limited to, one or more peptide synthesizer units 420, one or more sourcing units 432, one or more monitoring units 440, one or more controller units 422, one or more computing units 426, one or more tRNA charging units 428, and/or one or more nucleic acid synthesizer units 430. In some embodiments, one or more of the units may be internal or external to the apparatus.

In some embodiments, one or more apparatus 410 further includes one or more fluid flows. In some embodiments, the one or more fluid flows connect and/or allow the transfer of one or more peptide synthesis components among one or more of the optional one or more units of the apparatus 410. In some embodiments, the one or more fluid flows are operable to provide, co-localize, remove and/or separate, optionally sequentially, one or more peptide synthesis components. In some embodiments, the one or more fluid flows are operable to provide, co-localize, remove and/or separate, optionally sequentially, one or more peptide synthesis components at one or more identifiable time intervals.

Figure 2:
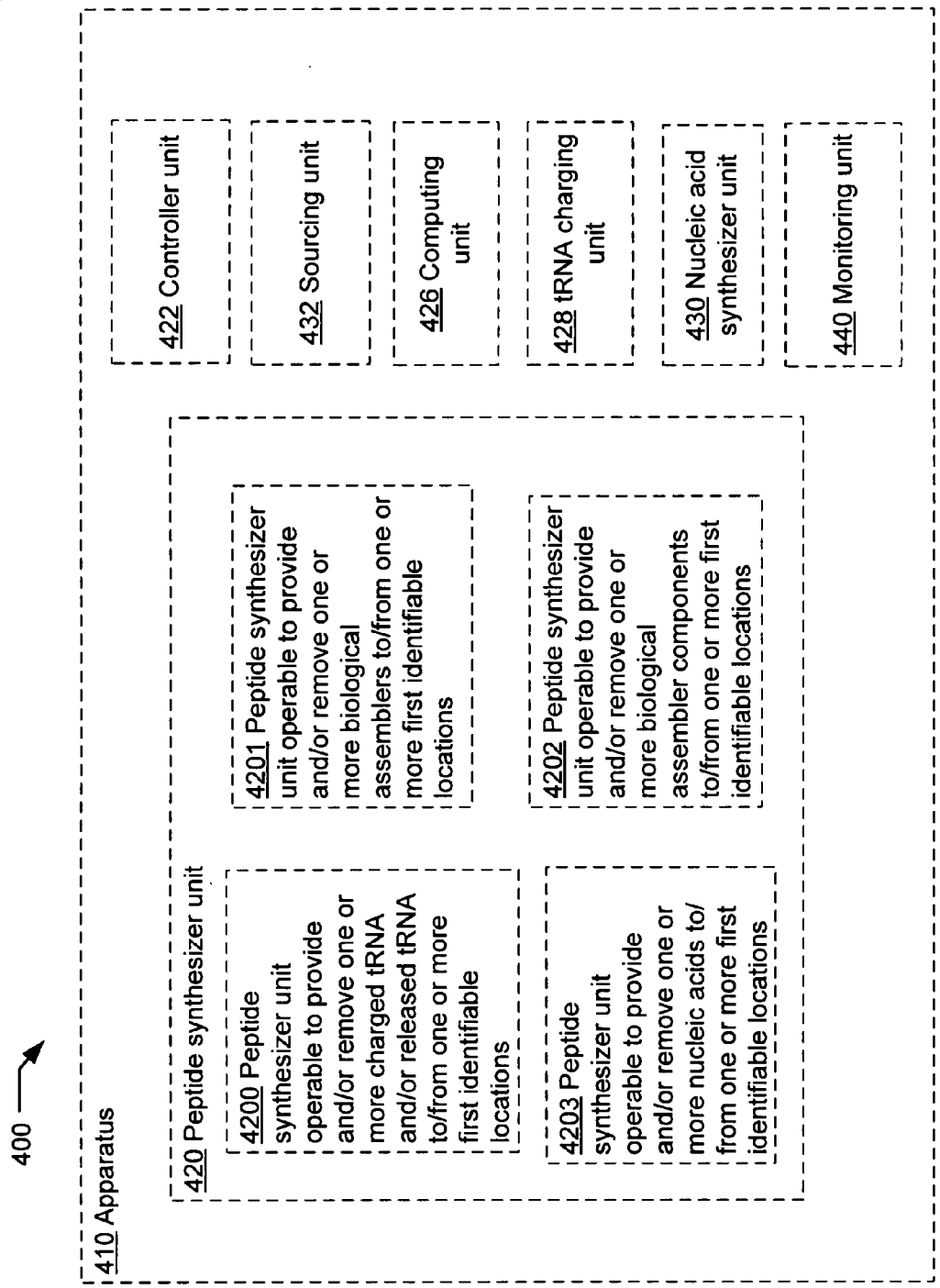
FIG. 2 shows schematics of illustrative embodiments of the apparatus of FIG. 1, with illustrative examples of a peptide synthesizer unit.

FIG. 2 shows a schematic 400 of illustrative embodiments of the optional apparatus 410 of FIG. 1, with specific illustrative embodiments of one or more peptide synthesizer units 420, including unit 4200, unit 4201, unit 4202, and unit 4203. In some embodiments, one or more peptide synthesizer units are operable to provide, optionally sequentially, one or more peptide synthesis components to one or more identifiable locations. In some embodiments, one or more peptide synthesizer units are operable to co-localize, optionally sequentially, one or more peptide synthesis components. In some embodiments, one or more peptide synthesizer units are operable to remove, optionally sequentially, one or more peptide synthesis components from one or more identifiable locations. In some embodiments, one or more peptide synthesizer units are operable to separate, optionally sequentially, one or more peptide synthesis components.

In some embodiments, the one or more peptide synthesizer units are operable to provide, co-localize, remove, and/or separate, optionally sequentially, one or more peptide synthesis components at one or more first identifiable locations, wherein the one or more identifiable locations include one more temporal-spatial locations. In some embodiments, one or more temporal-spatial locations are moving along predictable time or other sequential path. In some embodiments, the one or more identifiable locations are one location. In some embodiments, the one or more identifiable locations are external to the apparatus. In some embodiments, the one or more identifiable locations are internal to the apparatus, and/or one or more of the optional units within the apparatus. In some embodiments, each operable element may have a different identifiable location or one or more operable elements may have similar and/or identical identifiable locations.

In some embodiments, the one or more peptide synthesizer units are operable to provide, co-localize, remove, and/or separate, optionally sequentially, one or more peptide synthesis components at one or more identifiable time intervals. In some embodiments, the one or more first identifiable time intervals are at least partially based on a predicted rate of incorporation of two or more amino acids into one or more peptides, a predicted rate of activity of one or more biological assemblers, a predicted rate of translocation of one or more nucleic acids, and/or a predicted rate of release of tRNA. In some embodiments, the one or more first identifiable time intervals are from approximately 0.001 seconds to approximately 0.01 seconds, or are approximately 0.01 seconds, and/or other appropriate time intervals as described elsewhere. In some embodiments, each operable element may have a different identifiable time interval or one or more operable elements may have a similar and/or identical identifiable time interval.

In some embodiments, the one or more peptide synthesizer units include one or more fluid flows. The one or more fluid flows may be used to provide and/or co-localize components for peptide synthesis in one or more identifiable locations. The one or more fluid flows may be used to remove and/or separate components for peptide synthesis from the one or more identifiable locations. The one or more fluid flows may be used to transfer one or more charged tRNA, one or more biological assemblers, one or more biological assembler components, and/or one or more nucleic acids to and/or from one or more identifiable locations. In some embodiments, the one or more fluid flows are operable to transfer one or more peptide synthesis components to one or more identifiable locations at one or more identifiable time intervals.

In some embodiments, the one or more peptide synthesizer units are operable to optionally affix one or more peptide synthesis components, including but not limited to, one or more biological assemblers, one or more charged tRNA, one or more nucleic acids, and/or one or more biological assembler components. In some embodiments, one or more peptide synthesis components are affixed at one or more identifiable locations.

In some embodiments, one or more peptide synthesizer units are optionally operable to isolate one or more target peptides following partial complete synthesis.

In one aspect, the disclosure is drawn to one or more apparatus comprising one or more peptide synthesizer units that are operable to co-localize two or more charged tRNA with one or more biological assemblers at one or more first identifiable locations. Unit 4200 is optionally one or more peptide synthesizer units operable to provide and/or to remove one or more charged tRNA and/or released tRNA to and/or from one or more first identifiable locations. In some embodiments, one or more peptide synthesizer units are operable to sequentially provide two or more charged tRNA to one or more first identifiable locations. In some embodiments, one or more peptide synthesizer units are further operable to remove and/or separate, optionally sequentially, two or more charged tRNA and/or tRNA and/or other components from one or more first identifiable locations. In some embodiments, one or more peptide synthesizer units are operable to provide, optionally sequentially, two or more charged tRNA to one or more first identifiable locations, and to remove and/or separate, optionally sequentially, two or more charged tRNA and/or one or more tRNA from one or more first identifiable locations.

In some embodiments, the one or more peptide synthesizer units are operable to optionally sequentially provide two or more charged tRNA to one or more identifiable locations at one or more first identifiable time intervals. In some embodiments, the one or more peptide synthesizer units are further operable to optionally sequentially separate two or more charged tRNA from one or more identifiable locations at one or more second identifiable time intervals.

Unit 4201 is optionally one or more peptide synthesizer units operable to provide and/or to remove one or more biological assemblers to and/or from one or more identifiable locations. In some embodiments, one or more apparatus include one or more peptide synthesizer units that are operable to provide, optionally sequentially, one or more biological assemblers to one or more first identifiable locations. In some embodiments, one or more units are further operable to remove, optionally sequentially, one or more biological assemblers from one or more first identifiable locations.

In some embodiments, the one or more peptide synthesizer units are further operable to affix one or more biological assemblers at one or more first identifiable locations. In some embodiments, the one or more biological assemblers are affixed at one or more first identifiable locations.

In some embodiments, the one or more peptide synthesizer units are operable to co-localize, optionally sequentially, one or more biological assemblers with two or more charged tRNA, wherein at least two of the two or more charged tRNA are at one or more different locations. In some embodiments, one or more units are further operable to separate, optionally sequentially, the one or more biological assemblers from the two or more charged tRNA. In some embodiments, one or more apparatus include one or more peptide synthesizer units that are operable to co-localize, optionally sequentially, one or more biological assemblers and two or more charged tRNA, at one or more identifiable locations. In some embodiments, one or more units are further operable to separate, optionally sequentially, the one or more biological assemblers and the two or more charged tRNA.

In some embodiments, the one or more biological assemblers may be one or more peptide assemblers, one or more ribosome-based biological assemblers, and/or one or more non-ribosome-based biological assemblers. The one or more ribosome-based biological assemblers may be eukaryotic, mitochondrial and/or prokaryotic, among others.

Unit 4202 is optionally one or more peptide synthesizer units operable to provide and/or to remove one or more biological assembler components to and/or from one or more identifiable locations. In some embodiments, one or more apparatus include one or more peptide synthesizer units that are operable to provide, optionally sequentially, one or more biological assemblers components to one or more second identifiable locations. In some embodiments, one or more peptide synthesizer units are operable to remove, optionally sequentially, one or more biological assembler components from one or more second identifiable locations. The one or more second identifiable locations are optionally the same as, or optionally different from the first one or more identifiable locations.

The one or more biological assembler components, may be one or more peptide assembler components, one or more ribosome-based biological assembler components, and/or one or more non-ribosome-based biological assembler components. The one or more ribosome-based biological assembler components may be eukaryotic, mitochondrial and/or prokaryotic, among others.

Unit 4203 is optionally one or more peptide synthesizer units operable to provide and/or to remove one or more nucleic acids to and/or from one or more identifiable locations. In some embodiments, one or more apparatus include one or more peptide synthesizer units that are operable to provide, optionally sequentially, one or more nucleic acids to one or more first identifiable locations. In some embodiments, one or more apparatus includes one or more peptide synthesizer units that are operable to remove, optionally sequentially, one or more nucleic acids from one or more first identifiable locations. In some embodiments, one or more nucleic acids are one or more DNA, one of more cDNA, one or more RNA and/or one or more mRNA.

Figure 3:
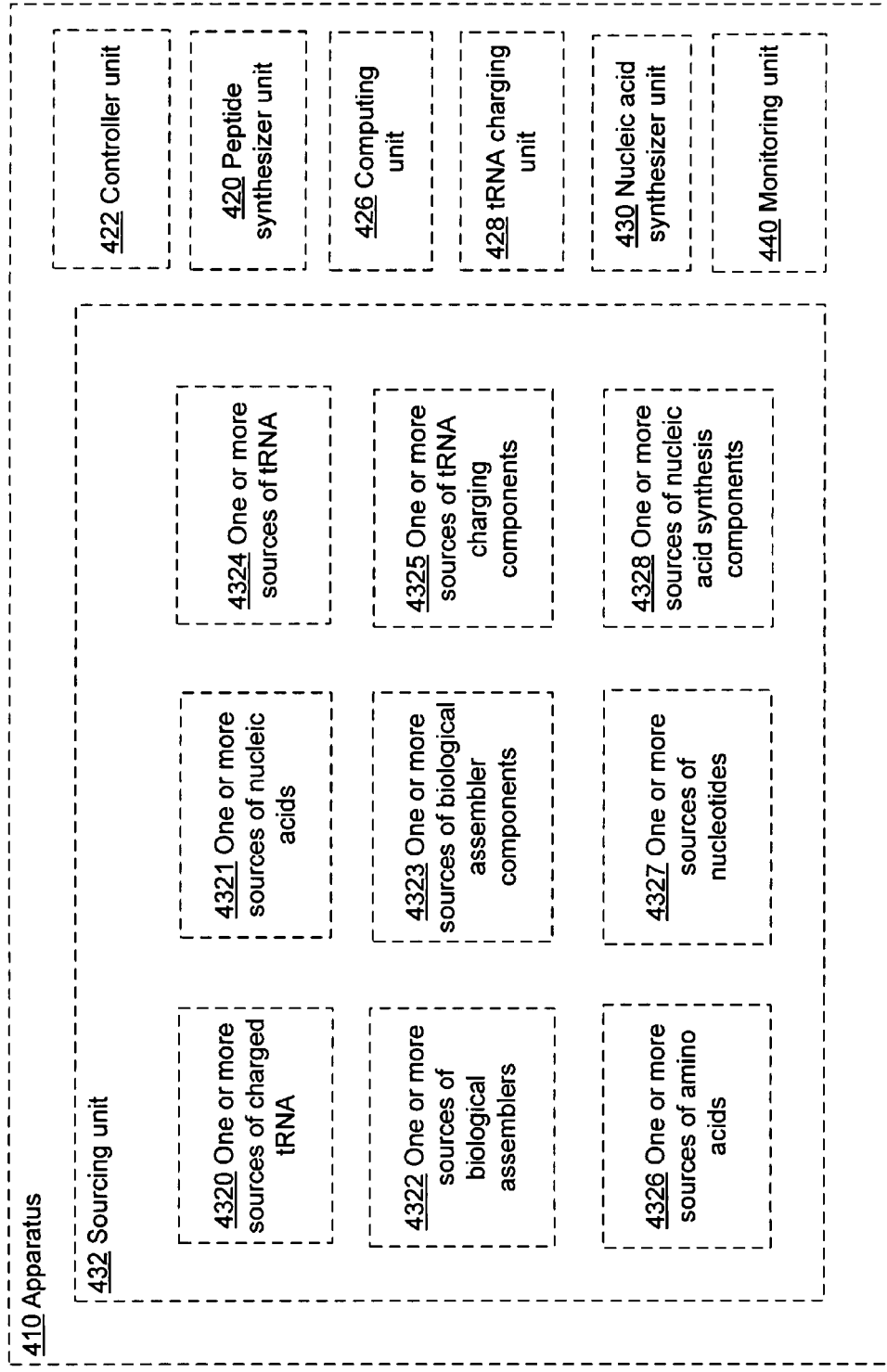
FIG. 3 shows schematics of illustrative embodiments of the apparatus of FIG. 1, with specific examples of a sourcing unit.

FIG. 3 shows a schematic 400 of illustrative embodiments of the apparatus 410 of FIG. 1, with specific illustrative embodiments of one or more sourcing units 432, including unit 4320, unit 4322, unit 4321, unit 4323, unit 4324, unit 4325, unit 4326, unit 4327, and/or unit 4328. In some embodiments, one or more sourcing units 432 optionally contain one or more peptide synthesis components. In some embodiments, one or more apparatus includes, but is not limited to, one or more peptide synthesizer units 420 and one or more sourcing units 432. In some embodiments, one or more of the one or more peptide synthesizer units 420 and one or more of the one or more sourcing units 432 are the same unit. In some embodiments, one or more sourcing units 432 include one or more fluid flows. In some embodiments, one or more sourcing units 432 are operable to provide/co-localize/remove/separate one or more peptide synthesis components from one or more identifiable locations.

In some embodiments, one or more sourcing units 432 are operable to provide/co-localize/remove/separate one or more peptide synthesis components from one or more identifiable locations at one or more identifiable time intervals. In some embodiments, the one or more identifiable time intervals are at least partially based on a predicted rate of incorporation of two or more amino acids into one or more peptides, a predicted rate of activity of one or more biological assemblers, a predicted rate of translocation of one or more nucleic acids, and/or a predicted rate of release of tRNA. In some embodiments, the one or more identifiable time intervals are from approximately 0.001 seconds to approximately 0.1 seconds and/or approximately 0.01 seconds, or other appropriate time interval.

In some embodiments, one or more sourcing units include one or more sources of charged tRNA 4320, one or more sources of biological assemblers 4322, one or more sources of biological assembler components 4323, one or more sources the nucleic acids 4321, one or more sources of DNA, one or more sources of cDNA, one or more sources of mRNA, one or more sources of RNA, one or more sources of tRNA 4324, one or more sources of amino acids 4326 one or more sources of nucleotides 4327, one or more sources of tRNA charging components 4325, and/or one or more sources of nucleic acid synthesis components 4328. In some embodiments, one or more sourcing units 432 include one or more of one or more sources of tRNA 4324 (including, but not limited to, natural, unnatural, and arbitrary tRNA), one or more sources of amino acids 4326 (including, but not limited to, natural, unnatural, and arbitrary amino acids), and/or one or more sources of tRNA charging components 4325 (including, but not limited to, natural, unnatural, and arbitrary).

Unit 4320 is optionally one or more sourcing units containing one or more sources of charged tRNA, and is optionally operable to provide and/or to remove one or more charged tRNA and/or released tRNA to and/or from one or more identifiable locations. In some embodiments, one or more apparatus includes one or more or two or more sources of charged tRNA 4320 optionally operable to provide two or more charged tRNA to one or more identifiable locations at one or more first identifiable time intervals, and/or to remove one or more charged tRNA and/or released tRNA from one or more identifiable locations at one or more second identifiable time intervals.

In some embodiments, one or more apparatus includes two or more sources of charged tRNA 4320, wherein one or more first source of the two or more sources of charged tRNA includes a supply of one or more first type of charged tRNA, and one or more second source of the two or more sources of charged tRNA includes one or more second type of charged tRNA. In some embodiments, the one or more first type of charged tRNA is different from, or the same as, the one or more second type of charged tRNA. In some embodiments, one or more apparatus further includes one or more third source of the two or more sources of charged tRNA that includes a supply of one or more third type of charged tRNA. In some embodiments, the one or more third type of charged tRNA is different from, or the same as, the one or more first type of charged tRNA and/or the one or more second type of charged tRNA. In some embodiments, the first type of charged tRNA includes one or more natural charged tRNA, one or more unnatural charged tRNA, and/or one or more arbitrary charged tRNA and the second type of charged tRNA includes one or more natural charged tRNA, one or more unnatural charged tRNA, and/or one or more arbitrary charged tRNA. In some embodiments, the two or more sources of charged tRNA include one or more fluid flows.

Unit 4322 is optionally one or more sourcing units containing one or more sources of biological assemblers, and is optionally operable to provide and/or to remove one or more biological assemblers to and/or from one or more identifiable locations. In some embodiments, one or more apparatus includes one or more sources of biological assemblers 4322 optionally operable to provide and/or to remove one or more biological assemblers to and/or from one or more identifiable locations at one or more third identifiable time intervals. In some embodiments, one or more apparatus includes one or more sources of biological assemblers 4322, wherein one or more first source of the one or more biological assemblers includes a supply of one or more first type of biological assemblers, and one or more second source of the one or more sources of biological assemblers includes one or more second type of biological assemblers. In some embodiments, the one or more first type of biological assemblers is different from, or the same as, the one or more second type of biological assemblers. In some embodiments, one or more apparatus further includes one or more third source of the one or more sources of biological assemblers that includes a supply of one or more third type of biological assemblers. In some embodiments, the one or more third type of biological assemblers is different from, or the same as, the one or more first type of biological assemblers and/or the one or more second type of biological assemblers. In some embodiments, the first type of biological assemblers is prokaryotic, and the second type of biological assemblers in eukaryotic. In some embodiments, the one or more sources of biological assemblers include one or more fluid flows.

Unit 4321 is optionally one or more sourcing units containing one or more sources of nucleic acids, and is optionally operable to provide and/or to remove one or more nucleic acids to and/or from one or more identifiable locations. In some embodiments, one or more apparatus includes one or more sources of nucleic acids 4321 optionally operable to provide and/or to remove one or more nucleic acids to and/or from one or more identifiable locations at one or more fourth identifiable time intervals. In some embodiments, one or more apparatus includes one or more sources of nucleic acids 4321, wherein one or more first source of the one or more nucleic acids includes a supply of one or more first type of nucleic acids, and one or more second source of the one or more sources of nucleic acids includes one or more second type of nucleic acids. In some embodiments, the one or more first type of nucleic acids is different from, or the same as, the one or more second type of nucleic acids. In some embodiments, one or more apparatus further includes one or more third source of the one or more sources of nucleic acids that includes a supply of one or more third type of nucleic acids. In some embodiments, the one or more third type of nucleic acids is different from, or the same as, the one or more first type of nucleic acids and/or the one or more second type of nucleic acids. In some embodiments, the first type of nucleic acids is DNA and the second type of nucleic acids is RNA. In some embodiments, the one or more sources of nucleic acids are one or more sources of RNA, one or more sources of mRNA, one or more sources of DNA, and/or one or more sources of cDNA. In some embodiments, the one or more sources of nucleic acids include one or more fluid flows. In some embodiments, the one or more third locations are included in the two or more first locations and/or are optionally the same as one or more second locations.

Unit 4323 is optionally one or more sourcing units containing one or more sources of biological assembler components, and is optionally operable to provide and/or to remove one or more biological assembler components to and/or from one or more identifiable locations. In some embodiments, one or more apparatus includes one or more sources of biological assembler components 4323, each source positioned to provide one or more biological assembler components to one or more fourth locations. In some embodiments, one or more of the one or more sources of biological assembler components includes one or more fluid flows. In some embodiments, the one or more fourth locations are one or more temporal-spatial locations and/or are moving along a predictable time or other sequential path. In some embodiments, the one or more fourth locations are optionally the same as the one or more sources of one or more biological assemblers and/or the one or more first locations. In some embodiments, the one or more sources of biological assembler components are positioned to provide the biological assembler components to one or more sources of one or more biological assemblers and/or the one or more first locations.

In some embodiments, one or more apparatus includes one or more sources of biological assembler components 4323, wherein one or more first source of the one or more biological assembler components includes a supply of one or more first type of biological assembler components, and one or more second source of the one or more sources of biological assembler components includes one or more second type of biological assembler components. In some embodiments, the one or more first type of biological assembler components is different from, or the same as, the one or more second type of biological assembler components. In some embodiments, one or more apparatus further includes one or more third source of the one or more sources of biological assembler components that includes a supply of one or more third type of biological assembler components. In some embodiments, the one or more third type of biological assembler components is different from, or the same as, the one or more first type of biological assembler components and/or the one or more second type of biological assembler components. In some embodiments, the one or more sources of biological assembler components include one or more fluid flows.

In some embodiments, one or more apparatus includes one or more sources of tRNA 4324, each source positioned to provide one or more tRNA to one or more second locations; one or more sources of amino acids 4326, each source positioned to provide one or more amino acids to the one or more second locations; and one or more sources of tRNA charging components 4325, each source positioned to provide one or more tRNA charging components to the one or more second locations. In some embodiments, one or more of the one or more sources of tRNA, the one or more sources of amino acids, and/or the one or more sources of tRNA charging components include one or more fluid flows. In some embodiments, the one or more second locations are one or more temporal-spatial locations and/or the one or more temporal-spatial locations are moving along a predictable time or other sequential path. In some embodiments, the one or more second locations are positioned to provide charged tRNA to the two or more sources of charged tRNA. In some embodiments, the one or more second locations are one or more sources of charged tRNA.

Unit 4324 is optionally one or more sourcing units containing one or more sources of tRNA, and is optionally operable to provide and/or to remove one or more tRNA to and/or from one or more identifiable locations. In some embodiments, one or more first source of the one or more sources of tRNA includes a supply of one or more first type of tRNA and one or more second source of the one or more sources of tRNA includes a supply of one or more second type of tRNA. In some embodiments, the one or more first type of tRNA is different from, or the same as, the one or more second type of tRNA. In some embodiments, the one or more first type of tRNA includes one or more natural tRNA, and the one or more second type of tRNA includes one or more unnatural tRNA.

Unit 4326 is optionally one or more sourcing units containing one or more sources of amino acids, and is optionally operable to provide and/or to remove one or more amino acids to and/or from one or more identifiable locations. In some embodiments, one or more first source of the one or more sources of amino acids includes a supply of one or more first type of amino acids and one or more second source of the one or more sources of amino acids includes a supply of one or more second type of amino acids. In some embodiments, the one or more first type of amino acids is different from, or the same as, the one or more second type of amino acids. In some embodiments, the one or more first type of amino acids includes one or more natural amino acids, and the one or more second type of amino acids includes one or more unnatural amino acids.

Unit 4325 is optionally one or more sourcing units containing one or more sources of tRNA charging components, and is optionally operable to provide and/or to remove one or more tRNA charging components to and/or from one or more identifiable locations. In some embodiments, one or more first source of the one or more sources of tRNA charging components includes a supply of one or more first type of tRNA charging components, and one or more second source of the one or more sources of tRNA charging components includes a supply of one or more second type of tRNA charging components. In some embodiments, the one or more first type of tRNA charging components is different from, or the same as, the one or more second type of tRNA charging components. In some embodiments, the one or more first type of tRNA charging components include one or more tRNA synthetases, and the one or more second type of tRNA charging components includes one or more non-natural tRNA charging components. In some embodiments, the first type of tRNA charging components include one or more prokaryotic tRNA synthetases, and the second type of tRNA charging components include one or more eukaryotic tRNA synthetases.

Unit 4327 is optionally one or more sourcing units containing one or more sources of nucleotides, and is optionally operable to provide and/or to remove one or more nucleotides to and/or from one or more identifiable locations. Unit 4328 is optionally one or more sourcing units containing one or more sources of nucleic acid synthesis components, and is optionally operable to provide and/or to remove one or more nucleic acid synthesis components to and/or from one or more identifiable locations. In some embodiments, one or more apparatus includes one or more sources of nucleotides 4327, each source positioned to provide one or more nucleotides to one or more third locations, and one or more sources of nucleic acid synthesis components 4328, each source positioned to provide one or more nucleic acid synthesis components to the one or more third locations. In some embodiments, one or more of the one or more sources of nucleotides, each source positioned to provide one or more nucleotides to one or more third locations, and one or more sources of nucleic acid synthesis components, each source positioned to provide one or more nucleic acid synthesis components to the one or more third locations include fluid flows. In some embodiments, the one or more third locations is one or more temporal-spatial locations and/or the one or more temporal-spatial locations are moving along a predictable time or other sequential path. In some embodiments, the one or more third locations are positioned to provide nucleic acids to one or more sources of nucleic acids. In some embodiments, the one or more third locations are one or more sources of nucleic acids 4321.

In one aspect, the disclosure is drawn to one or more apparatus comprising two or more sources of charged tRNA, each source positioned to sequentially provide one or more charged tRNA to one or more first locations. In some embodiments, one or more apparatus includes two or more sources of charged tRNA 4320, each source positioned to sequentially provide one or more charged tRNA to one or more first locations, and optionally to remove one or more charged tRNA and/or one or more tRNA from one or more first locations. In some embodiments, one or more apparatus includes two or more sources of charged tRNA 4320, each source positioned to sequentially provide one or more charged tRNA to one or more first locations containing one or more biological assemblers, and optionally to remove one or more charged tRNA and/or one or more tRNA from one or more first locations containing one or more biological assemblers.

In some embodiments, one or more apparatus includes two or more sources of charged tRNA 4320, each source positioned to sequentially provide one or more charged tRNA to one or more first locations and optionally to remove one or more charged tRNA and/or one or more tRNA from one or more first locations; and one or more sources of biological assemblers 4322. In some embodiments, one or more apparatus includes two or more sources of charged tRNA 4320, each source positioned to sequentially provide one or more charged tRNA to one or more first locations and optionally to remove one or more charged tRNA and/or one or more tRNA from one or more first locations; and one or more sources of biological assemblers 4322, each source positioned to provide, and optionally to remove, one or more biological assemblers to/from the one or more first locations. In some embodiments, the one or more biological assemblers are affixed.

In some embodiments, one or more apparatus includes two or more sources of charged tRNA 4320, each source positioned to sequentially provide one or more charged tRNA to one or more first locations at one or more first identifiable time intervals, and optionally to remove one or more charged tRNA and/or one or more tRNA from one or more first locations at one or more second identifiable time intervals. In some embodiments, one or more apparatus includes two or more sources of charged tRNA 4320, each source positioned to sequentially co-localize one or more charged tRNA with one or more first locations containing one or more biological assemblers at one or more first identifiable time intervals, and optionally to remove and/or separate one or more charged tRNA and/or one or more tRNA from one or more first locations containing one or more biological assemblers at one or more second identifiable time intervals.

In some embodiments, one or more apparatus includes two or more sources of charged tRNA 4320, each source positioned to sequentially provide one or more charged tRNA to one or more first locations at one or more first identifiable time intervals, and optionally to remove one or more charged tRNA and/or one or more tRNA from one or more first locations at one or more second identifiable time intervals; and one or more sources of biological assemblers 4322. In some embodiments, one or more apparatus includes two or more sources of charged tRNA 4320, each source positioned to sequentially provide one or more charged tRNA to one or more first locations at one or more first identifiable time intervals, and optionally to remove one or more charged tRNA and/or one or more tRNA from one or more first locations at one or more second identifiable time intervals; and one or more sources of biological assemblers 4322, each source positioned to provide, and optionally to remove, one or more biological assemblers to/from the one or more first locations at one or more third identifiable time intervals. In some embodiments, the one or more biological assemblers are affixed.

In some embodiments, one or more apparatus includes two or more sources of charged tRNA, each source further positioned to provide, optionally sequentially, two or more charged tRNA to one or more first locations, and further includes one or more fluid flows. In some embodiments, the one or more fluid flows provide, optionally sequentially, the two or more charged tRNA to the one or more locations, and optionally remove, optionally sequentially, one or more charged tRNA and/or one or more tRNA from the one or more first locations. In some embodiments, the one or more fluid flows provide, optionally sequentially, the one or more biological assemblers to the one or more locations, and optionally remove, optionally sequentially, the one or more biological assemblers from the one or more first locations.

In one aspect, the disclosure is drawn to one or more apparatus comprising two or more sources of charged tRNA; and one or more sources of biological assemblers, each source positioned to sequentially provide one or more biological assemblers to two or more first locations, and to optionally remove, optionally sequentially, the one or more biological assemblers from the two or more first locations. In some embodiments, one or more apparatus includes two or more sources of charged tRNA 4320, each source positioned to provide, optionally sequentially, one or more charged tRNA to one or more second locations, and optionally to remove, optionally sequentially, one or more charged tRNA and/or one or more tRNA from one or more second locations; and one or more sources of biological assemblers 4322, each source positioned to sequentially provide one or more biological assemblers to two or more first locations and optionally to remove, optionally sequentially, the one or more biological assemblers from the two or more first locations. In some embodiments, one or more apparatus includes two or more sources of charged tRNA 4320, each source positioned to affix, optionally sequentially, one or more charged tRNA at one or more second locations. In some embodiments, one or more of the two or more charged tRNA are affixed optionally at the one or more second locations.

In some embodiments, one or more apparatus includes one or more sources of biological assemblers 4322 and/or two or more sources of charged tRNA 4320 each including one or more fluid flows. In some embodiments, one or more apparatus further includes one or more fluid flows, wherein one or more of the one or more fluid flows optionally sequentially provides the one or more biological assemblers to each of the two or more first locations and optionally sequentially removes the one or more biological assemblers from each of the two or more first locations. In some embodiments, one or more apparatus further includes one or more fluid flows, wherein one or more of the one or more fluid flows optionally sequentially provides the one or more charged tRNA to each of the two or more second locations and optionally sequentially removes the one or more charged tRNA and/or tRNA from each of the two or more second locations.

In some embodiments, one or more apparatus includes two or more sources of charged tRNA; and one or more sources of biological assemblers, each source positioned to sequentially provide one or more biological assemblers to two or more first locations at one or more first identifiable time intervals, and to optionally remove, optionally sequentially, the one or more biological assemblers from the two or more first locations at one or more second identifiable time intervals. In some embodiments, one or more apparatus further include two or more sources of charged tRNA 4320, each source positioned to provide one or more charged tRNA to one or more second locations at one or more third identifiable time intervals, and optionally to remove one or more charged tRNA from one or more second locations at one or more fourth identifiable time intervals.

In some embodiments, the first locations and/or second locations are one or more temporal-spatial locations and/or are moving along a predictable time or other sequential path. In some embodiments, the two or more first locations are the two or more sources of charged tRNA. In some embodiments, one or more of the one or more second locations are one or more of the one or more first locations.

Figure 4:
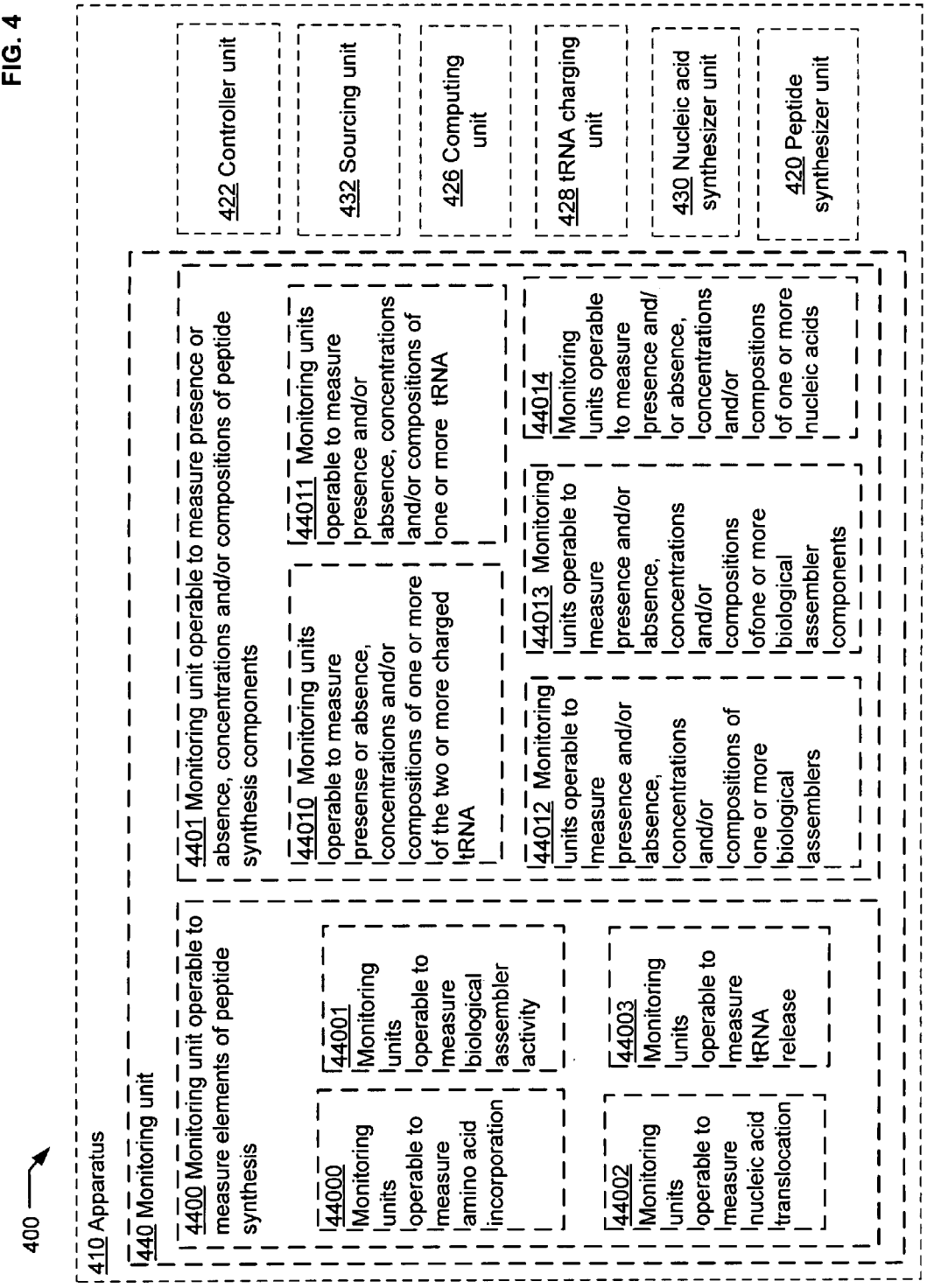
FIG. 4 shows schematics of illustrative embodiments of the apparatus of FIG. 1, with illustrative examples of a monitoring unit.

FIG. 4 shows a schematic 400 of illustrative embodiments of the apparatus 410 of FIG. 1, with specific illustrative embodiments of one or more monitoring units 440, including unit 4400 and unit 4401. In some embodiments, one or more apparatus includes, but is not limited to, one or more peptide synthesizer units 420 and one or more monitoring units 440. In some embodiments, the one or more peptide synthesizer units 420 and the one or more monitoring units 440 are the same one or more units. In some embodiments, one or more apparatus includes, but is not limited to one or more peptide synthesizer units 420, one or more sourcing units 432, and one or more monitoring units 440. In some embodiments, the one or more peptide synthesizer units 420, one or more sourcing units 432, and the one or more monitoring units 440 are the same unit.

Unit 4400 is optionally one or more monitoring units operable to measure one or more elements of peptide synthesis. Specific illustrative embodiments of unit 4400, include but are not limited to, one or more monitoring units operable to measure amino acid incorporation 44000, one or more monitoring units operable to measure biological assembler activity 44001, one or more monitoring units operable to measure nucleic acid translocation 44002, and/or one or more monitoring units operable to measure tRNA release 44003.

Unit 4401 is optionally one or more monitoring units, operable to measure presence and/or absence, concentration, and/or composition of one or more peptide synthesis components. Specific illustrative embodiments of unit 4401 include, but are not limited to, unit 44010, unit 44011, unit 44012, unit 44013, and/or 44014. Unit 44010 is optionally one or more monitoring units operable to measure presence and/or absence, concentration, and/or composition of one or more of the two or more charged tRNA. Unit 44011 is optionally one or more monitoring units operable to measure presence and/or absence, concentration, and/or composition of one or more tRNA. Unit 44012 is optionally one or more monitoring units operable to measure presence and/or absence, concentration, and/or composition of one or more biological assemblers. Unit 44013 is optionally one or more monitoring units operable to measure presence and/or absence, concentration, and/or composition of one or more biological assembler components. Unit 44014 is optionally one or more monitoring units operable to measure presence and/or absence, concentration, and/or composition of one or more nucleic acids.

Figure 5:
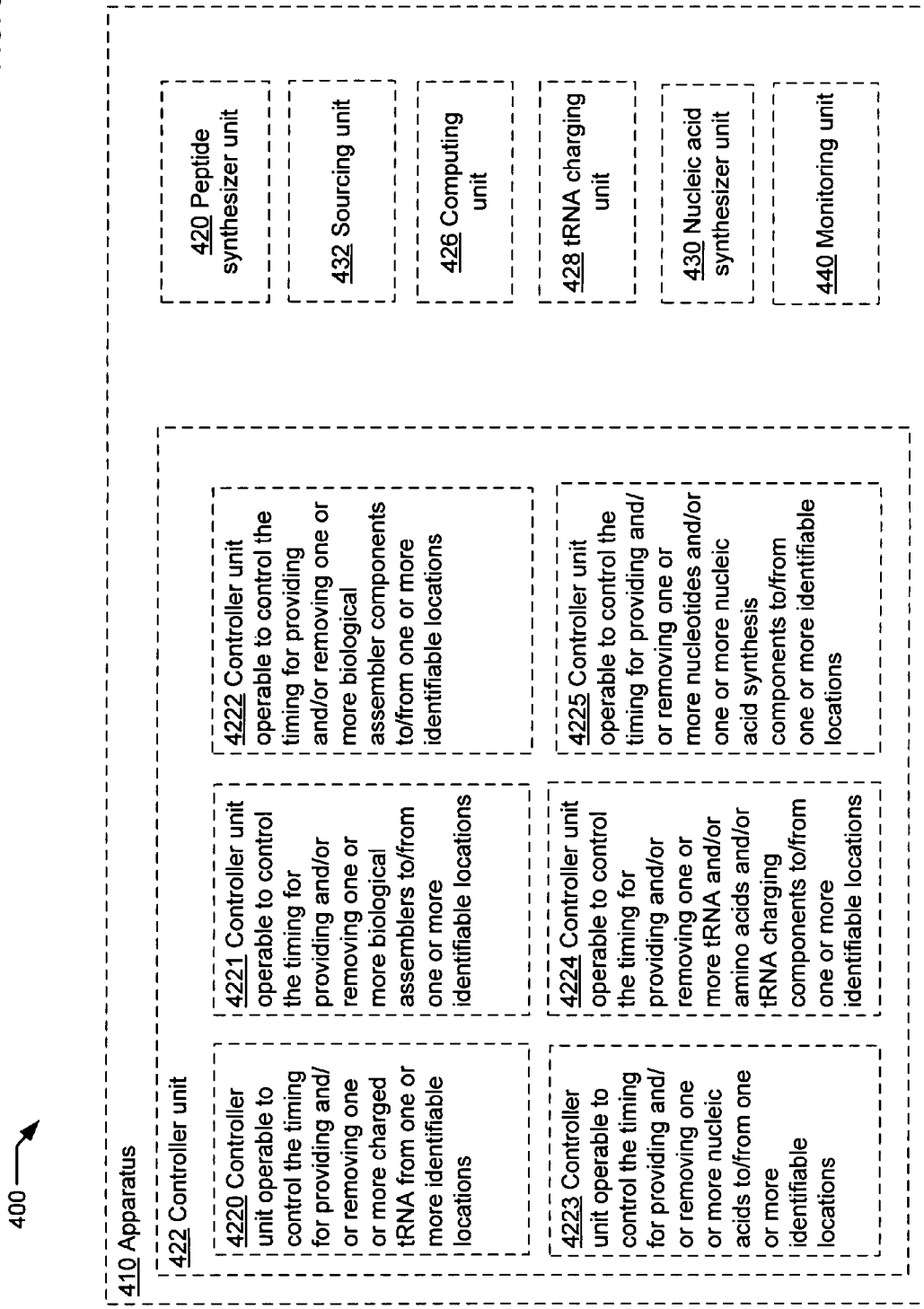
FIG. 5 shows schematics of illustrative embodiments of the apparatus of FIG. 1, with illustrative examples of a controller unit.

FIG. 5 shows a schematic 400 of illustrative embodiments of the apparatus 410 of FIG. 1, with specific illustrative embodiments of one or more controller units 422, including unit 4220, unit 4221, unit 4222, unit 4223, unit 4224, and unit 4225, wherein one or more of these units are optionally the same unit. In some embodiments, one or more apparatus includes, but is not limited to, one or more peptide synthesizer units 420 and one or more controller units 422. In some embodiments, the one or more peptide synthesizer units 420 and the one or more controller units 422 are the same one or more units. In some embodiments, one or more apparatus includes, but is not limited to one or more peptide synthesizer units 420, one or more sourcing units 432, one or more controller units 422 and one or more monitoring units 440. In some embodiments, the one or more peptide synthesizer units 420, one or more sourcing units 432, the one or more controller units 422 and the one or more monitoring units 440 are the same unit. In some embodiments, the one or more controller units 422 control the activity of the one or more units of one or more apparatus 410.

In some embodiments, one or more controller units 422 are operable to control the timing and/or the order for providing and/or co-localizing one or more peptide synthesis components at one or more identifiable locations, and optionally further operable to control the timing and/or the order for removing and/or separating one or more peptide synthesis components from one or more identifiable locations. The one or more peptide synthesis components include, but are not limited to, one or more charged tRNA, one or more tRNA, one or more biological assemblers, one or more biological assembler components, one or more nucleic acids and/or one or more nucleic acid synthesizing components.

In some embodiments, one or more controller units 422 are further operable to control an order and/or timing for providing and/or co-localizing one or more charged tRNA assembly components at one or more identifiable locations, and optionally further operable to control the timing and/or the order for removing and/or separating one or more charged tRNA assembly components from one or more identifiable locations. The one or more charged tRNA assembly components include, but are not limited to, one or more tRNA, one or more amino acids, and/or one or more tRNA charging components.

In some embodiments, one or more controller units 422 are further operable to control an order and/or timing for providing and/or co-localizing one or more nucleic acid assembly components at one or more identifiable locations, and optionally further operable to control the timing and/or the order for removing and/or separating one or more nucleic acid assembly components from one or more identifiable locations. The one or more nucleic acid assembly components include, but are not limited to, one or more nucleotides, and/or one or more nucleic acid synthesis components.

In some embodiments, the timing is at least partially based on the mechanism of peptide synthesis performed by the apparatus. Mechanisms of peptide synthesis include, but are not limited to, charged tRNA being provided sequentially to one or more locations, charged tRNA being provided sequentially to affixed biological assemblers; biological assemblers being provided sequentially to affixed charged tRNA; and/or biological assemblers and charged tRNA being co-localized at one or more locations. Depending on the mechanism of peptide synthesis, the timing related to providing/removing charged tRNA and/or the timing related to providing/removing biological assemblers, for example, optionally changes. Timing for each element may be different, and may change depending on the mechanism of synthesis and/or the biological synthesis components.

In some embodiments, the timing includes, but is not limited to, sequential timing, fixed timing, variable timing, predicted timing, and data-driven timing. In some embodiments, the timing is one or more identifiable time intervals. In some embodiments, the one or more identifiable time intervals are from approximately 0.001 seconds to 0.1 seconds and/or approximately 0.01 seconds, or other appropriate time intervals described elsewhere.

In some embodiments, the order and/or the timing for providing, co-localizing, removing and/or separating one or more peptide synthesis components is at least partially based on a target peptide sequence and/or a nucleic acid protein coding sequence. In some embodiments, the order and/or the timing for providing, co-localizing, removing and/or separating one or more peptide synthesis components is at least partially based on a predicted rate of incorporation of two or more amino acids into one or more peptides, a predicted rate of activity of one or more biological assemblers, a predicted rate of translocation of one or more nucleic acids, and/or a predicted rate of release of tRNA.

In some embodiments, one or more controller units is operable to control the order and/or the timing for providing, co-localizing, removing and/or separating one or more peptide synthesis components at least partially based on monitoring of amino acid incorporation into one or more peptides, biological assembler activity, nucleic acid translocation, and/or tRNA release. In some embodiments, one or more monitoring units 440 are operable to perform the monitoring of amino acid incorporation into one or more peptides, biological assembler activity, nucleic acid translocation, and/or tRNA release. In some embodiments, one or more of the one or more monitoring units 440 and one or more of the one or more controller units 422 are the same units.

In some embodiments, one or more controller units 422 is operable to control the order and/or the timing for providing, co-localizing, removing and/or separating one or more peptide synthesis components at least partially based on measurements including, but not limited to, availability of one or more nucleic acid codons, concentrations of one or more of the two or more charged tRNA or the one or more tRNA, presence or absence of one or more of the two or more charged tRNA or the one or more tRNA, or presence or absence of one or more anti-codons on one or more of the two or more charged tRNA or the one or more tRNA. In some embodiments, one or more of these measurements is at least partially determined extrinsically. In some embodiments, one or more of these measurements are determined based at least partially on measurements by one or more monitoring units 440. In some embodiments, one or more of these measurements are provided in real time.

In illustrative embodiments, one or more controller units are operable to provide (and optionally to remove) two or more charged tRNA in a sequence at one or more identifiable time intervals to one or more biological assemblers at one or more identifiable locations, and are further operable to co-localize (and optionally to remove) at one or more identifiable time intervals the one or more biological assemblers at the one or more identifiable locations. The one or more identifiable time intervals are optionally different for the co-localization of the two or more charged tRNA, the co-localization of one or more biological assemblers, the removal of one or more charged tRNA and/or one or more tRNA, and/or the removal of one or more biological assemblers.

In illustrative embodiments, one or more controller units are operable to co-localize (and optionally to separate) one or more biological receptors with two or more charged tRNA in a sequence at one or more identifiable time intervals, wherein at least two of the two or more charged tRNA are at one or more different locations. The one or more identifiable time intervals are optionally different for the co-localization of the one or more biological assemblers with the two or more charged tRNA, the separation of the one or more biological assemblers from the two or more charged tRNA, the co-localization of the two or more charged tRNA at the one or more different locations and/or the removal of the two or more charged tRNA from the one or more different locations.

In illustrative embodiments, one or more controller units are operable to co-localize (and optionally to separate) two or more charged tRNA and one or more biological assemblers in a sequence at one or more identifiable locations and at one or more identifiable time intervals. The one or more identifiable time intervals are optionally different for the co-localization of two or more charged tRNA, the co-localization of one or more biological assemblers, the removal of one or more charged tRNA and/or one or more tRNA, and/or the removal of one or more biological assemblers.

Unit 4220 is optionally one or more controller units, operable to control the timing and/or order for providing and/or removing one or more or two or more charged tRNA and/or released tRNA to and/or from one or more identifiable locations. In some embodiments, one or more apparatus include, but are not limited to, one or more peptide synthesizer units and one or more controller units that are operable to control the timing for providing and optionally for removing one or more charged tRNA and/or one or more tRNA. In some embodiments, one or more of the one or more peptide synthesizer units and one or more of the one or more charged tRNA controller units are the same unit.

In some embodiments, one or more controller units are operable to control the timing and/or the order for providing, optionally sequentially, two or more charged tRNA to one or more first identifiable locations, and optionally further operable to control the timing and/or the order for removing, optionally sequentially, two or more charged tRNA and/or one or more tRNA from one or more first identifiable locations. In some embodiments, one or more controller units are operable to control the timing and/or order for sequentially co-localizing two or more charged tRNA with one or more biological assemblers, and optionally sequentially removing two or more charged tRNA and/or one or more tRNA from the one or more biological assemblers. In some embodiments, one or more controller units are operable to control the timing and/or order for sequentially co-localizing two or more charged tRNA and one or more biological assemblers, and optionally sequentially separating the two or more charged tRNA and/or one or more tRNA and the one or more biological assemblers.

Unit 4221 is optionally one or more controller units, operable to control the timing and/or order for providing and/or removing, optionally sequentially, one or more biological assemblers to and/or from one or more identifiable locations. In some embodiments, one or more apparatus include, but are not limited to, one or more peptide synthesizer units and one or more controller units that are operable to control the timing for providing and optionally for removing one or more biological assemblers. In some embodiments, one or more of the one or more peptide synthesizer units and one or more of the one or more biological assembler controller units are the same unit.

In some embodiments, one or more controller units are operable to control the timing and/or order for, optionally sequentially, co-localizing one or more biological assemblers, and optionally further operable to control the timing and/or order for, optionally sequentially, removing the one or more biological assemblers following peptide synthesis. In some embodiments, one or more controller units are operable to control the timing and/or order for, optionally sequentially, co-localizing one or more biological assemblers with two or more charged tRNA, wherein at least two of the two or more charged tRNA are at one or more different locations, and optionally further operable to control the timing and/or order for, optionally sequentially, separating the one or more biological assemblers from the two or more charged tRNA and/or one or more tRNA. In some embodiments, one or more controller units are operable to control the timing and/or order for, optionally sequentially, co-localizing one or more biological assemblers and two or more charged tRNA, and optionally further operable to control the timing and/or order for, optionally sequentially, separating the one or more biological assemblers and the two or more charged tRNA and/or one or more tRNA.

Unit 4222 is optionally one or more controller units, operable to control the timing for providing and/or removing one or more biological assembler components to and/or from one or more identifiable locations. In some embodiments, one or more apparatus includes one or more controller units to control an order and/or timing in which each source provides one or more biological assembler components to one or more fourth locations. In some embodiments, one or more apparatus include, but are not limited to, one or more peptide synthesizer units and one or more controller units that are operable to control the timing for providing and optionally for removing one or more biological assembler components. In some embodiments, one or more of the one or more peptide synthesizer units and one or more of the one or more biological assembler components controller units are the same unit.

In some embodiments, one or more controller units are operable to control the timing and/or order for providing, optionally sequentially, one or more biological assembler components, and optionally further operable to control the timing and/or order for removing one or more biological assembler components. In some embodiments, one or more controller units are operable to control the timing and/or order for, optionally sequentially, co-localizing one or more biological assembler components with two or more charged tRNA, wherein at least two of the two or more charged tRNA are at one or more different locations, and optionally further operable to control the timing and/or order for, optionally sequentially, separating the one or more biological assembler components from the two or more charged tRNA and/or one or more tRNA. In some embodiments, one or more controller units are operable to control the timing and/or order for, optionally sequentially, co-localizing one or more biological assembler components and two or more charged tRNA, and optionally further operable to control the timing and/or order for, optionally sequentially, separating the one or more biological assembler components and the two or more charged tRNA and/or one or more tRNA.

Unit 4223 is optionally one or more controller units, operable to control the timing and/or the order for providing and/or removing one or more nucleic acids to and/or from one or more identifiable locations. In some embodiments, one or more apparatus include, but are not limited to, one or more peptide synthesizer units and one or more controller units that are operable to control the timing for providing and optionally for removing one or more nucleic acids. In some embodiments, one or more of the one or more peptide synthesizer units and one or more of the one or more biological assembler components controller units are the same unit.

In some embodiments, one or more controller units are operable to control the timing and/or the order for co-localizing, optionally sequentially, one or more nucleic acids, and optionally further operable to control the timing and/or the order for removing, optionally sequentially, one or more nucleic acids. In some embodiments, one or more apparatus includes one or more controller units operable to control an order and/or timing in which each source optionally provides, optionally sequentially, one or more nucleic acids to one or more third locations, and/or optionally removes, optionally sequentially, one or more nucleic acids from one or more third locations. In some embodiments, one or more controller units are operable to control the timing and/or the order for providing and optionally for removing one or more DNA, one or more cDNA, one or more RNA, and/or one or more mRNA. In some embodiments, the one or more nucleic acids are provided to one or more identifiable locations and/or to one or more biological assemblers, or one or more biological assembler components.

Unit 4224 is optionally one or more controller units, operable to control the timing for providing and/or removing one or more tRNA, one or more amino acids, and/or one or more tRNA charging components to and/or from one or more identifiable locations. In some embodiments, one or more apparatus include, but are not limited to, one or more peptide synthesizer units and one or more controller units that are operable to control the timing for providing and optionally for removing one or more tRNA, one or more amino acids, and/or one or more tRNA charging components. In some embodiments, the one or more peptide synthesizer units and the one or more tRNA charging in controller units are the same unit. In some embodiments, one or more controller units are operable to control timing and/or order for charging one or more tRNA. In some embodiments, one or more controller units 422 include one or more first controller units 4224 operable to control one or more of an order or timing in which each source provides one or more tRNA to one or more second locations; one or more second controller units operable to control one or more of the order or the timing in which each source provides one or more amino acids to the one or more second locations; and one or more third controller units operable to control one or more of the order or the timing in which each source provides one or more tRNA charging components to the one or more second locations; and wherein one or more of the one or more first controller units are optionally the same as one or more of the one or more second controller units, and optionally the same as one or more of the one or more third controller units.

Unit 4225 is optionally one or more controller units, operable to control the timing and/or the order for providing and/or removing one or more nucleotides and/or one or more nucleic acid synthesis components to and/or from one or more identifiable locations. In some embodiments, one or more apparatus include, but are not limited to, one or more peptide synthesizer units and one or more controller units that are operable to control the timing and or the order for providing and optionally for removing one or more nucleotides and/or one or more nucleic acid synthesis components. In some embodiments, the one or more peptide synthesizer units and the one or more nucleic acid synthesis controller units are the same unit. In some embodiments, one or more controller units are operable to control the timing and/or the order for synthesizing one or more DNA, one or more cDNA, one or more RNA, and/or one or more mRNA. In some embodiments, one or more apparatus include one or more first controller units to control one or more of an order or timing in which each source provides one or more nucleotides to the one or more third locations; and one or more second controller units to control one more of the order or the timing in which each source provides one or more nucleic acid synthesis components to the one or more third locations; wherein the one or more first controller units are optionally the same as the one or more second controller units.

Figure 6:
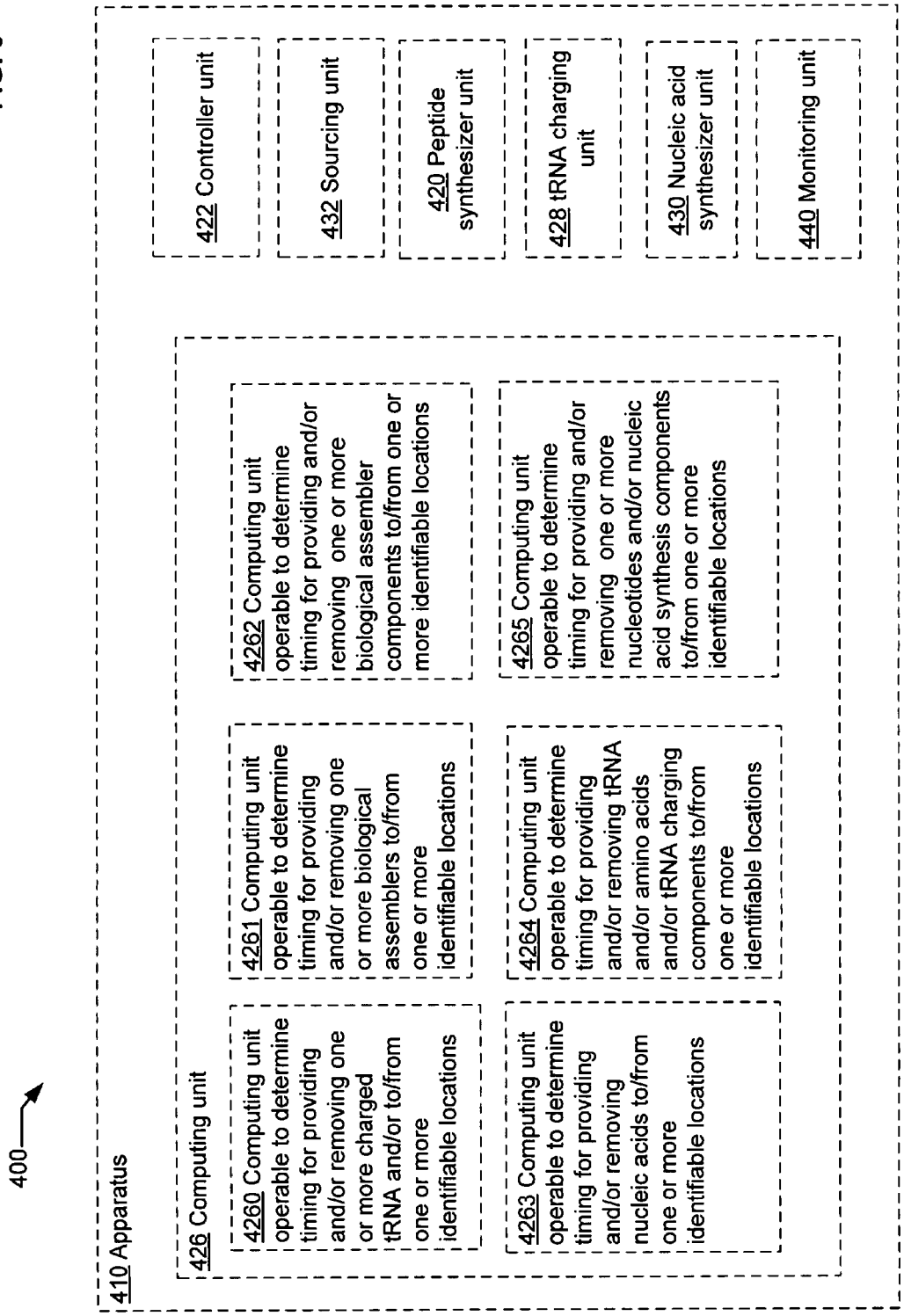
FIG. 6 shows schematics of illustrative embodiments of the apparatus of FIG. 1, with illustrative examples of a computing unit.

FIG. 6 shows a schematic 400 of illustrative embodiments of the apparatus 410 of FIG. 1, with specific illustrative embodiments of one or more computing units 426, including unit 4260, unit 4261, unit 4262, unit 4263, unit 4264, and unit 4265, wherein one or more of these units are optionally the same unit. In some embodiments, one or more apparatus include, but are not limited to, one or more peptide synthesizer units 420 and one or more computing units 426. In some embodiments, the one or more peptide synthesizer units 420 and the one or more computing units 426 are the same one or more units. In some embodiments, one or more apparatus optionally further includes, but is not limited to, one or more controller units 422, one or more sourcing units 432, and one or more monitoring units 440. In some embodiments, the one or more peptide synthesizer units 420, the one or more sourcing units 432, the one or more controller units 422, the one or more computing units 426, and the one or more monitoring units 440 are the same unit. In some embodiments one or more of the one or more controller units are optionally the same as one or more of the one or more computing units.

In some embodiments, one or more computing units 426 are operable to determine the timing and/or the order for providing and/or co-localizing one or more peptide synthesis components at one or more identifiable locations, and optionally further operable to determine the timing and/or the order for removing and/or separating one or more peptide synthesis components from one or more identifiable locations. The one or more peptide synthesis components include, but are not limited to, one or more charged tRNA, one or more tRNA, one or more biological assemblers, one or more biological assembler components, one or more nucleic acids, and/or nucleic acid synthesizing components.

In some embodiments, the timing is at least partially based on the mechanism of peptide synthesis performed by the apparatus. Mechanisms of peptide synthesis include, but are not limited to, charged tRNA being provided sequentially to one or more locations, charged tRNA being provided sequentially to affixed biological assemblers; biological assemblers being provided sequentially to affixed charged tRNA; and/or biological assemblers and charged tRNA being co-localized at one or more locations. Depending on the mechanism of peptide synthesis, the timing related to providing/removing charged tRNA and/or the timing related to providing/removing biological assemblers, for example, optionally changes. Timing for each element may be different, and may change depending on the mechanism of synthesis.

In some embodiments, the timing includes, but is not limited to, sequential timing, fixed timing, variable timing, predicted timing, and data-driven timing. In some embodiments, the timing is one or more identifiable time intervals. In some embodiments, the one or more identifiable time intervals are from approximately 0.001 seconds to 0.1 seconds and/or approximately 0.01 seconds, or other appropriate time intervals described elsewhere.

In some embodiments, the order and/or the timing for providing, co-localizing, removing and/or separating one or more peptide synthesis components is at least partially based on a target peptide sequence and/or a nucleic acid protein coding sequence. In some embodiments, the order and/or the timing for providing, co-localizing, removing and/or separating one or more peptide synthesis components is at least partially based on a predicted rate of incorporation of two or more amino acids into one or more peptides, a predicted rate of activity of one or more biological assemblers, a predicted rate of translocation of one or more nucleic acids, and/or a predicted rate of release of tRNA.

In some embodiments, one or more computing units 426 are operable to determine the order and/or the timing for providing, co-localizing, removing and/or separating one or more peptide synthesis components at least partially based on monitoring of amino acid incorporation into one or more peptides, biological assembler activity, nucleic acid translocation, and/or tRNA release. In some embodiments, one or more monitoring units 440 are operable to perform the monitoring of amino acid incorporation into one or more peptides, biological assembler activity, nucleic acid translocation, and/or tRNA release. In some embodiments, one or more of the one or more monitoring units 440 and one or more of the one or more computing units 426 are the same units.

In some embodiments, one or more computing units 426 are operable to determine the order and/or the timing for providing, co-localizing, removing and/or separating one or more peptide synthesis components at least partially based on measurements including, but not limited to, availability of one or more nucleic acid codons, concentrations of one or more of the two or more charged tRNA or the one or more tRNA, presence or absence of one or more of the two or more charged tRNA or the one or more tRNA, or presence or absence of one or more anti-codons on one or more of the two or more charged tRNA or the one or more tRNA. In some embodiments, one or more of these measurements is at least partially determined extrinsically. In some embodiments, one or more of these measurements are determined based at least partially on measurements by one or more monitoring units 440. In some embodiments, one or more of these measurements are provided in real time.

Unit 4260 is optionally one or more computing units, operable for determining the timing for providing and/or removing one or more or two or more charged tRNA and/or released tRNA to and/or from one or more identifiable locations. In some embodiments, one or more apparatus include, but are not limited to, one or more peptide synthesizer units and one or more computing units that are operable to determine the timing and/or order for providing and optionally for removing one or more charged tRNA and/or one or more tRNA. In some embodiments, one or more of the one or more peptide synthesizer units and one or more of the one or more charged tRNA computing units are the same unit.

In some embodiments, one or more computing units are operable to determine the timing and/or the order for providing, optionally sequentially, two or more charged tRNA to one or more first identifiable locations, and optionally further operable to determine the timing and/or the order for removing, optionally sequentially, two or more charged tRNA and/or one or more tRNA from one or more first identifiable locations. In some embodiments, one or more computing units are operable to determine the timing and/or order for sequentially co-localizing two or more charged tRNA with one or more biological assemblers, and optionally sequentially removing two or more charged tRNA and/or one or more tRNA from the one or more biological assemblers. In some embodiments, one or more computing units are operable to determine the timing and/or order for sequentially co-localizing two or more charged tRNA and one or more biological assemblers, and optionally sequentially separating the two or more charged tRNA and/or one or more tRNA and the one or more biological assemblers.

Unit 4261 is optionally one or more computing units operable for determining the timing and/or order for providing and/or removing one or more biological assemblers to and/or from one or more identifiable locations. In some embodiments, one or more apparatus include, but are not limited to, one or more peptide synthesizer units and one or more computing units that are operable to determine the timing for providing and optionally for removing one or more biological assemblers. In some embodiments, one or more of the one or more peptide synthesizer units and one or more of the one or more biological assembler computing units are the same unit.

In some embodiments, one or more computing units operable for determining the timing and/or order for, optionally sequentially, co-localizing one or more biological assemblers, and optionally further operable to determine the timing and/or order for, optionally sequentially, removing the one or more biological assemblers following peptide synthesis. In some embodiments, one or more computing units operable for determining the timing and/or order for, optionally sequentially, co-localizing one or more biological assemblers with two or more charged tRNA, wherein at least two of the two or more charged tRNA are at one or more different locations, and optionally further operable to determine the timing and/or order for, optionally sequentially, separating the one or more biological assemblers from the two or more charged tRNA and/or one or more tRNA. In some embodiments, one or more computing units operable for determining the timing and/or order for, optionally sequentially, co-localizing one or more biological assemblers and two or more charged tRNA, and optionally further operable to determine the timing and/or order for, optionally sequentially, separating the one or more biological assemblers and the two or more charged tRNA and/or one or more tRNA.

Unit 4262 is optionally one or more computing units operable for determining the timing and/or order for providing and/or removing one or more biological assembler components to and/or from one or more identifiable locations. In some embodiments, one or more apparatus includes one or more computing units to determine an order and/or timing in which each source provides one or more biological assembler components to one or more fourth locations. In some embodiments, one or more apparatus include, but are not limited to, one or more peptide synthesizer units and one or more computing units that are operable to determine timing and/or order for providing one or more biological assembler components to one or more identifiable locations. In some embodiments, one or more of the one or more peptide synthesizer units and one or more of the one or more biological assembler components computing units are the same unit.

In some embodiments, one or more computing units operable for determining the timing and/or order for providing, optionally sequentially, one or more biological assembler components, and optionally further operable to determine the timing and/or order for removing one or more biological assembler components. In some embodiments, one or more computing units operable for determining the timing and/or order for, optionally sequentially, co-localizing one or more biological assembler components with two or more charged tRNA, wherein at least two of the two or more charged tRNA are at one or more different locations, and optionally further operable to determine the timing and/or order for, optionally sequentially, separating the one or more biological assembler components from the two or more charged tRNA and/or one or more tRNA. In some embodiments, one or more computing units operable for determining the timing and/or order for, optionally sequentially, co-localizing one or more biological assembler components and two or more charged tRNA, and optionally further operable to determine the timing and/or order for, optionally sequentially, separating the one or more biological assembler components and the two or more charged tRNA and/or one or more tRNA.

Unit 4263 is optionally one or more computing units, operable for determining the timing and/or order for providing and/or removing one or more nucleic acids to and/or from one or more identifiable locations. In some embodiments, one or more apparatus include, but are not limited to, one or more peptide synthesizer units and one or more computing units that are operable to determine timing and/or order for providing one or more nucleic acids to one or more first identifiable locations. In some embodiments, one or more of the one or more peptide synthesizer units and one or more of the one or more nucleic acid computing units are the same unit.

In some embodiments, one or more computing units are operable to determine the timing and/or the order for co-localizing, optionally sequentially, one or more nucleic acids, and optionally further operable to determine the timing and/or the order for removing, optionally sequentially, one or more nucleic acids. In some embodiments, one or more apparatus further includes one or more computing units operable to determine the order and/or the timing in which each source optionally provides one or more nucleic acids to one or more third locations, and optionally removes one or more nucleic acids from one or more third locations. In some embodiments, one or more computing units are operable to determine the timing and/or the order for providing and optionally for removing one or more DNA, one or more cDNA, one or more RNA, and/or one or more mRNA. In some embodiments, the one or more nucleic acids are provided to one or more identifiable locations and/or to one or more biological assemblers, or one or more biological assembler components.

Unit 4264 is optionally one or more computing units operable for determining the timing and/or order for providing and/or removing one or more tRNA, one or more amino acids, and/or one or more tRNA charging components to and/or from one or more identifiable locations. In some embodiments, one or more apparatus include, but are not limited to, one or more peptide synthesizer units and one or more computing units that are operable to determine timing and/or order for providing one or more tRNA, one or more amino acids, and/or one or more tRNA charging components to one or more first identifiable locations. In some embodiments, the one or more peptide synthesizer units and the one or more tRNA charging controller units are the same unit. In some embodiments, one or more computing units are operable to determine timing and/or order for charging one or more tRNA. In some embodiments, one or more apparatus include one or more first computing units to determine one or more of an order or timing in which each source provides one or more tRNA to the one or more second locations; one or more second computing units to determine one or more of the order or the timing in which each source provides one or more amino acids to the one or more second locations; and one or more third computing units to determine one or more of the order or the timing in which each source provides the one or more tRNA charging components to the one or more second locations; and wherein one or more of the one or more first computing units are optionally the same as the one or more second computing units, and optionally the same as the one or more third computing units.

Unit 4265 is optionally one or more computing units, operable for determining the timing and/or order for providing and/or removing one or more nucleotides and/or one or more nucleic acid synthesis components to and/or from one or more identifiable locations. In some embodiments, one or more apparatus 410 include, but are not limited to, one or more peptide synthesizer units 420 and one or more computing units that are operable to determine timing and/or order for providing one or more nucleotides and/or one or more nucleic acid synthesis components 4265 to one or more identifiable locations. In some embodiments, the one or more peptide synthesizer units 420 and the one or more nucleic acid synthesis computing units 4265 are the same unit. In some embodiments, one or more computing units 4265 are operable to determine timing and/or order for synthesizing one or more DNA, one or more cDNA, one or more RNA, and/or one or more mRNA. In some embodiments, one or more apparatus include one or more first computing units to determine one or more of an order or timing in which each source provides one or more nucleotides to the one or more third locations; and one or more second computing units to determine one more of the order or the timing in which each source provides one or more nucleic acid synthesis components to the one or more third locations; wherein the one or more first computing units are optionally the same as the one or more second computing units.

In some embodiments, one or more apparatus 410 include, but are not limited to, one or more tRNA charging units 428 operable to charge one or more tRNA with one or more amino acids. In some embodiments, one or more apparatus 410 include, but are not limited to, one or more peptide synthesizer units 420 and one or more tRNA charging units 428. In some embodiments, one or more of the one or more tRNA charging units 428 and one or more of the one or more peptide synthesizer units 420 are the same unit. In some embodiments, one or more tRNA charging units 428 are operable to co-localize one or more tRNA, one or more amino acids, and one or more tRNA charging components in one or more third identifiable locations. In some embodiments, the one or more tRNA charging units 428 are operable to provide one or more charged tRNA to one or more peptide synthesizer units and/or to one or more sources of charged tRNA 4320. In some embodiments, one or more of the one or more third identifiable locations are the same as one or more of the one or more first locations and/or the one or more second locations. In some embodiments, one or more of the one or more third identifiable locations are the same as one or more sources of charged tRNA 4320. In some embodiments, one or more third identifiable locations are located in one or more peptide synthesizer units 420. In some embodiments, the one or more tRNA charging units 428 include one or more fluid flows.

In some embodiments, one or more apparatus include, but are not limited in, one or more peptide synthesizer units 420 and one or more tRNA charging units 428 that are operable to charge one or more natural tRNA with one or more amino acids, one or more unnatural tRNA with one or more amino acids, one or more arbitrary tRNA with one or more amino acids, one or more tRNA with one or more natural amino acids, one or more tRNA with one or more unnatural amino acids, and/or one or more tRNA with one or more arbitrary amino acids. In some embodiments, the one or more apparatus 410 include, but are not limited to one or more sources of tRNA 4324, one or more sources of amino acids 4326, and/or one or more sources of tRNA charging components 4325.

In some embodiments, one or more apparatus include one or more nucleic acid synthesizer units 430 operable to synthesize nucleic acids. In some embodiments, one or more apparatus 410 include, but are not limited to, one or more peptide synthesizer units 420 and one or more nucleic acid synthesizer units 430. In some embodiments, one or more of the one or more peptide synthesizer units 420 and one or more of the one or more nucleic acid synthesizer units 430 are the same unit. In some embodiments, one or more nucleic acid synthesizer units 430 are operable to synthesize one or more RNA, one or more mRNA, one or more cDNA, and/or one or more DNA. In some embodiments, one or more nucleic acid synthesizer units 430 are operable to co-localize one or more nucleotides and/or one or more nucleic acid synthesis components in one or more fourth identifiable locations. In some embodiments, one or more nucleic acid synthesis components include, but are not limited to, one or more DNA synthesis components, one or more cDNA synthesis components, one or more RNA synthesis components, and one or more mRNA synthesis components.

In some embodiments, one or more of the apparatus 410 include, but are not limited to, one or more nucleic acid synthesizer units 430 operable to provide one or more nucleic acids to one or more peptide synthesizer units 420. In some embodiments, one or more of the one or more fourth identifiable locations are optionally the same as one or more of the one or more first identifiable locations, and/or one or more sources of nucleic acids 4321. In some embodiments one or more fourth identifiable locations are located in one or more peptide synthesizer units 420. In some embodiments, the one or more nucleic acid synthesizer units 430 include one or more fluid flows.

EXAMPLES

The following Examples are provided to illustrate, not to limit, aspects of the present invention. Materials and reagents described in the Examples are commercially available unless otherwise specified.

Example 1

Arbitrary Synthesis of Polypeptides—Basic Protocol

Ribosomal assemblies, either derived from a cell lysate or reconstituted from one or more individual components, are incubated with a nucleic acid sequence, for example mRNA, either before or after addition to a reaction chamber to form an initiation complex. Then, assembly of a target polypeptide is achieved through sequentially combining the ribosome initiation complex with appropriate aminoacylated tRNAs (aa-tRNA; charged tRNA) using one of several methods described herein or below.

For example, aminoacylated tRNAs may be added sequentially to the reaction chamber such that the amino acids are provided in the order of the target protein sequence and the anti-codons align with the codons of the template nucleic acid. After a fixed or variable interval, unused aa-tRNA and used deacylated tRNA may be cleared and the next aa-tRNA in the sequence added to the ribosomes. Sequential additions of aa-tRNAs are continued until termination of translation has been achieved. The translated polypeptide is optionally isolated from the translation mix.

Alternatively, the ribosome complex may be exposed sequentially to aa-tRNA such that the amino acids are available in the order of the target protein sequence and the anti-codons align with the codons of the template nucleic acid. After a fixed or variable interval, the ribosome complex with nascent polypeptide strand may be separated from unused aa-tRNA and used deacylated tRNA, and then exposed to the next aa-tRNA in the sequence. Sequential exposure of the ribosome complex including the nascent polypeptide strand to aa-tRNAs is continued until termination of translation has been achieved. The translated polypeptide may be isolated from the translation mix.

Translation is terminated once the nucleic acid template has reached the end of the target coding sequence. In a cell free lysate, termination and release of the nascent polypeptide chain may occur once the ribosome assembly has reached a series of one or more stop codons and no additional aa-tRNAs are added to the system. Under these conditions, release factors associated with the cell free lysate facilitate termination and release of the polypeptide. In a reconstituted system, termination and release of the nascent polypeptide chain is facilitated by the addition of release factors to the reaction once the ribosome assembly has reached a series of one or more stop codons and no additional aa-tRNAs are added to the system.

Example 2

Timing of Sequential Addition of Each aa-tRNA

The addition and incubation of each aa-tRNA in the translation reaction can be set to a uniform interval or a variable interval. The uniform interval can be set, for example, from 0.001 to 0.1 seconds for each aa-tRNA. The rate of translation with natural amino acids in an optimized in vitro system is approximately 10 codons per second (Arch. Biochem. Biophys. (1996) 328:9-16).

A variable interval which might, for example, be dependent upon the specific aa-tRNA can be determined empirically for each individual aa-tRNA or can be determined in real time during translation. Fluorescence resonance energy transfer (FRET) can be used to measure tRNA interactions within the ribosomes. This type of analysis can be used to determine the kinetics of ribosome interaction for each of the synthesized aa-tRNAs, and these numbers used, for example, to set the time interval for addition and clearance of each individual aa-tRNA.

For example, FRET can be used to measure the interaction of tRNA species in the P and A sites of the ribosome as described by Blanchard et al. (Nat. Struct. Mol. Biol. (2004) 11:1008-1014). E. coli ribosomes are initiated in vitro with fluorescently labeled fMet-tRNA$^{fMet}$ (Cy3) in the P site and tethered to a streptavidin derivatized quartz microscope slide via biotinylated mRNA. The aa-tRNA of interest, for example Phe-tRNA$^{Phe}$, is labeled with Cy5 on a naturally occurring modified nucleotide (acp$^3$U/position 47) using standard procedures. Phe-tRNA$^{Phe}$ (Cy5) is complexed with the elongation factor ET-Tu as previously described (J. Biol. Chem. (2005) 280:36065-36072) and immediately added by stopped-flow delivery to the surface-immobilized ribosomes.

A total internal reflection (TIR) fluorescence microscope may be used to measure the changes in Cy3 and Cy5 fluorescence as the labeled tRNAs move into proximity of one another within the ribosome. Maximal FRET signal will occur when, for example, Phe-tRNA$^{Phe}$ (Cy5) is in the A site, has been released from ET-Tu, and is in close proximity to fMet-tRNA$^{fMet}$ (Cy3) during peptide bond formation (Nat. Struct. Mol. Biol. (2004) 11:1008-1014). The time to reach this maximal signal can be used to determine, for example, the time interval required for a specific aa-tRNA to bind to the ribosome, transfer the associated amino acid, and dissociate from the ribosome. Similar FRET analysis can be done, for example, using labeled ribosomes and aa-tRNA (Nucleic Acids Res. (2005) 33:182-189).

Alternatively, empirical rates of amino acid incorporation for each aa-tRNA can be determined for example by using a puromycin assay system as described by Beringer et al. (J. Biol. Chem. (2005) 280:36065-36072). This assay measures the rate of peptidyl transferase (i.e. transfer of amino acid to a nascent peptide chain) by monitoring transfer of the growing peptide chain to puromycin.

As an example, fMet-aa-tRNA$^{Met}$ labeled with Cy3 on the Met is loaded into the P site of ribosomes and this complex is immobilized on a surface as described by Blanchard et al. (Proc. Nat. Acad. Sci. (2004) 101:12893-12898). Association of the Cy3 label with the surface restricted ribosomes creates surface localized fluorescence. Upon addition of puromycin, the Cy3-Met-aa-tRNA$^{Met}$ is transferred to the puromycin which is quickly released from the ribosome and the surface-localized fluorescence disappears. The rate at which fluorescence disappears can be used to determine the rate at which a peptide bond forms for a given amino acid.

The calculated empirical rate at which a given tRNA either binds to or is released from the ribosome assembly can be used to modulate the time interval over which specific aa-tRNAs are sequentially added to fixed ribosomes or over which ribosomes are moved sequentially passed fixed aatRNAs. These calculated rates can also be used to modulate the time interval over which free aa-tRNAs and ribosomes interact.

Real-Time Assessment of Translation

Real-time assessment of translation progression with a specific aa-tRNA can be measured and a feedback loop used to indicate when the next aa-tRNA should be added. Various components of the translation system can be monitored for change during each cycle.

For example, the release of phosphate (Pi) from the hydrolysis of GTP to GDP during translation can be used to monitor progression of the process. GTP is hydrolyzed to GDP by a conformation change in the elongation factor/aa-tRNA ternary complex once the complex has bound to the ribosome. In addition, GTP is hydrolyzed to GDP by an elongation factor during the process of translocation and removal of deacylated tRNA from the ribosomal complex.

Release of Pi can be measured using a phosphate binding protein assay. Phosphate binding protein (PBP) from *E. coli*, for example, is purified as described (Methods (2005) 37:183-189). Alternatively, PBP can be cloned from, for example, the *E. coli* phoS gene by standard molecular biology techniques. Alternatively, cDNA encoding PBP from, for example, *E. coli* can be synthesized de novo by a commercial source (e.g. Blue Heron Biotechnology, Bothell, Wash.), based on the published nucleotide sequence (J. Bacteriol. (1984) 157:909-917).

Purified PBP is labeled, for example, with a fluorescent dye such as 7-diethylamino-3-((((2-maleimidyl)ethyl)amino)carbonyl)))) couramin (MDCC) as described previously (Methods (2005) 37:183-189). Briefly, 100 µM PBP is incubated with 150 µM MDCC, 5 µM MnCl2, 200 µM 7-methylguanosine, 1 µM glucose 1,6-bisphosphate, and 0.2 U/ml purine nucleoside phosphorylase in 20 mM Tris-HCl (pH 8.2) in the dark for 45 min at room temperature. The MDCC-PBP solution is then passed over a BioGel size exclusion column to separate the labeled protein from the smaller reaction components. PBP is extremely stable and once conjugated to MDCC can be stored at −80° C. for years (Methods (2005) 37:183-189). Alternatively, PBP can be labeled with other fluorescent dyes such as rhodamine (Biochemistry (2006) 45:14764-14771).

Alternatively, a PhosphoSensor system for measuring Pi via a phosphate-binding protein is commercially available (e.g. Invitrogen, Carlsbad, Calif.). The binding of Pi to MDCC-labeled PBP increases the fluorescence emission by as much as 12 fold at a wavelength of 464 nm when the complex is excited at 425 nm (Methods (2005) 37:183-189). Fresh GTP and labeled PBP are added coincident with each tRNA addition. As translation proceeds during a given cycle, the Pi associated fluorescence increases to a plateau level. At the end of a given cycle, under conditions where the ribosomes are fixed or size excluded, the reaction chamber is flushed of unused aa-tRNA and deacylated tRNA and the next aa-tRNA is added to the chamber with additional GTP and labeled PBP. Alternatively, under conditions where the aa-tRNAs are fixed or tethered, the ribosomes move away from the unused aa-tRNA and deacylated tRNA to a new location in the reaction chamber to interact with the next aa-tRNA in the presence of additional GTP and labeled PBP.

Alternatively, real-time assessment of translation can be monitored by measuring depletion of aa-tRNA or appearance of deacylated tRNA. For example, once tRNA is deacylated, the acceptor stalk at the 3' end of the tRNA sequence is revealed and becomes accessible to hybridization by, for example, a peptide nucleic acid (PNA) labeled, for example, with biotin, digoxigenin, fluorescent dyes, or reporter enzymes. Sequence specific Cy3-labeled PNAs are available through custom synthesis services (e.g. Panagene, Daejeon, Korea).

The selective PNA can be bound to a biosensor that emits a signal once binding with the deacylated tRNA occurs. For example, evanescent field fluorescence can be used to measure fluorescence changes at the surface in response to Cy3-deacylated tRNA binding to immobilized PNA. Alternatively, the tRNA and the PNA can be labeled with Cy3 and Cy5, respectively, and FRET used to measure the interaction of the two species. Molecules can be labeled with Cy3 and Cy5 using commercially available labeling kits (e.g. Amersham Biosciences, Piscataway, N.J.).

Interaction of PNA and deacylated tRNA can be measured without labeling the components by, for example, surface plasmon resonance. The specific PNA is immobilized on a surface plasmon resonance-based biosensor and the change in mass associated with binding of deacylated tRNAs are monitored.

A selective PNA can be synthesized using an Applied Biosystems 3400 DNA Synthesizer or an ABI 3900 Synthesizer, or using custom commercial services (e.g. Panagene, Daejeon, Korea). The PNA is further purified by reverse phase HPLC on an Ultrasphere ODS C-18, 4.6*250 mm column (Beckman) using an acetonitrile/TFA gradient (from A to B linear in 30 min: A, water/0.1% TFA; B, acetonitrile/0.1% TFA) as described by Jankowsky et al. (Nucleic Acids Res. (1997) 25:2690-2693).

Under conditions in which the aa-tRNA is fixed or tethered to a surface, the transition from the aa-tRNA to the deacylated state can be measured based on the change in mass of the deacylated tRNA using a MEMS device (see, e.g. U.S. Pat. No. 6,722,200 and U.S. Pat. No. 6,457,361). Similarly, if the ribosome complex is tethered, the docking of aa-tRNA and release of the amino acid and the deacylated tRNA can be measured based on the change in mass.

Example 3

Ribosomal Complexes for the Arbitrary Synthesis of Polypeptides

The ribosome system used in the translation reaction may be derived from cell free lysates or from reconstitution of purified native or recombinant components. Cell-free protein synthesis systems consisting of a cell extract are prepared, for example, from *E. coli*, wheat germ or rabbit reticulocytes.

The cell lysate is prepared, for example, from rabbit reticulocytes following the protocol of Jagus et al. (Current Protocols in Cell Biology (1998) Juan S. Bonifacino, Mary Dasso, Joe B. Harford, Jennifer Lippincott-Schwartz, and Kenneth M. Yamada (eds.) John Wiley & Sons, Inc). Whole blood is centrifuged for 10 minutes at 1400×g and subsequently lysed for 5 minutes with RNase-free distilled water. The resulting lysate is centrifuged for 20 minutes at 20,000×g to remove cell membranes and mitochondria. The resulting supernatant contains all of the protein components necessary to accomplish protein synthesis in the presence of an added nucleic acid template. Cell-lysates for in vitro translation are also available from commercial sources (e.g. Invitrogen, Carlsbad, Calif.; Ambion, Austin, Tex.).

For some syntheses, the lysate is depleted of endogenous aa-tRNA. Depletion of aa-tRNA from a commercially available rabbit reticulocyte lysate (Invitrogen, Carlsbad, Calif.) is accomplished by passing the lysate over a 1 ml ethanolaminesepharose column equilibrated with 25 mM KCl, 10 mM NaCl, 1.1 mM MgCl$_2$, 0.1 mM EDTA, 1 mM dithiothreitol, 10 mM HEPES-KOH (pH 7.4) supplemented with 80 mM potassium acetate and 0.5 mM magnesium acetate to match the ionic concentration of the lysate. Under these conditions, aa-tRNA has been shown to selectively bind to the column matrix (RNA (2001) 7:765-773).

Alternatively, a reconstituted ribosomal complex can be used that contains ribosomes, various protein factors, and the nucleic acid template of interest. An example of a reconstituted ribosomal complex includes hexahistidine-tagged recombinant initiation factors (IF1, IF2, and IF3), elongation factors (EF-G, EF-Tu, and EF-Ts), release factors (RF1, RF2, and RF3), and termination factor RRF generated by PCR, expressed in E. coli and purified using a nickel-chelating resin that binds the His tag (Nature Biotech. (2001) 19:751-755; Methods (2005) 36:299-304). NTPs, creatine phosphatase, creatine kinase, myokinase, and nucleoside diphosphate kinase, for example, are added as part of an energy-recycling system. Ribosomes are isolated from E. coli, for example, by centrifugation of a cell lysate at 30,000×g followed by repeated centrifugation of the 30,000×g supernatant at 100,000×g and washing in 10 mM Tris-acetate, pH 8.2, 14 mM magnesium acetate, 60 mM potassium acetate, 1 mM dithiothreitol, and 1 M ammonium chloride (Methods (2005) 36:279-290).

The ribosome complex may be free in translation solution, but retained in a "flow cell" reaction chamber by size exclusion mediated by, for example, the limiting size of an out flow channel. Alternatively, the ribosome complex may be selectively retained by a semi-permeable membrane. Semi-permeable membranes include those available from commercial sources (e.g. Millipore, Bellerica, Mass.) for example Biomax or Amicon PM high flow ultrafiltration membranes. Membranes are chosen with molecular weight cut-offs that would retain the ribosome complex but allow free-flow of added tRNA, for example 30-50 kilodalton (kDa).

Alternatively, ribosomes may be attached to a solid surface. In one example, the solid surface may be a thin mica sheet that forms, for example, one or more surfaces of a flow cell. 70S ribosomes may be attached non-specifically to the mica sheet. In one method, ribosomes are incubated for 5 minutes with the mica sheet in a buffer having, for example, 5 mM KH$_2$PO$_4$, pH 7.3, 95 mM KCl, 5 mM NH$_4$Cl, 5 mM Mg acetate, 0.5 mM CaCl$_2$, 8 mM putrescine, 1 mM spermidine, 1 mM dithiothreitol. The attached ribosomes are washed 3 times with 50 mM Tris-HCl, pH 7.4, 50 mM KCl, 10 mM Mg Cl$_2$, washed 1 time with protein-based blocking solution such as 5% bovine serum albumin treated with an RNase inhibitor, followed by 3 final washes with buffer. To the ribosomes are then added the template nucleotide and for example purified elongation factors as well as components of an energy recycling system. (RNA (2003) 9:1174-1179).

Alternatively, ribosomes may be attached to a glass surface (e.g., a microscope cover slip) by a chemical reaction (Biophys. J. (2005) 89:1909-1919). Glass cover slips may be functionalized with amine groups using, for example, 3-aminopropyltriethoxysilane (APTES, United Chemical Technologies, Bristol, Pa.). The cover slips are then treated with N-[k-maleimidoundecanoyloxyl]sulfosuccinimide ester (Sulfo-KMUS); Pierce, Rockford, Ill.), a heterobifunctional cross-linker which carries a succinimide group at one end and a maleimide group at the other end, separated by a 11 carbon linker chain. The succinimide group reacts with the amines on the glass surface, leaving the maleimide groups exposed and reactive toward protein sulfhydryls at the surface of the ribosome. The length of the linker carbon chain can be varied by using commercially available sulfo-NHS reagents with spacer arms ranging for example from 4-16 angstrom (e.g. Pierce, Rockford, Ill.).

Ribosomes may also be immobilized via association with an affixed strand of nucleic acid sequence, for example 5' or 3' biotinylated mRNA. The mRNA is biotinylated at the 5' end, for example, by a one step transcription procedure using biotinylated AMP or GMP as a transcription initiator (Nucleic Acids Res. (2005) 33:e129). Alternatively, nucleotides can be biotinylated using, for example, EZ-Link PFP-Biotin ((+)-Biotin pentafluorophenyl-ester) per the instructions provided by the manufacturer (TFP-PEO-Biotin; Pierce, Rockford, Ill.).

The 70S ribosome complexes are initiated on the biotinylated mRNA in vitro in 50 mM Tris acetate (pH 7.5), 100 mM KCl, 5 mM ammonium acetate, 0.5 mM calcium acetate, 5 mM magnesium acetate, 6 mM 2-mercaptoethanol, 5 mM putrescine, and 1 mM spermidine, and subsequently purified by sucrose density ultracentrifugation in the above buffer with 20 mM magnesium acetate as described by Pavlov & Ehrenberg (Arch. Biochem. Biophys. (1996) 328:9-16). The resulting initiation complexes containing the biotinylated mRNA are immobilized, for example, on the surface of a quartz microscope slide coated with a combination of polyethylene glycol (PEG) and streptavidin-biotin-PEG. Alternatively, the biotinylated ribosome complex is bound to the surface of a microchip or a polystyrene bead coated with streptavidin. The surfaces are further treated with a blocking solution containing 10 µM BSA/10 µM double-stranded DNA.

Example 4

Nucleic Acid Templates for the Arbitrary Synthesis of Polypeptides

The nucleic acid template used in the translation reaction can be DNA, RNA or mRNA, and may be, for example, a traditional protein coding nucleic acid sequence, or an arbitrary nucleic acid sequence used as a template for arbitrary protein synthesis. The nucleic acid sequence may contain a ribosomal binding site, for example, a Shine-Dalgarno sequence as well as an initiation codon, for example AUG.

Traditional mRNA used in the translation reaction may be transcribed from a cDNA construct containing the nucleotide sequence corresponding to the polypeptide sequence of interest. The cDNA construct contains polymerase promoter sequences allowing for runoff transcription using, for example, the T7 RNA polymerase with standard reagents available from commercial sources (e.g. Stratagene, La Jolla, Calif.).

The cDNA corresponding to the polypeptide of interest can be derived from screening of cDNA libraries, amplification of cDNA libraries or genomic DNA using specific oligonucleotide primers and the polymerase chain reaction (PCR), or cDNA purchased intact from commercial sources (e.g. Origene, Rockville, Md.). DNA may also be synthesized de novo using custom commercial services (e.g. Blue Heron Biotechnology, Bothell, Wash.).

As an illustrative example, the arbitrary nucleic acid template is composed of a single nucleotide. Synthesis and use of high-molecular weight poly(U) (average length 8,000-10,000 bases) is known in the art and is prepared by polynucleotide phosphorylase polymerization of UDP and fractionated by Sephacryl column chromatography (Biophys. J. (2005) 89:1909-1919). In this instance, only one, two or three tRNA species are needed, with a three-base, four-base, or five-base anticodon containing three, four, or five As, respectively. A variety of natural and unnatural amino acids (optionally including the entire set of natural amino acids) are acylated to these tRNA species.

Alternatively, the arbitrary nucleic acid sequence could be composed entirely of alternating or repeating stop codons as described herein. Alternatively, the arbitrary nucleic acid sequence could be composed of a set of optionally repeating 3-base, 4-base or 5-base codons which are not stop codons. In general, any subset of the natural codons can be used to create the nucleic acid sequence (2, 3, 4, 5, 6, 7, 8, 9, 10, etc.), so long as the corresponding tRNAs are available and acylated with the required natural and/or unnatural amino acids. The codons may be used in a repeating or a non-repeating pattern. The nucleic acid sequence may also be optimized for codon usage and easy translation, as well as to avoid using the same codon for different amino acids when the codons are adjacent, or optionally within one, two, three, four, five, six, seven, eight, nine, or ten codons of the same codon among other things.

Example 5

Recovery of Translation Product from the Arbitrary Synthesis of Polypeptides

At the end of translation, the peptide or protein product may be recovered from the reaction vessel. Protein can be isolated in a variety of ways, including by virtue of a small tag engineered into the protein sequence.

Hexahistidine, a string of 6 histidines, is inserted, for example, at some point along the length of the protein sequence. The polyhistidine binds strongly to divalent metal ions such as nickel and cobalt and can be immobilized on, for example, a matrix or surface containing nickel ions. After extensive washing to remove unbound material, the bound His-tagged protein is eluted from the matrix or surface with, for example, imidazole or low pH (Nucleic Acids Res. (1991) 19:6337-6338).

Alternative methods for tagging the protein include, for example, a Myc epitope tag (Mol. Cell. Biol. (1993) 13:5861-5876) or some other small epitope or recognition sequence recognized by a specific antibody or aptamer.

Alternatively, tags associated with the components of a reconstituted ribosomal complex can be used to selectively separate these components from the un-tagged translation product. At the completion of translation, large particles, for example, a microsphere, are introduced into the reaction vessel. The particles have associated nickel or cobalt affixed to their surface which then binds the His-tagged proteins. Particles of this type are available from commercial sources (e.g. Dynabeads® TALON™, Invitrogen, Carlsbad, Calif.). Flow is directed towards an outlet that excludes both the large ribosome complex and the particles, allowing the un-tagged protein to be expelled.

Example 6 aa-tRNAs for the Arbitrary Synthesis of Polypeptides

There are 20 common amino acids that are naturally incorporated into polypeptides during translation in eukaryotes and that can be used in the methods and apparatus described herein. In addition, incorporation of an unnatural amino acid into a polypeptide sequence is possible, for example, by addition of the unnatural amino acid on a natural tRNA. Both unnatural and natural amino acids may also be incorporated into a polypeptide sequence using unnatural tRNA, for example tRNA with modified anti-codon sequences. During translation, the natural (or modified) aa-tRNA then places the unnatural (or natural) amino acid into the elongating polypeptide sequence based on the anticodon sequence of the aa-tRNA and the respective codon sequence within the nucleic acid template.

Each aa-tRNA may be added to the translation reaction by itself, or already pre-complexed with an elongation factor, for example ET-Tu. The formation of this complex is initiated, for example, by incubation of EF-Tu•GDP (~300 pmol) with GTP (1 mM), phosphoenol pyrovate (3 mM), and pyruvate kinase (100 µg/ml) in 20 µl of 50 mM Tris-HCl (pH 7.5), 40 mM NH4Cl, 10 mM MgCl2, and 1 mM DTT for 10 min at 37° C. to exchange the bound GDP with GTP. Equimolar aa-tRNA is added in the same buffer and further incubated for 5 min at 37° C. (J. Biol. Chem. (2005) 280:36065-36072).

The aa-tRNA/ET-Tu complex may be free in solution or tethered to a substrate, for example, via interaction of ET-Tu with an affixed anti-ET-Tu antibody. Upon engagement of aa-tRNA in ribosome, GTP is converted back to GDP and the aa-tRNA/ET-Tu complex is broken.

The aa-tRNAs may be immobilized using a variety of methods including, for example, by electrostatic binding to poly-L-lysine. Alternatively, biotinylated aa-tRNAs may be immobilized by binding to avidin or streptavidin on the surface of the reaction chamber or to beads, for example.

Another option is to immobilize the aa-tRNAs via a linker molecule. For example, the aa-tRNAs can be immobilized through hybridization to, for example, the T-loop of the tRNA, with a selective peptide nucleic acid (PNA) (see, e.g. Methods (2005) 36:270-278; Bioorg. Med. Chem. Lett. (2006) 16:4757:4759). The PNA can be bound through a linker to the surface of the chamber or beads, among others. A selective PNA conjugated to a peptide can be synthesized, for example, using custom services (e.g. Panagene, Daejeon, Korea). The PNA-peptide is linked to the surface of the chamber or beads by, for example, N-hydroxysuccinimide (NHS) ester (see, e.g. Trends Biotechnol. 22:617-622 (2004)).

Alternatively, the aa-tRNA is modified, for example, with Cy3 or Cy5 as described herein and subsequently attached to the surface of the reaction chamber or beads, for example, via an immobilized anti-Cy3/Cy5 monoclonal antibody (Sigma Aldrich).

Alternatively, aa-tRNAs may be immobilized in association with an elongation factor. For example, ET-Tu is biotinylated using standard procedures and is attached to a streptavidin-modified surface of the reaction chamber or beads, for example. aa-tRNA is subsequently bound to ET-Tu in a GTP-dependent manner as described herein. Alternatively, aa-tRNA/ET-Tu complexes are generated external to the reaction chamber and then added to the streptavidin-modified reaction chamber. Alternatively, the aa-tRNA/ET-Tu complexes may be attached, for example, via an anti-ET-Tu polyclonal antibody (e.g., BET-A300-957, Axxora Life Sciences Inc. San Diego, Calif.) immobilized to the reaction chamber surface (or surface of beads, among others) using standard procedures.

Synthesis of Natural tRNAs tRNA species with anti-codons corresponding to the complement of natural codons on mRNA can be generated de novo using standard molecular biology techniques. tRNA nucleotide sequence information for a variety of organisms is available in public databases (e.g. available at //www-.staff.uni-bareuth.de/).

Phenylalanine (Phe) specific tRNA is generated, for example, by annealing complementary oligomers containing the nucleotide sequence of tRNA(Phe). The complementary oligomers may be synthesized using an Applied Biosystems 3400 DNA Synthesizer or an ABI 3900 Synthesizer, or using custom commercial services. The oligomers are designed to contain restriction sites at the 5' and 3' ends, for example Kpn and HindIII, enabling ligation of the fragment into a transcription compatible vector, such as Bluescript® II KS +/− (Stratagene, La Jolla, Calif.). The fragment is oriented 5' to 3' relative to an RNA polymerase promoter sequence within Bluescript® II KS +/−, such as that for T7 polymerase. Additional restrictions sites, for example BstNI and FokI, are engineered into the 3' end of the sequence within the acceptor stem. Linearization of the construct at BstNI or FokI followed by T7 polymerase mediated run-off transcription generates tRNA(Phe) with either an intact acceptor stem compatible for example with enzymatic aminoacylation or a truncated acceptor stem lacking the 3' terminal CA compatible for example with chemical aminoacylation (Nucleic Acids Res. (1990) 18:83-88).

Alternatively, a transcription template for tRNA synthesis can be generated in the absence of cDNA cloning by generating two oligonucleotides of disparate size (Korencic et al. Nucleic Acids Res. (2002) 30:e105). The first and larger oligonucleotide comprises the tRNA gene. The second is for example 23 nucleotides and complementary to the 3' end of the first oligonucleotide. The two oligonucleotides are annealed, forming a double stranded T7 promoter site. Transcription using, for example, the aforementioned template is carried out in a reaction containing 40 mM Tris-HCl, pH 8.0, 22 mM $MgCl_2$, 1 mM spermidine, 5 mM DTT, 0.5% Triton-X100, 4 mM each NTP, 5 mM GMP and 30 nM T7 RNA polymerase for 3 h at 37° C. The reaction mix is extracted with phenol/chloroform and ethanol precipitated. The tRNA is subsequently purified on and extracted from a 12% polyacrylamide gel.

Methods for purifying tRNA species from native sources such as E. coli and yeast have also been described (J. Biol. Chem. (1968) 243:5761-5769). Alternatively, purified native tRNA species are available from commercial sources (e.g. Sigma-Aldrich, St. Louis, Mo.).

Synthesis of Unnatural tRNAs

Unnatural tRNAs may be defined as tRNAs with primary nucleotide sequence not normally found in nature and may be synthesized de novo or derived from natural tRNA by, for example, site-directed mutagenesis.

Unnatural tRNA can be synthesized by site-directed mutagenesis of a natural tRNA. Site-directed mutagenesis can be used to modify, for example, the anticodon region, amino acid acceptor stem, or other parts of the primary tRNA sequence of, for example, $tRNA^{Gln}$. A cDNA construct containing the $tRNA^{Gln}$ sequence is generated using, for example, one of the methods described herein. Point mutations in the primary sequence are generated using user-defined oligonucleotides of, for example, 20 bases and a commercially available site-directed mutagenesis kit (e.g. QuikChange® XL, Stratagene, La Jolla, Calif.).

Alternatively, unnatural tRNA can be synthesized de novo using the methods described herein, including the two oligonucleotide primer strategy above and the overlapping oligonucleotides with primer extension strategy described in Example 8 (Methods (2005) 36:270-278). Alternatively, the nucleotide sequence for an unnatural tRNA can be synthesized de novo using custom commercial services (e.g. Blue Heron Biotechnology, Bothell, Wash.).

Aminoacylation of Natural and Unnatural tRNA with Natural Amino Acids

Charged or acylated tRNAs (aa-tRNA) used in the translation reaction are generated by addition of an amino acid to a tRNA via enzymatic or chemical aminoacylation. Enzymatic aminoacylation may be achieved using the aminoacyl tRNA synthetases specific for each of the twenty natural amino acids.

For example, phenylalanyl-$tRNA^{Phe}$ can be generated in vitro by enzymatic aminoacylation following the methods of Sampson & Uhlenbeck (PNAS (1988) 85:1033-1037). $tRNA^{Phe}$ is heated to 60° C. and slowly cooled to 25° C. prior to addition of aminoacylation reaction mixture. To the tRNA is added 30 mM Hepes KOH (pH 7.45), 10 µM phenylalanine, 2 mM ATP, 15 mM $MgCl_2$, 25 mM KCl, and 4 mM dithiothreitol. The reaction is initiated by addition of phenylalanyl-tRNA synthetase at 0.07 to 0.3 units/ml. The reaction is carried out for 4 minutes at 37° C.

Enzymatic aminoacylation using aminoacyl tRNA synthetases can also be used to incorporate natural amino acids into unnatural tRNA. For example, unnatural tRNA containing a four-base anticodon can by aminoacylated by endogenous E. coli aminoacyl-tRNA synthetases (Nucleic Acids Res. (2006) 34:1653-1662).

Amino acid specific aminoacyl tRNA synthetases can be purified from E. coli and yeast, for example, (e.g. Nucleic Acids Res. (1986) 14:7529-7539) or through standard cDNA cloning techniques (e.g. Nucleic Acids Res. (1998) 26:521-4). Alternatively, full-length cDNA encoding various aminoacyl tRNA synthetases are commercially available (e.g. Origene, Rockville, Md.) or can be synthesized de novo (e.g. Blue Heron Biotechnology, Bothell, Wash.) based on published sequence information.

Chemical aminoacylation of natural and unnatural tRNA may be achieved using for example aminoacylated pdCpA derivatives (Nucleic Acids Res. (1989) 17:9649-9660), or an N-pentenoyl protecting group (Methods (2005) 36:245-251).

For example, phenylalanyl-$tRNA^{Phe}$, can be generated by chemical aminoacylation using the N-pentenoyl protection method as described by Lodder et al. (Methods (2005) 36:245-251). Pentenoic acid (49 mmol) and N-hydroxysuccinimide (49 mmol) in $CH_2Cl_2$ are added to N,N'-dicyclohexylcarbodiimide (50 mmol). After 1.5 hours at room temperature, the reaction product is passed over a silica column, eluted with 7:3 hexane-ethyl acetate, and crystallized from ether-petroleum ether (35-60° C.). The resulting 4-pentenoyloxy succinimide ester is incubated with 1 mmol phenylalanine and 2 mmol $NaHCO_3$ in 1:1 $H_2O$:dioxane. After 16 hours at room temperature, the reaction mixture is diluted with 1N $NaHSO_4$ and extracted with ethyl acetate. The organic extract is dried ($MgSO_4$) and concentrated under diminished pressure. The crude product is redissolved in acetonitrile and chloroacetonitrile and incubated for 20 hours at room temperature. The reaction mixture is diluted with ethyl acetate, washed with 1 N $NaHSO_4$, and the organic extract dried ($MgSO_4$) and concentrated under diminished pressure. The crude product is applied to a silica gel column and eluted with 4:1 ethyl acetate-hexanes. The resulting N-4-pentenoyl amino acid cyanomethyl ester is added to a solution of the tris(tetrabutylammonium) salt of pdCpA in DMF. The reaction mixture is incubated for 3 hours at room temperature, diluted in 1:2 CH$_3$CN-50 mM NH$_4$OAc (pH 4.5) and purified on a semi-preparative C$_{18}$ reversed phase column, resulting in N-4-pentenoyl-aminoacyl pdCpA. The last step in this chemical aminoacylation procedure involves ligation of the aminoacyl-pdCpA to tRNA$^{Phe}$ lacking the 3'-terminal pCpA in 50 mM Hepes buffer (pH 7.5) containing 15 mM MgCl$_2$, 0.75 mM ATP, 10% DMSO, and 100 units of T4 RNA ligase. After incubation for 1 hour at 37° C., the N-(4-penenoyl)-phenylalanyl-tRNA is precipitated with ethanol and the resulting pellet dissolved in H$_2$O. Removal of the pentenoyl protection group prior to translation is accomplished by incubating the tRNA with I$_2$ (25 mM in 1:1 THF-H$_2$O). The aminoacyl-tRNA is purified by ethanol precipitation and can be stored dissolved in buffered aqueous solution at pH 5.0 at low temperature for several weeks (Methods (2005) 36:245-251).

Alternatively, a precursor tRNA with self-aminoacylation activity may be used to aminoacylate itself (EMBO (2001) 20:1797-1806).

Aminoacylation of Natural and Unnatural tRNA Using Unnatural Amino Acids

Unnatural amino acids are known in the art including, but not limited to, those containing spectroscopic probes, post-translational modification, metal chelators, photoaffinity labels, D-enantiomers, as well as other functional groups and modified structures (e.g. Methods (2005) 36:227-238; Ann. Rev. Biochem. (2004) 73:147-176; Science (2003) 301:964-967; Royal Society of Chemistry (2004) 33:422-430). A variety of unnatural amino acids are available from commercial sources (e.g. Sigma-Aldrich, St. Louis Mo.; EMD Biosciences, San Diego, Calif.).

Naturally occurring aminoacyl tRNA synthetases may be used to incorporate unnatural amino acids into natural tRNAs. For example, homoallylglycine and trifluoroleucine can be incorporated into protein using wild type aminoacyl tRNA synthetases in E. coli starved for the nature amino acids glycine and leucine, respectively (Methods (2005) 36:291-298). In vitro, wild-type aminoacyl tRNA synthetases incorporate a wide variety of unnatural amino acids into natural tRNAs as demonstrated by Hartmann et al. (Proc. Natl. Acad. Sci. (2006) 103:4356-4361). In this example, the 20 aminoacyl tRNA synthetases are purified and incubated in vitro with total tRNA and a variety of natural and unnatural tRNAs and mass spectrometry is used to determine the structures of the resulting aa-tRNAs species. Alternatively, genetic screening methods have been described for developing mutant aminoacyl tRNA synthetases in, for example, Saccharomyces cerevisiae that can enzymatically transfer an unnatural amino acid to a specific tRNA (Science (2003) 301:964-967).

Similarly, endogenous E. coli aminoacyl-tRNA synthetases can be used to incorporate unnatural amino acids into an unnatural tRNA such as, for example, a suppressor tRNA containing a modified anticodon (Chem. Soc. Rev. (2004) 33:422-30).

Unnatural amino acids can also be incorporated into natural and/or unnatural tRNA by, for example, a chemical aminoacylation procedure as described herein and/or known in the art (see, e.g. Nucleic Acids Res. (1989) 17:9649-9660 and Methods (2005) 36:245-251). In general, any amino acid can be chemically aminoacylated to any tRNA. For example, tRNA$^{Phe}$ can be used to selectively incorporate phenylalanine, p-nitrophenylalanine, or any other amino acid at specific sites in the polypeptide at a phenylalanine codon. As an example, p-nitrophenylalanine can be chemically aminoacylated to tRNA$^{Phe}$, and can be incorporated into the polypeptide sequence in place of phenylalanine. p-nitrophenylalanine can also be arbitrarily added to tRNA$^{Tyr}$, for example, and can be incorporated into the polypeptide sequence in place of tyrosine.

Alternatively, an unnatural amino acid can be incorporated into a natural or unnatural tRNA through the use of a peptide nucleic acid (PNA) carrier as described by Sisido et al. (Methods (2005) 36:270-278). In this procedure, a PNA molecule is designed with sequence complementary to the 3' end of the acceptor stock of the tRNA to be aminoacylated. A natural or unnatural amino acid is attached via an amino acid thioester linkage to the PNA. Upon incubation with the tRNA, a PNA/tRNA hybrid is formed. The natural or unnatural amino acid is transferred to the tRNA via an ester exchange and the PNA is released. The aminoacylated tRNA is then separated from the PNA by phenol/chloroform extraction and ethanol precipitation.

Example 7

Incorporation of Natural and Unnatural Amino Acids into a Polypeptide Using an Anti-Stop Codon tRNA Stop codons in mRNA, represented by UAG, UAA, and UGA, usually signify the end of the coding sequence and the point at which translation is terminated. However, suppressor tRNA can compete with release factors and read through the termination signal. Suppressor tRNA have a mutation in the anticodon sequence which allows stop codon recognition. For example, a supD mutation in E. coli changes the anticodon sequence of tRNA$^{Ser}$ from CGA to CUA, allowing it to recognize the UAG codon (Nucleic Acids Res. (1983) 11:3823-3832).

The ability of suppressor tRNAs to incorporate amino acids at stop codons allows for incorporation of up to three unnatural amino acids into a single protein using the traditional in vitro translation system (Nucleic Acids Res. (2004) 32:6200-6211).

In the current invention, in which aa-tRNAs are sequentially added and optionally cleared, multiple stop codons within a coding sequence can be used to arbitrarily incorporate multiple natural and unnatural amino acids.

Generation of aa-tRNA with Anti-Stop Codon

The anticodon of a naturally occurring tRNA, for example tRNA$^{Gln}$, can be modified to recognize a stop codon by site-directed mutagenesis. A cDNA construct containing the tRNA$^{Gln}$ sequence is generated using, for example, one of the methods described herein. Point mutations in the anticodon are generated using user-defined oligonucleotides of, for example, 20 bases and a commercially available site-directed mutagenesis kit (e.g. QuikChange® XL, Stratagene, La Jolla, Calif.). The natural anticodons of tRNA$^{Gln}$ are CUG and UUG at bases 34-36. Mutating, for example, G36 to A36 of CUG generates an anticodon that corresponds to the UAG stop codon.

Alternatively, modifications to the anticodon of tRNA$^{Gln}$ can be introduced using the two oligonucleotide primer strategy of Korencic et al. (Nucleic Acids Res. (2002) 30:105) as described in Example 6. The long primer is designed, for example, to include one or more point mutations that generate anti-stop codons in the anticodon sequence of a natural tRNA sequence.

Suppressor tRNA derived from, for example, tRNA$^{Gln}$, can be aminoacylated with a natural amino acid by either enzymatic or chemical methods as described herein or known in the art. Unnatural amino acids are added to suppressor tRNA by chemical aminoacylation as described herein or known in the art.

Because of the step-wise addition and optional clearance of aa-tRNAs in the invention, a single suppressor tRNA can be used for aminoacylation and incorporation of, for example, multiple natural and unnatural amino acids. Alternatively, the three individual suppressor tRNAs can all be aminoacylated with the same natural or unnatural amino acid.

Generation of Nucleic Acid Template

A nucleic acid template with multiple stop codons can be generated from a cDNA encoding a naturally occurring mRNA using established methods of site-directed mutagenesis. For example, a naturally occurring 3-base codon for phenylalanine UUU is replaced by the stop codon UAG at one or more sites within the cDNA, maintaining the appropriate reading frame. mRNA with one or more anticodon sites is generated by, for example, transcription run-off as previously described. Alternatively, nucleic acid sequence is generated de novo by a custom commercial service (e.g. Blue Heron Biotechnology, Bothell, Wash.) based on a user-defined sequence. For example, a template sequence can be generated that is composed entirely of alternating UAG, UAA, and UGA stop codons.

All three anti-stop codon aa-tRNAs can be charged with all of the canonical amino acids as well as with unnatural amino acids, depending upon placement in the amino acid sequence. This would allow, for example, incorporation of phenylalanine at the UAG, UAA, or UGA codons using, for example, Phe-tRNA$^{Phe}_{UAG}$, Phe-tRNA$^{Phe}_{UAA}$, or Phe-tRNA$^{Phe}_{UGA}$, respectively.

Translation Reaction

The nucleic acid template with one or more anticodon sequences is added to the ribosomal complex and translation initiated. Release factors may be omitted from the ribosomal complex to prevent premature termination at the engineered stop codons. Appropriate aa-tRNAs are added and optionally cleared sequentially from the reaction. When a stop codon is translocated into the A site of the ribosome, a suppressor aa-tRNA with the corresponding anti-stop codon is added to the reaction mix. The suppressor aa-tRNA incorporates a natural or unnatural amino acid at the site. Translation is terminated, for example, when the polypeptide of interest has been fully synthesized. The end of the coding sequence may correspond to one or more stop codons. At this point, release factors, for example RF1, RF2, and RF3, are added to the reaction mix to release the translation product from the ribosome.

Example 8

Synthesis of Polypeptides from a Nucleic Acid Template Using a Four-Base Codon/Anticodon Strategy with an Arbitrary aa-tRNA Generation of aa-tRNA with a Four-Base Anticodon Four-base codons on a nucleic acid template can be recognized by aa-tRNAs containing complementary four-base anticodons (e.g. Methods (2005) 36:270-278; Nucleic Acids Res. (2006) 34:1653-1662). User-defined tRNAs are specifically designed to contain an extra base in the anticodon loop, expanding the codon recognition from three to four bases. For example, the anticodon for phenylalanine is GAA at base pairs 34-36 of the human tRNA$^{Phe}$. Addition of an extra base, for example, a G between the As generates a four base anticodon GAGA corresponding to the codon UCUC.

A modified tRNA with a specified sequence in the anticodon region can be generated de novo using the protocols described herein. An alternative scheme for preparing a 4-base anticodon tRNA involves overlapping oligonucleotides and primer extension (Methods (2005) 36:270-278). A first primer spans half of the desired tRNA sequence and contains, for example, sequence for the T7 promoter at the 5' end. A second reverse primer spans the complementary sequence of the second half of the tRNA with sufficient overlap, for example 20 nucleotides, with the 3' end of the first oligonucleotide to facilitate annealing of the two oligonucleotides. The reverse primer contains the four base anticodon and variants of the anticodon can be obtained, for example, by modifying the design of the reverse primer.

Primer extension to generate a double stranded piece of DNA is carried out using PCR. The reaction mix contains 1 µM each of the two primers, 0.2 mM dNTPS and 25 U of Pfu DNA polymerase in 20 mM Tris-HCl (pH 8.8), 2 mM MgSO$_4$, 10 mM KCl, 10 mM (NH$_4$)$_2$SO$_4$, 0.1% Triton X-100, and 0.1 mg/ml nuclease free bovine serum albumin (BSA). Amplification is carried out using, for example, 20-30 cycles with a temperature program of 94° C. for 90 s, 55° C. for 2 s, and 72° C. for 30 s. The resulting double stranded piece of DNA contains a T7 promoter at the 5' end and the full sequence of the user-defined tRNA with the 4-base codon. The final tRNA is generated using transcription run-off with T7 polymerase as described above.

The resulting tRNA is extracted with phenol and chloroform, precipitated with ethanol and further purified by separation on a 10% denaturing polyacrylamide gel. The RNA on the gel is detected by UV shadowing, excised and extracted from the gel using 2 mM EDTA at room temperature overnight. After filtration to remove residual gel, the tRNA is again precipitated with ethanol. The resulting pellet is dissolved in water. Similar procedures have been used to generate tRNA with five-base anticodons as described by Hohsaka et al. (Nucleic Acids Res. (2001) 29:3646-3651)

Incorporation efficiency for different four-base anticodon sequences has been determined using a tRNA library with random mutations in the four-base anticodon (Biochemistry (2001) 40:11060-11064). Each tRNA is assessed for its ability to incorporate, for example, an unnatural amino acid such as fluorescently labeled p-nitrophenylalanine into a target translation product. A similar approach can be used to change the nucleotides adjacent to the 4-base anticodon in the anticodon loop to improve efficiency of amino acid incorporation as described by Taira et al. (Nucleic Acids Res. (2006) 34:1653-1662).

Chemical or enzymatic aminoacylation of the resulting tRNA with either natural or unnatural amino acids is carried out using the various techniques described herein or known in the art.

Nucleic Acid Template

The nucleic acid template for polypeptide synthesis using aa-tRNA with a four-base anticodon can be derived, for example, from modification of a natural mRNA. Site-specific base pair additions in the corresponding cDNA can be accomplished using user-defined primers and site-directed mutagenesis with, for example, a QuikChange® XL Site-Directed Mutagenesis Kit (Stratagene, La Jolla, Calif.) or similar kit from other commercial sources (e.g. Invitrogen, Carlsbad, Calif.). mRNA is generated from the modified cDNA using, for example, T7 polymerase and transcription run-off as described above. Similar methods can be used to generate five-base anticodons.

Alternatively, a user-defined nucleic acid template containing, for example, only 4-base or 5-base codons or a combination thereof with or with or without 3-base codons can be generated de novo using custom commercial services (e.g. Blue Heron Biotechnology, Bothell, Wash.).

Translation Reaction

The translation reaction is carried out to termination as described herein with sequential addition of each aa-tRNA, in which the aa-tRNA may have, for example, a 3-base, 4-base, or 5-base anticodon depending upon the corresponding nucleic acid template.

Example 9

Synthesis of Polypeptides by Sequential Addition of aa-tRNAs Using a Mitochondrial Translation System An in vitro translation system can be isolated from mitochondria as an alternative to the cytosolic ribosome complexes described herein.

For example, a reconstructed mitochondrial translation system can be isolated from yeast as described by Pfisterer and Buetow (Proc. Natl. Acad. Sci. (1981) 78:4917-4921). A culture of Saccharomyces carlsbergensis, for example, are grown to high density ($OD_{660}$ 12) and protoplasts formed by incubation with Glusulase in 1.2 M sorbitol, 10 mM Tris maleate (pH 5.7), 1 mM EDTA, and 0.1 M 2-mercaptoethanol for 30 minutes at 30° C. followed by centrifugation at 3000× g. The protoplasts are swollen for 20 minutes in 0.6 M sorbitol, 10 mM Tris maleate (pH 6.7) 1 mM EDTA, and 0.1% bovine serum albumin (BSA) and lysed using a French press at 3000 psi. The lysate is centrifuged for 10 min at 1500×g and the resulting supernatant further centrifuged at 13,000×g for 10 minutes. The pellet is washed and resuspended in 50 mM NH4Cl, 10 mM Mg acetate, 10 mM Tris HCl (pH 7.5), and 5 mM 2-mercaptoethanol. Mitochondria are lysed by addition of 5% sodium deoxycholate and rapid pipetting. The lysate is first centrifuged for 10 minutes at 18,000×g and then layered on top of a 1.5 M sucrose gradient and centrifuged for 16 hr at 120,000×g. The supernatant is saved and contains components necessary for efficient translation (Proc. Natl. Acad. Sci. (1981) 78:4917-4921). Endogenous mitochondrial tRNAs can be removed by running the supernatant over a DEAE-cellulose column (Proc. Natl. Acad. Sci. (1981) 78:4917-4921). The ribosome pellet is resuspended in 40 mM Tris HCl (pH 7.8), 10 mM Mg acetate, 30 mM NH4Cl, 5 mM 2-mercaptoethanol, 1 mM ATP, 8 mM creatine phosphate with 1.6 µg creatine phosphokinase and 20 µM GTP. To this is added the tRNA depleted supernatant in preparation for translation.

Alternatively, mitochondrial ribosomes can be isolated from rat livers and used for in vitro translation as described, for example, by Ulbrich et al. (Eur. J. Biochem. (1980) 108: 337-343. The mitochondrial ribosomes are prepared using a 1.5 M sucrose gradient and the combination of supernatant and ribosome pellet are necessary for efficient translation. As with the yeast system described above, endogenous mitochondrial tRNAs can be removed from the mammalian system by running the supernatant over a DEAE-cellulose column.

Aminoacylated tRNAs are generated as described here in. Alternatively, mitochondrial tRNAs can be used in the mitochondrial translation system. There are 22 mitochondrial tRNAs in human and other mammalian mitochondria. The nucleic acid sequence of these tRNAs can be found in public databases (e.g. available at //mamit-trna.u-strasbg.fr/). This sequence information is used to generate natural and unnatural mitochondrial tRNA using the molecular biology techniques described herein and known in the art. The mitochondrial tRNAs are aminoacylated using the methods described herein or known in the art.

A natural or user-defined nucleic acid sequence is used as the template for translation. Poly(U) mRNA, for example, has been successfully translated to polyphenylalanine using in vitro mitochondrial translation systems from yeast and rat liver (J. Biol. Chem. (1974) 249:6806-6811; Eur. J. Biochem. (1980) 108:337-343; Proc. Natl. Acad. Sci. (1981) 78:4917-4721).

Translation proceeds in the reaction chamber using the mitochondrial ribosomes and one or more of the methods for sequential combination with natural or unnatural aa-tRNAs as described herein.

Example 10

Peptide Synthesizing Apparatus

Figure 24:
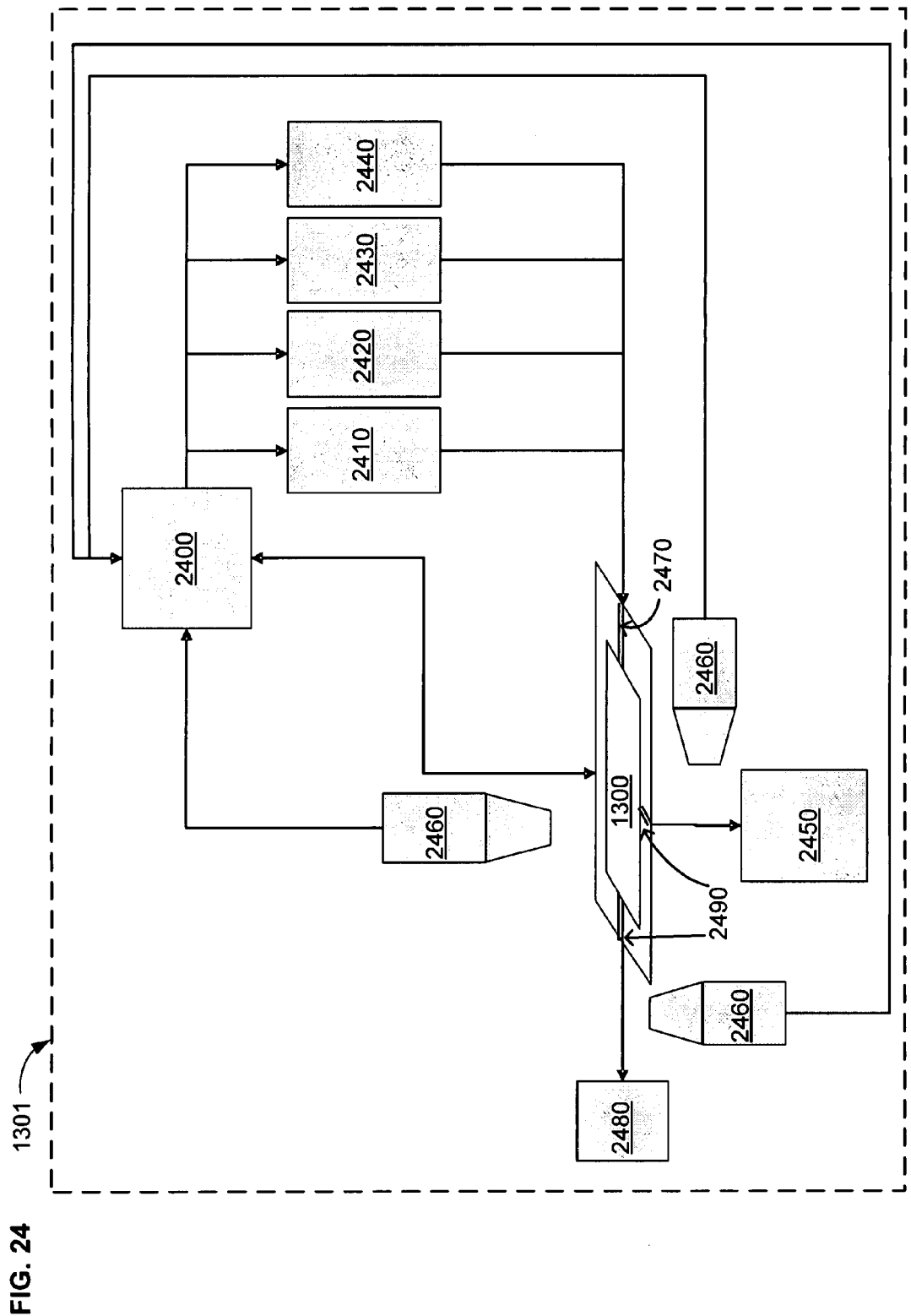
FIG. 24 shows a schematic of an illustrative apparatus for biologically synthesizing peptides.

FIG. 24 shows a schematic of an apparatus 1301 (e.g. optionally the same as apparatus 410 shown in FIG. 1) for biologically synthesizing peptides, optionally including, for example, a reaction chamber 1300 (e.g. optionally the same as one or more peptide synthesizer units 420 shown in FIG. 1) connected to one or more reservoirs 2410, 2420, 2430, 2440, 2450, 2480 (e.g. optionally the same as one or more sourcing units 432 shown in FIG. 1), and where the synthesis is optionally monitored by one or more detectors 2460 (e.g. optionally the same as one or more monitoring units 440 shown in FIG. 1), and controlled by control circuitry (e.g. optionally the same as one or more controller units 422 and/or one or more computing units 426 shown in FIG. 1).

The reservoirs 2410, 2420, 2430, 2440, 2450, 2480 optionally include, for example, a reservoir 2410 for ribosomes and initiation components, a reservoir 2420 for buffers, a reservoir 2430 for aa-tRNAs, a reservoir 2440 for termination components, a reservoir 2450 for waste, and a reservoir 2480 for translation product, among others. One or more detectors 2460 may monitor reactions within the reaction chamber 1300, as well as materials flowing to the waste reservoir 2450 or the translation product reservoir 2480, among others. Another part of the apparatus may include control circuitry 2400 for all or part of the process for peptide synthesis described herein, and optionally including the translation process, for example.

The reaction chamber 1300 may have one or more input ports 2470 to accommodate addition of reaction components, including components from one or more reservoirs, and one or more output ports 2490 to eliminate waste and to recover translation product, for example. The reaction chamber may contain a sensor such as a biosensor or a photodiode. Accordingly, detectors 2460 may include fluorescence detectors, among others. The reaction chamber 1300 optionally includes a mechanism for controlling fluid temperature, flow rate, and reaction component mixing. Fluids and/or reaction components are moved through the system, for example, via diffusion, capillary action, centrifugal force, electromotive force, magnetic field, or a pump, among others.

Figure 25:
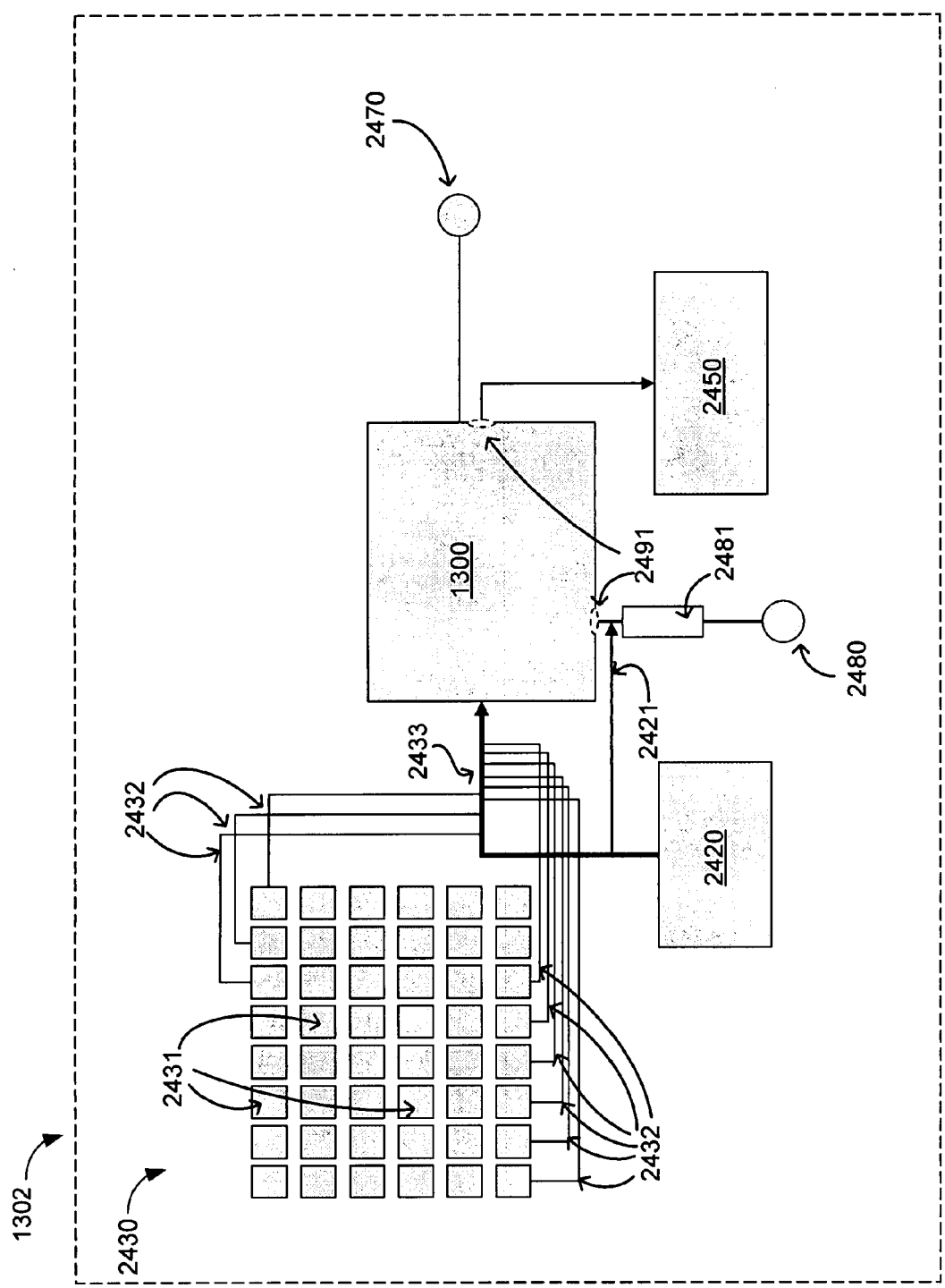
FIG. 25 shows a schematic of an illustrative embodiment of the illustrative apparatus of FIG. 24, including an illustrative example of a microchip as part of the reaction chamber.

The reaction chamber 1300 may be part of a microchip (see, e.g. microchip 1302 in FIG. 25). Solid substrates for the microchip include, for example, glass (e.g., functionalized glass, a glass slide, porous silicate glass, a single crystal silicon, quartz, UV-transparent quartz), plastics and polymers (e.g., polystyrene, polypropylene, polyvinylidene difluoride, poly-tetrafluoroethylene, polycarbonate, PDMS, acrylic), metal coated substrates (e.g., gold), silicon substrates, latex, membranes (e.g., nitrocellulose, nylon), or a glass slide suitable for surface plasmon resonance (Annu. Rev. Biomed. Eng. (2002) 4:261-286). The surface of the microchip can be modified to facilitate the stable attachment of linkers, capture probes, or binding agents, for example. A surface can be amidated by treating the substrate aminosilane, for example. Silane-treated surfaces can be further derivatized with homobifunctional and heterobifunctional linkers. The substrate can be derivatized, for example, so it has a hydroxy, an amino or carboxyl group, N-hydroxy-succinimidyl ester, photoactivatable group, sulfhydryl, ketone, or other functional group available for reaction (see, e.g. U.S. Pat. No. 6,846,638, US 2005/0260653B1).

Figure 28:
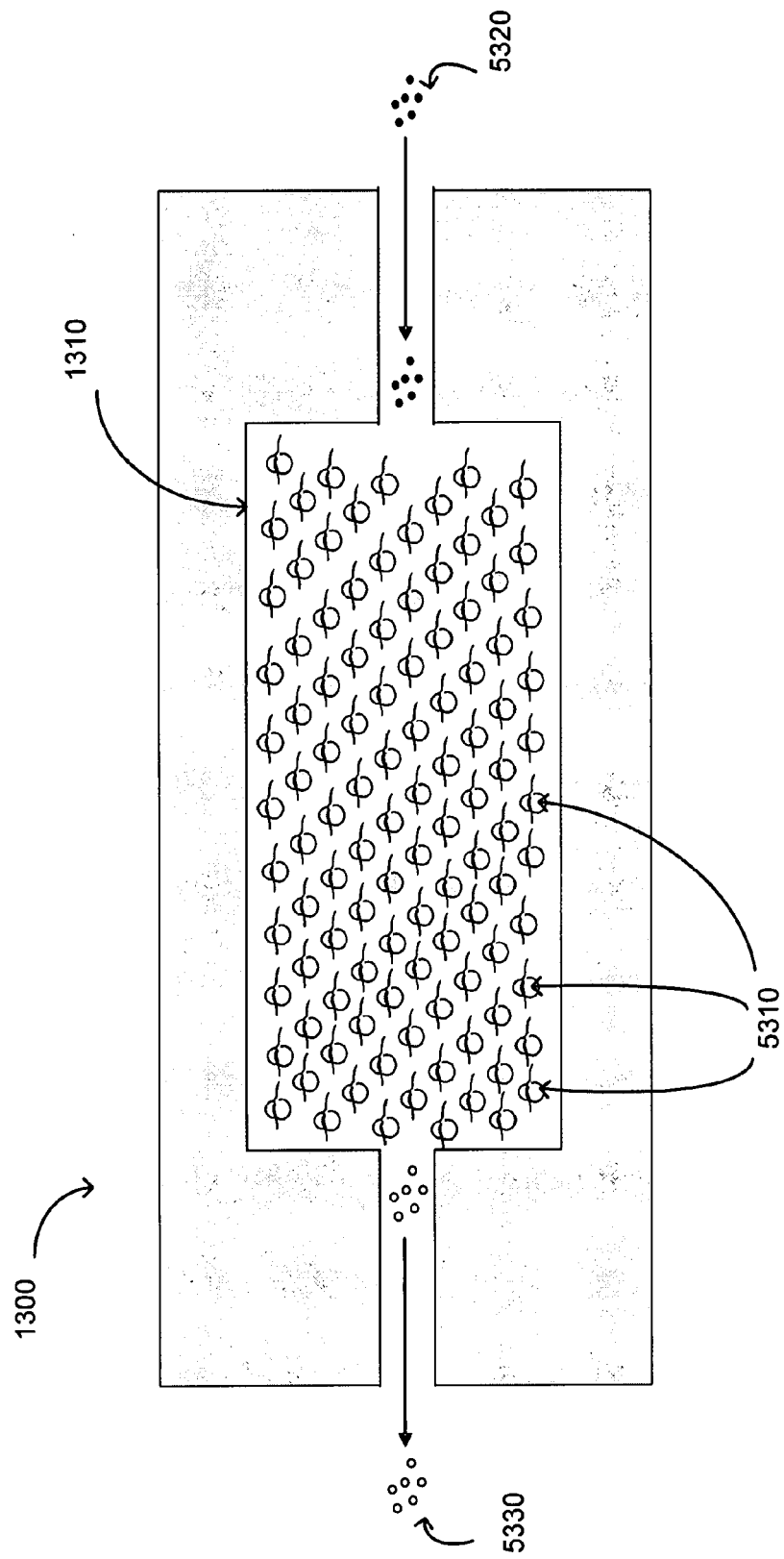
FIG. 28 shows a schematic of an illustrative embodiment of the illustrative apparatus of FIG. 24, including an illustrative example of a reaction chamber.

The reaction chamber 1300 may be a single chamber with a square, rectangular, circular or oval surface configuration, for example (see, e.g. FIG. 25, FIG. 28). The reaction chamber 1300 may also include a series of channels, for example, in a linear, serpentine, or spiral configuration (see, e.g. FIG. 29, FIG. 30, FIG. 31, FIG. 32, FIG. 33, FIG. 35), or it may have a central channel with one or more side channels (see, e.g. FIG. 34, FIG. 36, FIG. 37). In some configurations, the reaction chamber may be composed of multiple layers of chambers and/or channels, connected by additional channels, allowing components and/or fluids to move on multiple planes (see, e.g. FIG. 32, FIG. 38). Although typically described herein in the singular, reaction chambers 1300 may be run in multiples depending on the desired throughput and connected serially or in parallel, for example. Reaction chambers 1300 my also be scaled up and/or scaled down depending on the desired implementation.

Chambers and/or channels may be fabricated into the solid substrate of the reaction chamber using methods known in the art, for example, micromachining, lithography, embossing, in situ construction, injection molding and laser ablation (see, e.g. Annu. Rev. Biomed. Eng. (2002) 4:261-286). Alternatively, elastomeric nanochannels may be used, for example (see, e.g. Nature Materials (2007) 6:424-428).

FIG. 25, FIG. 26, FIG. 27, and FIG. 36 show schematic representations of illustrative configurations of at least part of one or more apparatus 410 for biologically synthesizing peptides.

FIG. 25 shows a schematic of an illustrative configuration of at least part of an apparatus 1301 in which a microchip 1302 optionally contains an array of aa-tRNA reservoirs 2430 connected to a reaction chamber 1300 by a series of microfabricated channels 2432. In one configuration, for example, individual aa-tRNA reservoirs 2431 are aligned in a grid with channels 2432 converging on a central channel 2433 which inputs into the reaction chamber 1300. A wash reservoir 2420 may also converge on this central input channel 2433 and may be used to flush the central channel as well as the reaction chamber 1300 after each aa-tRNA addition, for example. Waste from each cycle exits through a separate output channel to a waste reservoir 2450. Ribosomes are added via an injection port 2470 and the final translation product exits through an output port 2480. The reaction chamber 1300 may have optional size exclusion membranes 2491 that allow outflow of deacylated tRNA and excess aa-tRNA, for example, but not the ribosomal complexes. The translation outflow port 2480 may have an optional affinity chromatography matrix 2481, for example nickel or cobalt, that allows for purification of the translation product as described herein and/or known in the art. An optional channel 2421 provides buffers or other components to the chromatography matrix.

Figure 26:
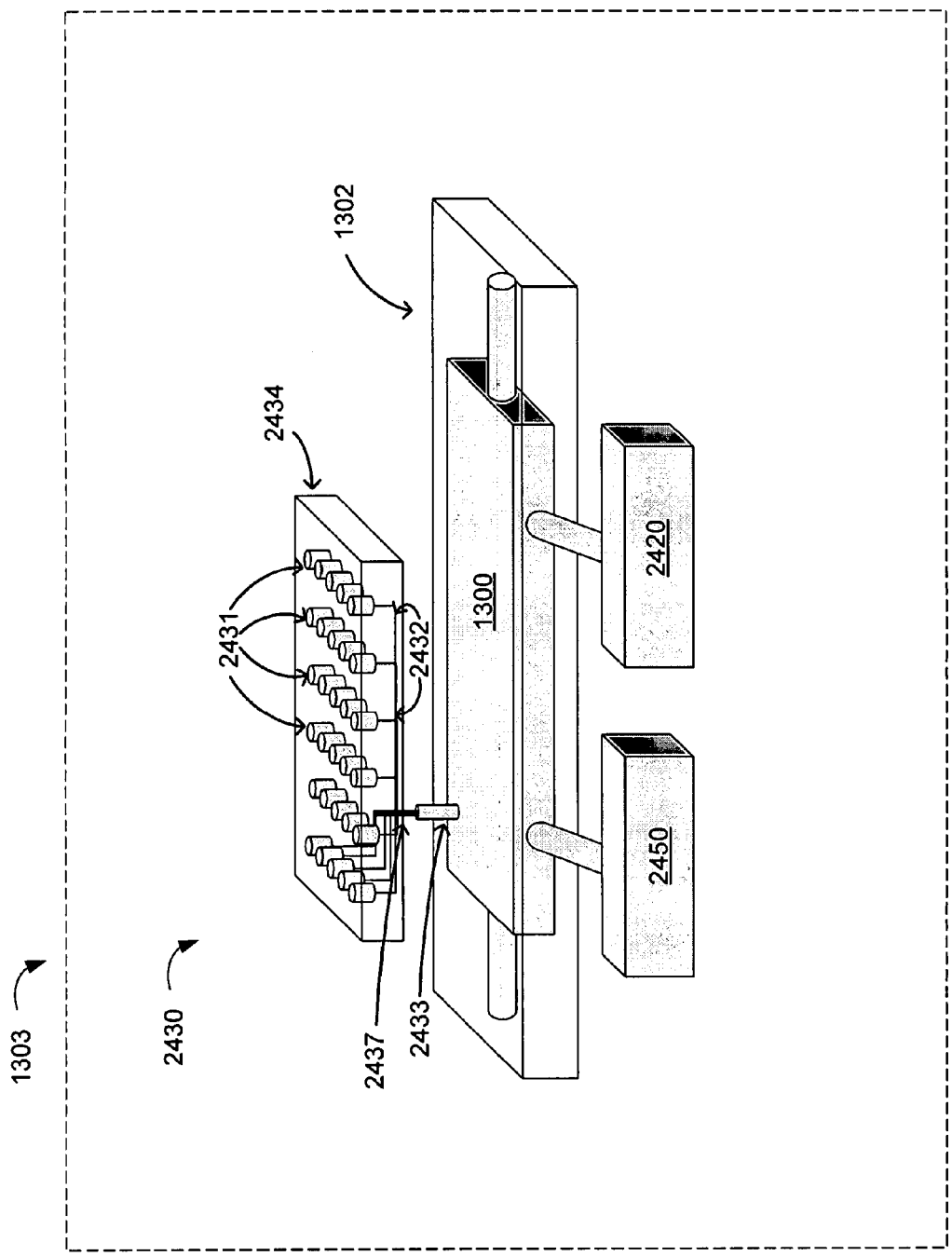
FIG. 26 shows a schematic of an illustrative embodiment of the illustrative apparatus of FIG. 24, including an illustrative example of a dispensing unit.

FIG. 26 shows a schematic of an illustrative configuration of at least part of an apparatus 1303 in which the aa-tRNAs are sourced from a reservoir 2430 external to an optional microchip 1302 containing the reaction chamber 1300, and optionally including one or more reservoirs such as, but not limited to, reservoir 2450 for waste and reservoir 2420 for buffers. In one configuration, the aa-tRNA reservoir 2430 is, for example, a multiwell plate 2434.

In some configurations, the multiwell plate 2434 is directly and optionally fixedly connected to an input channel 2433 on the reaction chamber 1300 through a main channel 2437 that is fed by channels 2432 running from each aa-tRNA reservoir 2431. In some configurations, the channels 2432 running from each aa-tRNA reservoir 2431 are directly connected and optionally fixedly connected to the reaction chamber 1300 (not shown).

In some configurations, the reaction chamber 1300 may move relative to the multiwell plate 2434 and/or the multiwell plate 2434 may move relative to the reaction chamber 1300 (not shown). In this case, each of the channels 2432 running from each aa-tRNA reservoir 2431 include an optional output port (not shown) that can be aligned with the input channel 2433 on the reaction chamber 1300, as appropriate, by movement of either or both of the reaction chamber 1300 and the multiwell plate 2434.

Figure 27:
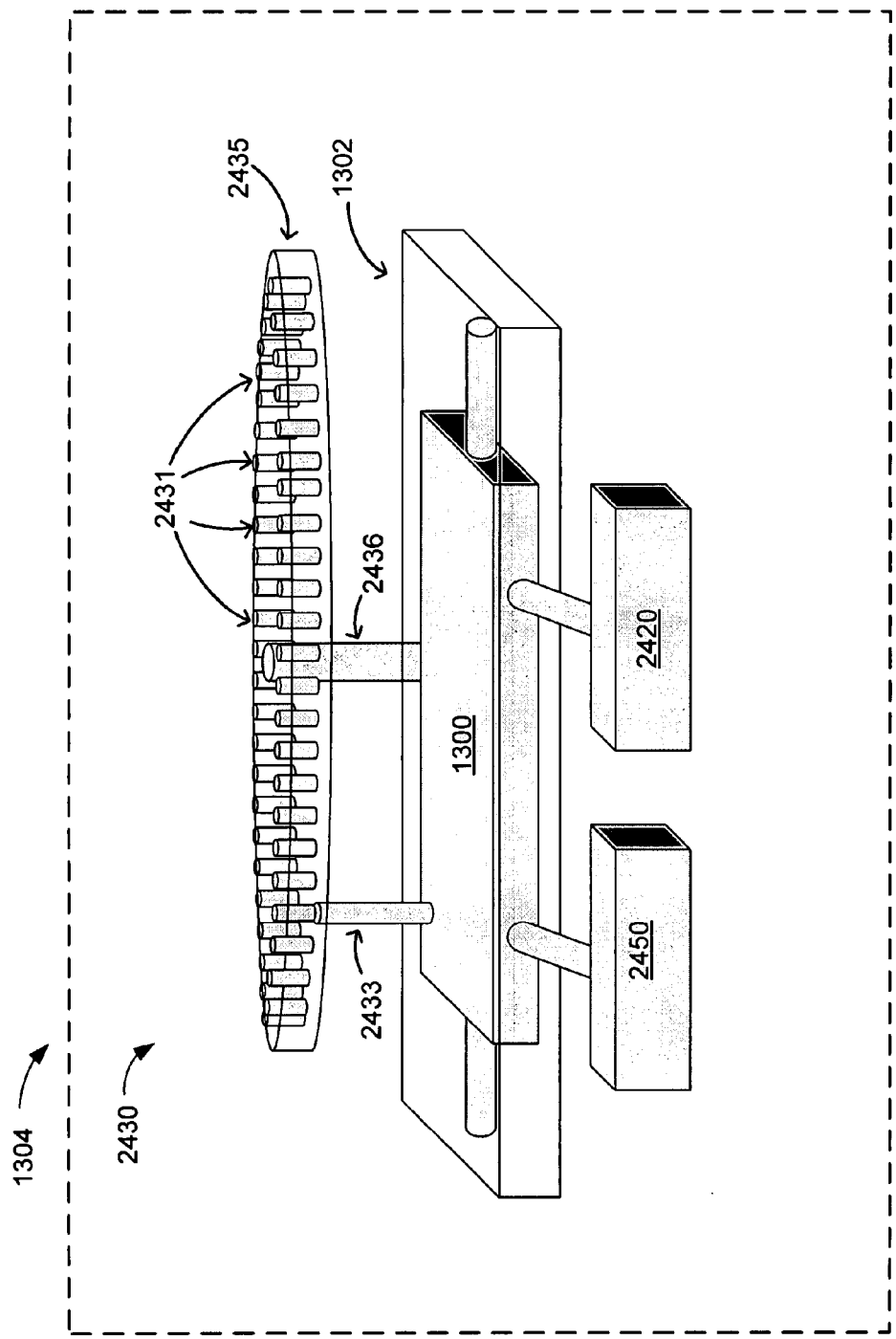
FIG. 27 shows a schematic of an illustrative embodiment of the illustrative apparatus of FIG. 24, including an illustrative example of a dispensing unit.

FIG. 27 shows a schematic of an illustrative configuration of at least part of an apparatus 1304 in which the aa-tRNAs are sourced from a reservoir 2430 external to an optional microchip 1302 containing the reaction chamber 1300, and optionally including one or more reservoirs such as, but not limited to, reservoir 2450 for waste and reservoir 2420 for buffers. In one configuration, the aa-tRNA reservoir 2430 is, for example, a disk 2435. In some configurations, the reservoirs 2431 containing aa-tRNAs are optionally arrayed on the perimeter of the disc 2435. The disc 2435 is optionally rotated back and forth around a fixed central core 2436 to align the appropriate aa-tRNA reservoir 2431 with an input channel 2433 of the reaction chamber 1300.

Figure 29:
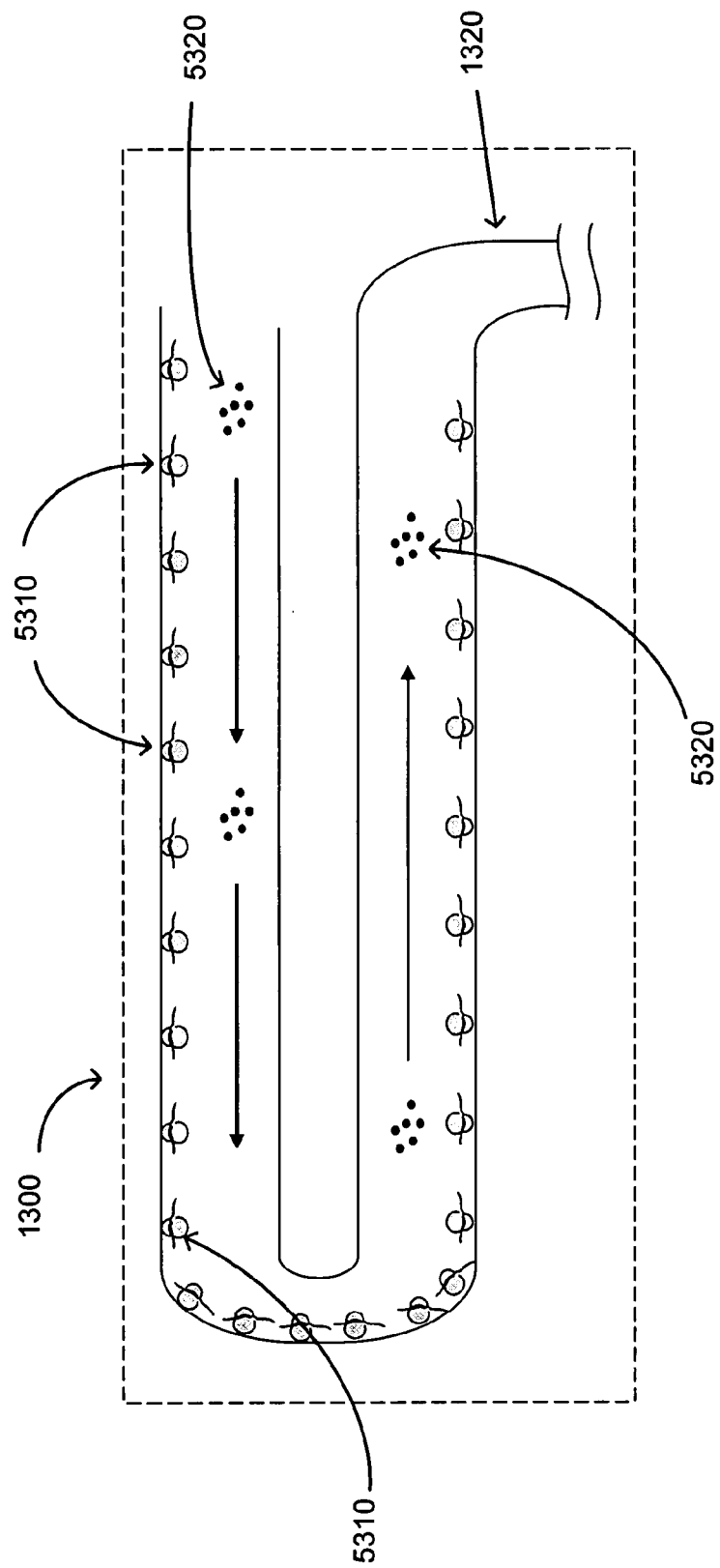
FIG. 29 shows a schematic of an illustrative embodiment of the illustrative apparatus of FIG. 24, including an illustrative example of a reaction chamber.
Figure 30:
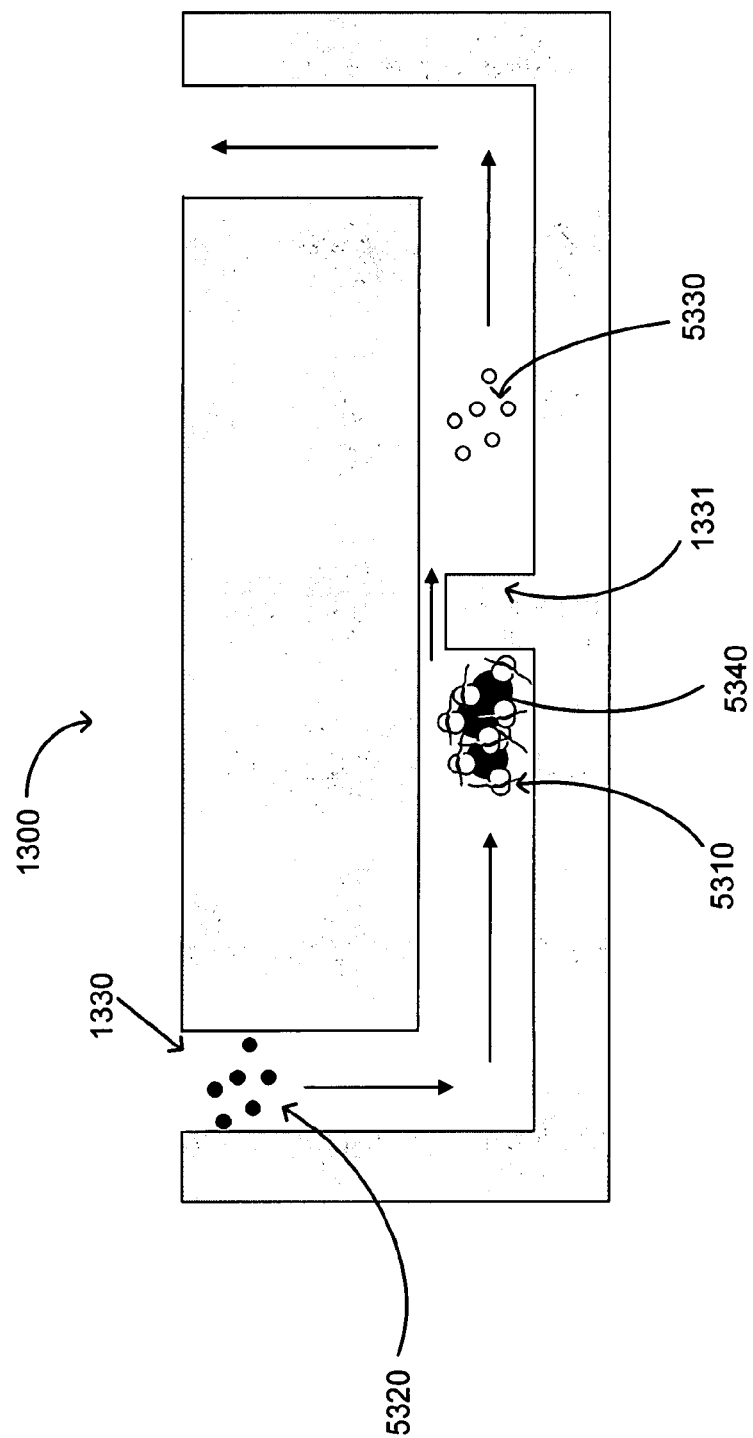
FIG. 30 shows a schematic of an illustrative embodiment of the illustrative apparatus of FIG. 24, including an illustrative example of a reaction chamber.

FIG. 28, FIG. 29, and FIG. 30 show schematic representations of illustrative configurations of reaction chambers 1300 that are optionally part of one or more apparatus 410 for biologically synthesizing peptides. Although the reaction chambers 1300 are illustratively described for use in one or more of the methods described herein in which the ribosomes 5310 are fixed in space while the aa-tRNAs 5320 are free flowing, they are optionally useful for one or more of the other methods described herein as well.

Ribosomes can be attached to a surface, for example, via a biotin/streptavidin interaction as described herein and/or known in the art (see, e.g. Biosensors & Bioelectronics (2001) 16:745-755). For example, a silicon surface of the reaction chamber 1300 may be treated with an aminosilane reagent, such as 3-aminopropyltriethoxysilane using standard procedures (e.g. Tech Tip #5, Pierce, Rockford, Ill.). The silanized silica is subsequently coated with sulfo-NHS-biotin as described herein and/or known in the art. Streptavidin is then added as the final layer. In one configuration, the ribosomes, biotinylated via the associated mRNA, are affixed by injection into the input channel 2433 and binding to the streptavidin modified surface of the reaction chamber 1300.

FIG. 28 shows a schematic representation of an illustrative configuration of a reaction chamber 1300 composed of a single chamber 1310. Ribosomes 5310 are attached to the surface of the chamber 1310 optionally after initiation via a streptavidin/biotin interaction. The aa-tRNAs 5320 are added sequentially, incubated with the ribosomes 5310 for a defined or variable interval as determined using methods described herein, including, for example, as determined by control circuitry 2400. After incubation, the deacylated tRNAs 5330, among other components, are washed from the reaction chamber 1300.

FIG. 29 shows a schematic representation of an illustrative configuration of a reaction chamber 1300 in which ribosomes 5310 are attached to the surface of a continuous serpentine channel 1320. The aa-tRNAs 5320 enter one end of the channel and pass by the immobilized ribosomes 5310. The continuous channel may be a variety of shapes including, for example, linear or spiral, among others.

FIG. 30 shows a schematic representation of an illustrative configuration of a reaction chamber 1300 designed for protein synthesis using ribosomes 5310 fixed to beads 5340, for example, and fixed in space by size exclusion. The reaction chamber 1300 may be constructed from, for example, a quartz glass (fused quartz, fused silica) plate into which a channel 1330 has been cut with an intervening dam 1331 that allows for fluid flow but limits particle flow, as described in Sato et al. (Anal. Chem. (2000) 72:1144-1147). Beads 5340 with attached ribosomes 5310 as well as free aa-tRNA 5320 are injected into one side of the channel 1330 and as fluid flows through the channel, the beads become restricted at the dam 1331, while the deacylated tRNA 5330 pass beyond the dam 1331. Reversing the fluid flow allows the used beads to be flushed from the system.

The reaction chamber 1300 may be composed of three quartz glass plates (cover, middle, bottom) with thicknesses, for example, of 170 µm, 100 µm and 1 mm respectively. Two access holes of 0.5 mm diameter for an inlet and an outlet are bored on the cover glass. Two deep channels, for example, in line with one another and separated by, for example, 3 mm are etched into the middle plate with a $CO_2$ laser beam. The middle plate is attached to the bottom plate by fusing the optically-smooth surfaces at 1150° C., creating a two part reaction chamber 100 µm in depth separated by a 3 mm thick dam. Additional etching is used to shave 10 µm off the top of the dam, allowing for flow of fluid between the two reaction chambers. A similar microchip device can be made using photolithography and wet etching as described by Sato et al. (Lab. Chip. (2004) 4:570-575). Small microspheres pre-coated, for example, with avidin, streptavidin, or biotin are commercially available (e.g. Luminex, Pierce, Polyscience Inc.). Ribosomes are attached to the microspheres, for example, using a biotinylated mRNA as described herein and/or known in the art.

Figure 31:
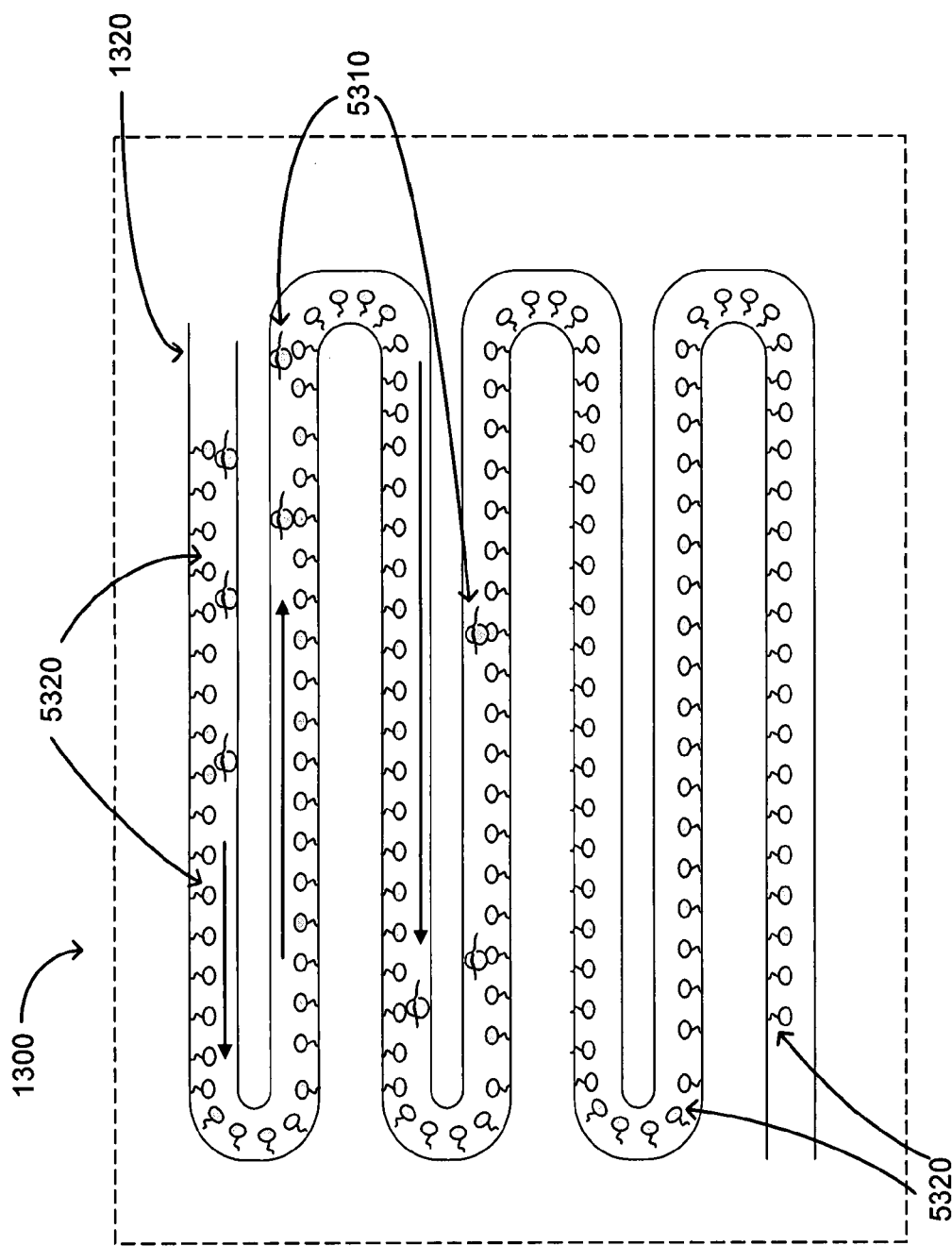
FIG. 31 shows a schematic of an illustrative embodiment of the illustrative apparatus of FIG. 24, including an illustrative example of a reaction chamber.
Figure 32:
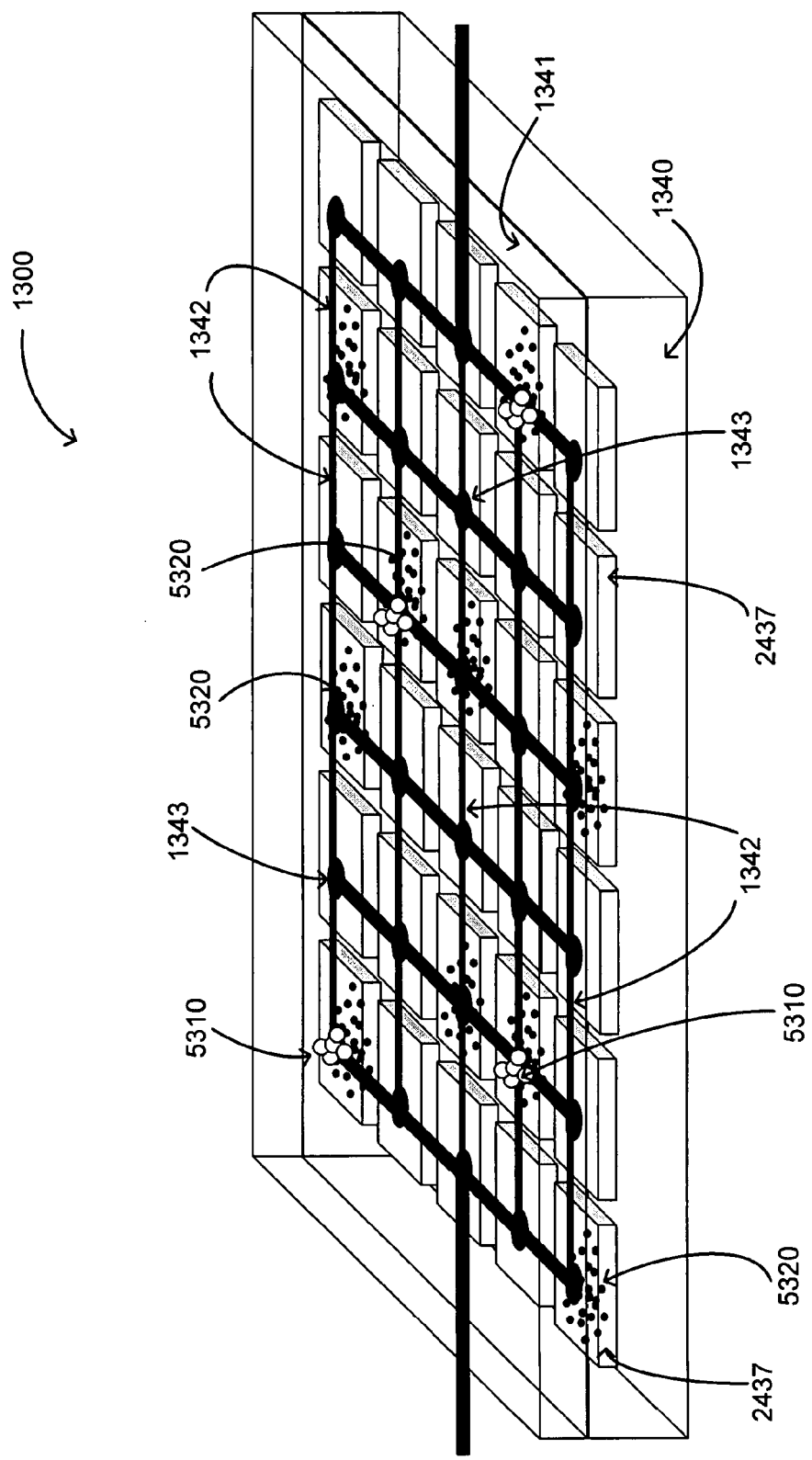
FIG. 32 shows a schematic of an illustrative embodiment of the illustrative apparatus of FIG. 24, including an illustrative example of a reaction chamber.

FIG. 31 and FIG. 32 show schematic representations of illustrative configurations of reaction chambers 1300 that are optionally part of one or more apparatus 410 for biologically synthesizing peptides. Although the reaction chambers 1300 are illustratively described for use in one or more of the methods described herein in which the aa-tRNAs 5320 are tethered to a surface while the ribosomes 5310 are free flowing, they are optionally useful for one or more of the other methods described herein as well.

FIG. 31 shows a schematic representation of an illustrative configuration of a reaction chamber 1300 in which the aa-tRNAs 5320 are attached to the surface of a channel 1320 with a serpentine configuration. Ribosome complexes 5310 pass through the channel 1320, interacting with the tethered aa-tRNA 5320. The aa-tRNA 5320 are optionally tethered in the order required for target peptide synthesis.

FIG. 32 shows a schematic representation of an illustrative configuration of a reaction chamber 1300 in which the specific aa-tRNAs 5320 are tethered in discrete wells 2437 of a multiwell plate 1340. An upper chamber 1341 above the multiwell plate 1340 has a grid of channels 1342 with openings 1343 down to each discrete well 2437. The ribosomes 5310 are attached to magnetic beads, for example, as described herein and/or known in the art. The beads are moved along the channels 1342 of the grid by magnetic force. The beads are directed to the next aa-tRNA in the target peptide sequence optionally using control circuitry 2400, and dropped into the well. After a defined or variable time interval, as described herein, magnetic force may be used to lift the beads out of the well and to move the beads along the grid to the next appropriate well. Tethered aa-tRNAs may be replenished, for example, by swapping out exhausted wells 2437. In some configurations, the specific aa-tRNAs 5320 are free in solution in each discrete well 2437, and are replenished by adding more aa-tRNA 5320 to the well from an optional external reservoir.

FIG. 33, FIG. 34, FIG. 35, FIG. 36, FIG. 37, and FIG. 38 show schematic representations of illustrative configurations of reaction chambers 1300 that are optionally part of one or more apparatus 410 for biologically synthesizing peptides. Although the reaction chambers 1300 are illustratively described for use in one or more of the methods described herein in which the ribosomes 5310 and the aa-tRNAs 5320 are both free in solution, encapsulated in aqueous bubbles, or attached to movable microspheres, the reaction chambers are optionally useful for one or more of the other methods described herein as well. The reaction chamber 1300 may be a continuous channel optionally linear, serpentine, square, and/or spiral (among others) in configuration, optionally with multiple side channels through which ribosomes 5310 and/or aa-tRNAs 5320 flow.

Figure 33:
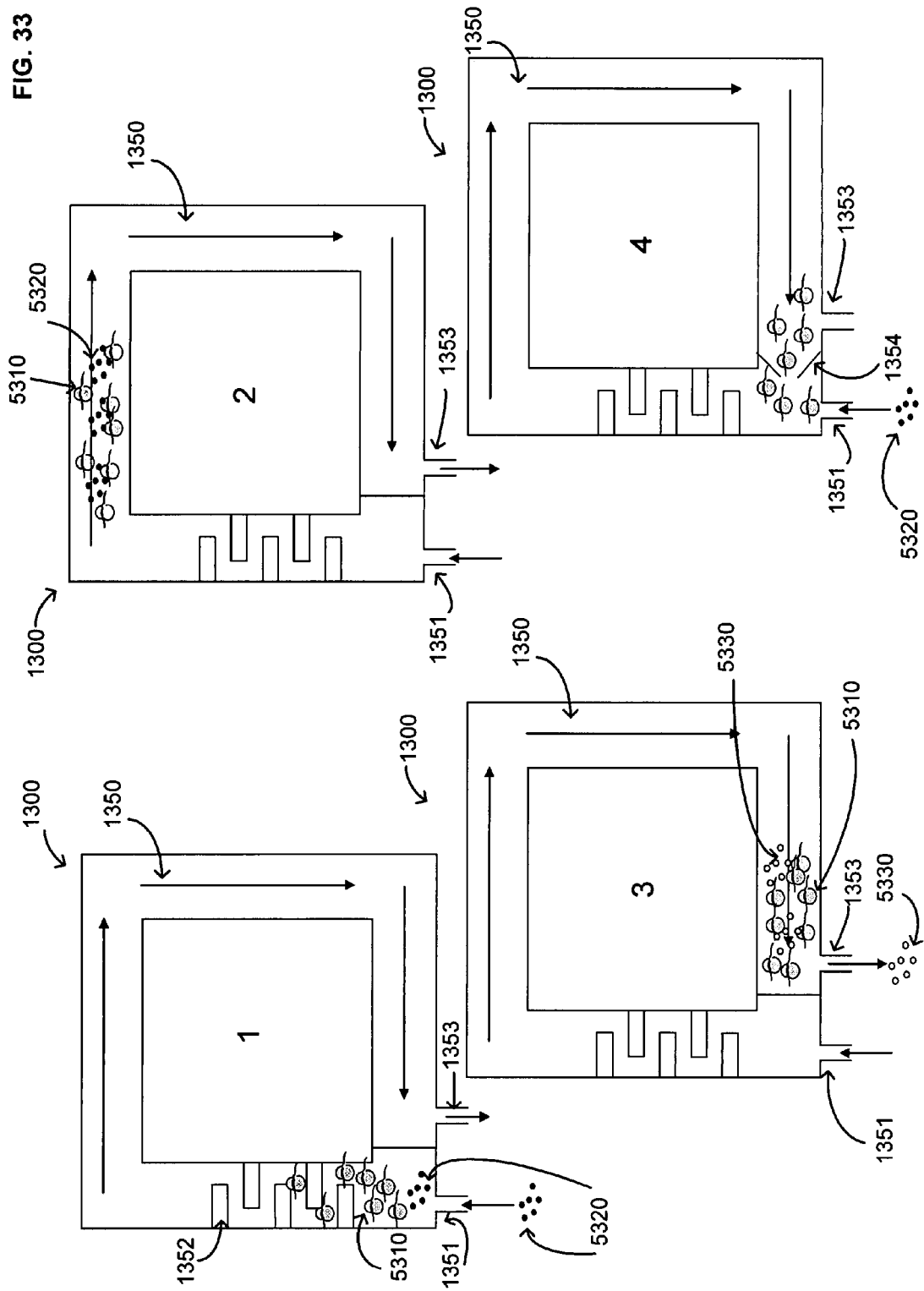
FIG. 33 shows a schematic of an illustrative embodiment of the illustrative apparatus of FIG. 24, including an illustrative example of a reaction chamber.

FIG. 33 shows a schematic representation of an illustrative configuration of a reaction chamber 1300 at four different stages during an illustrative round of peptide synthesis. The reaction chamber 1300 includes a channel 1350 optionally configured in a square (or, for example, an oval or circle (not shown)). In the reaction chamber 1300, an input port 1351 allows for addition of reagents and components, including aa-tRNA 5320. The output port 1353 allows for removal of waste, deacylated tRNAs 5330, and retrieval of the translation product, among other components.

The numbered diagrams (1, 2, 3, 4) indicate the progressive movement of ribosomes 5310 and aa-tRNA 5320 during a round of peptide synthesis. In Part 1, ribosomes 5310, either free or attached to beads, for example, are loaded into the channel 1350. Specific aa-tRNAs 5320 are added in an appropriate sequence through the input port 1351, and the ribosomes 5310 and aa-tRNAs 5320 flow through a mixer 1352 consisting of obstructions to the flow of buffer. In Part 2, the ribosomes 5310 and aa-tRNAs 5320 travel along the channel 1350 for a specified or variable time interval defined by methods described herein optionally including using control circuitry 2400. In Part 3, the ribosomes 5310 with associated nascent polypeptide chain and deacylated tRNAs 5330 reach the output port 1353. The ribosomes are excluded from passage through the output port 1353 by size exclusion, either because of the size of the ribosome complex 5310 alone or because of the size of an associated bead, for example. The deacylated tRNAs 5330 pass out of the reaction chamber 1300 through the output port 1353. In Part 4, a valve 1354 is opened which allows the ribosomes 5310 to return to the start of the channel, whereupon the next aa-tRNAs 5320 are encountered. The cycle is repeated until translation is complete.

Figure 34:
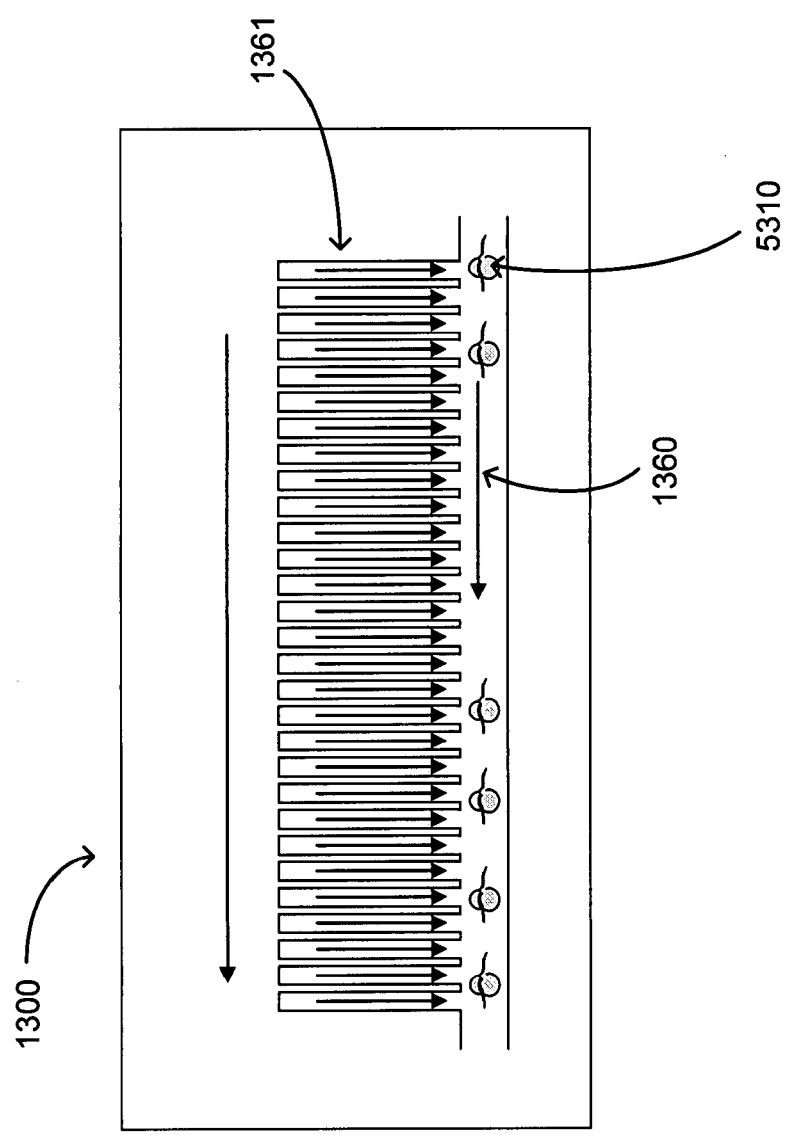
FIG. 34 shows a schematic of an illustrative embodiment of the illustrative apparatus of FIG. 24, including an illustrative example of a reaction chamber.

FIG. 34 shows a schematic representation of an illustrative configuration of a reaction chamber 1300 in which the main channel 1360 is linear with multiple side channels 1361. The number of side channels 1361 may be higher or lower than the 29 shown depending on the target peptide to be sequenced, among other considerations. The channel is optionally looped, so that the ribosomes 5310 pass the same side channels 1361 multiple times.

Each side channel 1361 is optionally sourced with one type of aa-tRNA 5320 at a given time. The aa-tRNAs 5320 are optionally loaded into the multiple side channels in the same sequence as the desired coding sequence, or are optionally loaded in a set sequence, but then released in the correct order as the ribosomes 5310 approach. The ribosome complex 5310, preinitiated with nucleic acid is injected into one end of the continuous channel. The complex flows through the main channel 1360, spending a defined or variable interval optionally determined by control circuitry 2400 at appropriate side channels 1361 in association with appropriate aa-tRNA 5320.

Figure 35:
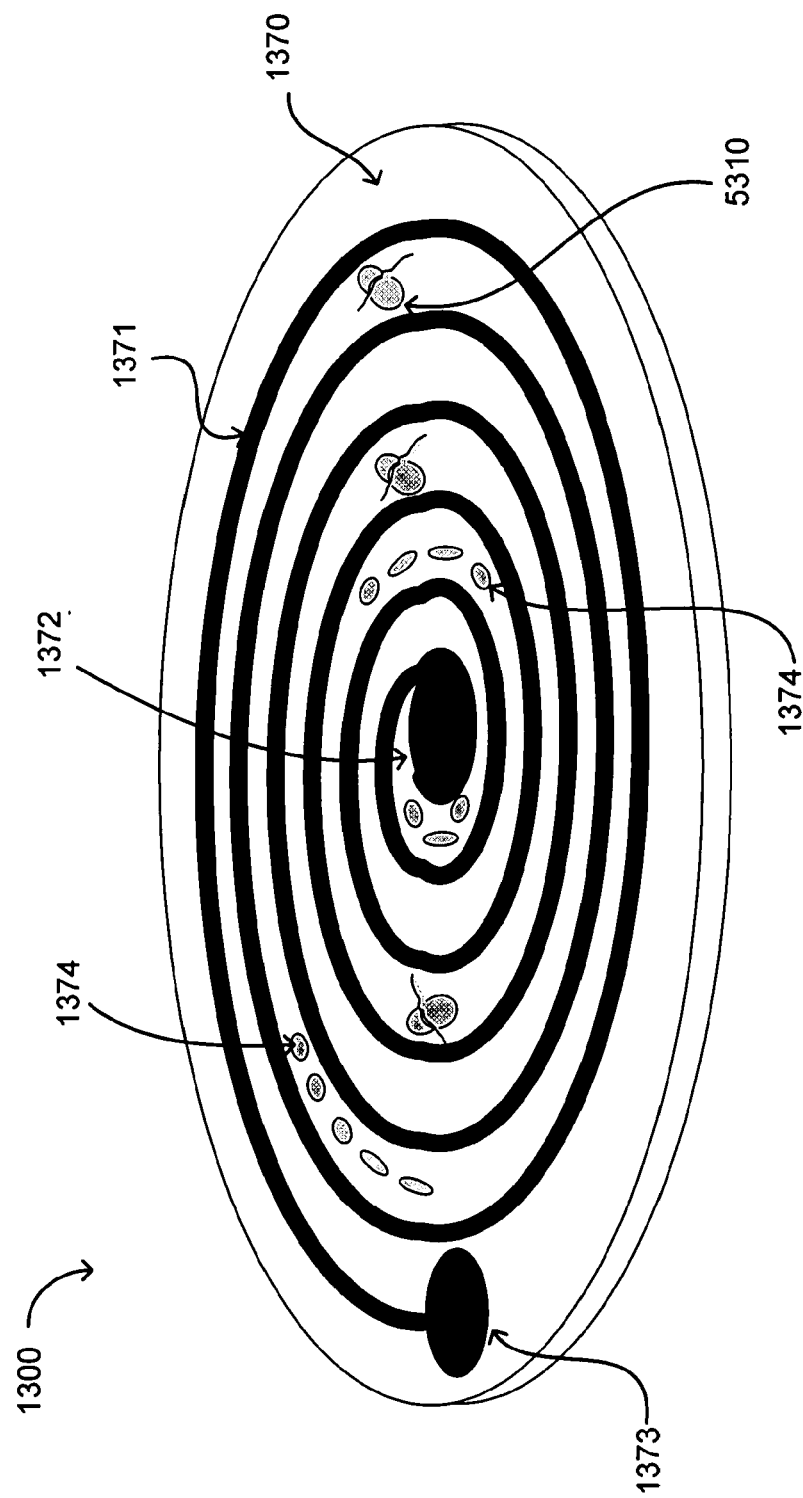
FIG. 35 shows a schematic of an illustrative embodiment of the illustrative apparatus of FIG. 24, including an illustrative example of a reaction chamber.

FIG. 35 shows a schematic representation of an illustrative configuration of a reaction chamber 1300 in which the reaction chamber 1300 is a disc 1370 (e.g. a CD) into which a spiral channel 1371 has been etched. Ribosomes 5310 are loaded into the channel 1371 at a central input 1372. The ribosomes 5310 move down the channel by, for example, centrifugal force. Multiple side channels 1374 are optionally pre-loaded with aa-tRNA 5320 in a target sequence or are optionally attached to multiple sources of aa-tRNA 5320 that can optionally be released according to control-circuitry 2400. As the ribosomes move past the side channels 1374 aa-tRNA 5320 are optionally released in a target sequence for incorporation into the nascent polypeptide which may be accessed at an outlet port 1373 at the termination of the spiral.

Figure 36:
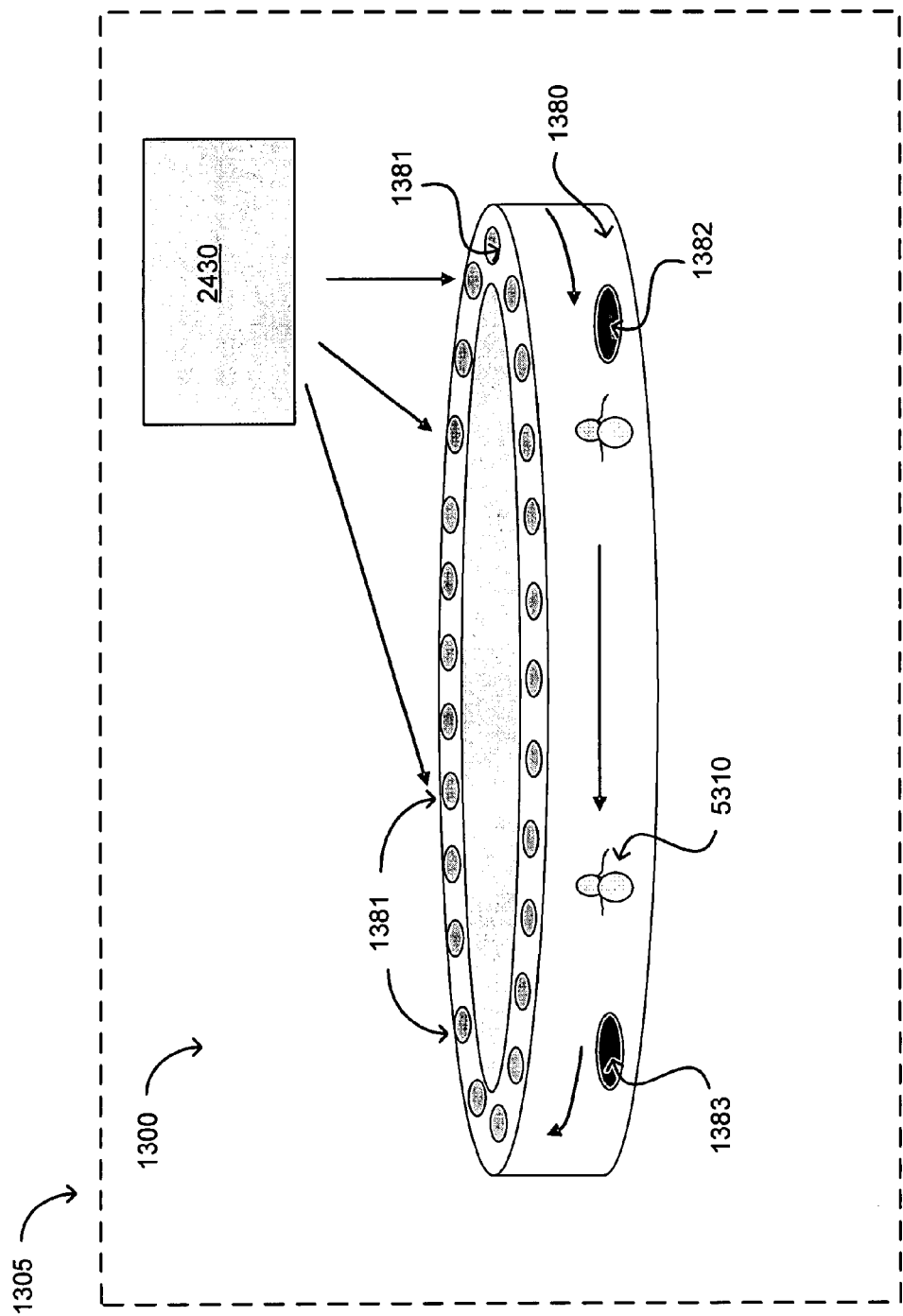
FIG. 36 shows a schematic of an illustrative embodiment of the illustrative apparatus of FIG. 24, including an illustrative example of a dispensing unit.

FIG. 36 shows a schematic representation of an illustrative configuration of at least part of one or more apparatus 410 for biologically synthesizing peptides, including a reaction chamber 1300 and a reservoir 2430. The reaction chamber 1300 is a circular channel 1380 with multiple side channels 1381. Each side channel 1381 optionally contains one type of aa-tRNA at a time. The ribosome complexes 5310 are added to the channel at input 1382. The ribosome complexes 5310 move from one side channel 1381 to the next. In one illustrative configuration, for example, there are 25 side channels 1381 (shown). As each aa-tRNA is added via a side channel 1381 to the reaction chamber 1300, the side channel is refilled from, for example, an external reservoir 2430 with the aa-tRNA that will be needed 25 steps in the future. The waste and translation products, for example, are collected from an output 1383.

Figure 37:
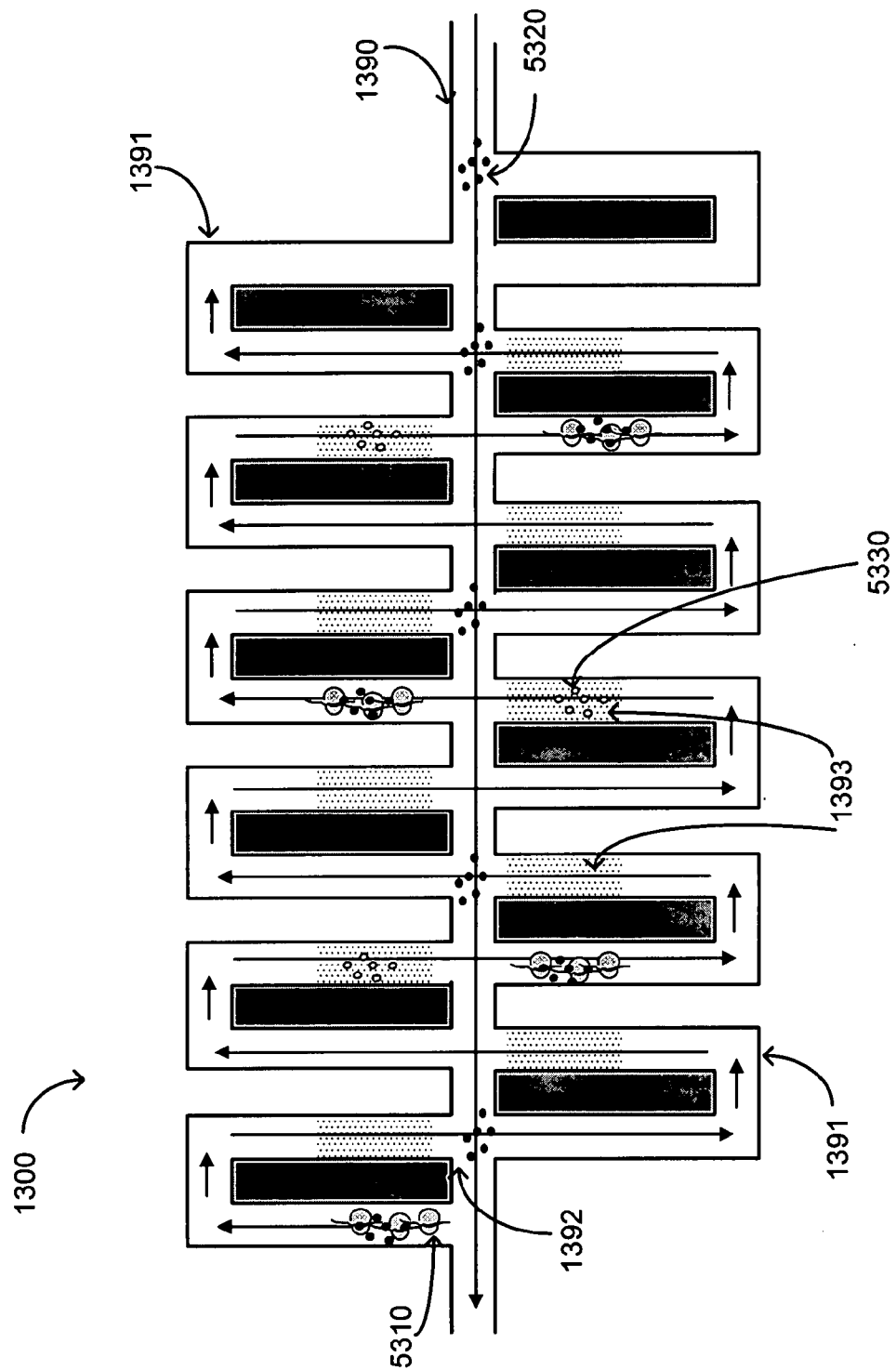
FIG. 37 shows a schematic of an illustrative embodiment of the illustrative apparatus of FIG. 24, including an illustrative example of a reaction chamber.

FIG. 37 shows a schematic representation of an illustrative configuration of a reaction chamber 1300 in which the reaction chamber 1300 is composed of a main linear channel 1390 which overlaps with a serpentine channel 1391. The aa-tRNAs 5320 move in a continuous stream along channel 1390. The ribosomes 5310 move in a serpentine pattern in channel 1391, crossing through the flow of aa-tRNAs at the junction 1392 of the two channels. The ribosomes 5310 and/or aa-tRNAs 5320 may be free in solution, encapsulated in an aqueous bubble, or affixed to microspheres. The ribosomes 5310 and aa-tRNAs 5320 optionally move in opposite directions, such that the ribosomes 5310 pick up each successive aa-tRNA 5320 in an order calculated to achieve the target protein sequence. A portion of the channel 1393 traversed by the ribosome 5310 is optionally coated with a peptide nucleic acid (PNA), for example, that recognizes and binds deacylated t-RNA 5330.

Figure 38:
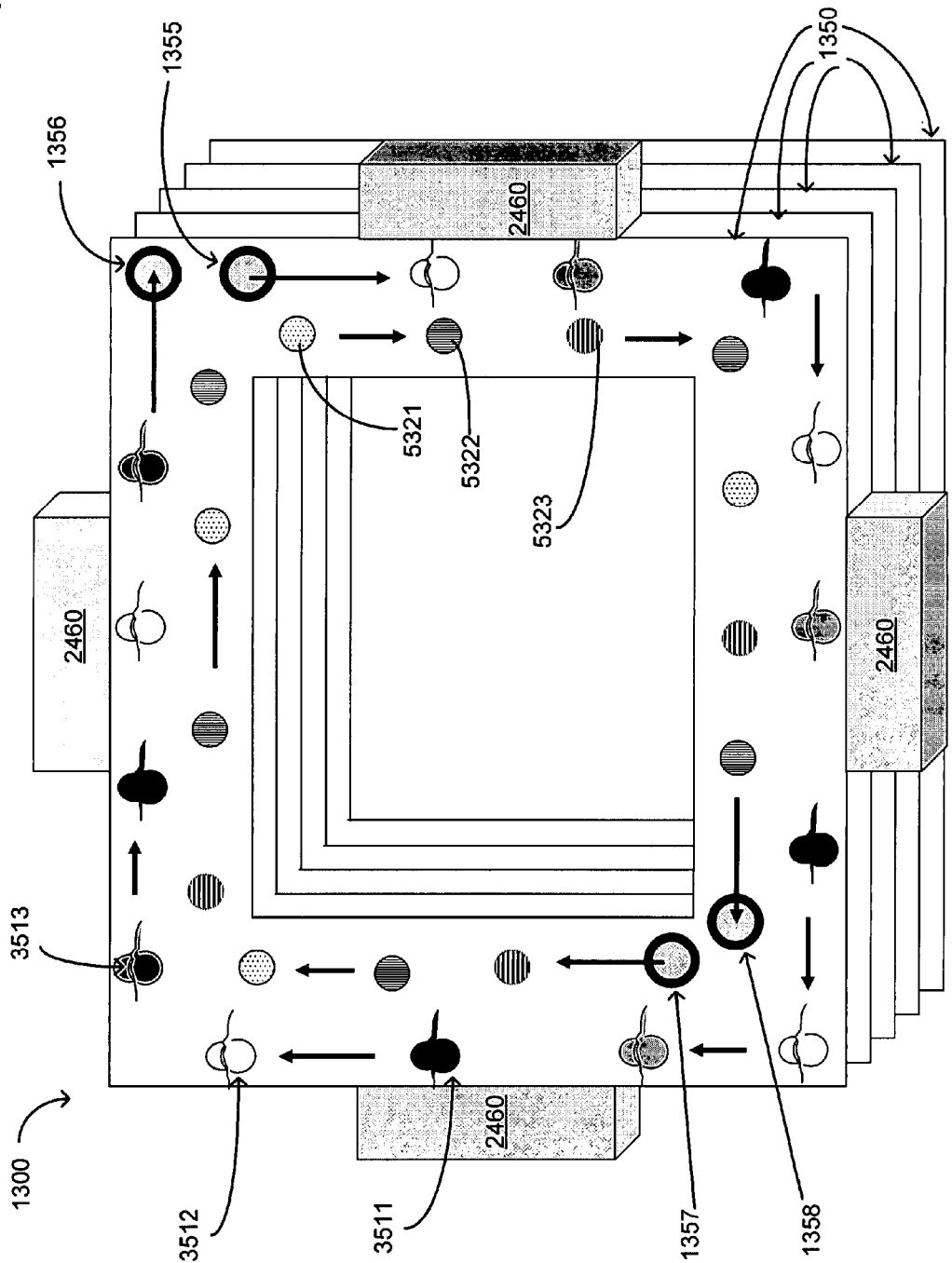
FIG. 38 shows a schematic of an illustrative embodiment of the illustrative apparatus of FIG. 24, including an illustrative example of a reaction chamber.

FIG. 38 shows a schematic representation of an illustrative configuration of a multilayer reaction chamber 1300 in which ribosomes and aa-tRNAs may be free flowing. In one configuration, the ribosomes 5311, 5312, 5313 and aa-tRNAs 5321, 5322, 5323 move in parallel streams along a square channel 1350 (optionally oval or circular, among others (not shown)). There are optionally multiple stacked channels 1350. The ribosomes flow into each channel 1350 via input 1355 and pass to another channel through output 1356. Similarly aa-tRNAs flow into each channel 1350 via input 1357 and pass to another channel through output 1358. Each set of ribosome complexes 5311, 5312, and 5313 and aa-tRNAs 5321, 5322, and 5323 are labeled, for example, with a unique fluorescent dye. There may be a single population of ribosomes initiated with a unique coding sequence. Alternatively, there may be a mixed population of ribosomes initiated with more than one coding sequence, with each coding sequence/ribosome type having a unique fluorescence identifier. Similarly, each aa-tRNA is optionally labeled with a unique fluorescent dye. Detectors 2460 monitor the fluorescence. When the appropriate combinations of ribosome-associated and aa-tRNA-associated fluorescence are detected in proximity to one another, the two streams are pushed together by the lowering of a partial barrier, for example, to allow for interaction between the ribosome and the aa-tRNA. In one configuration, the ribosomes and/or the aa-tRNAs are affixed to magnetic beads and magnetic force is used to push the two components together. For example, magnetic microspheres of varied size and fluorescence are commercially available (Luminex, Austin, Tex.) and can be used in combination with fluorescence monitoring to detect proximity of appropriate ribosome and aa-tRNA pair.

In one aspect, the disclosure is drawn to one or more methods comprising receiving a first input associated with a first possible dataset, the first possible dataset including data representative of one or more charged tRNA sequences; and determining temporal-spatial parameters for synthesizing one or more peptides based on a first possible data set. One or more of these methods may be used as part of one or more methods of target peptide synthesis and/or implemented on one or more apparatus 410 for target peptide synthesis.

Figure 7:
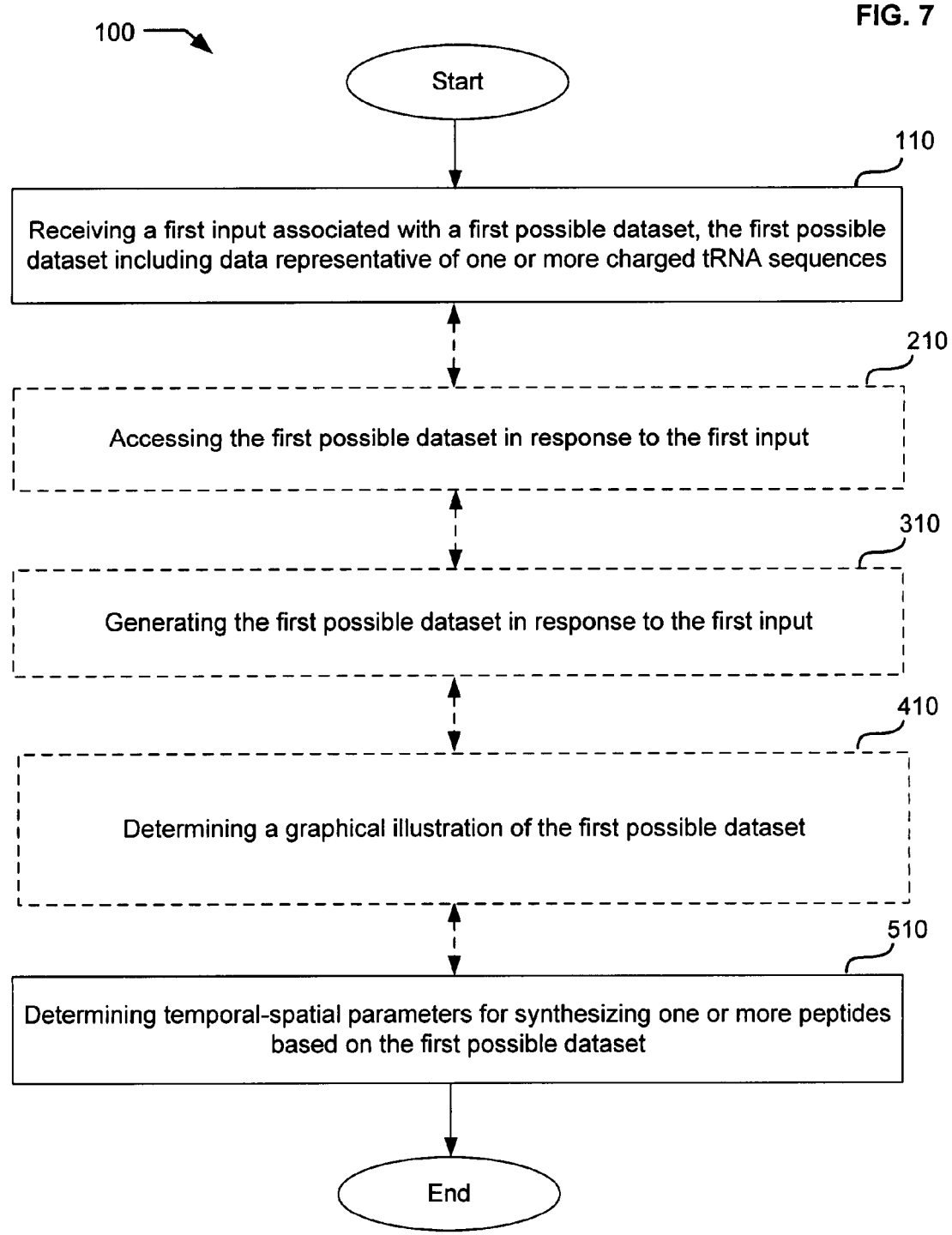
FIG. 7 shows an operational flow representing illustrative embodiments of operations related to determining temporal-spatial parameters for synthesizing one or more peptides based on a first possible dataset.

FIG. 7 shows an operational flow 100 representing illustrative embodiments of operations related to determining temporal-spatial parameters for synthesizing one or more peptides based on a first possible dataset. In FIG. 7, and in the following figures that include various illustrative embodiments of operational flows, discussion and explanation may be provided with respect to apparatus and methods described herein, and/or with respect to other examples and contexts. The operational flows may also be executed in a variety of other contexts and environments, and or in modified versions of those described herein. In addition, although some of the operational flows are presented in sequence, the various operations may be performed in various repetitions, concurrently, and/or in other orders than those that are illustrated.

After a start operation, the operational flow 100 moves to a receiving operation 110 where receiving a first input may be associated with a first possible dataset, the first possible dataset including data representative of one or more charged tRNA sequences. For example, a first input may include data representative of a target peptide sequence, a target nucleic acid sequence, a target biological assembler, and/or target biological assembler components. A first input may also include data representative of the identity and sequence of charged tRNA.

An optional accessing operation 210 accesses the first possible dataset in response to the first input. For example, data representative of a target peptide sequence, a target nucleic acid sequence, a target biological assembler, and/or target biological assembler components may be accessed. Data representative of the identity and sequence of charged tRNA may also be accessed.

An optional generating operation 310 generates the first possible dataset in response to the first input. For example, data representative of a target peptide sequence, a target nucleic acid sequence, a target biological assembler, and/or target biological assembler components may be generated. Data representative of the identity and sequence of charged tRNA may also be generated.

An optional determining operation 410 determines a graphical illustration of the first possible dataset. For example, data representative of a target peptide sequence, a target nucleic acid sequence, a target biological assembler, and/or target biological assembler components may be graphically represented. Data representative of the identity and sequence of charged tRNA may also be graphically represented.

Then, a determining operation 510, determines temporal-spatial parameters for synthesizing one or more peptides based on the first possible dataset. For example, data representative of temporal-spatial parameters for synthesizing one or more peptides based on a target peptide sequence, a target nucleic acid sequence, a target biological assembler, and/or target biological assembler components may be determined. Data representative of temporal-spatial parameters for synthesizing one or more peptides based on the sequence of charged tRNA may also be determined.

Operations 110 to 510 may be performed with respect to a digital representation (e.g. digital data) of, for example, data representative of a target peptide sequence, a target nucleic acid sequence, a target biological assembler, and/or target biological assembler components. The logic may accept a digital or analog (for conversion into digital) representation of an input and/or provide a digitally-encoded representation of a graphical illustration, where the input may be implemented and/or accessed locally or remotely.

Operations 110 to 510 may be performed related to either a local or a remote storage of the digital data, or to another type of transmission of the digital data. In addition to inputting, accessing querying, recalling, calculating, determining or otherwise obtaining the digital data, operations may be performed related to storing, assigning, associating, displaying or otherwise archiving the digital data to a memory, including for example, sending and/or receiving a transmission of the digital data from a remote memory. Accordingly, any such operations may involve elements including at least an operator (e.g. human or computer) directing the operation, a transmitting computer, and/or receiving computer, and should be understood to occur in the United States as long as at least one of these elements resides in the United States.

Figure 8:
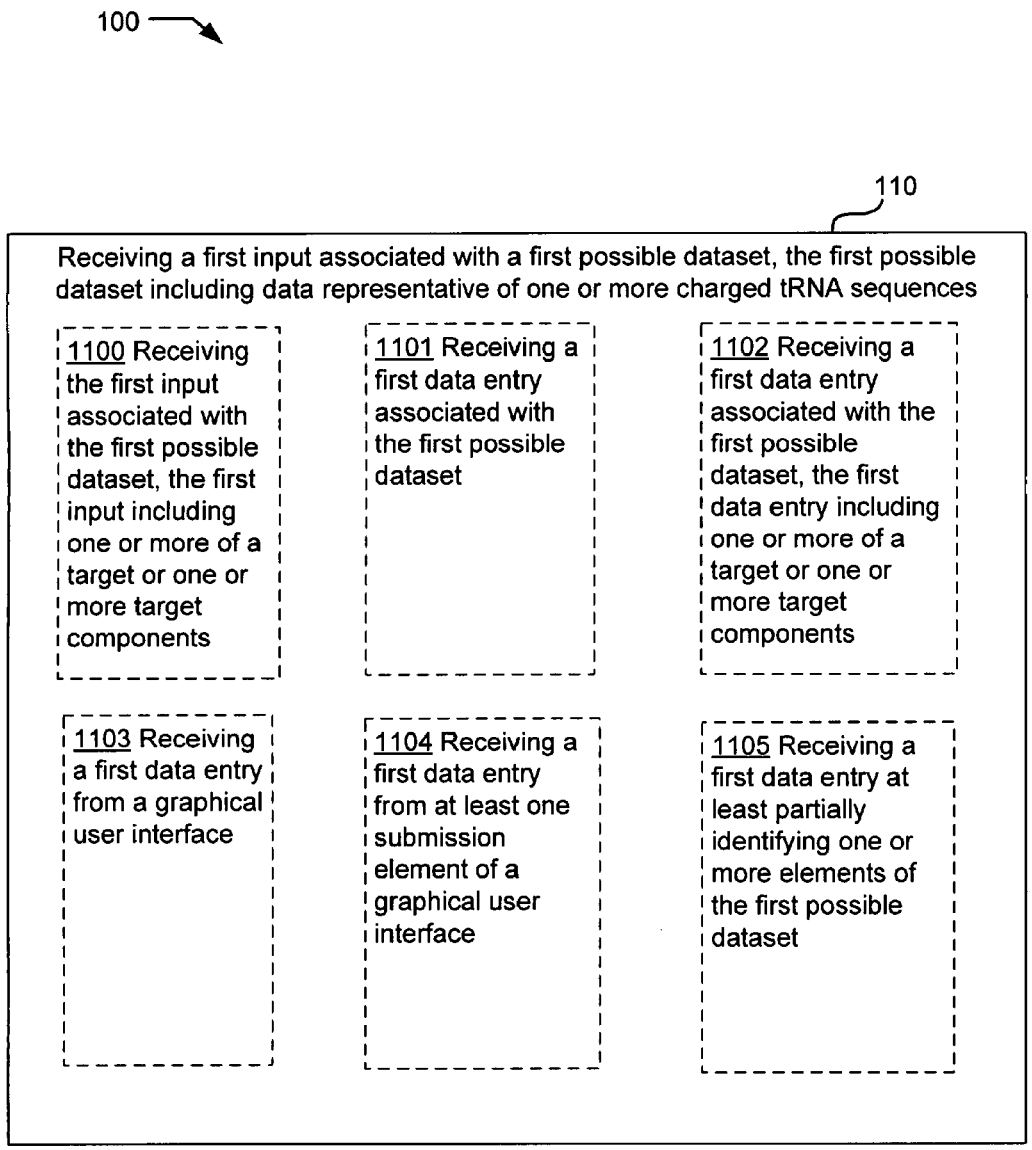
FIG. 8 shows optional embodiments of the operational flow of FIG. 7.

FIG. 8 illustrates optional embodiments of the operational flow 100 of FIG. 7. FIG. 8 shows illustrative embodiments of the receiving operation 110, receiving a first input associated with a first possible dataset, the first possible dataset including data representative of one or more charged tRNA sequences, including operations receiving types of inputs and data entry and may include at least one additional operation. Receiving operations may optionally include, but are not limited to, operation 1100, operation 1101, operation 1102, operation 1103, operation 1104, and/or operation 1105.

At the optional operation 1100, the first input may include one or more of a target or one or more target components. At the optional operation 1101, a first data entry associated with a first possible dataset may be received. At the optional operation 1105, a first data entry at least partially identifying one or more elements of the first possible dataset may be received.

At the optional operation 1102, a first data entry associated with a first possible dataset may be received that may include one or more of a target or one or more target components. A first data entry associated with a first possible dataset may be received that may include at least partially identifying one or more of a target structure, a peptide sequence, a nucleic acid sequence, a biological assembler, one or more biological assembler components, one or more amino acids, one or more charged tRNA, or one or more tRNA. A first data entry associated with a first possible dataset may be received that may include receiving a first data entry at least partially identifying one or more of one or more domains of a target structure, one or more shapes of the target structure, one or more charges of a target structure, one or more functions of a target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA.

At the optional operation 1103, a first data entry may be received from a graphical user interface, or at the optional operation 1104, from at least one submission element of a graphical user interface.

Figure 9:
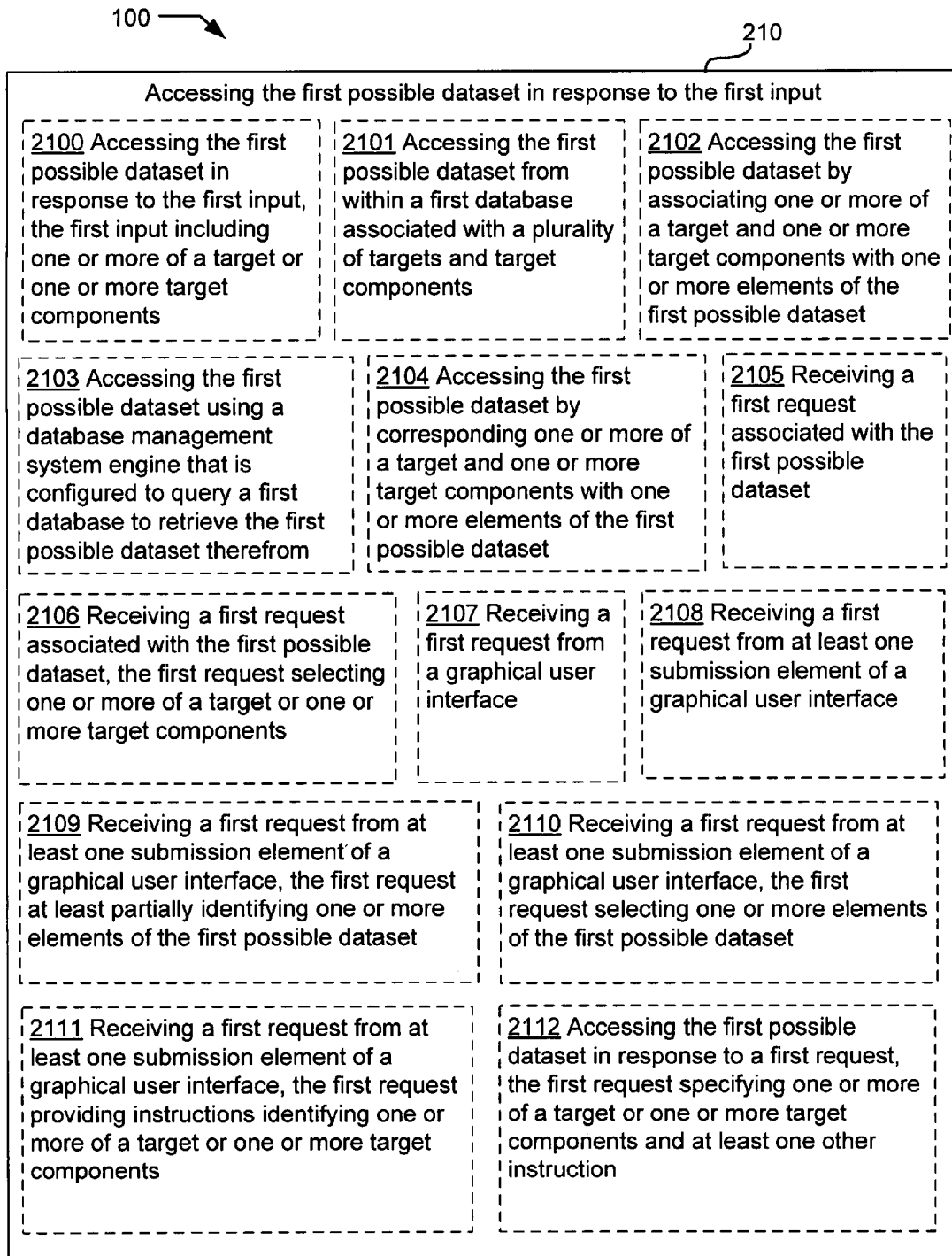
FIG. 9 shows optional embodiments of the operational flow of FIG. 7.

FIG. 9 illustrates optional embodiments of the operational flow 100 of FIG. 7. FIG. 9 shows illustrative embodiments of the optional accessing operation 210, accessing the first possible dataset in response to the first input, including operations accessing the first possible dataset and may include at least one additional operation. Accessing operations may optionally include, but are not limited to, operation 2100, operation 2101, operation 2102, operation 2103, operation 2104, operation 2105, operation 2106, operation 2107, operation 2108, operation 2109, operation 2110, operation 2111, and operation 2112.

At the optional operation 2100, a first possible dataset may be accessed in response to a first input, the first input including one or more of a target or one or more target components. At the optional operation 2101, a first possible dataset may be accessed from within a first database associated with a plurality of targets and target components. At the optional operation 2102, a first possible dataset may be accessed by associating one or more of a target and/or one or more target components with one or more elements of the first possible dataset. At the optional operation 2103, a first possible dataset may be accessed using a database management system engine that is configured to query a first database to retrieve a first possible dataset therefrom. At the optional operation 2104, a first possible dataset may be accessed by corresponding one or more of a target and one or more target components with one or more elements of a first possible dataset.

A first possible dataset may be accessed by associating one or more of a target, one or more of a target structure, a peptide sequence, a nucleic acid sequence, a biological assembler, one or more biological assembler components, one or more amino acids, one or more charged tRNA, or one or more tRNA with one or more elements of the first possible dataset. A first possible dataset may be accessed by associating one or more of one or more domains of a target structure, one or more shapes of a target structure, one or more charges of a target structure, one or more functions of a target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA with one or more elements of the first possible dataset. A first possible dataset may be accessed as being associated with one or more of a target or one or more target components, based on one or more characterizations stored in association with one or more elements of the first possible dataset and related to one or more of a peptide sequence, a nucleic acid sequence, biological assembler, one or more biological assembler components, one or more amino acids, one or more charged tRNA, or one or more tRNA.

At the optional operation 2105, a first request associated with a first possible dataset may be received. At the optional operation 2106, a first request associated with a first possible dataset may be received, the first request selecting one or more of a target or one or more target components. At the optional operation 2107, a first request from a graphical user interface may be received. At the optional operation 2108, a first request from at least one submission element of a graphical user interface may be received. At the optional operation 2109, a first request from at least one submission element of a graphical user interface may be received, one or more first requests at least partially identifying one or more elements of a first possible dataset. At the optional operation 2110, a first request from at least one submission element of a graphical user interface may be received, one or more first requests at least partially selecting one or more elements of a first possible dataset. At the optional operation 2111, a first request from at least one submission element of a graphical user interface may be received, one or more first requests providing instructions identifying one or more of a target or one or more target components.

A first request from at least one submission element of a graphical user interface may be received, one or more first requests providing instructions identifying a target structure, a peptide sequence, a nucleic acid sequence, a biological assembler, one or more biological assembler components, one or more amino acids, one or more charged tRNA, or one or more tRNA. A first request from at least one submission element of a graphical user interface may be received, one or more first requests providing instructions identifying one or more domains of a target structure, one or more shapes of the target structure, one or more charges of a target structure, one or more functions of a target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA.

At the optional operation 2112, a first possible dataset may be accessed in response to a first request, the first request specifying one or more of a target or one or more target components and at least one other instruction.

Figure 10:
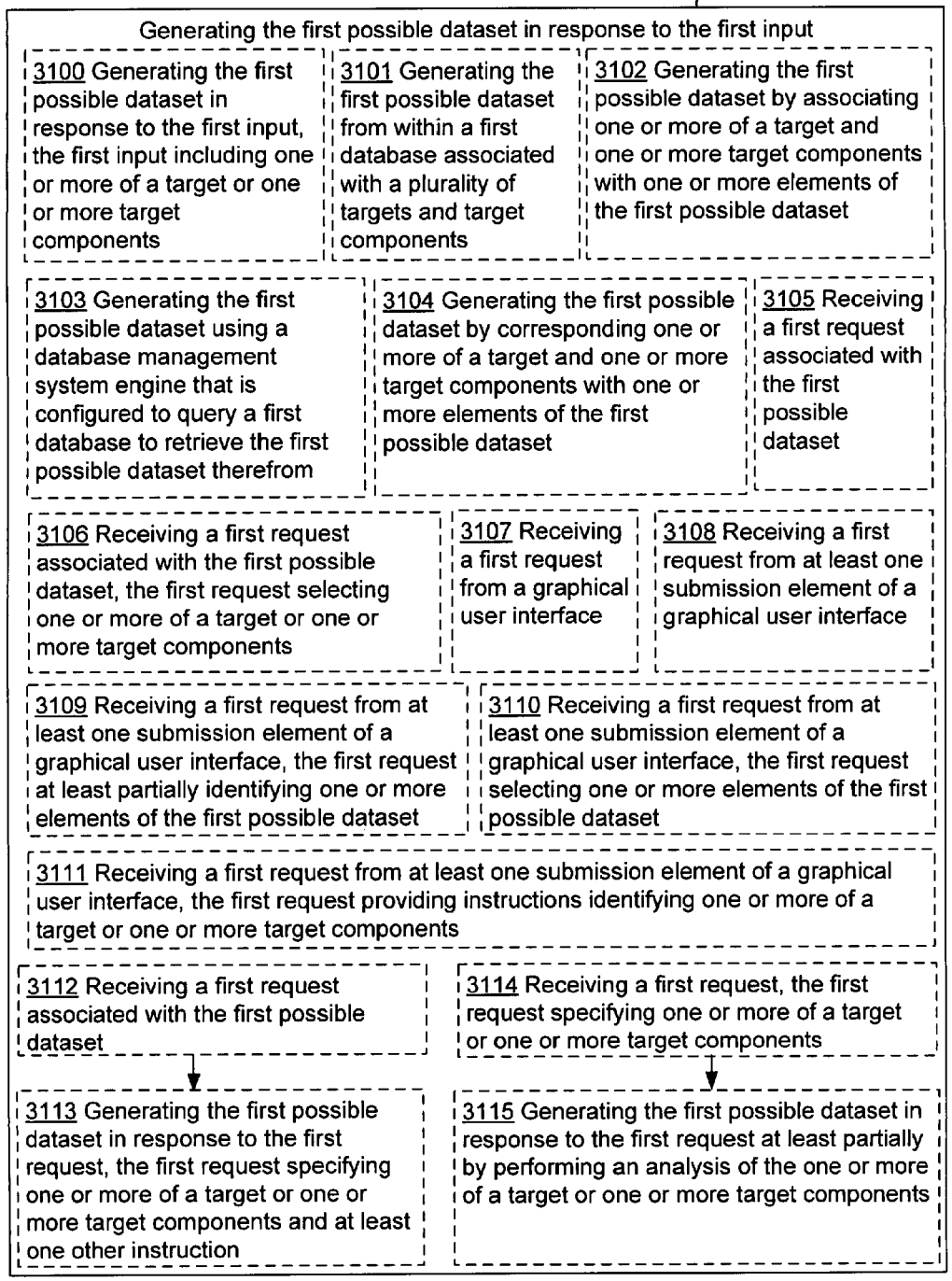
FIG. 10 shows optional embodiments of the operational flow of FIG. 7.

FIG. 10 illustrates optional embodiments of the operational flow 100 of FIG. 7. FIG. 10 shows illustrative embodiments of the optional generating operation 310, generating the first possible dataset in response to the first input, including operations generating the first possible dataset and may include at least one additional operation. Generating operations may optionally include, but are not limited to, operation 3100, operation 3101, operation 3102, operation 3103, operation 3104, operation 3105, operation 3106; operation 3107, operation 3108, operation 3109, operation 3110, operation 3111, operation 3112, operation 3113, operation 3114, operation 3115.

At the optional operation 3100, a first possible dataset may be generated in response to a first input, the first input including one or more of a target or one or more target components. At the optional operation 3101, a first possible dataset may be generated from within the first database associated with a plurality of targets and target components. At the optional operation 3102, a first possible dataset may be generated by associating one or more of a target and one or more target component with one or more elements of the first possible dataset. At the optional operation 3103, a first possible dataset may be generated using a database management system engine that is configured to query a first database to retrieve a first possible dataset therefrom. At the optional operation 3104, a first possible dataset may be generated by corresponding one or more of a target and one or more target components with one or more elements of the first possible dataset.

A first possible dataset may be generated by associating one or more of the target structure, at peptide sequence, a nucleic acid sequence, a biological assembler, one or more biological assembler components, one or more amino acids, one or more charged tRNA, or one or more tRNA, with one or more elements of the first possible dataset. A first possible dataset may be generated by associating one or more of one or more domains of the target structure, one or more shapes of the target structure, one or more charges of the target structure, one or more functions of the target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA, with one or more elements of the first possible dataset.

At the optional operation 3105, a first request associated with a first possible dataset may be received. At the optional operation 3106, a first request associated with the first possible dataset may be received, the first request selecting one or more of a target or one or more target components. At the optional operation 3107, a first request from a graphical user interface may be received. At the optional operation 3108, a first request may be received from at least one submission element of a graphical user interface. At the optional operation 3109, a first request may be received from at least one submission element of a graphical user interface, the first request at least partially identifying one or more elements of the first possible dataset. At the optional operation 3110, a first request may be received from at least one submission element of a graphical user interface, the first request selecting one or more elements of the first possible dataset. At the optional operation 3111, a first request may be received from at least one submission element of the graphical user interface, the first request providing instructions identifying one or more of a target or one or more target components.

A first request may be received from at least one submission element of the graphical user interface, the first request providing instructions identifying the target structure, a peptide sequence, a nucleic acid sequence, a biological assembler, one or more biological assembler components, one or more amino acids, one or more charged tRNA, or one or more tRNA. A first request may be received from at least one submission element of the graphical user interface, the first request providing instructions identifying one or more domains of the target structure, one or more shapes of the target structure, one or more charges of the structure, one or more functions of a target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA.

At the optional operation 3112, a first request associated with the first possible dataset may be received, and at the optional operation 3113, the first possible dataset may be generated in response to the first request, the first request specifying one or more of a target or one or more target components and at least one other instruction. At the optional operation 3114, a first request may be received, the first request specifying one or more of a target or one or more target components, and at the optional operation 3115, the first possible dataset may be generated in response to the first request at least partially by performing an analysis of the one or more of a target or one or more target components.

Figure 11:
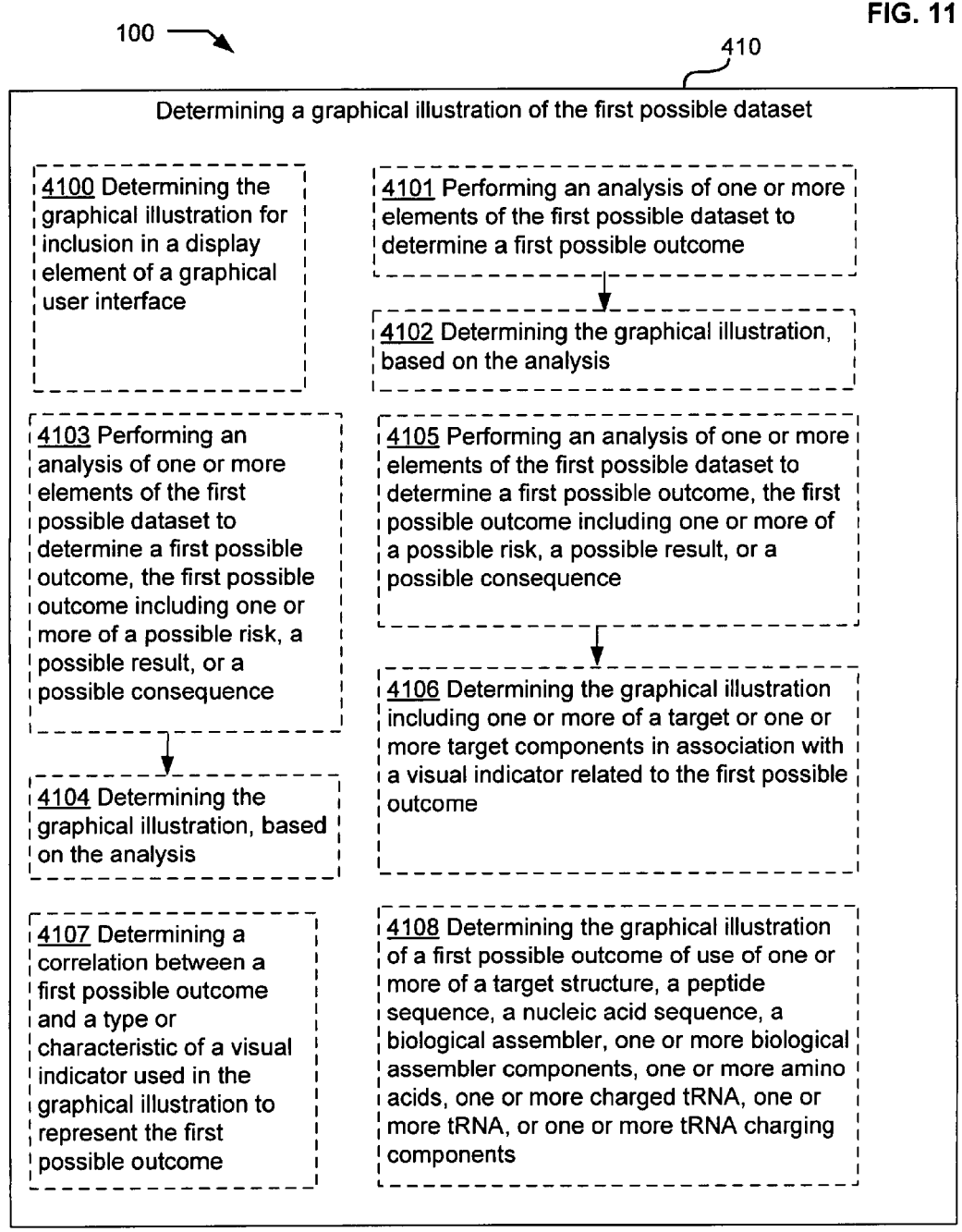
FIG. 11 shows optional embodiments of the operational flow of FIG. 7.

FIG. 11 illustrates optional embodiments of the operational flow 100 of FIG. 7. FIG. 11 shows illustrative embodiments of the optional determining operation 410, determining a graphical illustration of the first possible dataset, including operations determining a graphical illustration of the first possible dataset and may include at least one additional operation. Determining operations may optionally include, but are not limited to, operation 4100, operation 4101, operation 4102, operation 4103, operation 4104, operation 4105, operation 4106, operation 4107, and operation 4108.

At the optional operation 4100, a graphical illustration for inclusion in a display element of a graphical user interface may be determined. At the optional operation 4101, an analysis of one or more elements of the first possible dataset may be performed to determine a first possible outcome, and at the optional operation 4102 the graphical illustration may be determined based on the analysis. At the optional operation 4103, analysis of one or more elements of the first possible dataset may be performed to determine a first possible outcome, the first possible outcome including one or more of a possible risk, a possible result, or a possible consequence; and at the optional operation 4104 the graphical illustration may be determined based on the analysis. At the optional operation 4105, an analysis of one or more elements of the first possible dataset may be performed to determine the first possible outcome, the first possible outcome including one or more of a possible risk, a possible result, or a possible consequence, and at the optional operation 4106, the graphical illustration may be determined including one or more of a target or one or more target components in association with a visual indicator related to the first possible outcome. At the optional operation 4107, correlation between the first possible outcome and a type or characteristic of a visual indicator used in the graphical illustration to represent the first possible outcome may be determined. At the optional operation 4108, the graphical illustration of the first possible outcome of use of one or more of the target structure, a peptide sequence, a nucleic acid sequence, a biological assembler, one or more biological assembler components, one or more amino acids, one or more charged tRNA, one or more tRNA, or one or more tRNA charging components may be determined. The graphical illustration of a first possible outcome of use of one or more of one or more domains of the target structure, one or more shapes of the target structure, one or more charges of the structure, one or more functions of a target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA may be determined.

Figure 12:
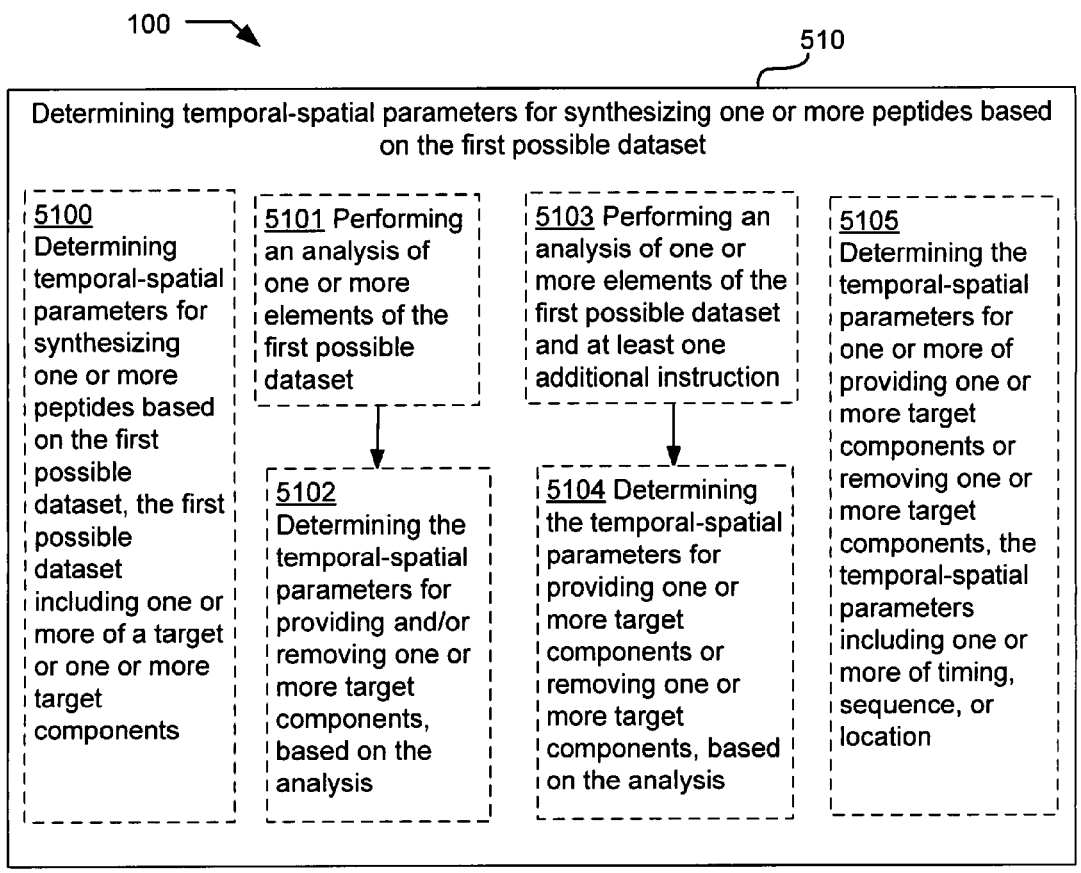
FIG. 12 shows optional embodiments of the operational flow of FIG. 7.

FIG. 12 illustrates optional embodiments of the operational flow 100 of FIG. 7. FIG. 12 shows illustrative embodiments of the determining operation 510, determining temporal-spatial parameters for synthesizing one or more target peptides based on the first possible dataset, including operations determining temporal-spatial parameters for implementing the first possible dataset and may include at least one additional operation. Determining operations may optionally include, but are not limited to, operation 5100, operation 5101, operation 5102, operation 5103, operation 5104, and operation 5105.

At the optional operation 5100, temporal-spatial parameters for synthesizing one or more peptides based on the first possible dataset may be determined, the first possible dataset including one or more of a target or one or more target components. At the optional operation 5101, an analysis of one or more elements of the first possible dataset may be performed, and at the optional operation 5102, the temporal spatial parameters for providing one or more target components may be determined, based on the analysis. At the optional operation 5103, an analysis of one or more elements of the first possible dataset and at least one additional instruction may be performed, and at the optional operation 5104, the temporal-spatial parameters for providing one or more target components and/or removing one or more target components may be determined, based on the analysis. At the optional operation 5105, the temporal-spatial parameters for providing one or more target components and/or removing one or more target components may be determined, the temporal-spatial parameters including one or more of timing, sequence, or location.

Figure 13:
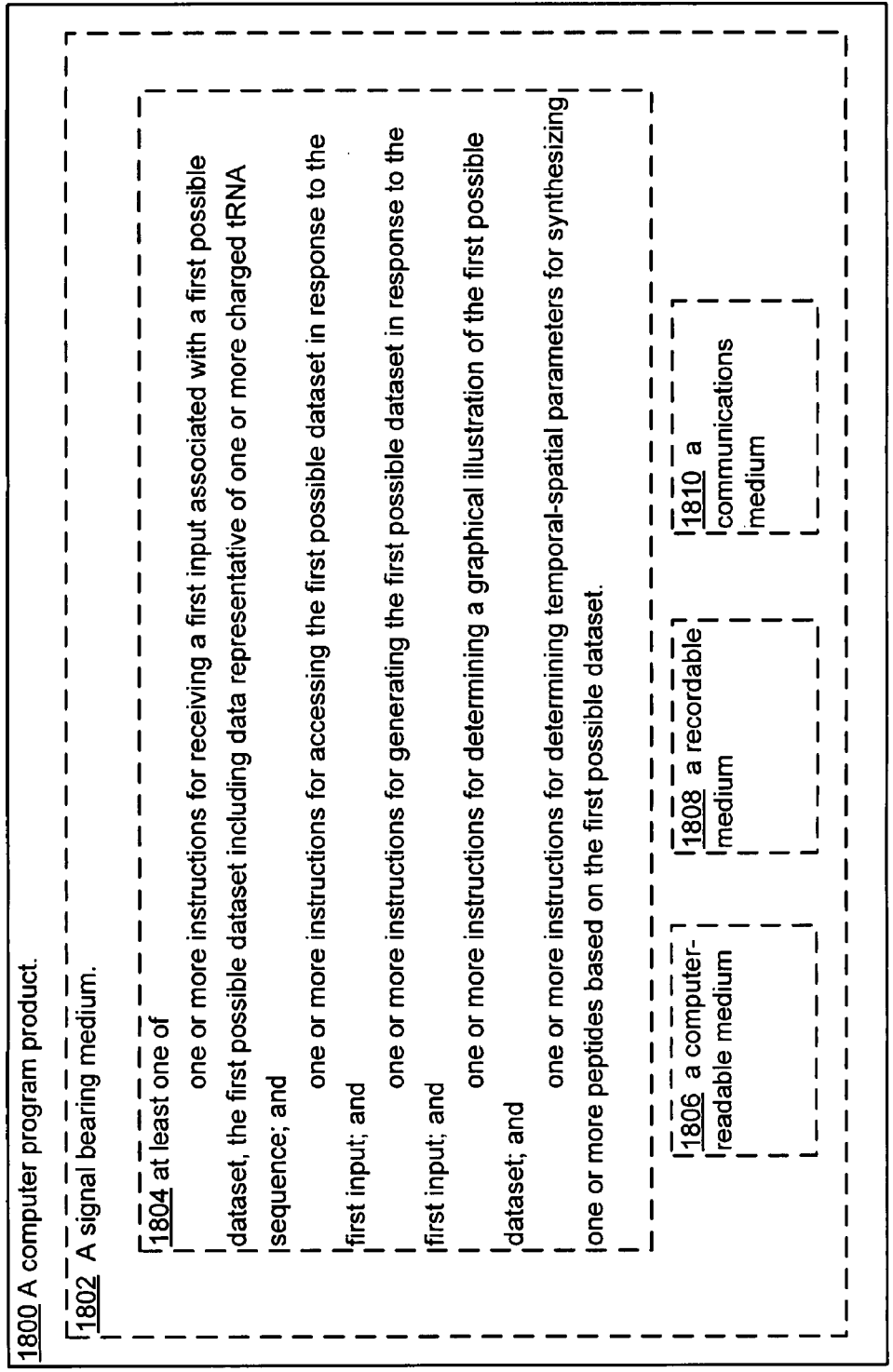
FIG. 13 shows a partial view of an illustrative embodiment of a computer program product that includes a computer program for executing a computer process on a computing device.

FIG. 13 shows a schematic of a partial view of an illustrative computer program product 1800 that includes a computer program for executing a computer process on a computing device. An illustrative embodiment of the example computer program product is provided using a signal bearing medium 1802, and may include at least one instruction of 1804: one or more instructions for receiving a first input associated with a first possible dataset, the first possible dataset including data representative of one or more charged tRNA sequence; one or more instructions for accessing the first possible dataset in response to the first input; one or more instructions for generating the first possible dataset in response to the first input; one or more instructions for determining a graphical illustration of the first possible dataset; or one or more instructions for determining temporal-spatial parameters for synthesizing one or more peptides based on the first possible dataset. The one or more instructions may be, for example, computer executable and/or logic implemented instructions. In some embodiments, the signal bearing medium 1802 of the one or more computer program 1800 products include a computer readable medium 1806, a recordable medium 1808, and/or a communications medium 1810.

Figure 14:
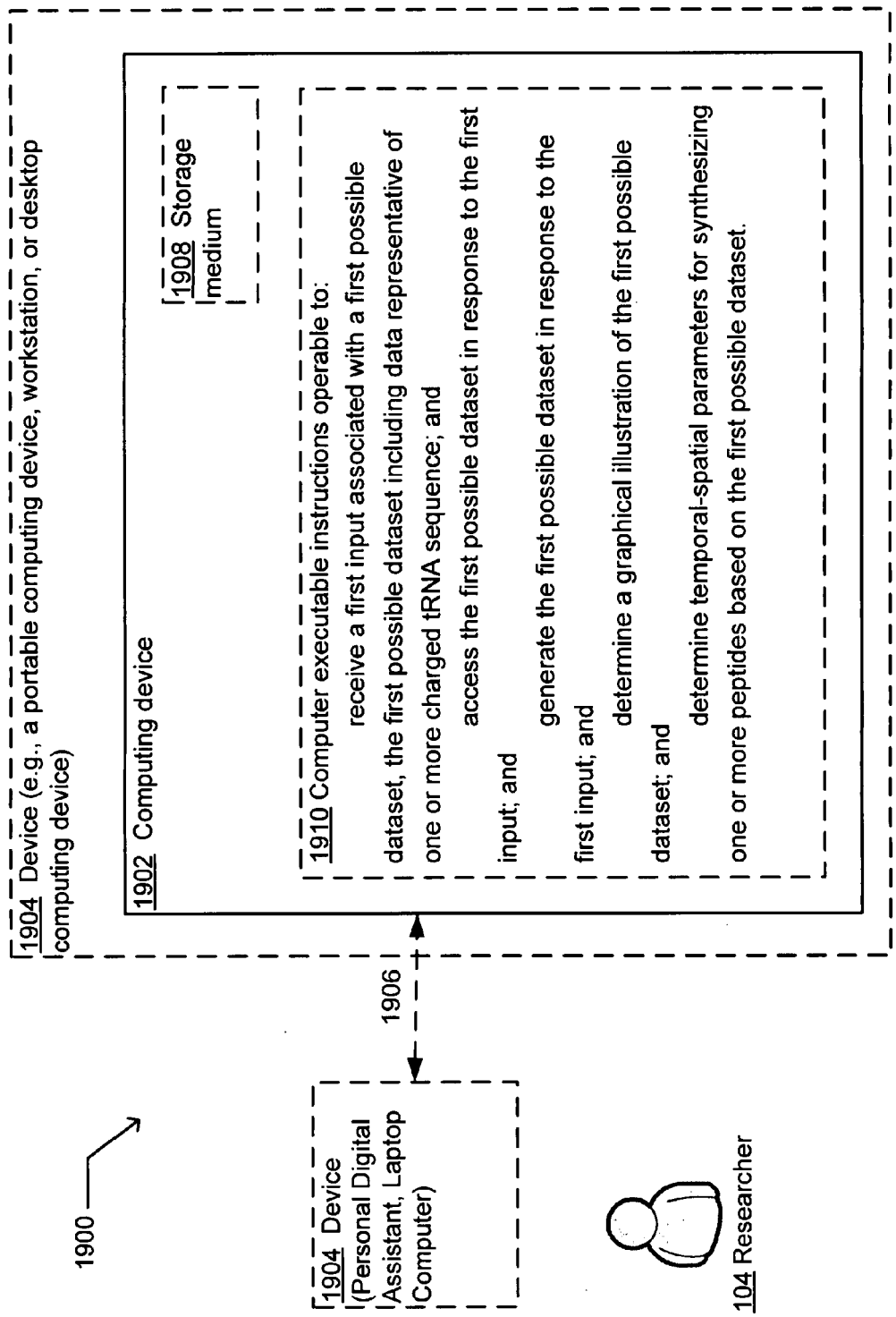
FIG. 14 shows an illustrative embodiment of a system in which embodiments may be implemented.

FIG. 14 shows a schematic of an illustrative system 1900 in which embodiments may be implemented. The system 1900 may include a computing system environment. The system 1900 also illustrates a researcher/scientist/investigator/operator 104 using a device 1904, that is optionally shown as being in communication with a computing device 1902 by way of an optional coupling 1906. The optional coupling may represent a local, wide area, or peer-to-peer network, or may represent a bus that is internal to a computing device (e.g. in illustrative embodiments the computing device 1902 is contained in whole or in part within the device 1904 or within one or more apparatus 410, or one or more computing units 426, or one or more controller units 422, or one or more monitoring units 440). An optional storage medium 1908 may be any computer storage medium.

The computing device 1902 includes one or more computer executable instructions 1910 that when executed on the computing device 1902 cause the computing device 1902 to receive the first input associated with the first possible dataset, the first possible dataset including data representative of one or more charged tRNA sequences; optionally access the first possible dataset in response to the first input; optionally generate the first possible dataset in response to the first input; optionally determine a graphical illustration of the first possible dataset; and determine temporal-spatial parameters for synthesizing one or more peptides at least partially based on a first possible dataset. In some illustrative embodiments, the computing device 1902 may optionally be contained in whole or in part within an apparatus 410 and/or one or more peptide synthesizer units 420 of FIG. 1 (e.g. one or more computing units 426, and/or one or more controller units 422, and/or one or more monitoring units 440), or may optionally be contained in whole or in part within the researcher device 1904.

The system 1900 includes at least one computing device (e.g. 1904 and/or 1902 and/or one or more computing units 426 of FIG. 1) on which the computer-executable instructions 1910 may be executed. For example, one or more of the computing devices (e.g. 1902, 1904, 426) may execute the one or more computer executable instructions 1910 and output a result and/or receive information from the researcher (optionally from one or more monitoring unit 440) on the same or a different computing device (e.g. 1902, 1904, 426) and/or output a result and/or receive information from one or more peptide synthesizer units 420 and/or one or more monitoring units 440 and/or one or more computing units 426 and/or one or more controller units 422 in order to perform and/or implement one or more of the techniques, processes, or methods described herein, or other techniques.

The computing device (e.g. 1902 and/or 1904 and/or 426) may include one or more of a desktop computer, a workstation computer, a computing system comprised a cluster of processors, a networked computer, a tablet personal computer, a laptop computer, or a personal digital assistant, or any other suitable computing unit or may be part of any one of the apparatus 410 described herein. In some embodiments, an apparatus 410, one or more peptide synthesizer units 420 and/or one or more monitoring units 440 and/or one or more controller units 422 may be operable to communicate with any one of the one or more computing devices (e.g. 1902 and/or 1904 and/or 426) that may be operable to communicate with a database to access the first possible dataset and/or subsequent datasets. In some embodiments, the computing device (e.g. 1902 and/or 1904 and/or 426) is operable to communicate with the peptide biological synthesis apparatus 410.

In one aspect, the disclosure is drawn to one or more methods comprising receiving a first input associated with a first possible dataset, the first possible dataset including data representative of one or more aspects of target peptide synthesis; and determining temporal-spatial parameters for sequentially co-localizing one or more target components based on the first possible dataset and/or for separating one or more target components based on the first possible dataset. One or more of these methods may be used as part of one or more methods of target peptide synthesis and/or implemented on one or more apparatus 410 for target peptide synthesis.

FIG. 15 shows an operational flow 600 representing illustrative embodiments of operations related to determining temporal-spatial parameters for sequentially co-localizing one or more target components based on the first possible dataset and/or for separating one or more target components based on the first possible dataset. In FIG. 15, and in the following figures that includes various illustrative embodiments of operational flows, discussion and explanation may be provided with respect to apparatus and methods described herein, and/or with respect to other examples and contexts. The operational flows may also be executed in a variety of other contexts and environments, and or in modified versions of those described herein. In addition, although some of the operational flows are presented in sequence, the various operations may be performed in various repetitions, concurrently, and/or in other orders than those that are illustrated. The operational flows may be performed in real time during target peptide synthesis.

After a start operation, the operational flow 600 moves to a receiving operation 610 where a first input may be associated with a first possible dataset, the first possible dataset including data representative of one or more aspects of target synthesis. For example, a first input may include data representative of the progress of target peptide synthesis. Data representative of the progress of target peptide synthesis may be manually or automatically gathered, or derived from monitoring the progress of target peptide synthesis. Monitoring may be optionally performed by one or more monitoring units 440.

An optional accessing operation 710 accesses the first possible dataset in response to the first input. For example, data representative of the progress of target peptide synthesis may be accessed. Such data may be manually or automatically generated, or derived from one or more monitoring units 440.

An optional generating operation 810 generates the first possible dataset in response to the first input. For example, data representative of the progress of target peptide synthesis may be generated. Such data may be manually or automatically generated, or derived from one or more monitoring units 440.

An optional determining operation 910 determines a graphical illustration of the first possible dataset. For example, data representative of the progress of target peptide synthesis may be graphically represented. Such data may be manually or automatically generated, or derived from one or more monitoring units 440.

Then, a determining operation 1010, determines temporal-spatial parameters for optionally sequentially co-localizing one or more target components based on the first possible dataset and/or for separating one or more target components based on the first possible dataset. For example, temporal-spatial parameters for sequentially co-localizing one or more target components based on the first possible dataset and/or for separating one or more target components based on the first possible dataset may be determined at least partially based on data representative of the progress of target peptide synthesis. Such data may be manually or automatically generated, or derived from one or more monitoring units 440.

Operations 610 to 1010 may be performed with respect to a digital representation (e.g. digital data) of, for example, data representative of progress of a target peptide synthesis. The logic may accept a digital or analog (for conversion into digital) representation of an input and/or provide a digitally-encoded representation of a graphical illustration, where the input may be implemented and/or accessed locally or remotely.

Operations 610 to 1010 may be performed related to either a local or a remote storage of the digital data, or to another type of transmission of the digital data. In addition to inputting, accessing querying, recalling, calculating, determining or otherwise obtaining the digital data, operations may be performed related to storing, assigning, associating, displaying or otherwise archiving the digital data to a memory, including for example, sending and/or receiving a transmission of the digital data from a remote memory. Accordingly, any such operations may involve elements including at least an operator (e.g. human or computer) directing the operation, a transmitting computer, and/or receiving computer, and should be understood to occur in the United States as long as at least one of these elements resides in the United States.

FIG. 16 illustrates optional embodiments of the operational flow 600 of FIG. 15. FIG. 16 shows illustrative embodiments of the receiving operation 610, including operations receiving a first input, optionally data entry, associated with a first possible dataset, the first input including data representative of one or more aspects of target synthesis, and optionally one or more additional operations. Receiving operations may optionally include, but are not limited to, operation 6100, operation 6101, operation 6102, operation 6103, operation 6104, operation 6105, operation 6106, operation 6107, operation 6108, operation 6109, operation 6110, and/or operation 6111.

At the optional operation 6100, the first input may include data representative of amino acid incorporation into one or more peptides, biological assembler activity, nucleic acid translocation, and/or tRNA release. At the optional operation 6101, the first input may include data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA.

At the optional operation 6110, the first input may be associated with monitoring amino acid incorporation, biological assembly activity, nucleic acid translocation, and/or tRNA release. At the optional operation 6111, the first input may be associated with monitoring availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA. Monitoring may be performed by one or more monitoring units 440.

At the optional operation 6102, a first data entry associated with the first possible dataset may be received. At the optional operation 6109, a first data entry at least partially identifying one or more elements of the first possible dataset may be received.

At the optional operation 6103, a first data entry associated with the first possible dataset may be received that may include receiving the first input associated with amino acid incorporation, biological assembly activity, nucleic acid translocation, and/or tRNA release. At the optional operation 6104, a first data entry associated with the first possible dataset may be received that may include data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA.

At the optional operation 6105, a first data entry from one or more peptide synthesizer units 420 may be received. At the optional operation 6106, a first data entry from one or more monitoring units 440, one or more computing units 426 and/or one or more controller units 422 may be received.

At the optional operation 6107, a first data entry may be received from a graphical user interface, or at the optional operation 6108 from at least one submission element of a graphical user interface.

FIG. 17 illustrates optional embodiments of the operational flow 600 of FIG. 15. FIG. 17 shows illustrative embodiments of the optional accessing operation 710, including operations accessing the first possible dataset in response to the first input, and may include at least one additional operation. Accessing operations may optionally include, but are not limited to, operation 7100, operation 7101, operation 7102, operation 7103, operation 7104, operation 7105, operation 7106, operation 7107, operation 7108, operation 7109, operation 7110, and/or operation 7111.

At the optional operation 7100, a first possible dataset may be accessed in response to a first input, the first input including data representative of amino acid incorporation into one or more peptides, biological assembler activity, nucleic acid translocation, and/or tRNA release. At the optional operation 7101, a first possible dataset may be accessed in response to a first input, the first input including data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA.

At the optional operation 7102, a first possible dataset may be accessed by associating data representative of amino acid incorporation into one or more peptides, biological assembler activity, nucleic acid translocation, and/or tRNA release with one or more elements of the first possible dataset. At the optional operation 7103, a first possible dataset may be accessed by associating data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA with one or more elements of the first possible dataset.

At the optional operation 7104, a first possible dataset may be accessed by corresponding data representative of amino acid incorporation into one or more peptides, biological assembler activity, nucleic acid translocation, and/or tRNA release with one or more elements of the first possible dataset. At the optional operation 7105, a first possible dataset may be accessed by corresponding data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA with one or more elements of the first possible dataset.

At the optional operation 7106, a first possible dataset may be accessed in response to the first input at least partially based on receiving a first request associated with the first possible dataset. At the optional operation 7107, a first possible dataset may be accessed in response to the first input at least partially based on receiving a first request associated with the first possible dataset, the first request selecting one or more target components. At the optional operation 7108, a first possible dataset may be accessed in response to the first input at least partially based on receiving a first request from a graphical user interface, or the optional operation 7109, receiving a first request from at least one submission element of a graphical user interface. At the optional operation 7110, a first possible dataset may be accessed in response to the first input at least partially based on receiving a first request from at least one submission element of a graphical user interface, the first request providing instructions identifying one or more target components. At the optional operation 7111, a first possible dataset may be accessed in response to the first input at least partially based on receiving a first request from at least one submission element of a graphical user interface, the first request specifying one or more target components and at least one other instruction.

Figure 19:
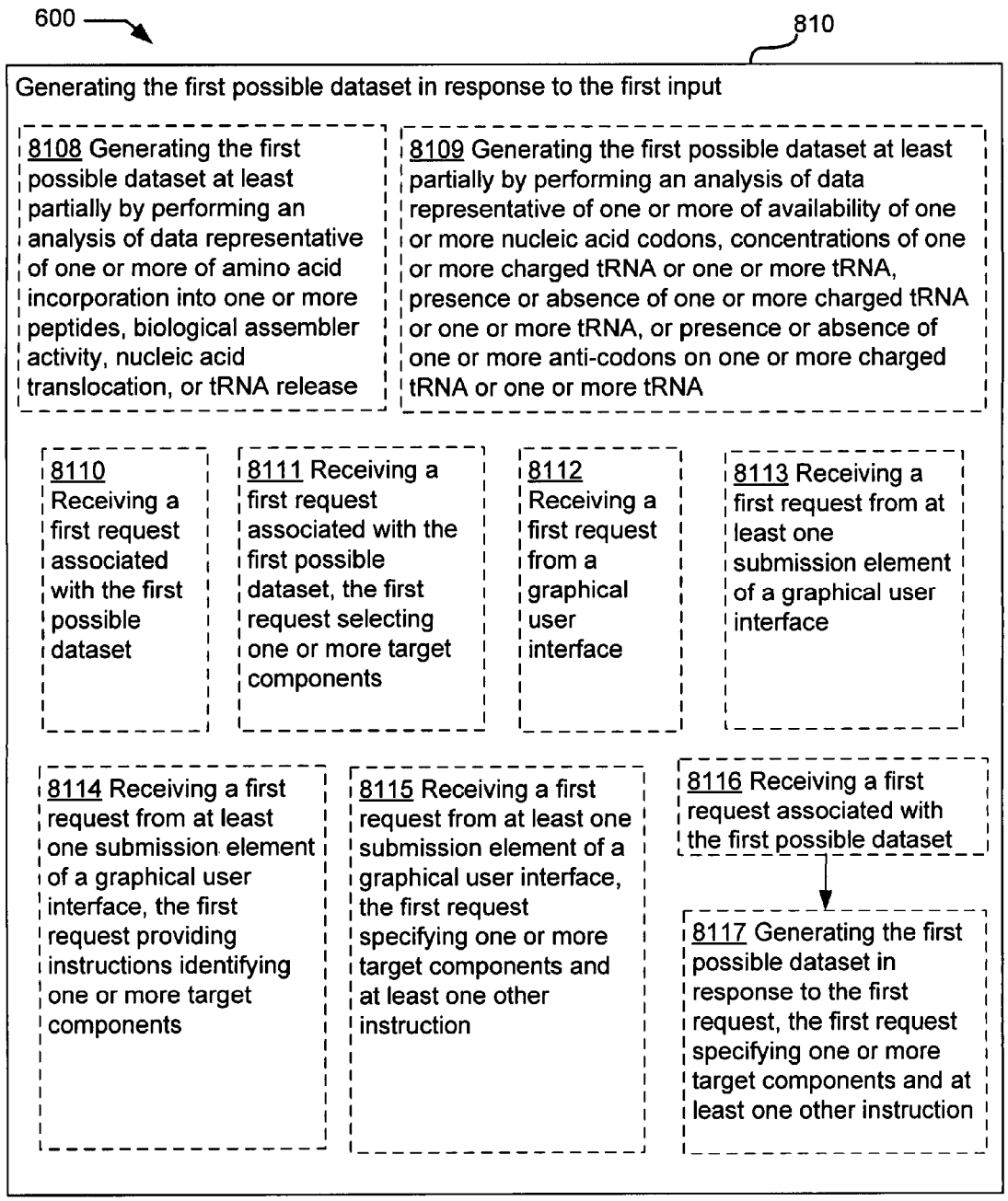
FIG. 19 shows optional embodiments of the operational flow of FIG. 15.

FIG. 18 and FIG. 19 illustrate optional embodiments of the operational flow 600 of FIG. 15. FIG. 18 and FIG. 19 show illustrative embodiments of the optional generating operation 810, including operations generating the first possible dataset in response to the first input, and may include at least one additional operation. Generating operations may optionally include, but are not limited to, operation 8100, operation 8101, operation 8102, operation 8103, operation 8104, operation 8105, operation 8108, operation 8109, operation 8110, operation 8111, operation 8112, operation 8113, operation 8114, operation 8115, operation 8116 and/or operation 8117.

At the optional operation 8100, the first possible dataset is generated in response to the first input, the first input including data representative of amino acid incorporation into one or more peptides, biological assembler activity, nucleic acid translocation, and/or tRNA release. At the optional operation 8101, the first possible dataset is generated in response to the first input, the first input including data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA.

At the optional operation 8102, the first possible dataset is generated in response to the first input by associating data representative of amino acid incorporation into one or more peptides, biological assembler activity, nucleic acid translocation, and/or tRNA release with one or more elements of the first possible dataset. At the optional operation 8103, the first possible dataset is generated in response to the first input by associating data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA with one or more elements of the first possible dataset.

At the optional operation 8104, the first possible dataset is generated in response to the first input by corresponding data representative of amino acid incorporation into one or more peptides, biological assembler activity, nucleic acid translocation, and/or tRNA release with one or more elements of the first possible dataset. At the optional operation 8105, the first possible dataset is generated by corresponding data representative of one or more of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA with one or more elements of the first possible dataset.

At the optional operation 8108, the first possible dataset is generated in response to the first input at least partially by performing an analysis of data representative of amino acid incorporation into one or more peptides, biological assembler activity, nucleic acid translocation, and/or tRNA release. At the optional operation 8109, the first possible dataset is generated in response to the first input at least partially by performing an analysis of data representative of one or more of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA.

In some embodiments, the first possible dataset is generated in response to the first input, wherein receiving a first input associated with a first possible dataset comprises receiving a first request associated with the first possible dataset 8110. In some embodiments, the first possible dataset is generated in response to the first input, wherein receiving a first input associated with a first possible dataset comprises receiving a first request associated with the first possible dataset, the first request selecting one or more target components 8111. In some embodiments, the first possible dataset is generated in response to the first input, wherein receiving a first input associated with a first possible dataset comprises receiving a first request from a graphical user interface 8112. In some embodiments, the first possible dataset is generated in response to the first input, wherein receiving a first input associated with a first possible dataset comprises receiving a first request from at least one submission element of a graphical user interface 8113. In some embodiments, the first possible dataset is generated in response to the first input, wherein receiving a first input associated with a first possible dataset comprises receiving a first request from at least one submission element of a graphical user interface, the first request providing instructions identifying one or more target components 8114. In some embodiments, the first possible dataset is generated in response to the first input, wherein receiving a first input associated with a first possible dataset comprises receiving a first request from at least one submission element of a graphical user interface, the first request specifying one or more target components and at least one other instruction 8115. In some embodiments, the first possible dataset is generated in response to the first input, wherein receiving a first input associated with a first possible dataset comprises receiving a first request associated with the first possible dataset 8116; and generating the first possible dataset in response to the first request, the first request specifying one or more target components and at least one other instruction 8117.

Figure 20:
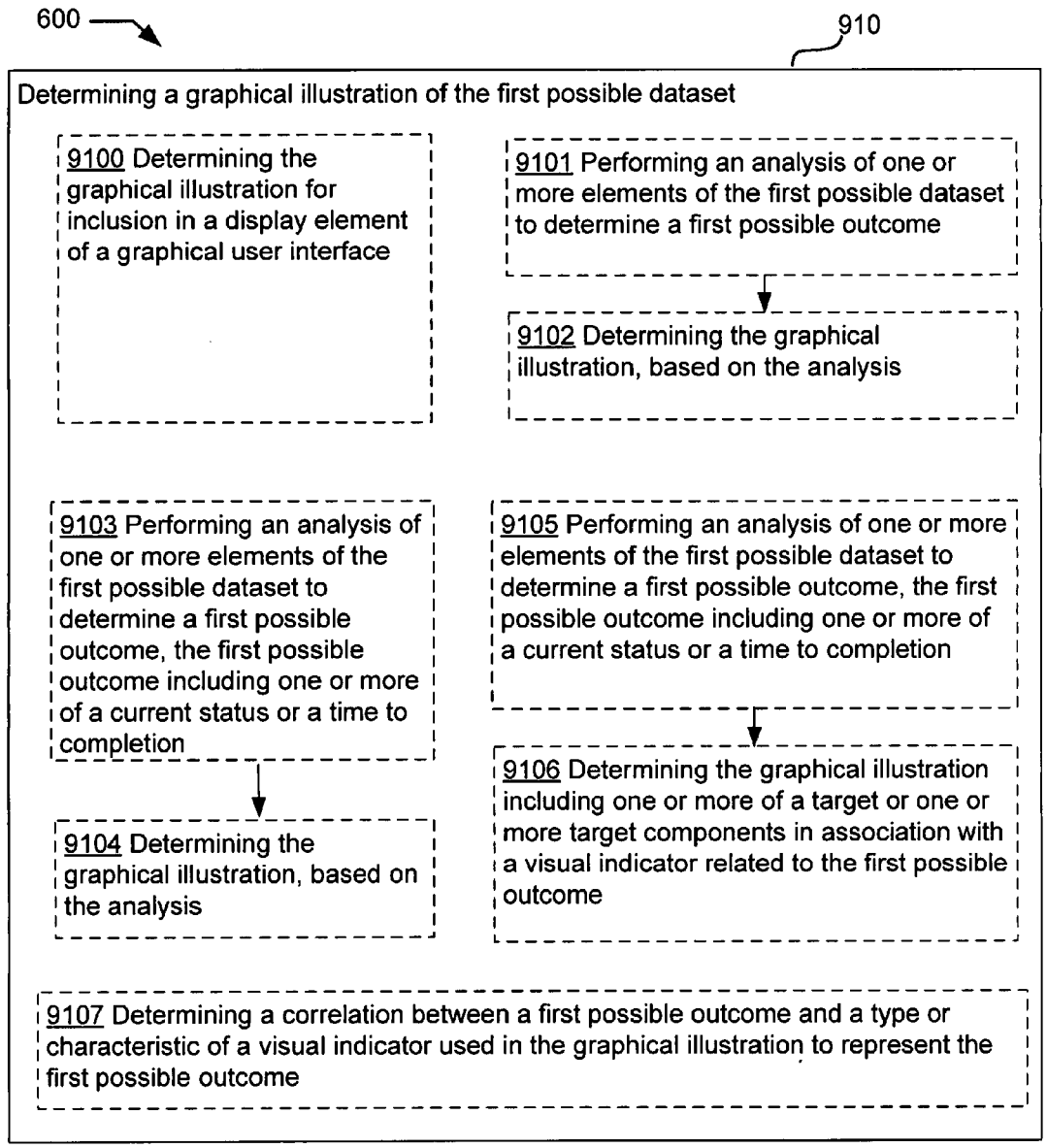
FIG. 20 shows optional embodiments of the operational flow of FIG. 15.

FIG. 20 illustrates optional embodiments of the operational flow 600 of FIG. 15. FIG. 20 shows illustrative embodiments of the optional determining operation 910, including operations determining a graphical illustration of the first possible dataset, and may include at least one additional operation. Determining operations may optionally include, but are not limited to, operation 9100, operation 9101, operation 9102, operation 9103, operation 9104, operation 9105, operation 9106, and/or operation 9107.

At the optional operation 9100, a graphical illustration of the first possible dataset is determined for inclusion in a display element of a graphical user interface. At the optional operation 9107, a graphical illustration of the first possible dataset is determined by determining a correlation between a first possible outcome and a type or characteristic of a visual indicator used in the graphical illustration to represent the first possible outcome.

In some embodiments, a graphical illustration of the first possible dataset is determined by performing an analysis of one or more elements of the first possible dataset to determine a first possible outcome 9101; and determining the graphical illustration, based on the analysis 9102. In some embodiments, a graphical illustration of the first possible dataset is determined by performing an analysis of one or more elements of the first possible dataset to determine a first possible outcome, the first possible outcome including one or more of a current status or a time to completion 9103; and determining the graphical illustration, based on the analysis 9104. In some embodiments, a graphical illustration of the first possible dataset is determined by performing an analysis of one or more elements of the first possible dataset to determine a first possible outcome, the first possible outcome including one or more of a current status or a time to completion 9105; and determining the graphical illustration including one or more of a target or one or more target components in association with a visual indicator related to the first possible outcome 9106.

Figure 21:
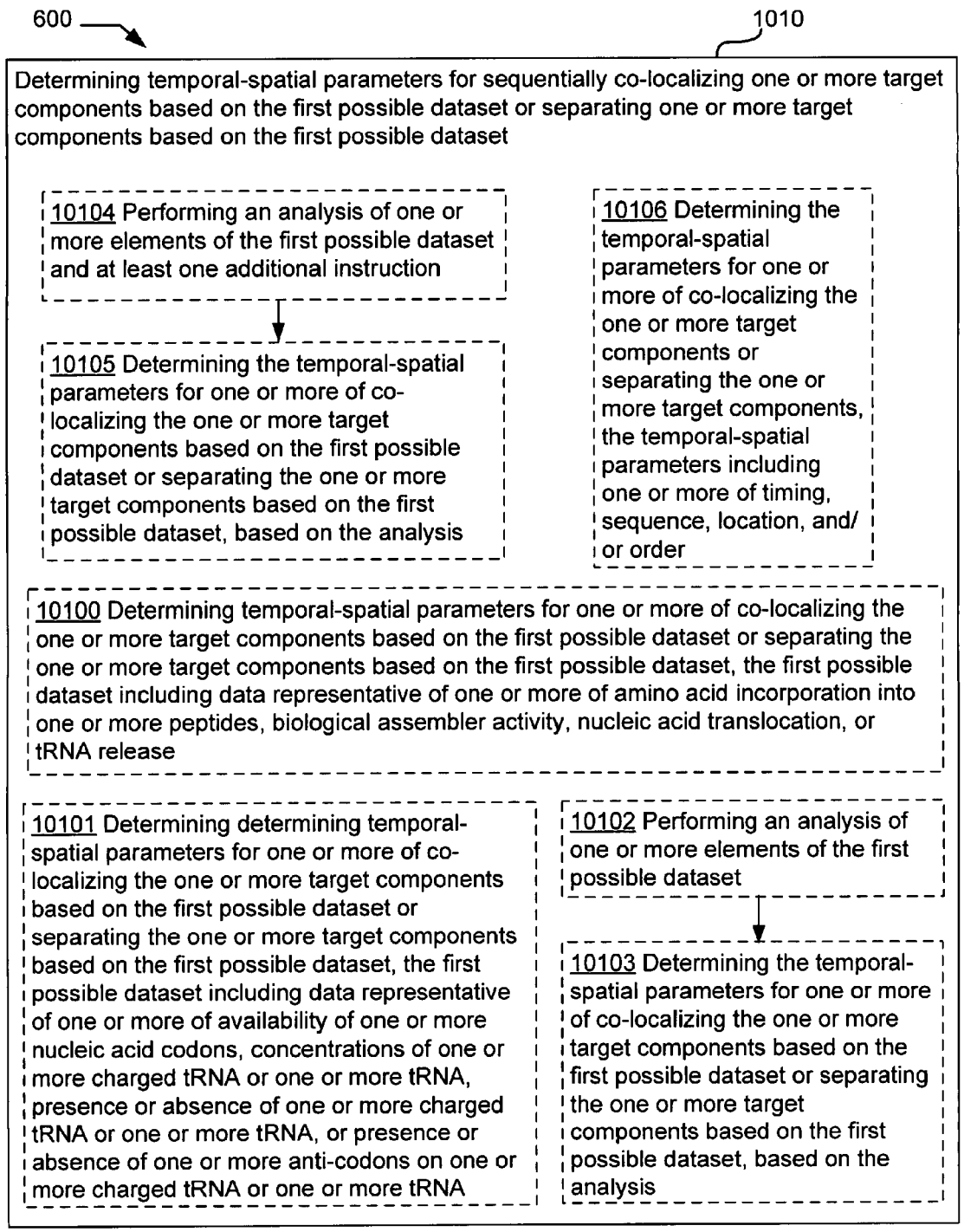
FIG. 21 shows optional embodiments of the operational flow of FIG. 15.

FIG. 21 illustrates optional embodiments of the operational flow 600 of FIG. 15. FIG. 21 shows illustrative embodiments of the determining operation 1010, including operations determining temporal-spatial parameters for optionally sequentially co-localizing one or more target components based on the first possible dataset or optionally sequentially separating one or more target components based on the first possible dataset, and may include at least one additional operation. Determining operations may optionally include, but are not limited to, operation 10100, operation 10101, operation 10102, operation 10103, operation 10104, operation 10105, and/or operation 10106.

At the optional operation 10100, temporal-spatial parameters are determined for optionally sequentially co-localizing the one or more target components based on the first possible dataset, and/or optionally sequentially separating the one or more target components based on the first possible dataset, the first possible dataset including data representative of one or more of amino acid incorporation into one or more peptides, biological assembler activity, nucleic acid translocation, or tRNA release. At the optional operation 10101, temporal-spatial parameters are determined for optionally sequentially co-localizing the one or more target components based on the first possible dataset, and/or optionally sequentially separating the one or more target components based on the first possible dataset, the first possible dataset including data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA. At the optional operation 10106, temporal-spatial parameters are determined for optionally sequentially co-localizing the one or more target components based on the first possible dataset, and/or optionally sequentially separating the one or more target components based on the first possible dataset, the temporal-spatial parameters including timing, sequence, location, and/or order.

In some embodiments, temporal-spatial parameters are determined for optionally sequentially co-localizing one or more target components based on the first possible dataset, and/or optionally sequentially separating one or more target components based on the first possible dataset by performing an analysis of one or more elements of the first possible dataset 10102; and determining the temporal-spatial parameters for optionally sequentially co-localizing the one or more target components based on the first possible dataset, and/or optionally sequentially separating the one or more target components based on the first possible dataset, based on the analysis 10103. In some embodiments, temporal-spatial parameters are determined for optionally sequentially co-localizing one or more target components based on the first possible dataset, and/or optionally sequentially separating one or more target components based on the first possible dataset by performing an analysis of one or more elements of the first possible dataset and at least one additional instruction 10104; and determining the temporal-spatial parameters for optionally sequentially co-localizing the one or more target components based on the first possible dataset, and/or optionally sequentially separating the one or more target components based on the first possible dataset, based on the analysis 10105.

Figure 22:
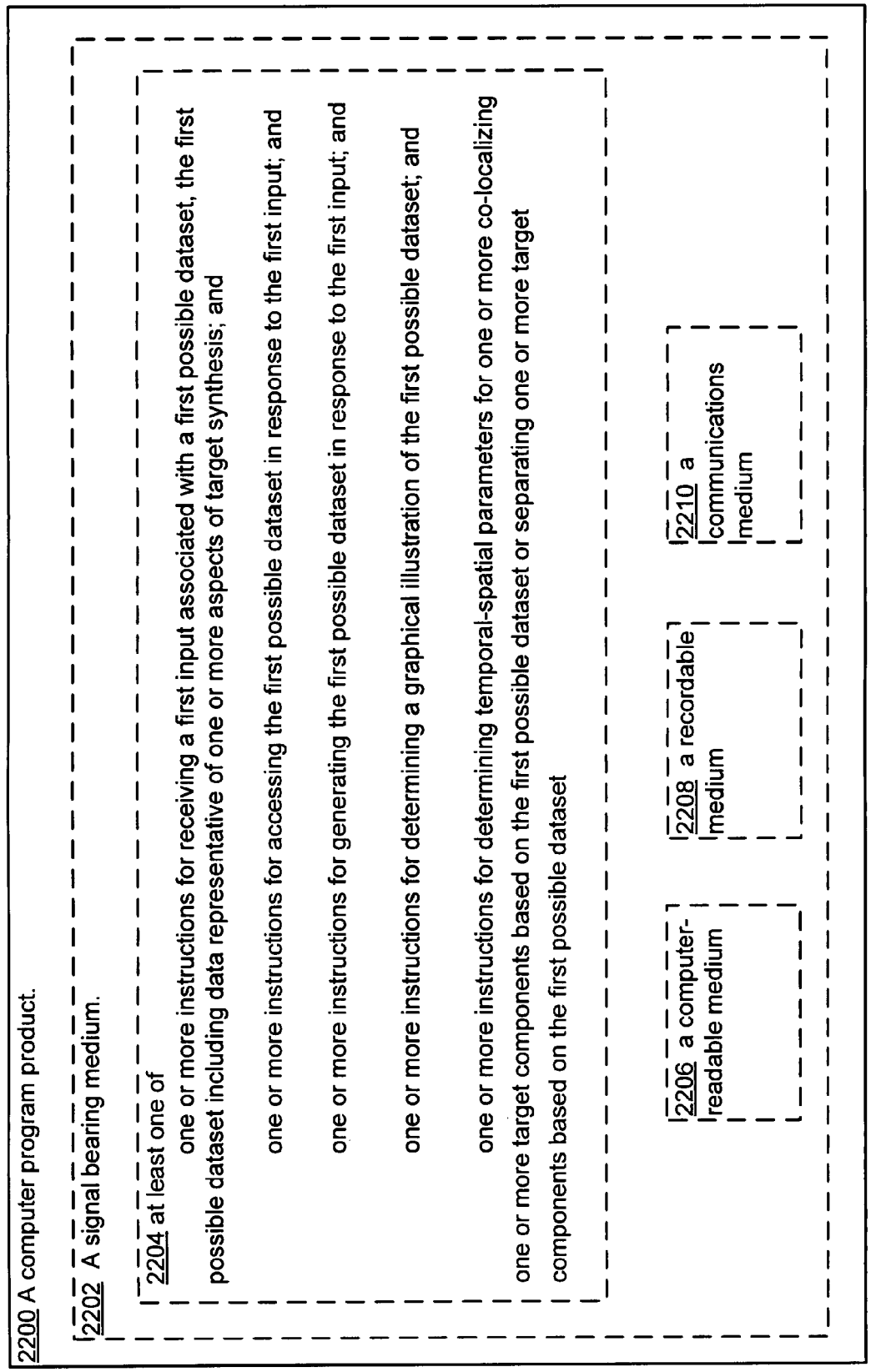
FIG. 22 shows a partial view of an illustrative embodiment of a computer program product that includes a computer program for executing a computer process on a computing device.

FIG. 22 shows a schematic of a partial view of an illustrative computer program product 2200 that includes a computer program for executing a computer process on a computing device. An illustrative embodiment of the example computer program product is provided using a signal bearing medium 2202, and may include at least one instruction of 2204: one or more instructions for receiving a first input associated with a first possible dataset, the first possible dataset including data representative of one or more aspects of target peptide synthesis; one or more instructions for accessing the first possible dataset in response to the first input; one or more instructions for generating the first possible dataset in response to the first input; one or more instructions for determining a graphical illustration of the first possible dataset; and/or one or more instructions for determining temporal-spatial parameters for one or more of sequentially co-localizing one or more target components based on the first possible dataset or optionally sequentially separating one or more target components based on the first possible dataset. The one or more instructions may be, for example, computer executable and/or logic implemented instructions. In some embodiments, the signal bearing medium 2202 of the one or more computer program products 2200 include a computer readable medium 2206, a recordable medium 2208, and/or a communications medium 2210.

Figure 23:
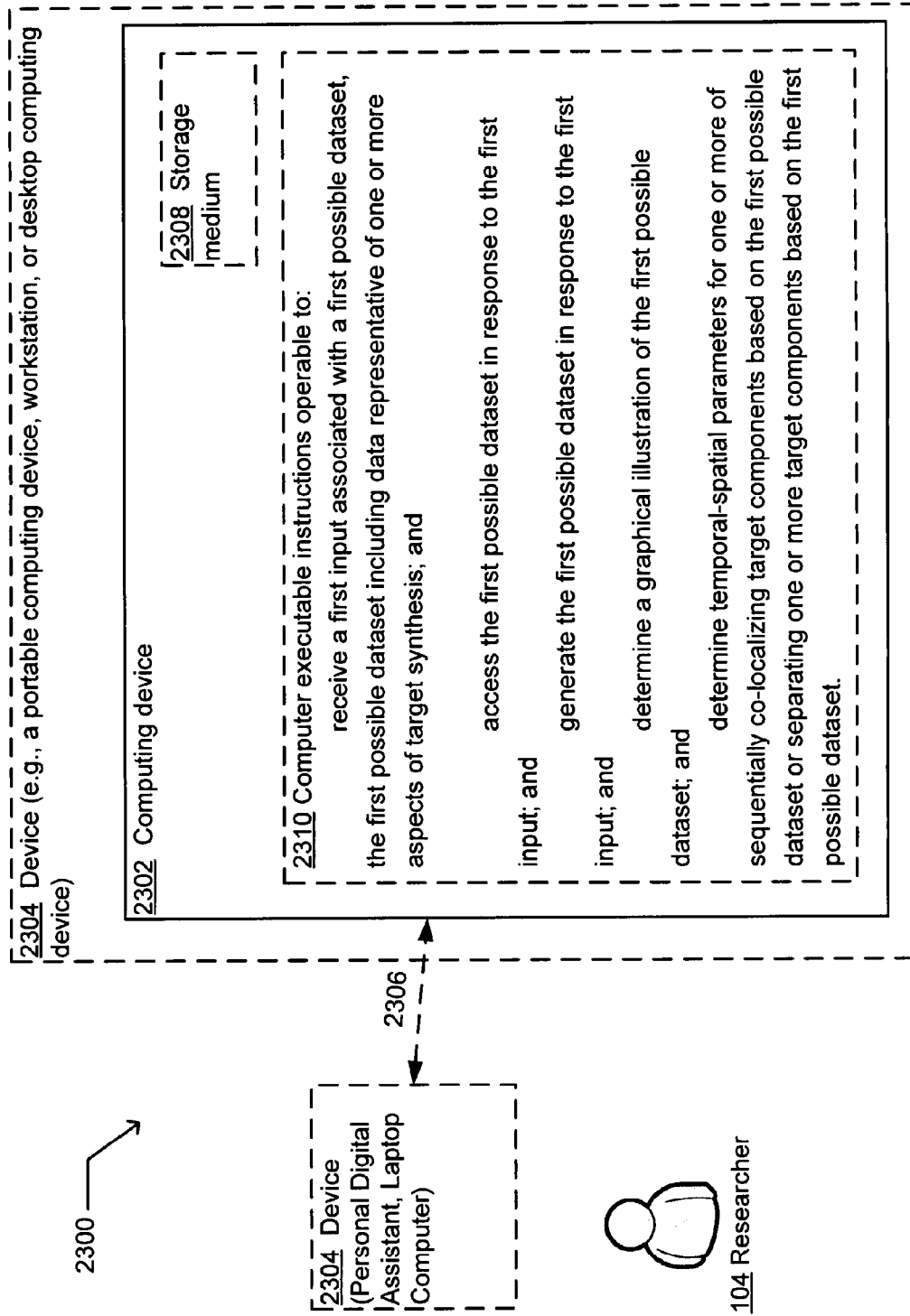
FIG. 23 shows an illustrative embodiment of a system in which embodiments may be implemented.

FIG. 23 shows a schematic of an illustrative system 2300 in which embodiments may be implemented. The system 2300 may include a computing system environment. The system 2300 also illustrates a researcher/scientist/investigator/operator 104 using a device 2304, that is optionally shown as being in communication with a computing device 2302 by way of an optional coupling 2306. The optional coupling may represent a local, wide area, or peer-to-peer network, or may represent a bus that is internal to a computing device (e.g. in illustrative embodiments the computing device 2302 is contained in whole or in part within the device 2304 or within one or more apparatus 410, or one or more computing units 426, or one or more controller units 422, or one or more monitoring units 440). An optional storage medium 2308 may be any computer storage medium.

The computing device 2302 includes one or more computer executable instructions 2310 that when executed on the computing device 2302 cause the computing device 2302 to receive a first input associated with a first possible dataset, the first possible dataset including data representative of one or more aspects of target peptide synthesis; optionally access the first possible dataset in response to the first input; optionally generate the first possible dataset in response to the first input; optionally determine a graphical illustration of the first possible dataset; and determine temporal-spatial parameters for one or more of optionally sequentially co-localizing one or more target components based on the first possible dataset or optionally sequentially separating one or more target components based on the first possible dataset. In some illustrative embodiments, the computing device 2302 may optionally be contained in whole or in part within one or more units of an apparatus 410 of FIG. 1 (e.g. one or more computing units 426 and/or one or more controller units 422 and/or one or more monitoring units 440), or may optionally be contained in whole or in part within the researcher device 2304.

The system 2300 includes at least one computing device (e.g. 2304 and/or 2302 and/or one or more computing units 426 of FIG. 1) on which the computer-executable instructions 2310 may be executed. For example, one or more of the computing devices (e.g. 2302, 2304, 426) may execute the one or more computer executable instructions 2310 and output a result and/or receive information from the researcher (optionally from one or more monitoring unit 440) on the same or a different computing device (e.g. 2302, 2304, 426) and/or output a result and/or receive information from an apparatus 410, one or more peptide synthesizer units 420, one or more controller units 422, and/or one or more monitoring units 440 in order to perform and/or implement one or more of the techniques, processes, or methods described herein, or other techniques.

The computing device (e.g. 2302 and/or 2304 and/or 426) may include one or more of a desktop computer, a workstation computer, a computing system comprised a cluster of processors, a networked computer, a tablet personal computer, a laptop computer, or a personal digital assistant, or any other suitable computing unit. In some embodiments, one or more peptide synthesis units 420 and/or one or more monitoring units 440 may be operable to communicate with any one of the computing devices (e.g. 2302 and/or 2304 and/or 426) that may be operable to communicate with a database to access the first possible dataset and/or subsequent datasets. In some embodiments, the computing device (e.g. 2302 and/or 2304 and/or 426) is operable to communicate with the peptide biological synthesizer apparatus 410.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

For ease of reading, all values described herein, and all numerical ranges described herein are approximate and should be read as including the word "about" or "approximately" prior to each numeral, unless context indicates otherwise. For example, the range "0.0001 to 0.01" is meant to read as "about 0.0001 to about 0.01."

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A peptide synthesis apparatus, comprising:
   at least one reaction chamber for synthesizing at least one target peptide;
   a plurality of aminoacylated tRNA ("aa-tRNA") sources, each of the plurality of aa-tRNA sources including aa-tRNA;
   a plurality of fluid channels fluidly coupling at least a portion of the plurality of aa-tRNA sources to the reaction chamber; and
   a computing device coupled to the at least a portion of the plurality of aa-tRNA sources, the computing device including a computer readable medium storing computer executable instructions that when executed by the computing device direct the at least a portion of the plurality of aa-tRNA sources to sequentially flow the aa-tRNA therefrom one type of the aa-tRNA at a time according to a predetermined order into the at least one reaction chamber, in which incorporation of amino acids from at least some of the sequentially flowed aa-tRNA into the at least one target peptide is not guided by the standard genetic code.

2. The peptide synthesis apparatus of claim 1, wherein the at least a portion of the plurality of aa-tRNA sources are fluidly coupled to a corresponding one of the plurality of fluid channels.

3. The peptide synthesis apparatus of claim 1, further comprising:
a common fluid channel fluidly coupled to the plurality of fluid channels; and
wherein the at least one reaction chamber includes an input port fluidly coupled to the common fluid channel and an output port through which a translation product generated during synthesis of the at least one target peptide in the at least one reaction chamber can exit.

4. The peptide synthesis apparatus of claim 1, further comprising:
a wash reservoir fluidly coupled to the at least one reaction chamber; and
wherein the computer executable instructions that when executed by the computing device further directs the wash reservoir to flush the at least one reaction chamber after the aa-tRNA from each of the at least a portion of the plurality of aa-tRNA sources is flowed into the at least one reaction chamber.

5. The peptide synthesis apparatus of claim 1, further comprising:
a source of ribosomes that is fluidly coupled to the at least one reaction chamber; and
wherein the computer executable instructions that when executed by the computing device further directs the source of ribosomes to inject ribosomes into the at least one reaction chamber.

6. The peptide synthesis apparatus of claim 1, wherein the at least one reaction chamber includes a size-exclusion membrane configured to selectively allow outflow of deacylated tRNA therethrough generated during synthesis of the at least one target peptide.

7. The peptide synthesis apparatus of claim 1, wherein the at least one reaction chamber and the at least a portion of the plurality of fluid channels are formed in a substrate.

8. The peptide synthesis apparatus of claim 7, wherein the plurality of aa-tRNA sources are not formed in the substrate.

9. The peptide synthesis apparatus of claim 7, wherein the plurality of aa-tRNA sources form an array that is formed in the substrate.

10. The peptide synthesis apparatus of claim 1, wherein the at least one reaction chamber includes a plurality of ribosomes fixed therein.

11. The peptide synthesis apparatus of claim 10, wherein the at least one reaction chamber includes a serpentine channel in which the plurality of ribosomes are fixed.

12. The peptide synthesis apparatus of claim 1, further comprising:
a source of ribosomes including beads having ribosomes attached thereto; and
wherein the at least one reaction chamber includes a dam dividing the at least one reaction chamber into an inlet portion and an outlet portion, the dam configured to restrict flow of the beads in the at least one reaction chamber, the inlet portion fluidly coupled to the at least a portion of the plurality of aa-tRNA sources and the source of ribosomes.

13. The peptide synthesis apparatus of claim 1, wherein some of the aa-tRNAs of the respective ones of the plurality of aa-tRNA sources are different types of aa-tRNA.

14. The peptide synthesis apparatus of claim 1, wherein the at least some of the sequentially flowed aa-tRNA includes an anti-codon and an amino acid that does not follow the standard genetic code.

15. The peptide synthesis apparatus of claim 1, further comprising:
a source of ribosomes including at least one bead having ribosomes attached thereto;
wherein the at least one reaction chamber includes a reaction channel defining a flow path; and
wherein the computer executable instructions that when executed by the computing device further directs the source of ribosomes to inject the at least one bead into the reaction channel, and direct the at least a portion of the plurality of aa-tRNA sources to sequentially inject different types of aa-tRNA in response to the at least one bead substantially completing traveling along the flow path until the at least one target peptide is synthesized.

16. The peptide synthesis apparatus of claim 1, further comprising:
a source of ribosomes;
wherein the at least one reaction chamber includes a main fluid channel fluidly coupled to the source of ribosomes;
wherein each of the at least a portion of the plurality of aa-tRNA sources is associated with a corresponding one of the plurality of fluid channels that is fluidly coupled to the main fluid channel, the plurality of fluid channels arranged in a selected spatial order corresponding to an amino acid sequence of the at least one target peptide to be synthesized; and
wherein the computer executable instructions that when executed by the computing device further directs the source of ribosomes to inject ribosomes into the main fluid channel and direct the at least a portion of the plurality of aa-tRNA sources to sequentially inject the aa-tRNA thereof into the corresponding one of the plurality of fluid channels as the ribosomes flow through the main fluid channel.

17. The peptide synthesis apparatus of claim 1, further comprising:
a source of ribosomes;
wherein the at least one reaction chamber includes a main fluid channel fluidly coupled to the plurality of fluid channels, and a serpentine ribosome channel fluidly coupled to the source of ribosomes; and
wherein the computer executable instructions that when executed by the computing device further directs the source of ribosomes to inject ribosomes into the main fluid channel and direct the at least a portion of the plurality of aa-tRNA sources to sequentially inject the aa-tRNA thereof direct the source of ribosomes to inject ribosomes into the serpentine ribosome channel and direct the at least a portion of the plurality of aa-tRNA sources to sequentially inject the aa-tRNA thereof into the main fluid channel as the ribosomes travel through the serpentine ribosome channel.

18. A peptide synthesis apparatus, comprising:
at least one reaction chamber for synthesizing at least one target peptide, the at least one reaction chamber having a plurality of aminoacylated tRNAs ("aa-tRNAs") disposed therein that are attached to a surface of the at least one reaction chamber;
at least one source of ribosomes;
at least one channel operably coupling the at least one source of ribosomes to the reaction chamber; and
a computing device coupled to the at least one source of ribosomes, the computing device including a computer readable medium storing computer executable instructions that when executed by the computing device direct the at least one source of ribosomes to provide ribosomes into the at least one reaction chamber to sequentially co-localize the ribosomes with at least a portion of the plurality of aa-tRNAs according to a predetermined order to direct synthesis of the at least one target peptide, in which at least some of the aa-tRNA does not follow the standard genetic code.

19. The peptide synthesis apparatus of claim 18, wherein the plurality of aa-tRNAs are tethered to the surface of the at least one reaction chamber in a selected spatial order for synthesizing the at least one target peptide.

20. The peptide synthesis apparatus of claim 18, wherein the at least one reaction chamber includes a serpentine channel in which the plurality of aa-tRNAs are fixed.

21. The peptide synthesis apparatus of claim 18, wherein at least a portion of the plurality of aa-tRNAs are different types of aa-tRNA.

22. The peptide synthesis apparatus of claim 18, wherein each of the plurality of aa-tRNAs are different types of aa-tRNA.

23. The peptide synthesis apparatus of claim 18, wherein the at least one channel is at least one fluid channel that fluidly couples the at least one source of ribosomes to the reaction chamber.

24. The peptide synthesis apparatus of claim 18, wherein:
the at least one reaction chamber includes a plurality of wells, each of at least a portion of the plurality of wells including a portion of the plurality of aa-tRNAs;
the at least one channel is configured as a grid overlying the plurality of wells;
the source of ribosomes includes at least one magnetic element having ribosomes attached thereto;
a magnetic actuator operably coupled to the computing devive; and
the computer executable instructions that when executed by the computing device further directs the magnetic actuator to move the at least one magnetic element through the grid and sequentially into selected ones of the plurality of wells.

25. The peptide synthesis apparatus of claim 24, wherein the computer executable instructions that when executed by the computing device further directs the magnetic actuator to move the at least one magnetic element through the grid and sequentially into selected ones of the plurality of wells in a selected time interval.

26. The peptide synthesis apparatus of claim 24, wherein the plurality of wells are removable.

27. The peptide synthesis apparatus of claim 24, wherein the portion of the plurality of aa-tRNAs is free in solution.

28. The peptide synthesis apparatus of claim 24, further comprising an additional source of aa-tRNAs configured to replenish aa-tRNA into the at least a portion of the plurality of wells consumed during synthesis of the at least one target peptide.

29. A microfluidic peptide synthesis apparatus, comprising:
a microchip substrate including,
at least one reaction chamber for synthesizing at least one target peptide formed in the microchip substrate;
an array formed in the microchip substrate, the array including a plurality of aminoacylated tRNA ("aa-tRNA") sources, each of the plurality of aa-tRNA sources including aa-tRNA; and
a plurality of microfluidic channels formed in the microchip substrate, the plurality of microfluidic channels fluidly coupling at least a portion of the plurality of aa-tRNA sources to the reaction chamber; and
a computing device coupled to the at least a portion of the plurality of aa-tRNA sources, the computing device including a computer readable medium storing computer executable instructions that when executed by the computing device direct the at least a portion of the plurality of aa-tRNA sources to sequentially flow the aa-tRNA therefrom one type of the aa-tRNA at a time according to a predetermined order into the at least one reaction chamber, in which incorporation of amino acids from at least some of the sequentially flowed aa-tRNA into the at least one target peptide is not guided by the standard genetic code.

* * * * *